United States Patent
Ohlmeyer et al.

(10) Patent No.: US 7,884,109 B2
(45) Date of Patent: *Feb. 8, 2011

(54) PURINE AND IMIDAZOPYRIDINE DERIVATIVES FOR IMMUNOSUPPRESSION

(75) Inventors: Michael J. Ohlmeyer, Plainsboro, NJ (US); Adolph C. Bohnstedt, Burlington, NJ (US); Celia Kingsbury, Cream Ridge, NJ (US); Koc-Kan Ho, West Windsor, NJ (US); Jorge Gabriel Quintero, Sayreville, NJ (US); Ming You, Plainsboro, NJ (US); Haengsoon Park, Plainsboro, NJ (US); Yingchun Lu, Kendall Park, NJ (US)

(73) Assignee: Wyeth LLC, Madison, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/870,802

(22) Filed: Oct. 11, 2007

(65) Prior Publication Data

US 2008/0287468 A1    Nov. 20, 2008

Related U.S. Application Data

(63) Continuation-in-part of application No. 11/398,357, filed on Apr. 5, 2006.

(60) Provisional application No. 60/668,286, filed on Apr. 5, 2005, provisional application No. 60/736,663, filed on Nov. 15, 2005.

(51) Int. Cl.
    *C07D 473/18*    (2006.01)
    *A61K 31/522*    (2006.01)
    *A61P 35/00*    (2006.01)
    *A61P 11/06*    (2006.01)
    *A61P 17/06*    (2006.01)
    *C07D 471/04*    (2006.01)

(52) U.S. Cl. ............... 514/263.2; 514/263.22; 544/118; 544/276; 544/229; 546/118

(58) Field of Classification Search ............ 514/234.2, 514/252.16, 263.2, 263.22, 263.23, 263.24; 544/118, 276

See application file for complete search history.

(56) References Cited

U.S. PATENT DOCUMENTS

| | | |
|---|---|---|
| 4,813,998 A | 3/1989 | Van Lommen et al. |
| 5,493,011 A | 2/1996 | Jung et al. |
| 5,705,625 A | 1/1998 | Civin et al. |
| 5,916,792 A | 6/1999 | Civin et al. |
| 6,313,129 B1 | 11/2001 | Uckun et al. |
| 6,372,740 B1 * | 4/2002 | Murata et al. ............ 514/234.2 |
| 6,432,947 B1 | 8/2002 | Arnaiz et al. |
| 6,452,005 B1 | 9/2002 | Uckun et al. |
| 6,506,738 B1 | 1/2003 | Yu et al. |
| 6,582,357 B2 | 6/2003 | Ouchi et al. |
| 2004/0116435 A1 | 6/2004 | Eriksson et al. |
| 2004/0116449 A1 | 6/2004 | Changelian |
| 2004/0157739 A1 | 8/2004 | Ahrens et al. |
| 2005/0032725 A1 | 2/2005 | Rao et al. |
| 2007/0021443 A1 * | 1/2007 | Ohlmeyer et al. ...... 514/263.22 |
| 2007/0253896 A1 * | 11/2007 | Le Brazidec et al. ....... 424/1.11 |
| 2008/0085898 A1 * | 4/2008 | Lu et al. .................. 514/234.2 |
| 2008/0085909 A1 * | 4/2008 | Roughton et al. ...... 514/263.22 |
| 2008/0207613 A1 * | 8/2008 | Styles et al. ............. 514/234.5 |
| 2008/0214580 A1 * | 9/2008 | Neagu et al. ............. 514/263.2 |
| 2008/0254029 A1 * | 10/2008 | Yanni et al. ............. 424/133.1 |
| 2008/0287468 A1 * | 11/2008 | Ohlmeyer et al. ......... 514/263.2 |
| 2009/0023723 A1 * | 1/2009 | Cole et al. ................ 514/234.2 |

FOREIGN PATENT DOCUMENTS

| | | |
|---|---|---|
| CA | 2238689 | 5/1997 |
| DE | 10 2005 042742 | 3/2007 |
| EP | 0 277 384 | 8/1988 |
| EP | 0 807 629 | 11/1997 |
| JP | 07075798 | 3/1995 |

(Continued)

OTHER PUBLICATIONS

Cetkovic-Cvrlje et al., "Dual Targeting of Burton's Tyrosine Kinase and Janus Kinase 3 with Rationally Designed Inhibitors Prevents Graft-Versus-Host Disease (GVHD)," *British Journal of Haematology*, vol. 126, pp. 821-827 (2004).

(Continued)

*Primary Examiner*—Mark L Berch
(74) *Attorney, Agent, or Firm*—Ram W. Sabnis

(57) ABSTRACT

The present invention provides novel purine and imidazopyridine derivatives useful for the prevention and treatment of autoimmune diseases, inflammatory disease, mast cell mediated disease and transplant rejection. The compounds are of the general formulas:

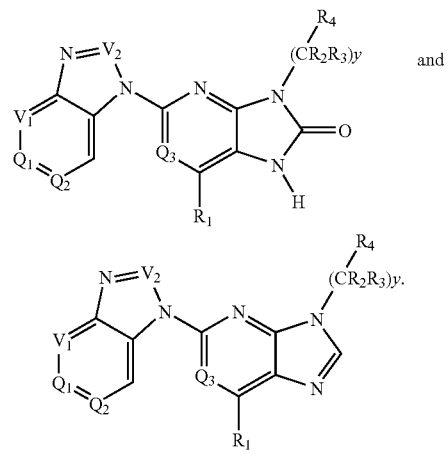

5 Claims, No Drawings

FOREIGN PATENT DOCUMENTS

| | | |
|---|---|---|
| JP | 2004 217582 | 8/2004 |
| WO | 99/41248 | 8/1999 |
| WO | 00/12089 | 3/2000 |
| WO | 01/19828 | 3/2001 |
| WO | 03/051277 | 6/2003 |
| WO | 2004/043386 | 5/2004 |
| WO | 2004/099204 | 11/2004 |
| WO | 2005/066156 | 7/2005 |
| WO | 2006/069080 | 6/2006 |
| WO | 2006/096270 | 9/2006 |
| WO | 2006/108103 | 10/2006 |
| WO | 2007/035873 | 3/2007 |
| WO | WO 2008060301 A1 * | 5/2008 |

OTHER PUBLICATIONS

Cetkovic-Cvrlje et al., "Targeting Janus kinase 3 in the treatment of leukemia and inflammatory diseases," *Arch. Immunol. Ther. Exp.*, vol. 52, pp. 69-82 (2004.).

Changelian et al., "Prevention of Organ Allograft Rejection by a Specific Janus Kinase 3 Inhibitor," *Science*, vol. 302, pp. 875-878 (2003).

O'Shea, J.J., "Cytokine signaling: new insights and new opportunities for therapeutic intervention?", *Arthristis Res.*, vol. 3(Suppl A): L018 (2001).

Ortmann et al., "Janus kinases and signal transducers and activators of transcription: their roles in cytokine signaling, development and immunoregulation," *Arthritis Res.*, vol. 2, pp. 16-32 (2000).

Yamaoka et al., "The Janus kinases (Jaks)," *Genome Biology*, vol. 5:253, pp. 253.1-253.6 (2004).

Uckun et al., "Structure-based Design of Novel Anticancer Agents," *Current Cancer Drug Targets*, vol. 1(1), pp. 59-71 (2001).

Kawahara et al., "Critical role of the interleukin 2 (IL-2) receptor γ-chain associated Jak3 in the IL-2-induced c-*fos* and c-*myc*, but not *bcl-2*, gene induction," *Proc. Natl. Acad. Sci.*, vol. 92, pp. 8724-8728 (1995).

O'Shea et al., "A New Modality for Immunosuppression: Targeting the Jak/Stat Pathway," *Nature Reviews*, vol. 3, pp. 555-564 (2004).

Papageorgiou et al., "Is Jak3 a new drug target for immunomodulation-based therapies?" *TRENDS in Pharmacological Sciences*, vol. 25(11), pp. 558-562 (2004).

Lin et al., "Constitutive Activation of Jak3/Stat3 in Colon Carcinoma Tumors and Cell Lines", *American Journal of Pathology*, vol. 167(4), pp. 969-980 (2005).

Dana et al, "Role of Immunity and Inflammation in Corneal and Ocular Surface Disease Associated with Dry Eye," *Lacrimal Gland, Tear Film and Dry Eye Syndromes 3*, pp. 729-738 (2002).

Nagelhout et al., "Preservation of Tear Film Integrity and Inhibition of Corneal Injury by Dexamethasone in a Rabbit Model of Lacrimal Gland Inflammation-Induced Dry Eye," *Journal of Ocular Pharmacology and Therapeutics*, vol. 21(2), pp. 139-148 (2005).

Pflugfelder, S., "Perspective Anti-inflammatory Therapy for Dry Eye," *American Journal of Ophthalmology*, vol. 137(2), pp. 337-342 (2004).

Amin et al, "Inhibition of Jak3 induces apoptosis and decreases anaplastic lymphoma kinase activity in anaplastic large cell lymphoma," *Oncogene*, vol. 22, pp. 5399-5407 (2003).

Harrington et al., "VX-680, a potent and selective small-molecule inhibitor of the Aurora kinases, suppresses tumor growth in vivo," *Nature Medicine*, vol. 10(3), pp. 262-267 (2004).

Jung et al., "Discovery of Novel and Potent Thiazoloquinazolines as Selective Aurora A and B Kinase," American Chem Soc., pp. 1-16 (2005).

Frantz, S., "Playing Dirty", *Nature*, vol. 437, pp. 942-943 (2005).

Martinez-Lostao et al., "Role of the STAT1 pathway in apoptosis induced by fludarabine and Jak kinase inhibitors in B-cell chronic lymphocytic leukemia," *Leuk Lymphoma*, vol. 46(3), pp. 435-442 (2005), Abstract only (PMID: 15621835).

Lai et al., "Jak3 activation is significantly associated with ALK expression in anaplastic large cell lymphoma," *Human Pathology*, vol. 36, pp. 939-944 (2005).

Pearson, H., "Designer transplant drug shows promise in monkeys," *News & Nature* (2003).

International Search Report from corresponding International Application No. PCT/US2006/012824.

Goldberg et. al., "Optimization of 2-Phenylaminoimidazo [4,5-*h*]isoquinolin-9-ones: Orally Active Inhibitors of Ick Kinase," *Journal of Medical Chem.*, vol. 46, pp. 1337-1349.

Beijersbergen van Henegouwen GM et al., Hydrolysis of RRR0alpha-tocopheryl acetate (vitamin # acetate) in the skin and its UV protecting activity (an in vivo study with the rat) *J Photochem Photobiol*, Jul. 29, 2005, vol. 1, pp. 45-51.

Hirota et all, "Synthesis and Biological Evaluation of 2,8-Disubstituted 9-Benzyladenines: Discovery of 8-Mercaptoadenines as Potent Interferon-Inducers," *Bioorganic & Medicinal Chemistry 11*, 2003, pp. 2715-2722.

International Search Report and Written Opinion from International Application No. PCT/US2006/061004.

International Search Report and Written Opinion from International Application No. PCT/US2007/080447.

International Search Report and Written Opinion from International Application No. PCT/US2007/080464.

International Search Report and Written Opinion from International Application No. PCT/US2007/081232.

International Search Report and Written Opinion from International Application No. PCT/US2007/069530.

* cited by examiner

PURINE AND IMIDAZOPYRIDINE DERIVATIVES FOR IMMUNOSUPPRESSION

CROSS-REFERENCE TO RELATED APPLICATIONS

This application is a Continuation-in-Part of U.S. patent application Ser. No. 11/398,357 filed Apr. 5, 2006, which claims priority from U.S. Provisional Application Ser. No. 60/668,286, filed Apr. 5, 2005, and U.S. Provisional Application Ser. No. 60/736,663, filed Nov. 15, 2005, the entire contents of the foregoing which are incorporated herein by reference.

FIELD OF THE INVENTION

The invention relates to purine and imidazopyridine derivatives useful as immunosuppressants.

BACKGROUND OF THE INVENTION

Immunosuppression is an important clinical approach in treating autoimmune disease and in preventing organ and tissue rejection. The clinically available immunosuppressants, including azathioprine, cyclosporine and tacrolimus, although effective, often cause undesirable side effects including nephrotoxicity, hypertension, gastrointestinal disturbances and gum inflammation. Inhibitors of the tyrosine kinase Jak3 are known to be useful as immunosuppressants (see U.S. Pat. No. 6,313,129).

The members of the Janus kinase (Jak) family of non-receptor intracellular tyrosine kinases are components of cytokine signal transduction. Four family members have been identified to date: Jak1, Jak2, Jak3 and Tyk2. The Jaks play a key role in the intracellular signaling mediated through cytokine receptors. Upon binding of cytokines to their receptors, Jaks are activated and phosphorylate the receptors, creating docking sites for other signaling molecules, in particular members of the signal transducer and activator of transcription (STAT) family. While expression of Jak1, Jak2 and Tyk2 is relatively ubiquitous, Jak3 expression is temporally and spatially regulated. Jak3 is predominantly expressed in cells of hematopoietic lineage; it is constitutively expressed in natural killer (NK) cells and thymocytes and is inducible in T cells, B cells and myeloid cells (reviewed in Ortmann, et al., 1999 and Yamaoka, et al., 2004). Jak3 is also is expressed in mast cells, and its enzymatic activity is enhanced by IgE receptor/Fc RI cross-linking (Malaviya and Uckun, 1999).

A specific, orally active Jak3 inhibitor, CP-690,550, has been shown to act as an effective immunosuppressant and prolong animal survival in a murine model of heart transplantation and a primate model of kidney transplantation (Changelian, et al., 2003).

Furthermore, aberrant Jak3 activity has been linked to a leukemic form of cutaneous T-cell lymphoma (Sezary's syndrome) and acute lymphoblastic leukemia (ALL), the most common form of childhood cancer. The identification of Jak3 inhibitors has provided the basis for new clinical approaches in treating leukemias and lymphomas (Cetkovic-Cvrlje, Marina; Uckun, Faith M.; Targeting Janus Kinase 3 in the treatment of Leukemia and Inflammatory Diseases. Archivum Immunologiae et Therapie Experimentalis (2004) and/or Uckun, Faith M.; Mao, Chen. Tyrosine kinases as new molecular targets in treatment of inflammatory disorders and leukemia. Current Parmaceutical Design (2004)). Two dimethoxyquinazoline derivatives, WHI-P131 (JANEX-1) and WHI-P154 (JANEX-2), have been reported to be selective inhibitors of Jak3 in leukemia cells (Sudbeck et al., 1999).

Jak3 has also been shown to play a role in mast-cell mediated allergic reactions and inflammatory diseases and serves as a target in indications such as asthma and anaphylaxis.

Therefore, compounds that inhibit Jak3 are useful for indications such as leukemias and lymphomas, organ and bone marrow transplant rejection, mast cell-mediated allergic reactions and inflammatory diseases and disorders.

SUMMARY OF THE INVENTION

It has now been found that compounds of general formula I and II are potent and selective inhibitors of Jak3:

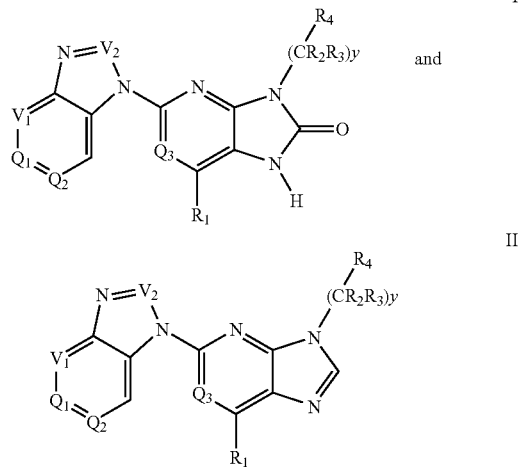

In these compounds, $Q_1$ and $Q_2$ are independently selected from the group consisting of $CX_1$, $CX_2$, and nitrogen;

$Q_3$ is N or CH;

$X_1$ and $X_2$ are independently selected from the group consisting of hydrogen, $(C_1$-$C_6)$alkyl, cyano, halo, halo$(C_1$-$C_6)$ alkyl, hydroxyl, $(C_1$-$C_6)$alkoxy, halo$(C_1$-$C_6)$alkoxy, nitro, carboxamido, and methylsulfonyl;

$V_1$ and $V_2$ are independently selected from CH and N;

$R_1$ is selected from the group consisting of hydrogen and methyl;

y is zero or an integer selected from 1, 2 and 3;

$R_2$ and $R_3$ are selected independently for each occurrence of $(CR_2R_3)$ from the group consisting of hydrogen and $(C_1$-$C_6)$ alkyl; and $R_4$ is selected from a group consisting of alkyl, heterocyclyl, aryl, substituted alkyl, substituted heterocyclyl, and substituted aryl.

The members of these genera are useful in inhibiting Jak3 activity and as such are useful in indications where clinical immunosuppression is desired and in the treatment of hematological cancers.

In another aspect, the invention relates to pharmaceutical compositions comprising a therapeutically effective amount of at least one compound of general formula I or general formula II, or a pharmaceutically acceptable salt thereof, and a pharmaceutically acceptable carrier.

In another aspect, the invention relates to a method for treating a disease by altering a response mediated by Jak3 tyrosine kinase. The method comprises bringing into contact with Jak3 at least one compound of general formula I or II.

In yet another aspect the present invention relates to a method of suppressing the immune system in a subject in need thereof comprising administering to the subject a therapeutically effective amount of at least one compound of general formula I or II.

Suppression of immune system activity is desirable for preventing or treating tissue or organ rejection following transplant surgery and for preventing and treating diseases and disorders arising from aberrant activity of the immune system, in particular autoimmune disorders and diseases. Exemplary autoimmune disorders include graft versus host disease (GVHD), insulin-dependent diabetes (Type I), Hashimoto's thyroiditis and Graves' disease, pernicious anemia, Addison's disease, chronic active hepatitis, Crohn's disease, ulcerative colitis, rheumatoid arthritis, multiple sclerosis, systemic lupus erythematosus, psoriasis, scleroderma and myasthenia gravis.

The compounds of the present invention are useful in preventing and treating diseases and disorders related to mast cell-mediated allergic reactions and inflammation.

Other indications in which the Jak3 inhibitors are useful include leukemias and lymphomas.

DETAILED DESCRIPTION OF THE INVENTION

Throughout this specification the substituents are defined when introduced and retain their definitions.

In a first aspect the invention relates to purinones and imidazopyridinones having general formula I:

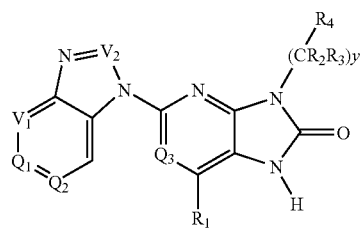

I

The members of the genus I may be conveniently divided into subgenera based on the values of Q and V. When $Q_1$ is carbon, $Q_2$ is nitrogen, $V_1$ is nitrogen, and $V_2$ is carbon a subgenus of purinones and imidazo[4,5-b]pyridinones having an attached purine arises. When $Q_1$ is carbon, $Q_2$ is nitrogen, and both $V_1$ and $V_2$ are carbon, a subgenus of purinones and imidazo[4,5-b]pyridinones having an attached imidazo[5,4-c]pyridine arises. When $Q_1$ and $Q_2$ are carbon, and both $V_1$ and $V_2$ are carbon, a subgenus of purinones and imidazo[4,5-b]pyridinones having an attached benzimidazole arises. When $Q_1$ and $Q_2$ are carbon, $V_1$ is carbon, and $V_2$ is nitrogen, a subgenus of purinones and imidazo[4,5-b]pyridinones having an attached benzotriazole arises. The genus could similarly be divided on the basis of $Q_3$. When $Q_3$ is nitrogen, a subgenus of purinones having an attached purine, imidazo[5,4-c]pyridine, benzimidazole or benzotriazole arises. When $Q_3$ is carbon, a subgenus of imidazo[4,5-b]pyridinones having an attached purine, imidazo[5,4-c]pyridine, benzimidazole or benzotriazole arises. The structures of these subgenera are shown below:

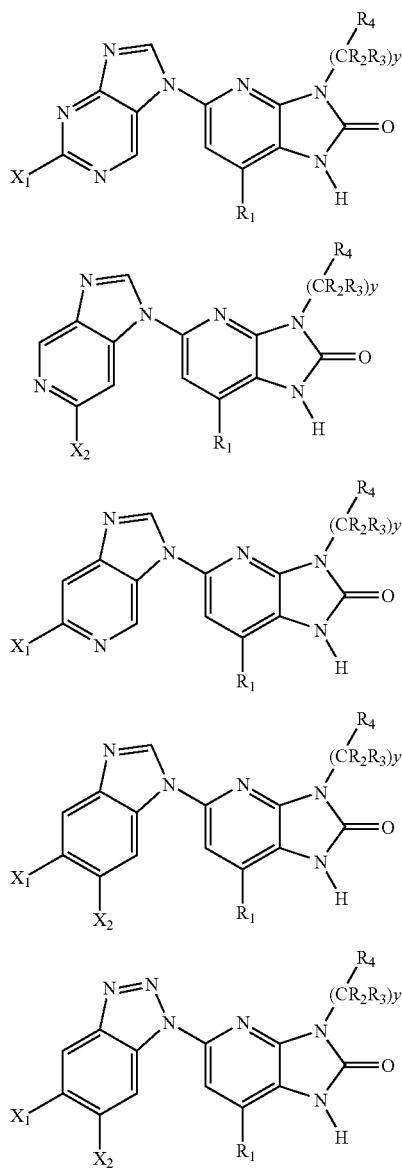

When $Q_3$ is nitrogen, a subgenus of purinones having an attached purine, imidazo[5,4-c]pyridine, benzimidazole or benzotriazole arises. The structures of these subgenera are shown below

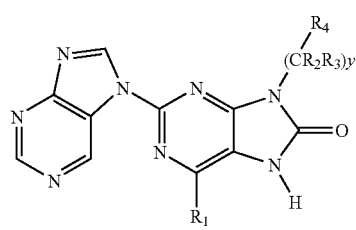

-continued

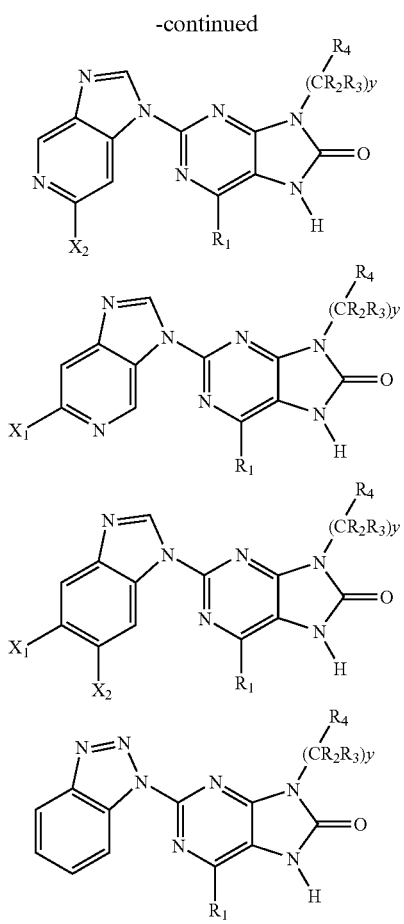

In another aspect the invention relates to purines and imidazopyridines having general formula II:

II

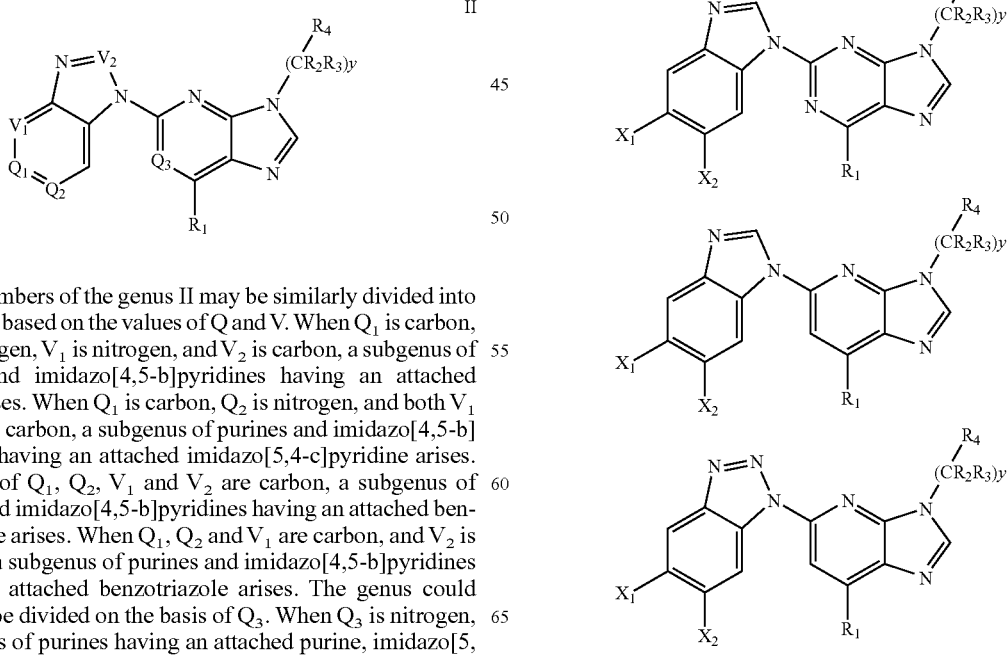

The members of the genus II may be similarly divided into subgenera based on the values of Q and V. When $Q_1$ is carbon, $Q_2$ is nitrogen, $V_1$ is nitrogen, and $V_2$ is carbon, a subgenus of purines and imidazo[4,5-b]pyridines having an attached purine arises. When $Q_1$ is carbon, $Q_2$ is nitrogen, and both $V_1$ and $V_2$ are carbon, a subgenus of purines and imidazo[4,5-b]pyridines having an attached imidazo[5,4-c]pyridine arises. When all of $Q_1$, $Q_2$, $V_1$ and $V_2$ are carbon, a subgenus of purines and imidazo[4,5-b]pyridines having an attached benzimidazole arises. When $Q_1$, $Q_2$ and $V_1$ are carbon, and $V_2$ is nitrogen, a subgenus of purines and imidazo[4,5-b]pyridines having an attached benzotriazole arises. The genus could similarly be divided on the basis of $Q_3$. When $Q_3$ is nitrogen, a subgenus of purines having an attached purine, imidazo[5,4-c]pyridine, benzimidazole or benzotriazole arises. When $Q_3$ is carbon, a subgenus of imidazo[4,5-b]pyridines having an attached purine, imidazo[5,4-c]pyridine, benzimidazole or benzotriazole arises. The structures of these subgenera are shown below:

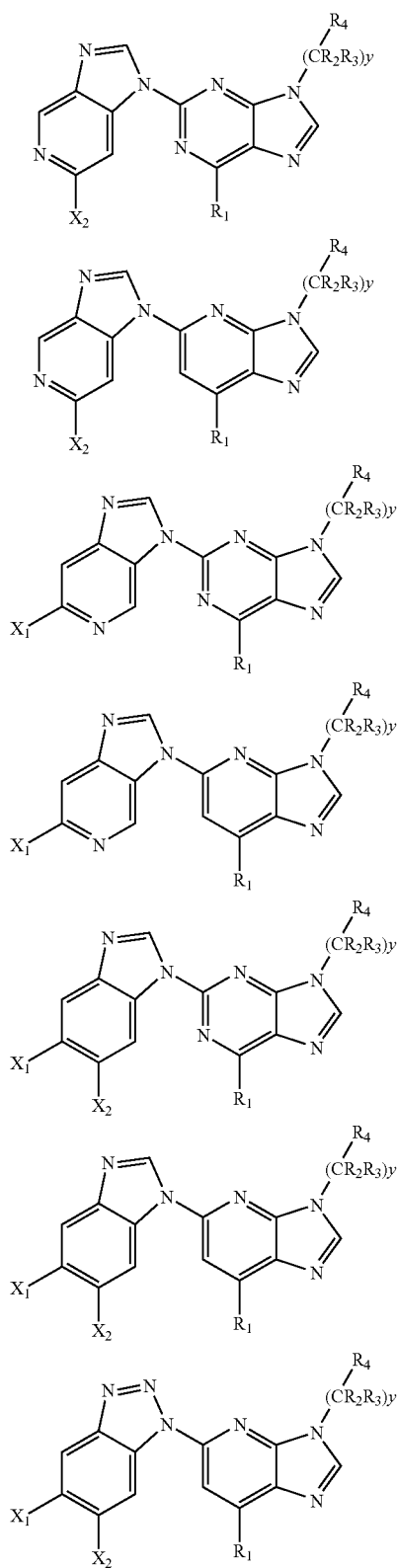

-continued

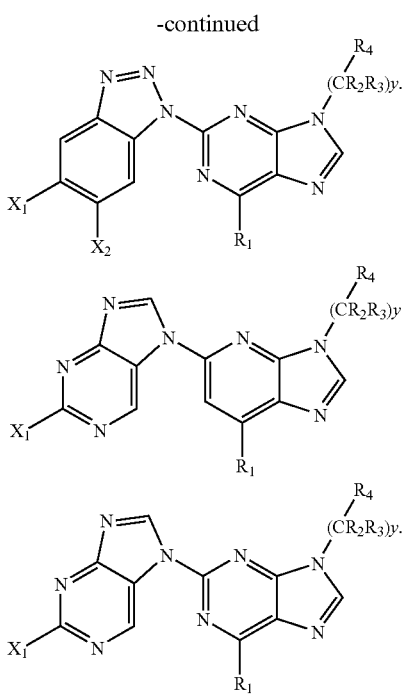

In certain embodiments, $X_1$ and $X_2$ are selected from hydrogen, cyano, chloro, fluoro, trifluoromethyl, trifluoromethoxy, carboxamido, and methyl; in other embodiments $R_1$ is H. In one subdivision, y is zero; in another y is 1 or 2 and $R_2$ and $R_3$ are hydrogen or methyl. Examples of $R_4$ include: cyclopentyl, cyclohexyl, piperidine, oxepane, benzoxepane, dihydrocyclopentapyridine, phenyl, tetralin, indane, tetrahydropyran, tetrahydrofuran, tetrahydroindole, isoquinoline, tetrahydroisoquinoline, quinoline, tetrahydroquinoline, chroman, isochroman, pyridine, pyrazine, pyrimidine, dihydropyran, dihydrobenzofuran, tetrahydrobenzofuran, tetrahydrobenzothiophene, furan, dihydropyrano[2,3-b]pyridine (see example below), tetrahydroquinoxaline, tetrahydrothiopyran(thiane), thiochroman(dihydrobenzothiin), thiochroman-1,1-dioxide, tetrahydronaphthalene, oxabicyclooctane, oxocane, tetrathiohydropyran-1,1-dioxide, tetrathiohydropyranoxide, or any of the foregoing rings carrying from 1-3 additional substituents, such as halogen, methyl, methoxy, trifluoromethyl, cyano, hydroxy, oxo, oxide and acetyl. Additional examples in which $R_4$ is alkyl or substituted alkyl include subgenera in which $R_4$ is oxaalkyl (alkoxyalkyl).

In certain embodiments of genus I, y is 1 or 2; $R_2$ and $R_3$ are hydrogen or methyl and $R_4$ is phenyl, quinoline, pyridine, pyrazine or substituted phenyl, quinoline, pyridine or pyrazine. In other embodiments of genus I, y is zero and $R_4$ is cyclopentyl, cyclohexyl, phenyl, piperidine, oxepane, benzoxepane, dihydrocyclopentapyridine, tetralin, indane, tetrahydropyran, tetrahydrofuran, tetrahydroindole, isoquinoline, tetrahydroisoquinoline, quinoline, tetrahydroquinoline, chroman, pyridine, pyrimidine, dihydropyran, dihydrobenzofuran, tetrahydrobenzofuran, tetrahydrobenzothiophene, dihydrobenzothiophene, furan, dihydropyrano[2,3-b]pyridine, tetrahydroquinoxaline, tetrahydrothiopyran(thiane), thiochroman(dihydrobenzothiin), thiochroman-1,1-dioxide, tetrahydronaphthalene, oxabicyclooctane, oxocane, tetrathiohydropyran-1,1-dioxide, tetrathiohydropyranoxide, or a substituted ring from the foregoing list. In further embodiments, (a) y is zero and $R_4$ is selected from cyclopentyl, cyclohexyl, oxepane, dihydrocyclopentapyridine, tetrahydropyran, tetrahydroquinoline, chroman, dihydrobenzofuran, tetrahydrobenzofuran, dihydropyrano[2,3-b]pyridine and tetrahydroquinoxaline, each optionally substituted with hydroxy, oxo, or halogen; or (b) y is 1 or 2, $R_2$ and $R_3$ are hydrogen or methyl and $R_4$ is selected from phenyl, pyridine and pyrazine, each optionally substituted with halogen. When y is zero, $R_4$ may be tetrahydropyran-4-yl, 4-hydroxycyclohexyl, 4-oxocyclohexyl, oxepan-4-yl, chroman-4-yl or fluoro substituted chroman-4-yl. It appears that, although both enantiomers are active, compounds in which the carbon at 4 of the chroman is of the (R) configuration have higher potency. Certain of the foregoing subgenera in which y is zero may also be described by a representation in which $R_4$ is

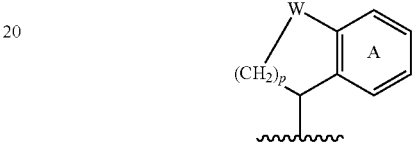

According to this representation, W is $CH_2$, C=O, CHOH, or O; p is 1, 2 or 3; and A is a six-membered heteroaromatic ring containing 1 or 2 nitrogens, a benzene ring optionally substituted with one or two fluorines, or a five-membered heterocyclic ring. The wavy line denotes the point of attachment to the purinone. Examples in which W is C=O include indanones, tetralones and benzosuberones. Examples in which W is $CH_2$ include indanes, tetralins and benzocycloheptanes. Examples in which W is CHOH include substituted tetralins. Examples in which W is O include dihydrobenzofuran, chroman, benzopyrans and benzoxepanes.

As before, compounds in which the carbon marked with an asterisk

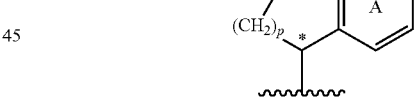

is of the (R) configuration appear to be more potent than their corresponding (S) enantiomers. An example of such a compound is

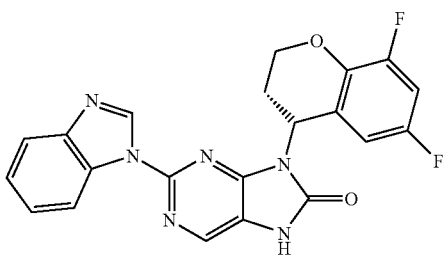

which is more potent than its corresponding (S) enantiomer

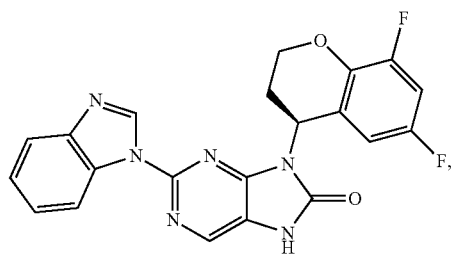

but both exhibit Jak3 kinase $IC_{50}$ below 1 micromolar. Examples below also include compounds in which y is 1 and $R_4$ is selected from difluorophenyl, fluorophenyl, chlorophenyl, chlorofluorophenyl, pyridin-3-yl and pyrazin-3-yl.

When $R^4$ is described by the representation below:

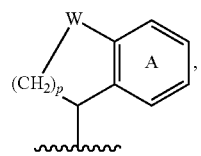

$R^4$ may be a substituted hydrxoytetralinyl of formula:

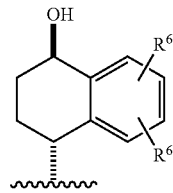

wherein $R^6$ is halogen or hydrogen. In other embodiments of genus I, y is zero and $R^4$ is a substituted hydroxytetralinyl of formula:

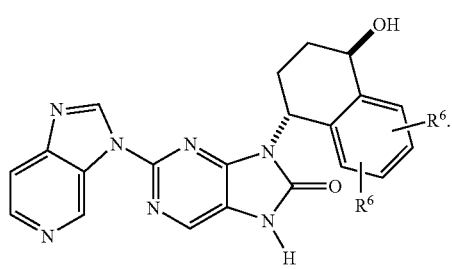

In further embodiments of genus I, y is zero and $R^4$ is a hydroxytetralinyl of formula:

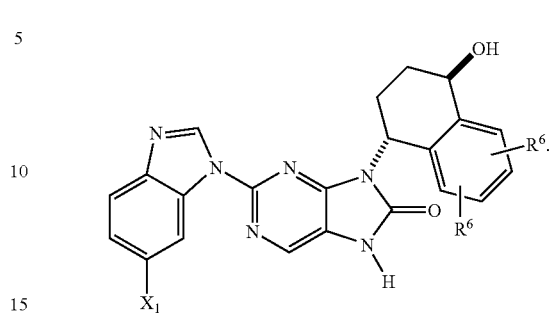

Examples of compounds that fall within the foregoing embodiments include but are not limited to:

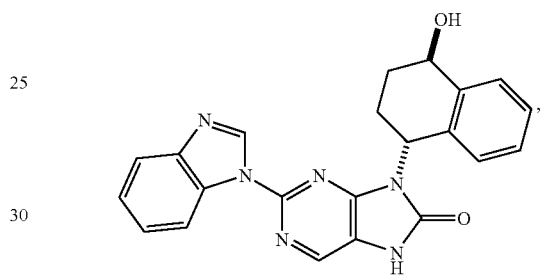

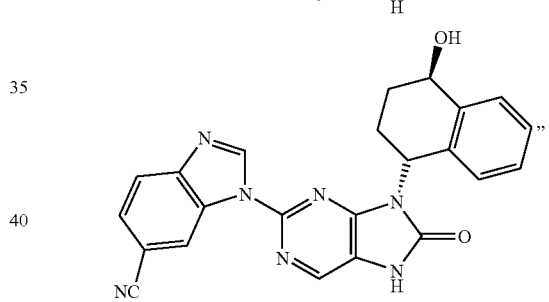

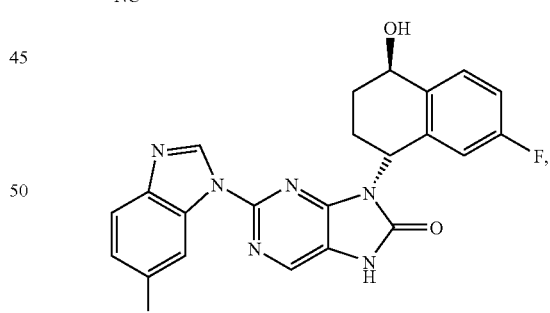

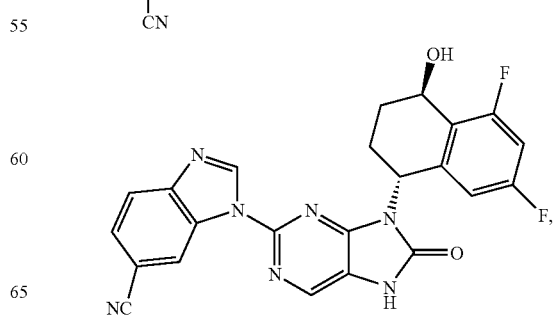

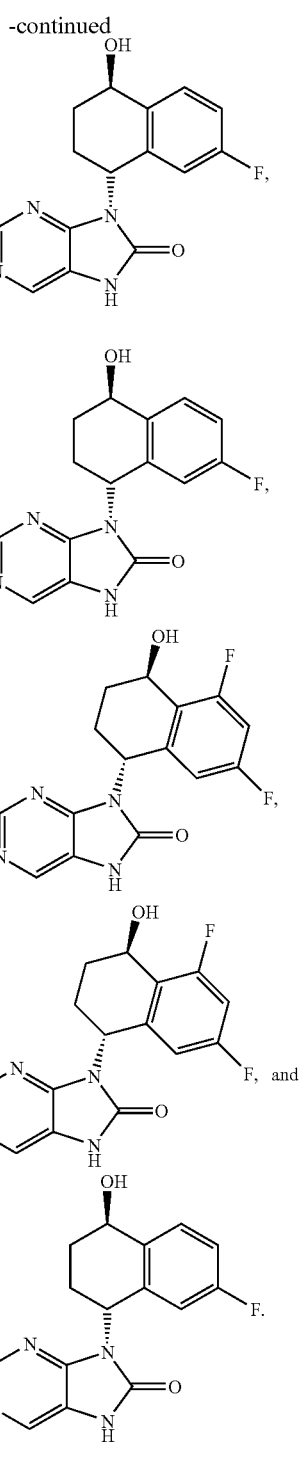

In certain embodiments of genus II, nitrogen is present at the 7 and 9 position on the 6,5 bicyclic heterocycle; $X_1$ is selected from hydrogen, cyano and fluoro; $Q_1$ is N and $R_1$ is H. In some embodiments, y is zero and $R_4$ is selected from phenyl, tetrahydropyran (e.g. tetrahydropyran-4-yl), isoquinoline (e.g. isoquinolin-8-yl), tetrahydroquinoline (e.g. 1,2,3,4-tetrahydroquinolin-5-yl), and their substituted counterparts. In other embodiments, y is 1 and $R_4$ is selected from difluorophenyl, fluorophenyl, chlorophenyl, chlorofluorophenyl, pyridin-3-yl and pyrazin-3-yl.

All of the compounds falling within the foregoing parent genera and their subgenera are useful as Jak3 inhibitors.

DEFINITIONS

For convenience and clarity certain terms employed in the specification, examples and claims are described herein.

Alkyl is intended to include linear, branched, or cyclic hydrocarbon structures and combinations thereof Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below; more preferred are $C_1$-$C_8$ alkyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, cyclohexyl, norbornyl, or other bridged systems and the like.

$C_1$ to $C_{20}$ hydrocarbon includes alkyl, cycloalkyl, alkenyl, alkynyl, aryl and combinations thereof Examples include phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons. Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127 (a)], i.e. it refers to compounds in which the oxygen is bonded via a single bond to its adjacent atoms (forming ether bonds); it does not refer to doubly bonded oxygen, as would be found in carbonyl groups.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and for the purposes of the present invention, fused moieties such as tetrahydronaphthalene (tetralin), and indane, in which one or more rings are aromatic, but not all need be. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyrazine, pyridine, pyridazine, pyrimidine, thiophene, furan, oxazole, oxazoline, isoxazole, dioxane, tetrahydrofuran and the like. Further examples include cyclic ethers (including bridged cyclic ethers), lactones, lactams, cyclicureas, and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl. A nitrogenous heterocycle is a heterocycle containing at least one nitrogen in the ring; it may contain additional nitrogens, as well as other heteroatoms. The nitrogenous heterocycle may be monocyclic, bicyclic, or multi-cyclic.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, hydroxyloweralkyl, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzenesulfonyl, benzyloxy, or heteroaryloxy. When the parent is a heterocycle that allows such substitution, the term also includes oxides, for example pyridine-N-oxide, thiopyran sulfoxide and thiopyran-S,S-dioxide. As mentioned above, two hydrogens on a single carbon may be replaced by a carbonyl to form an oxo derivative. Noteworthy oxo-substituted aryl residues include tetralone(3,4-dihydronaphthalen-1(2H)-one) and indanone(2,3-dihydroinden-1-one).

The terms "halogen" and "halo" refer to fluorine, chlorine, bromine or iodine.

Some of the compounds described herein may contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as, their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E or a mixture of the two in any proportion.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, chlorine and iodine include $^3$H, $^{14}$C, $^{35}$S, $^{18}$F, $^{36}$Cl and $^{125}$I, respectively. Compounds that contain those radioisotopes and/or other radioisotopes of other atoms are within the scope of this invention. Tritiated, i.e. $^3$H, and carbon-14, i.e., $^{14}$C, radioisotopes are particularly preferred for their ease in preparation and detectability. Radiolabeled compounds of this invention can generally be prepared by methods well known to those skilled in the art. Conveniently, such radiolabeled compounds can be prepared by carrying out the procedures disclosed in the Examples by substituting a readily available radiolabeled reagent for a non-radiolabeled reagent. Because of the high affinity for the JAK3 enzyme active site, radiolabeled compounds of the invention are useful for JAK3 assays.

In one embodiment, $R_4$ is a heterocycle selected from a nitrogenous heterocycle and an oxygenous heterocycle. Nitrogenous heterocycles that appear in the examples are monocyclic and bicyclic heterocycles or monocyclic and bicyclic heterocycles substituted with one or two substitutions. When y is not zero, heteroaryl is a preferred subset of heterocyclyl for $R_4$. Exemplary nitrogenous heterocycles include piperidine, pyridine, pyrazine, pyrimidine, pyridine, quinoline, isoquinoline, tetrahydroquinoline, tetrahydroisoquinoline, and their variously substituted derivatives, such as

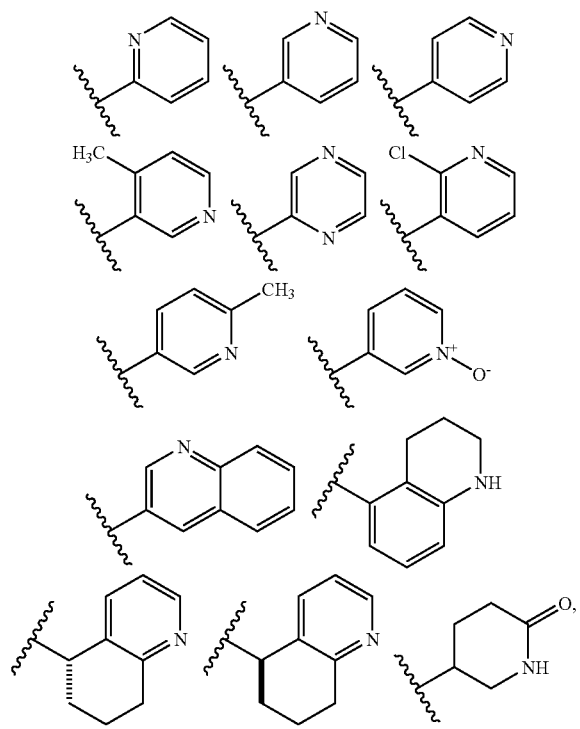

-continued

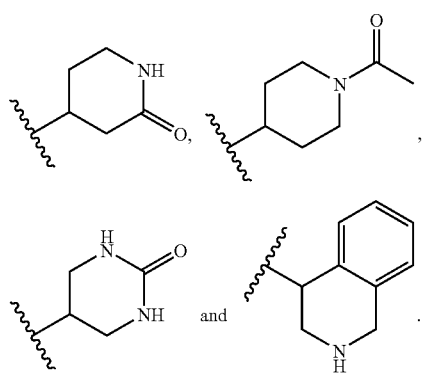

In another embodiment, R$_4$ is a substituted cycloalkyl. Substituents include hydroxyl, alkoxy, hydroxyalkyl, oxo, carboxamido(aminocarbonyl), carboxy, and carboalkoxy. Substituted cycloalkyls include:

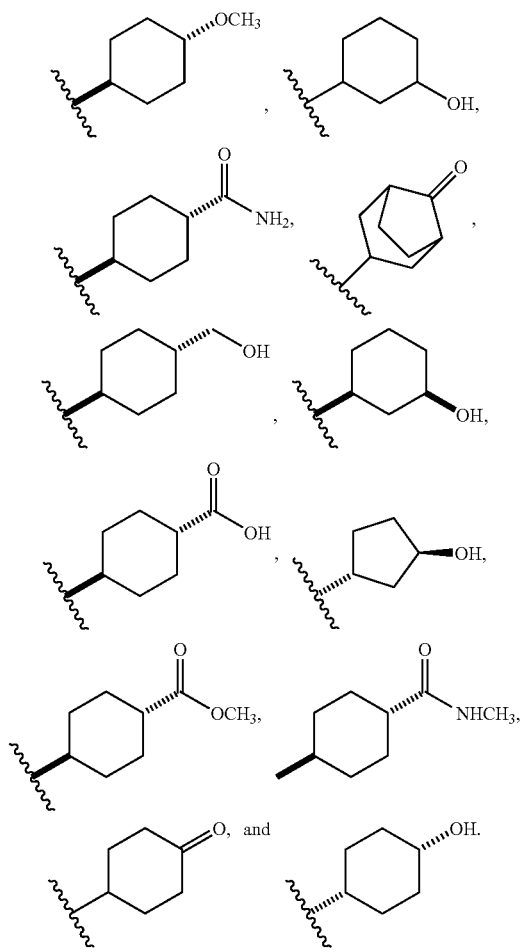

An oxygenous heterocycle is a heterocycle containing at least one oxygen in the ring; it may contain additional oxygens, as well as other heteroatoms. Exemplary oxygenous heterocycles include tetrahydropyran, chroman, pyran, oxocane and their variously substituted derivatives, such as:

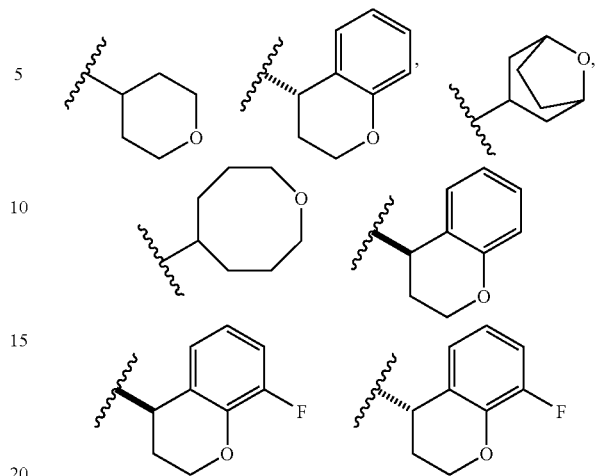

Chemical Synthesis

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art The present invention further provides pharmaceutical compositions comprising as active agents, the compounds described herein.

As used herein a "pharmaceutical composition" refers to a preparation of one or more of the compounds described herein, or physiologically acceptable salts or solvents thereof, with other chemical components such as physiologically suitable carriers and excipients.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Compounds that inhibit Jak-3 can be formulated as pharmaceutical compositions and administered to a mammalian subject, such as a human patient in a variety of forms adapted to the chosen route of administration, i.e., orally or parenterally, by intravenous, intramuscular, topical, transdermal or subcutaneous routes.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar or alginic acid or a salt thereof such as sodium alginate.

In addition, enteric coating may be useful as it is may be desirable to prevent exposure of the compounds of the invention to the gastric environment.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the composition. Such penetrants, including for example DMSO or polyethylene glycol, are known in the art.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The compounds of the present invention may also be formulated in rectal compositions such as suppositories or retention enemas, using, e.g., conventional suppository bases such as cocoa butter or other glycerides.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As used herein, and as would be understood by the person of skill in the art, the recitation of "a compound" is intended to include salts, solvates and inclusion complexes of that compound. The term "solvate" refers to a compound of Formula I or II in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic(besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine(N-methylglucamine) and procaine.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein.

It should be understood that in addition to the ingredients particularly mentioned above, the formulations of this invention may include other agents conventional in the art having regard to the type of formulation in question, for example those suitable for oral administration may include flavoring agents.

The compositions may be presented in a packaging device or dispenser, which may contain one or more unit dosage forms containing the active ingredient. Examples of a packaging device include metal or plastic foil, such as a blister pack and a nebulizer for inhalation. The packaging device or dispenser may be accompanied by instructions for administration. Compositions comprising a compound of the present invention formulated in a compatible pharmaceutical carrier may also be placed in an appropriate container and labeled for treatment of an indicated condition.

Indications

The compounds of the present invention are useful in inhibiting the activity if Jak3 or in inhibiting Jak3 mediated activity and are useful as immunosuppressive agents for tissue and organ transplants, including bone marrow and kidney transplant, and in the treatment of autoimmune and inflammatory diseases and of complications arising therefrom.

Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur anytime after transplantation.

There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Type I diabetes ensues from the selective aggression of autoreactive T-cells against insulin secreting β cells of the islets of Langerhans. Targeting Jak3 in this disease is based on the observation that multiple cytokines that signal through the Jak pathway are known to participate in the T-cell mediated autoimmune destruction of β cells. Indeed, a Jak3 inhibitor, JANEX-1 was shown to prevent spontaneous autoimmune diabetes development in the NOD mouse model of type I diabetes.

Graft-versus-host disease (GVHD) is a donor T-cell initiated pathological condition that frequently follows allogeneic bone marrow transplantation (BMT). Substantial experimental and clinical research have demonstrated that donor T-cells are the principal mediators and effectors of GVHD. Jak3 plays a key role in the induction of GVHD and treatment with a Jak3 inhibitor, JANEX-1, was shown to attenuate the severity of GVHD (reviewed in Cetkovic-Cvrlje and Ucken, 2004).

Mast cells express Jak3 and Jak3 is a key regulator of the IgE mediated mast cell responses including the release of inflammatory mediators. Jak3 was shown to be a valid target in the treatment of mast cell mediated allergic reaction.

Allergic disorders associated with mast cell activation include Type I immediate hypersensitivity reactions such as allergic rhinitis (hay fever), allergic urticaria (hives), angioedema, allergic asthma and anaphylaxis, i.e., "anaphylatic shock." These disorders are treated or prevented by inhibition of Jak3 activity, for example, by administration of a Jak3 inhibitor according to the present invention.

According to the present invention, the Jak3 inhibitors may be administered prophylactically, i.e., prior to onset of acute allergic reaction, or they may be administered after onset of the reaction, or at both times.

Inflammation of tissues and organs occurs in a wide range of disorders and diseases and in certain variations, results from activation of the cytokine family of receptors. Exemplary inflammatory disorders associated with activation of Jak3 include, in a non-limiting manner, skin inflammation due radiation exposure, asthma, allergic inflammation and chronic inflammation such as keratoconjunctivitis sicca.

The compounds of the present invention are also useful in treating certain malignancies, including skin cancer and hematological malignancy such as lymphomas and leukemias. An example of the lymphoma is anaplastic large cell lymphoma (ALCL). The utility of the Jak3 inhibitors of the present invention for treating ALCL have been demonstrated by the studies presented by Lai, R. et al. Jak3 activation is significantly associated with ALK expression in anaplastic large cell lymphoma. *Human Pathology* (2005) 36, 939-944 and Harrington et al. VX-680, a potent and selective small-molecule inhibitor of the Aurora kinases, suppresses tumor growth in vivo. *Nature Medicince* (2004) 3, 262-267 which are both incorporated in there entirety herein by reference.

An example of the leukemia is chronic myelogenous leukemia (CML). The utility of the Jak3 inhibitors of the present invention for treating CML have been demonstrated by the studies presented by Harrington et al. referenced above. The aforementioned study further has demonstrated the treatment of acute myelogenous leukemia (AML) via in vivo experiments.

The compounds of the present invention are also useful in treating non-hemotological malignancies, including pancreatic and colon cancer. [See Harrington et al., op. cit. for in vivo tests.]

The Jak3 inhibitors of the present invention are additionally useful in treating cardiovascular disease.

The following examples will further describe the invention, and are used for the purposes of illustration only, and should not be considered as limiting the invention being disclosed.

EXAMPLES

The following abbreviations and terms have the indicated meaning throughout:

Ac=acetyl
Bu=butyl
DCM=dichloromethane=methylene chloride=$CH_2Cl_2$
DEAD=diethyl azodicarboxylate
DIC=diisopropylcarbodiimide
DIEA=N,N-diisopropylethyl amine
DMF=N,N-dimethylformamide
DMSO=dimethyl sulfoxide
EA (EtOAc)=Ethyl Acetate
GC=gas chromatography
h=hours
HOAc=acetic acid
HOBt=hydroxybenzotriazole
Me=methyl
Pd(dppf)$_2$Cl$_2$=dichloro[1,1'-bis(diphenylphosphinoferrocene]palladium
Ph=phenyl
PhOH=phenol
RT=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl Examples 1-15 describe syntheses of certain precursors and intermediates of the invention.

Example 1

Synthesis of 3,4-Diaminobenzonitrile

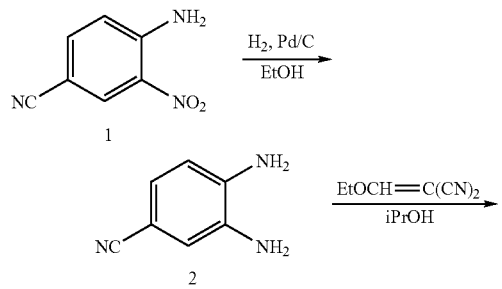

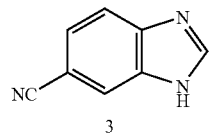

A solution of 4-amino-3-nitrobenzonitrile (1) (3.0 g) in ethanol (80 mL) was sparged for 5 minutes with nitrogen. Palladium on carbon (10%, 300 mg) was added and the mixture was saturated with hydrogen. The mixture was stirred under a hydrogen balloon for seven hours. The mixture was sparged with nitrogen and filtered through celite. The filtrate was concentrated in vacuo to provide the title compound, 3,4-diaminobenzonitrile (2).

Example 2

Synthesis of 3H-Benzo[d]imidazole-5-carbonitrile

A mixture of 3,4-diaminobenzonitrile (2) (1.0 g) and (ethoxymethylene)malononitrile (1.4 g) was refluxed in 50 mL of isopropyl alcohol for 16 h. The mixture was concentrated in vacuo to provide the title compound, 3H-benzo[d]imidazole-5-carbonitrile (3).

Example 3

Synthesis of 6-(Trifluoromethoxy)-1H-benzo[d]imidazole 6-(trifluoromethoxy)-1H-benzo[d]imidazole (4) was prepared in two steps from 2-nitro-4-(trifluoromethoxy)aniline (5) using procedures identical to those used to make 3H-benzo[d]imidazole-5-carbonitrile (3) from 4-amino-3-nitrobenzonitrile (1, examples 1, 2).

Example 4

Synthesis of 5,6-Difluoro-1H-benzo[d]imidazole

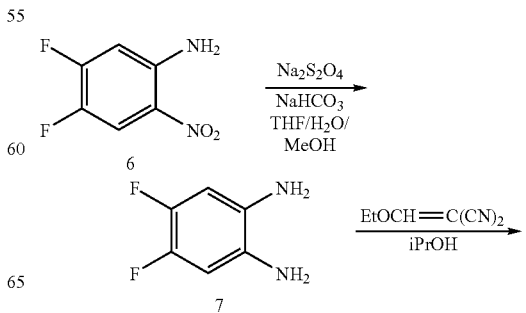

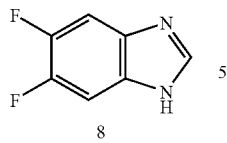

A solution of 4,5-difluoro-2-nitroaniline (6)(1.0 g) in 30 mL of THF was treated with a solution comprised of 6 g of $Na_2S_2O_4$ and 3 g $NaHCO_3$ in 30 mL of water. Methanol (10 mL) was added after the addition of the aqueous solution so that the mixture remained homogeneous. The mixture was stirred for two hours and then diluted with 100 mL of ethyl acetate and 100 mL of water. The organic layer was separated and the aqueous layer was extracted again with 100 mL of methylene chloride. The combined organic layers were dried over sodium sulfate, filtered, and concentrated to provide the crude intermediate 4,5-difluorobenzene-1,2-diamine (7). The intermediate was refluxed with (ethoxymethylene)malononitrile (1.1 g) in 25 mL of isopropyl alcohol for 16 h. The mixture was concentrated in vacuo and the resulting crude product was suspended in water and filtered. The precipitate was washed with water and air-dried to provide 380 mg of 5,6-difluoro-1H-benzo[d]imidazole (8).

Example 5

Synthesis of 5,6-Dimethoxy-1H-benzo[d]imidazole

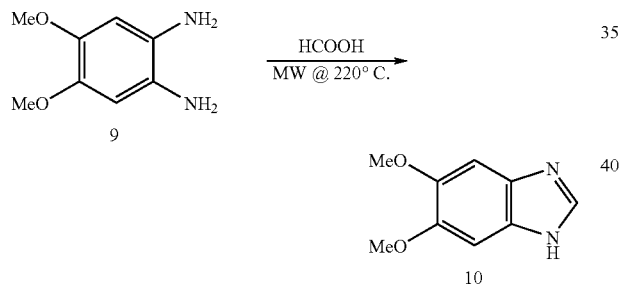

The title compound 5,6-dimethoxy-1H-benzo[d]imidazole (10) was made by heating 4,5-dimethoxy-1,2-phenylenediamine dihydrochloride (9) in formic acid at 220° C. in a microwave followed by concentration in vacuo.

Example 6

Synthesis of 6-Fluoro-1H-benzo[d]imidazole (11) and 6-(trifluoromethyl)-1H-benzo[d]imidazole (12)

The title compounds were by made as described in US Application Publication No. 2004/0087601, of some of the present inventors.

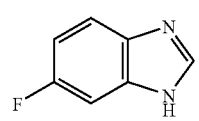

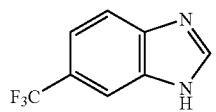

Example 7

Benzimidazole (13), 5-azabenzimidazole (14), 6-chloro-5-fluorobenzimidazole (15), and 5-methyl-benzimidazole (16)

The title compounds were commercially available.

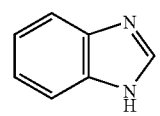

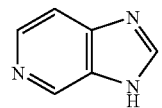

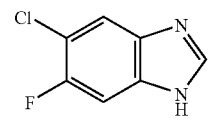

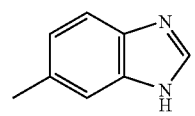

Example 8

Synthesis of the primary amine, pyrazin-2-ylmethanamine

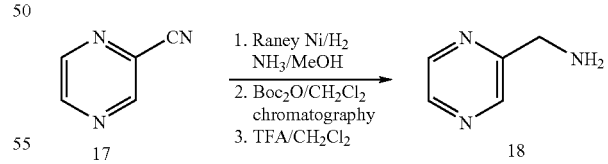

Raney nickel catalyst was carefully washed with THF and methanol making sure that the catalyst remained moist. The weight of the moist catalyst was 2.5 g after washing. This material was added to a solution of pyrazinecarbonitrile (17) (3.0 g) in 7N methanolic ammonia (120 mL). The mixture was shaken under a 50 p.s.i. atmosphere of hydrogen for 1.5 hours. The mixture was filtered and the filtrate was concentrated in vacuo to provide the crude title compound. Purification was accomplished by conversion of the crude amine to the tert-butyl carbamate with excess di-tert-butyl dicarbonate in methylene chloride. Column chromatography (70:27:3 hexanes:ethyl acetate:methanol) provided 0.50 g of pure tert-butyl pyrazin-2-ylmethylcarbamate. Pure pyrazin-2-yl-methanamine (18) was obtained as the TFA salt from deprotection of the carbamate with 1:1 TFA/CH$_2$Cl$_2$.

Example 9

Synthesis of 3-Aminomethyl-2-fluoropyridine

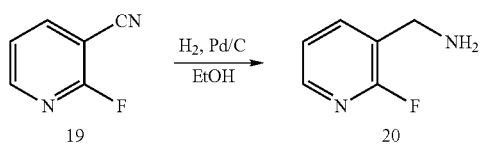

A round bottom flask was charged with 0.3 g (2.46 mM) of 3-cyano-2-fluoropyridine (19), which was then diluted in 20 mL EtOH. The solution was flushed with argon, and then while under a blanket of argon, 60 mg of 10% Pd/C (20% by weight), was added. The system was then sealed by septum and put under vacuum. A hydrogen balloon was then added, and the reaction was stirred for three hours (followed by TLC). The reaction was then put under vacuum again, then exposed to air, and filtered (keeping catalyst wet). The resulting solution was dried and evaporated to give 0.28 g (90%) of the title compound, 3-aminomethyl-2-fluoropyridine (20).

Example 10

Synthesis of 3-Aminomethyl-6-methoxypyridine (21), 3-Aminomethyl-6-methylpyridine (22), and 3-Aminomethylquinoline (23)

The title amines were obtained from the corresponding nitriles using the same procedure that was used to obtain 3-aminomethyl-2-fluoropyridine (20) from 3-cyano-2-fluoropyridine (see Example 9).

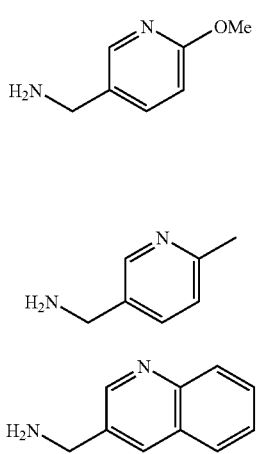

Example 11

Synthesis of 3-aminomethyl-2-methoxypyridine

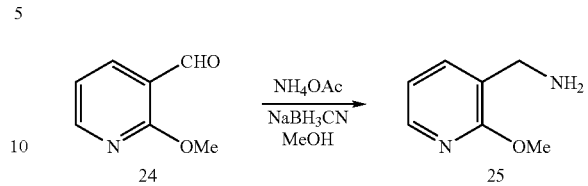

A round bottom flask was charged with 0.44 g (3.23 mM) of 2-methoxy-3-pyridine carboxaldehyde (24), 1.24 g (16.15 mM) of ammonium acetate, and 0.61 g (19.69 mM) of sodium cyanoborohydride. The flask was then flushed with argon, and then 50 mL of dry MeOH was added by syringe. The reaction was stirred for 2 days, at which point the MeOH was evaporated off 25 mL of water was added, and the mixture was brought to pH 2 with conc. HCl. This was extracted twice with EtOAc to remove the alcohol side product. The mixture was brought to pH 10 using sodium hydroxide pellets, saturated with NaCl, and extracted twice with DCM and once with EtOAc. The combined organics were dried and evaporated to give 0.31 g (69%) of 3-aminomethyl-2-methoxypyridine (25).

Example 12

Synthesis of 3-(α-aminoethyl)-2-chloropyridine (26)

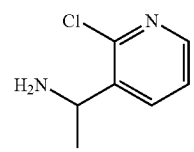

The title amine was obtained from the corresponding ketone using the same procedure that was used to obtain 3-aminomethyl-2-methoxypyridine from 2-methoxy-3-pyridine carboxaldehyde (24; Example 11).

Example 13

Synthesis of 3-aminomethyl-4-methylpyridine

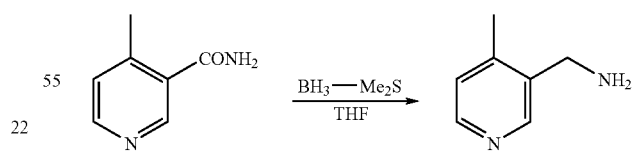

A round bottom flask was charged with 0.45 g (3.30 mM) of 4-methylnicotinamide (27). The flask was flushed with argon, and 50 mL of dry THF was added by syringe. The resulting solution was cooled to 0 dg C., and 2.5 mL (4.96 mM) of a 2M solution of borane-dimethylsulfide complex (in THF) was added. A bubbler was attached, and the solution was allowed to warm to RT overnight. The solution was quenched with MeOH, and dried and evaporated to give 0.38 g (95%) of 3-aminomethyl-4-methylpyridine (28).

Example 14

Synthesis of 5-fluoro-1,2,3,4-tetrahydronaphthalen-1-amine

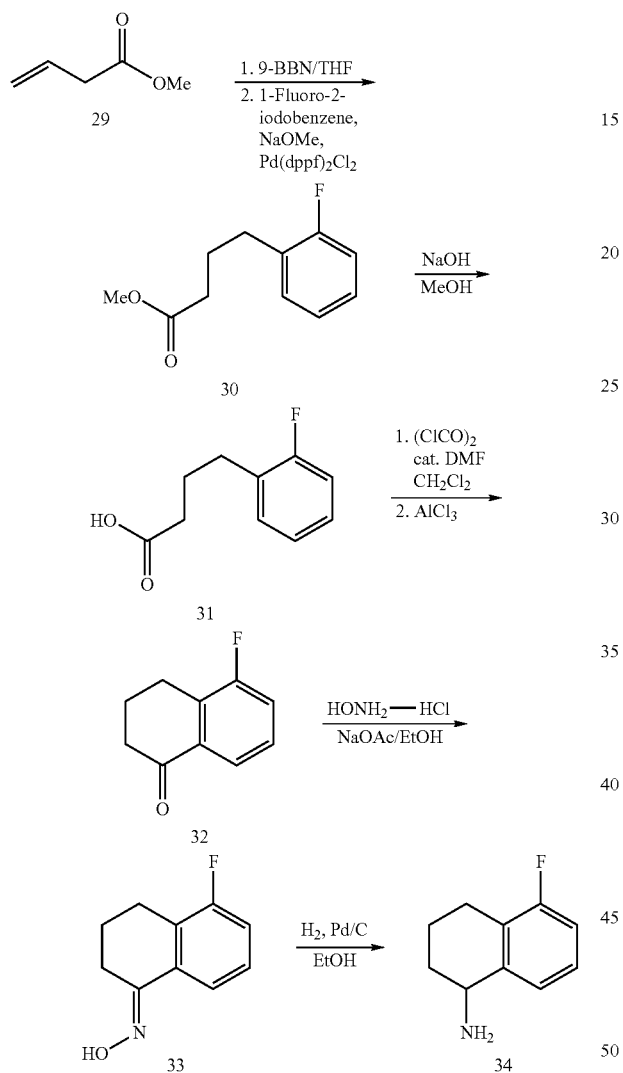

Methyl 4-(2-fluorophenyl)butanoate (2-(4-methylbutanoate)fluorobenzene, 30). A round bottom flask was sealed with a rubber septum, flushed with argon, then charged with 5.32 mL of methyl 3-buteneoate (29) and 100 mL of a 0.5M solution of 9-BBN in THF. The solution was stirred at RT for three hours. A 2-necked round bottom flask was equipped with a condenser and flushed with argon, then charged with 7.36 g of sodium methoxide and 1.11 g of Pd(dppf)$_2$Cl$_2$. To this mixture were added 20 mL of dry THF and 5.22 mL of 1-fluoro-2-iodobenzene. The hydroboration solution was added via canula and the resulting mixture was refluxed for 16 hours. The solution was cooled to RT, diluted with 150 mL of water, and extracted three times with ether. The combined organic layers were washed with brine, dried, and evaporated.

Column chromatography (5% EtOAc/hexanes) gave 1.79 g methyl 4-(2-fluorophenyl)butanoate (30).

4-(2-Fluorophenyl)butanoic acid (31). A round bottom flask was charged with 1.79 g of 2-(4-methylbutanoate)fluorobenzene, which was dissolved in 17 mL of MeOH. To this solution was added a solution of 1 g of sodium hydroxide. The resulting mixture was stirred 20 hours at RT. The solvent was evaporated and the crude material diluted with 15 mL of 0.5M HCl. Extraction with DCM three times gave 1.17 g (92%) of 4-(2-fluorophenyl)butanoic acid (31).

5-Fluoro-3,4-dihydronaphthalen-1(2H)-one (32). A round bottom flask was charged with 0.15 g of 4-(2-fluorophenyl) butanoic acid, which was dissolved in 20 mL DCM and cooled to 0° C. Oxalyl chloride (0.15 mL) was added, followed by 1 drop of DMF. A drying tube was attached, and the solution was stirred at 0° C. for two hours. Aluminum chloride (0.121 g) was added and the solution was allowed to slowly warm to RT overnight. The mixture was poured onto ice water, and extracted three times with DCM. The combined organic layers were washed with 0.5 M NaOH and brine. The organic phase was dried, evaporated, and purified by column chromatography (eluting with 20% EtOAc/Hexanes), to give 0.07 g (53%) of 5-fluoro-3,4-dihydronaphthalen-1(2H)-one (32).

5-Fluoro-1,2,3,4-tetrahydronaphthalen-1-amine (34). A round bottom flask was charged with 0.5 g of 5-fluoro-3,4-dihydronaphthalen-1(2H)-one, 0.28 g of hydroxylamine hydrochloride, and 0.34 g of sodium acetate. A condenser was attached, and the flask was purged with argon. 20 mL of dry EtOH was added, and the mixture was stirred at reflux for 18 hours. The solution was cooled to RT, diluted with EtOAc, and washed with water. The organic phase was dried with sodium sulfate and evaporated to give 0.5 g of the intermediate 5-fluoro-3,4-dihydronaphthalen-1(2H)-one oxime (33), which was reduced with Pd/C in EtOH with hydrogen (50 psi), to give 0.43 g (86%) of 5-fluoro-1,2,3,4-tetrahydronaphthalen-1-amine (34).

Example 15

Synthesis of 3-(9-((R)-6-fluorochroman-4-yl)-9H-purin-2-yl)-3H-benzo[d]imidazole-5-carbonitrile

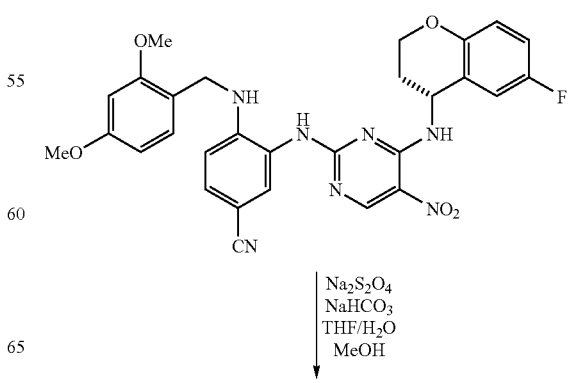

29

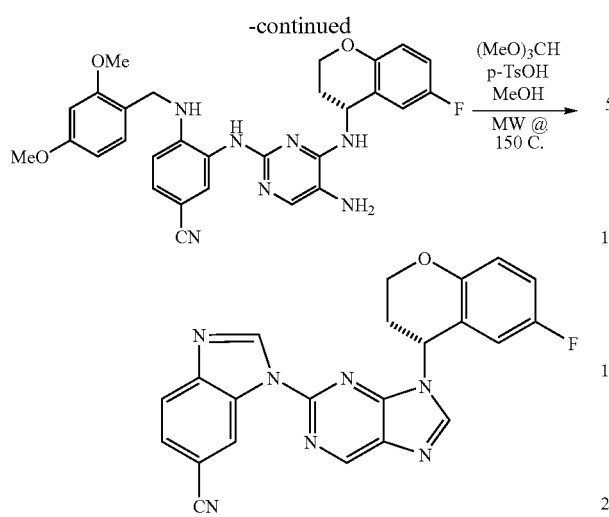

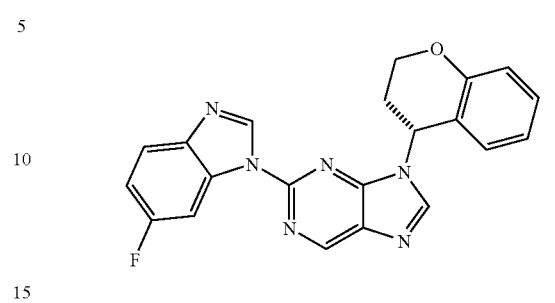

To a solution of (R)-4-(2,4-dimethoxybenzylamino)-3-(4-(6-fluorochroman-4-ylamino)-5-nitropyrimidin-2-ylamino)benzonitrile (prepared as described below in example 26, paragraph [0157]) (12 mg) in THF (5 mL) was added a premixed solution of sodium hydrosulfite (100 mg) and sodium bicarbonate (50 mg) in water (10 mL). MeOH (1 mL) was also added to aid solution of the mixture, which was stirred at room temperature for 30 min, when sodium chloride was added to saturate the solution. The resultant mixture was extracted with EtOAc (2×), the combined organics were dried, filtered and evaporated to yield (R)-4-(2,4-dimethoxybenzylamino)-3-(5-amino-4-(6-fluorochroman-4-ylamino)pyrimidin-2-ylamino)benzonitrile that was used as such for the next step, MH$^+$=542.

To a microwave vial was added the above amine, a catalytic amount of para-toluene sulfonic acid monohydrate, trimethyl orthoformate (0.5 mL) and MeOH (1 mL). The vial was capped and heated in an Emrys™ Optimizer microwave at 150.degree C. for 5 minutes. The mixture was concentrated in vacuo, and purified by RP HPLC to yield 4.6 mg of the titled product as the TFA salt, NMR CDCl$_3$ $^1$H δ 9.5 (br s, 1H), 9.3 (s, 1H), 9.0 (s, 1H), 8.2 (br s, 1H), 8.0 (d, 1H), 7.7 (d, 1H), 7.1-7.0 (m, 2H), 6.6 (dd, 1H), 6.0 (t, 1H), 4.4 (m, 1H), 4.3 (m, 1H), 2.7 (m, 2H); $^{19}$F δ −121, −76 ppm; MH$^+$=412.

30

Synthesis of 9-((R)-Chroman-4-yl)-2-(6-fluoro-1H-benzo[d]imidazol-1-yl)-9H-purine

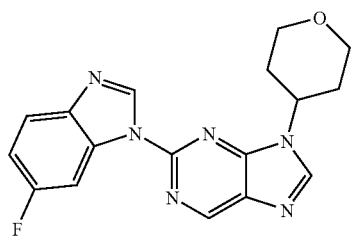

The title compound as a TFA salt was synthesized from (R)-tert-butyl 2-(4-(chroman-4-ylamino)-5-nitropyrimidin-2-ylamino)-4-fluorophenylcarbamate via the procedure described in Example 15. $^1$H NMR (300 MHz, CDCl$_3$): δ 9.15 (s, 2H), 8.27 (dd, 1H), 7.89 (s, 1H), 7.78 (dd, 1H), 7.32 (td, 1H), 7.32 (td, 1H), 7.13 (td, 1H), 7.1-6.9 (m, 3H), 6.00 (t, 1H), 4.4-4.3 (m, 2H), 4.2-4.1 (m, 2H), 2.7-2.5 (m, 2H). $^{19}$F NMR: δ −116.4.

Synthesis of 2-(6-Fluoro-1H-benzo[d]imidazol-1-yl)-9-(tetrahydro-2H-pyran-4-yl)-9H-purine The title compound as a TFA salt was synthesized from tert-butyl 4-fluoro-2-(5-nitro-4-(tetrahydro-2H-pyran-4-ylamino)pyrimidin-2-ylamino)phenylcarbamate via the procedure described in Example 15. $^1$H NMR (300 MHz, CDCl$_3$): δ 9.73 (s, 1H), 9.29 (s, 1H), 8.5-8.6 (m, 1H), 8.40 (s, 1H), 7.9-8.1 (m, 1H), 7.3-7.4 (m, 1H), 4.8-5.0 (m, 1H), 4.2-4.4 (m, 2H), 3.7-3.8 (m, 2H), 3.05 (d, 1H), 2.2-2.4 (m, 3H). $^{19}$F NMR: δ −112.4.

Example 16

Synthesis of 2-(1H-Benzo[d]imidazol-1-yl)-9-((R)-8-fluorochroman-4-yl)-7H-purin-8(9H)-one

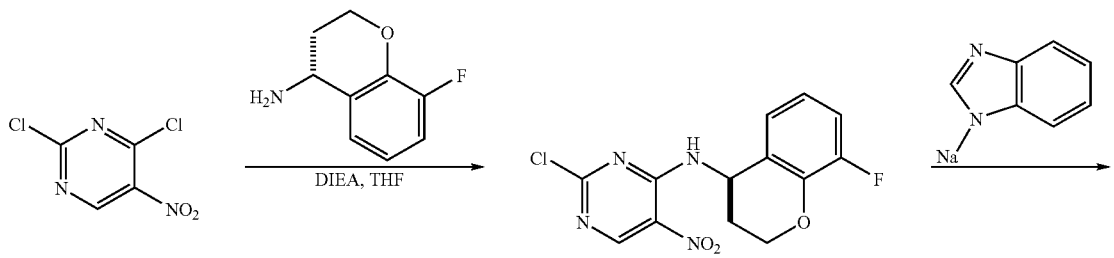

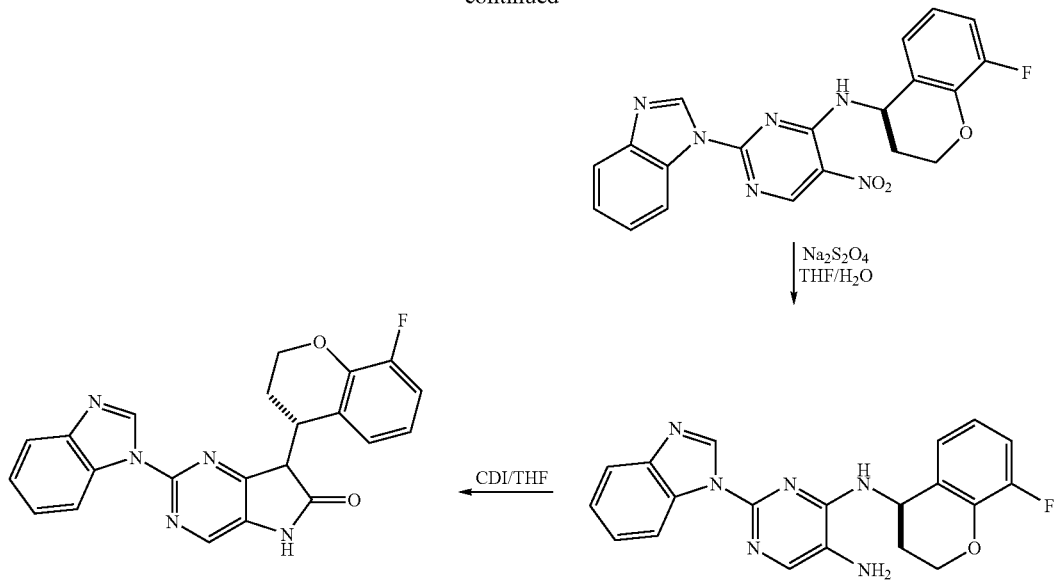

2-(1H-Benzo[d]imidazol-1-yl)-N—((R)-8-fluorochroman-4-yl)-5-nitropyrimidin-4-amine. (R)-8-fluorochroman-4-amine (60 mg, Example 29) was added to a solution of 2,4-dichloro-5-nitropyrimidine (70 mg) and DIEA (0.14 mL) in THF (5 mL) at −78° C. The reaction mixture was stirred for a further 15 min at −78° C. then removed from the cold bath and allowed to warm to RT. A one molar solution of the sodium salt of benzimidazole (0.7 ml, stock solution prepared via the addition of sodium hydride to a benzimidazole solution in THF) was added to the reaction intermediate ((R)-2-chloro-N-(8-fluorochroman-4-yl)-5-nitropyrimidin-4-amine) and the resulting mixture was stirred at RT overnight. Purification via column chromatography (elution with 1 MeOH/DCM) gave the titled compound (120 mg), MH$^+$=407.

2-(1H-Benzo[d]imidazol-1-yl)-9-((R)-8-fluorochroman-4-yl)-7H-purin-8(9H)-one. A freshly prepared solution of sodium hydrosulfite (tech, 0.5 g) and sodium bicarbonate (0.25 g) in H$_2$O (5 mL) was added to a solution of the above nitro compound (120 mg) in THF (10 mL). The mixture was stirred vigorously for 30 min then extracted with EtOAc (2×) and DCM (2×), the combined organics were washed with brine, dried, filtered and concentrated to yield the intermediate 2-(1H-benzo[d]imidazol-1-yl)-N$^4$—((R)-8-fluorochroman-4-yl)pyrimidine-4,5-diamine that was used as such in the next step.

Carbonyldiimidazole (0.2 g) was added to a solution of the above amine in THF (10 mL). The resulting mixture was stirred at RT overnight, silica gel was added, then the solvents were removed under reduced pressure and purified via column chromatography, elution with 5% MeOH/DCM, to yield the titled product (28 mg), MH$^+$=403, $^1$H NMR (CDCl$_3$) δ 10.6 (s, 1H), 8.9 (s, 1H), 8.3 (s, 1H), 7.8 (m, 2H), 7.3 (m, 2H), 7.0 (m, 1H), 6.7 (m, 1H), 5.9 (dd, 1H), 4.7 (m, 1H), 4.4 (t, 1H), 2.7 (m, 1H), 2.3 (m, 1H) ppm, $^{19}$F NMR δ −135.7 (m). Chiral HPLC—no evidence of other enantiomer, Method; Chiralcel™ OD-H (0.46×25 cm analytical column, Daicel Chemical Industries) isocratic 15% (0.05% TFA/EtOH) 85% (0.05% TFA/Hex), Rt=19.5 min (R)-enantiomer, Rt=22.4 min (S)-enantiomer.

Synthesis of 2-(1H-benzo[d]imidazol-1-yl)-9-((R)-6-fluorochroman-4-yl)-7H-purin-8(9H)-one

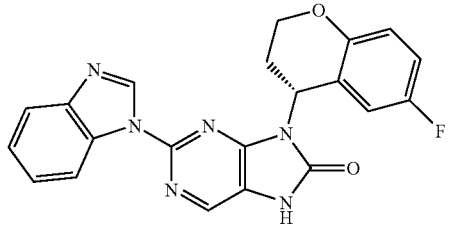

The title compound was synthesized from (R)-6-fluorochroman-4-amine using the procedures outline in Example 16. $^1$H NMR (300 MHz, CDCl$_3$): δ 10.28 (s, 1H), 8.82 (s, 1H), 8.28 (s, 1H), 7.94 (d, 1H), 7.79 (d, 1H), 7.2-7.4 (m, 2H), 6.8-7.1 (m, 2H), 6.66 (dd, 1H), 5.92 (br t, 1H), 4.55 (m, 1H), 4.33 (m, 1H), 2.90 (m, 1H), 2.31 (m, 1H).

Synthesis of 2-(1H-benzo[d]imidazol-1-yl)-9-((R)-5,6-difluorochroman-4-yl)-7H-purin-8(9H)-one

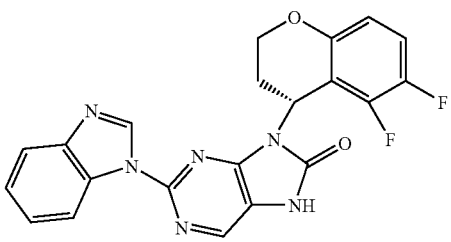

The title compound was synthesized from (R)-5,6-difluorochroman-4-amine (obtained by resolution of (+/−)-5,6-difluorochroman-4-amine using the resolution procedure outlined in Example 29) using the procedures outline in Example 16. $^1$H NMR (300 MHz, CDCl$_3$+5% CD$_3$OD): δ 8.62 (s, 1H), 8.18 (s, 1H), 8.0-8.1 (m, 1H), 7.6-7.7 (m, 1H), 7.2-7.3 (m, 1H), 6.9-7.1 (m, 2H), 6.7-6.8 (m, 1H), 5.86 (br t, 1H), 4.4-4.5 (m, 1H), 4.2-4.3 (m, 1H), 2.5-2.6 (m, 1H), 2.3-2.4 (m, 1H).

Synthesis of 2-(1H-Benzo[d]imidazol-1-yl)-9-((2-fluoropyridin-3-yl)methyl)-7H-purin-8(9H)-one

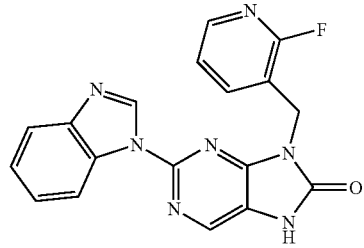

The title compound was synthesized from 3-aminomethyl-2-fluoropyridine via the procedure described in Example 16. $^1$H-NMR (CDCl$_3$) δ 9.2 (s, 1H), 9.0 (d, 1H), 8.4 (m, 1H), 8.2 (d, 1H), 7.8 (m, 2H), 7.4 (m, 3H), 7.2 (t, 1H), 4.3 (s, 2H), ppm.

Synthesis of 2-(1H-Benzo[d]imidazol-1-yl)-9-((2-methylpyridin-3-yl)methyl)-7H-purin-8(9H)-one

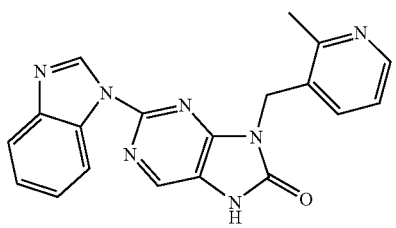

The title compound was synthesized from 3-aminomethyl-2-methylpyridine via the procedure described in Example 16. $^1$H-NMR (CDCl$_3$) δ 9.4 (s, 1H), 8.6 (d, 1H), 8.5 (d, 1H), 8.4 (d, 1H), 8.2 (s, 1H), 7.7 (d, 1H), 7.6 (t, 1H), 7.4 (m, 2H), 5.2 (s, 2H), 2.9 (s, 3H), ppm.

Synthesis of 2-(1H-Benzo[d]imidazol-1-yl)-9-((2-methoxypyridin-3-yl)methyl)-7H-purin-8(9H)-one

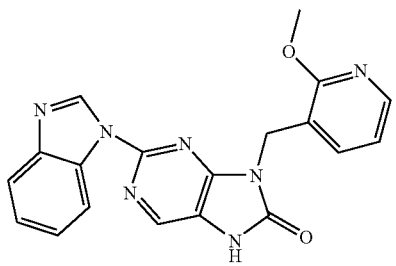

The title compound was synthesized from 3-aminomethyl-2-methoxypyridine via the procedure described in Example 16. $^1$H-NMR (CDCl$_3$) δ 9.1 (s, 1H), 8.6 (d, 1H), 8.2 (s, 1H), 8.0 (d, 1H), 7.7 (s, 1H), 7.7 (d, 1H), 7.5 (d, 1H), 7.3 (m, 2H), 6.80 (t, 1H), 5.1 (s, 2H), 3.9 (s, 3H), ppm.

Synthesis of 2-(1H-Benzo[d]imidazol-1-yl)-9-((4-methylpyridin-3-yl)methyl)-7H-purin-8(9H)-one

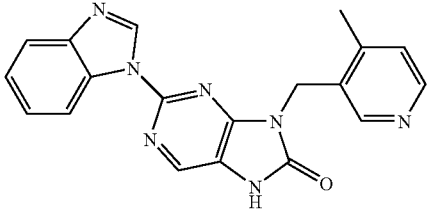

The title compound was synthesized from 3-aminomethyl-4-methylpyridine via the procedure described in Example 16. $^1$H-NMR (CDCl$_3$) δ 8.9 (s, 1H), 8.5 (s, 1H), 8.3 (m, 1H), 8.2 (m, 1H), 7.7 (m, 1H), 7.6 (m, 1H), 7.3 (m, 1H), 7.0 (m, 2H), 5.2 (s, 2H), 2.5 (s, 3H), ppm.

Synthesis of 2-(1H-Benzo[d]imidazol-1-yl)-9-(6,7-dihydro-5H-cyclopenta[b]pyridin-5-yl)-7H-purin-8(9H)-one

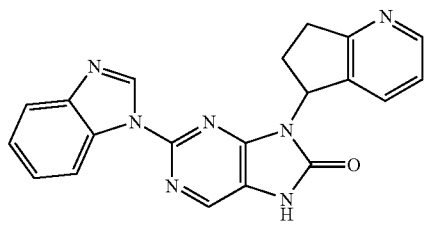

The title compound was synthesized from 6,7-dihydro-5H-cyclopenta[b]pyridin-5-amine (WO 2003/045924) via the procedure described in Example 16. $^1$H-NMR (CDCl$_3$) δ 8.8 (s, 1H), 8.6 (d, 1H), 8.3 (s, 1H), 7.8 (dd, 1H), 7.6 (dd, 1H), 7.4 (d, 1H), 7.3-7.1 (m, 3H), 6.3 (t, 1H), 3.6-3.5 (m, 1H), 3.4-3.2 (m, 1H), 2.9-2.6 (m, 2H) ppm.

Synthesis of 2-(1H-Benzo[d]imidazol-1-yl)-9-((6-methoxypyridin-3-yl)methyl)-7H-purin-8(9H)-one

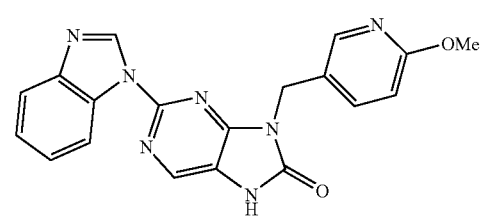

The title compound was synthesized from 3-aminomethyl-6-methoxypyridine via the procedure described in Example 16. $^1$H-NMR (CDCl$_3$) δ 9.2 (s, 1H), 8.5 (d, 1H), 8.3 (s, 1H), 8.2 (s, 1H), 7.8 (m, 2H), 7.4 (t, 2H), 6.7 (d, 1H), 5.1 (s, 2H), 3.8 (s, 3H) ppm.

Synthesis of 2-(1H-Benzo[d]imidazol-1-yl)-9-((6-methylpyridin-3-yl)methyl)-7H-purin-8(9H)-one

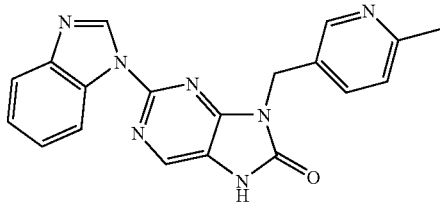

The title compound was synthesized from 3-aminomethyl-6-methylpyridine via the procedure described in Example 16. ¹H-NMR (CDCl₃) δ 9.5 (s, 1H), 9.2 (s, 1H), 8.9 (s, 1H), 8.7 (d, 1H), 8.4 (s, 1H), 8.1 (d, 1H), 7.9 (d, 1H), 7.5 (m, 2H), 5.5 (s, 2H), 2.6 (s, 3H) ppm.

Example 17

Non-regiospecific synthesis of benzimidazole purinone derivatives: Synthesis of 5-Nitro-N-(pyridin-3-ylmethyl)-2-(6-(trifluoromethoxy)-1H-benzo[d]imidazol-1-yl)pyrimidin-4-amine (42) AND 5-nitro-N-(pyridin-3-ylmethyl)-2-(5-(trifluoromethoxy)-1H-benzo[d]imidazol-1-yl)pyrimidin-4-amine (44)

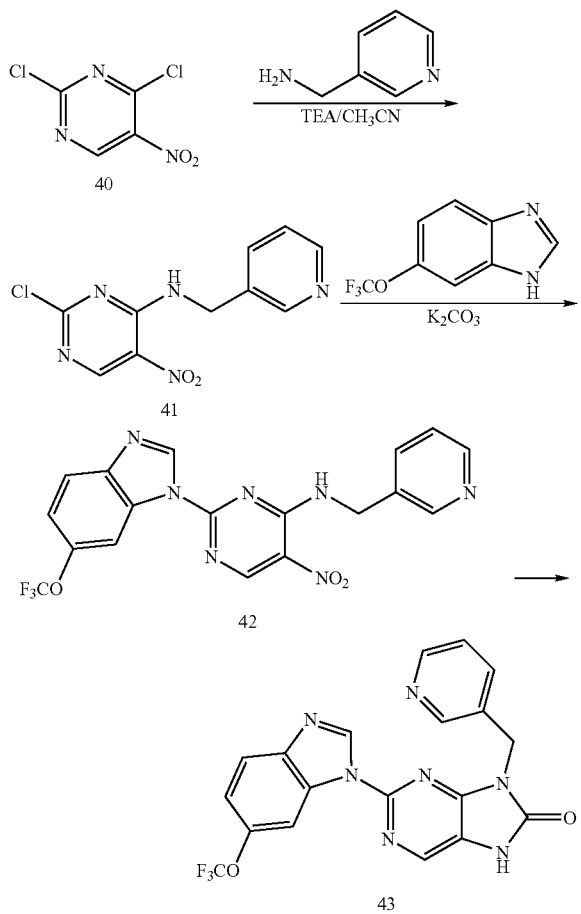

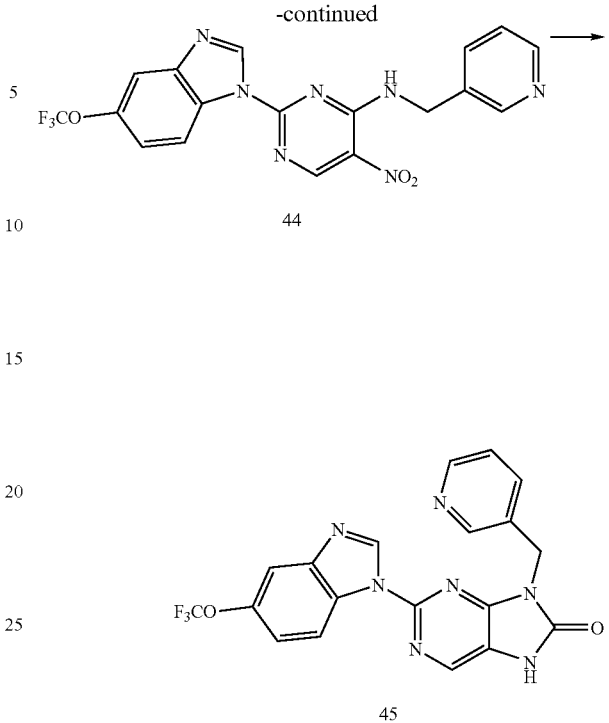

2-Chloro-5-nitro-N-(pyridin-3-ylmethyl)pyrimidin-4-amine (41). A solution of 2,4-dichloro-5-nitropyrimidine (40) (5 g) in methylene chloride (60 mL) was cooled to −78° C. and treated with 3-(aminomethyl)pyridine (2.8 g). The mixture was stirred at −78° C. for six hours, and concentrated in vacuo at RT to provide crude 2-chloro-5-nitro-N-(pyridin-3-ylmethyl)pyrimidin-4-amine (41), which was used without further purification.

5-Nitro-N-(pyridin-3-ylmethyl)-2-(6-(trifluoromethoxy)-1H-benzo[d]imidazol-1-yl)pyrimidin-4-amine (42) and 5-nitro-N-(pyridin-3-ylmethyl)-2-(5-(trifluoromethoxy)-1H-benzo[d]imidazol-1-yl)pyrimidin-4-amine (44). A suspension of crude 2-chloro-5-nitro-N-(pyridin-3-ylmethyl)pyrimidin-4-amine (52 mg) in acetonitrile (10 mL) was treated with 6-(trifluoromethoxy)-1H-benzo[d]imidazole (40 mg), potassium carbonate (0.5 g), and heated at 80° C. for four hours. The mixture was diluted with water and extracted with methylene chloride. The organic layer was separated, dried with sodium sulfate, filtered, and concentrated in vacuo. Column chromatography (70:22:8 methylene chloride:ethyl acetate:methanol) provided 12 mg of 5-nitro-N-(pyridin-3-ylmethyl)-2-(5-(trifluoromethoxy)-1H-benzo[d]imidazol-1-yl)pyrimidin-4-amine as the first eluting isomer and 15 mg of 5-nitro-N-(pyridin-3-ylmethyl)-2-(6-(trifluoromethoxy)-1H-benzo[d]imidazol-1-yl)pyrimidin-4-amine as the second eluting isomer.

High $R_f$ isomer: ¹H-NMR (CDCl₃) δ 9.2 (s, 1H), 8.9 (s, 1H), 8.8 (m, 1H), 8.6 (s, 1H), 8.5 (d, 1H), 8.2 (d, 1H, assign: H-7 of benzimidazole ring), 7.6 (d, 1H), 7.6 (s, 1H, assign: H-4 of benzimidazole ring), 7.2 (dd, 1H), 4.9 (d, 2H).

Low $R_f$ isomer: ¹H-NMR (CDCl₃) δ 9.2 (s, 1H), 8.9 (s, 1H), 8.8 (m, 1H), 8.6 (s, 1H), 8.5 (d, 1H), 8.2 (s, 1H, assign: H-7 of benzimidazole ring), 7.7 (d, 1H, assign: H-4 of benzimidazole ring), 7.6 (d, 1H), 7.2 (dd, 1H), 7.1 (d, 1H), 4.9 (d, 2H).

Example 18

Non-regiospecific synthesis of benzimidazole purinone derivatives: Synthesis of 9-(Pyridin-3-ylmethyl)-2-(6-(trifluoromethoxy)-1H-benzo[d]imidazol-1-yl)-7H-purin-8(9H)-one (43) and 9-(pyridin-3-ylmethyl)-2-(5-(trifluoromethoxy)-1H-benzo[d]imidazol-1-yl)-7H-purin-8(9H)-one (45)

The title compounds were synthesized from 5-nitro-N-(pyridin-3-ylmethyl)-2-(6-(trifluoromethoxy)-1H-benzo[d]imidazol-1-yl)pyrimidin-4-amine (42) and 5-nitro-N-(pyridin-3-ylmethyl)-2-(5-(trifluoromethoxy)-1H-benzo[d]imidazol-1-yl)pyrimidin-4-amine (44) using the same procedures that were used to convert (R)-tert-butyl 2,4-dimethoxybenzyl(5-nitro-6-(1-(pyridin-3-yl)ethylamino)pyridin-2-yl)carbamate to (R)-tert-butyl 2,4-dimethoxybenzyl(2-oxo-3-(1-(pyridin-3-yl)ethyl)-2,3-dihydro-1H-imidazo[4,5-b]pyridin-5-yl)carbamate (67; Example 22 below).

6-Trifluoromethoxy isomer (non-salt): $^1$H-NMR (CD$_3$OD) δ 9.3 (s, 1H), 8.8 (br s, 1H), 8.6 (s, 1H, assign: H-7 of benzimdazole ring), 8.6 (m, 1H), 8.4 (s, 1H), 8.1 (d, 1H), 7.9 (d, 1H, assign: H-4 of benzimidazole ring), 7.5 (dd, 1H), 7.4 (dd, 1H), 5.4 (s, 2H).

5-Trifluoromethoxy isomer (non-salt): $^1$H-NMR (CD$_3$OD) δ 9.3 (s, 1H), 8.8 (s, 1H), 8.7 (d, 1H, assign: H-7 of benzimdazole ring), 8.5 (d, 1H), 8.3 (s, 1H), 7.9 (d, 1H), 7.6 (s, 1H, assign: H-4 of benzimidazole ring), 7.4 (dd, 1H), 7.3 (dd, 1H), 5.3 (s, 2H).

Example 19

Non-regiospecific synthesis of an oxoimidazopyridine and an imidazopyridine derivative: Synthesis of 5-(1H-Benzo[d]imidazol-1-yl)-3-(pyridin-3-ylmethyl)-1H-imidazo[4,5-b]pyridin-2(3H)-one (50) and 5-(1H-benzo[d]imidazol-1-yl)3-(pyridin-3-ylmethyl)-3H-imidazo[4,5-b]pyridine (51)

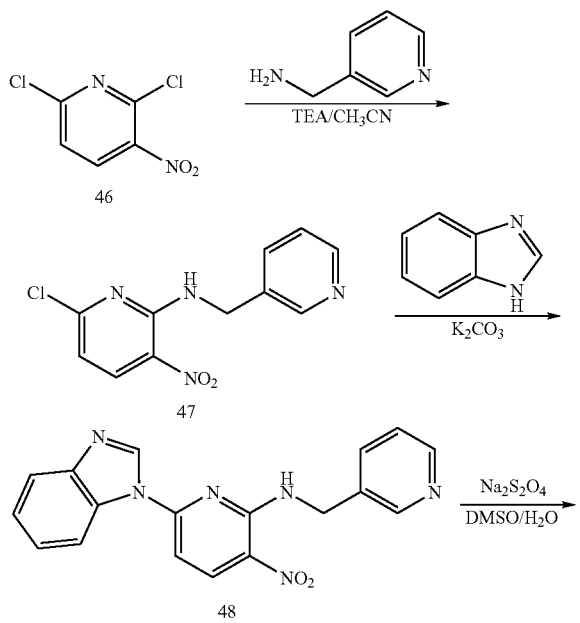

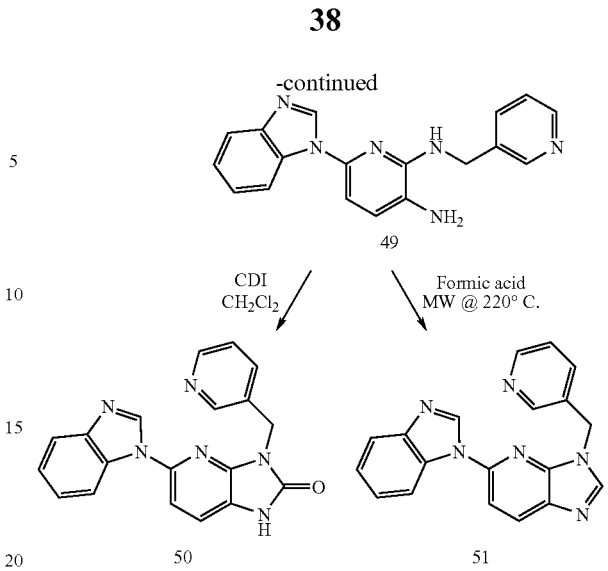

6-(1H-Benzo[d]imidazol-1-yl)-3-nitro-N-(pyridin-3-ylmethyl)pyridin-2-amine (48). A solution of 2,6-dichloro-3-nitropyridine (46) (0.5 g) in acetonitrile (20 mL) was cooled to 0° C. and treated with triethylamine (0.36 mL) followed by 3-(aminomethyl)pyridine (0.26 mL). The mixture was stirred for 30 minutes at 0° C. and eight hours at RT. The resulting solution, which contained the intermediate 6-chloro-3-nitro-N-(pyridin-3-ylmethyl)pyridin-2-amine (47), was transferred to a sealed tube containing benzimidazole (0.84 g) and potassium carbonate (3 g) and heated at 70° C. for 16 h. The mixture was cooled and filtered. The precipitated was washed with water and air-dried to provide 239 mg of the title compound (48).

5-(1H-Benzo[d]imidazol-1-yl)-3-(pyridin-3-ylmethyl)-1H-imidazo[4,5-b]pyridin-2(3H)-one (50) and 5-(1H-benzo[d]imidazol-1-yl)-3-(pyridin-3-ylmethyl)-3H-imidazo[4,5-b]pyridine (51). A solution of 6-(1H-benzo[d]imidazol-1-yl)-3-nitro-N-(pyridin-3-ylmethyl)pyridin-2-amine (48) (50 mg) in 1 mL of DMSO was treated with a solution of Na$_2$S$_2$O$_4$ (300 mg) in 1 mL of water. The mixture was stirred for two hours and diluted with 50 mL of ethyl acetate. The mixture was washed three times with 50 mL aliquots of saturated sodium chloride solution, dried over sodium sulfate, filtered, and concentrated in vacuo to provide the intermediate 6-(1H-benzo[d]imidazol-1-yl)-N2-(pyridin-3-ylmethyl)pyridine-2,3-diamine (49). Half of the intermediate was dissolved in methylene chloride (2 mL) and treated with 1,1'-carbonyldiimidazole (46 mg) at RT for 16 h. The resulting crude mixture was purified by preparative TLC (1000 microns, 5% MeOH/CH$_2$Cl$_2$) to provide 7.1 mg of 5-(1H-benzo[d]imidazol-1-yl)-3-(pyridin-3-ylmethyl)-1H-imidazo[4,5-b]pyridin-2(3H)-one (50): $^1$H-NMR (CDCl$_3$) δ 10.0 (br s, 1H), 8.9 (s, 1H), 8.6 (d, 1H), 8.5 (s, 1H), 7.9 (m, 2H), 7.8 (m, 1H), 7.6 (d, 1H), 7.4 (m, 2H), 7.4 (m, 1H), 7.3 (d, 1H), 5.2 (s, 2H). The other half of the reduced intermediate was dissolved in 1 mL of formic acid and heated in a microwave at 220° C. for 10 minutes. The mixture was concentrated in vacuo, diluted with methylene chloride, and washed with saturated aqueous sodium bicarbonate solution. The organic layer was separated, dried with sodium sulfate, filtered, and concentrated in vacuo.

Purification by preparative TLC (1000 microns, 5% MeOH/CH$_2$Cl$_2$) provided 3.5 mg of 5-(1H-benzo[d]imidazol-1-yl)-3-(pyridin-3-ylmethyl)-3H-imidazo[4,5-b]pyridine (51): $^1$H-NMR (CDCl$_3$) δ 8.8 (s, 1H), 8.6 (d, 1H), 8.6 (s, 1H), 8.3 (d, 1H), 8.2 (s, 1H), 8.0 (m, 1H), 7.9 (m, 1H), 7.7 (dd, 1H), 7.6 (d, 1H), 7.4 (m, 2H), 7.3 (m, 1H).

Example 20

Regiospecific synthesis: Synthesis of 3-(9-(2,6-Difluorobenzyl)-8-oxo-8,9-dihydro-7H-purin-2-yl)-3H-benzo[d]imidazole-5-carbonitrile

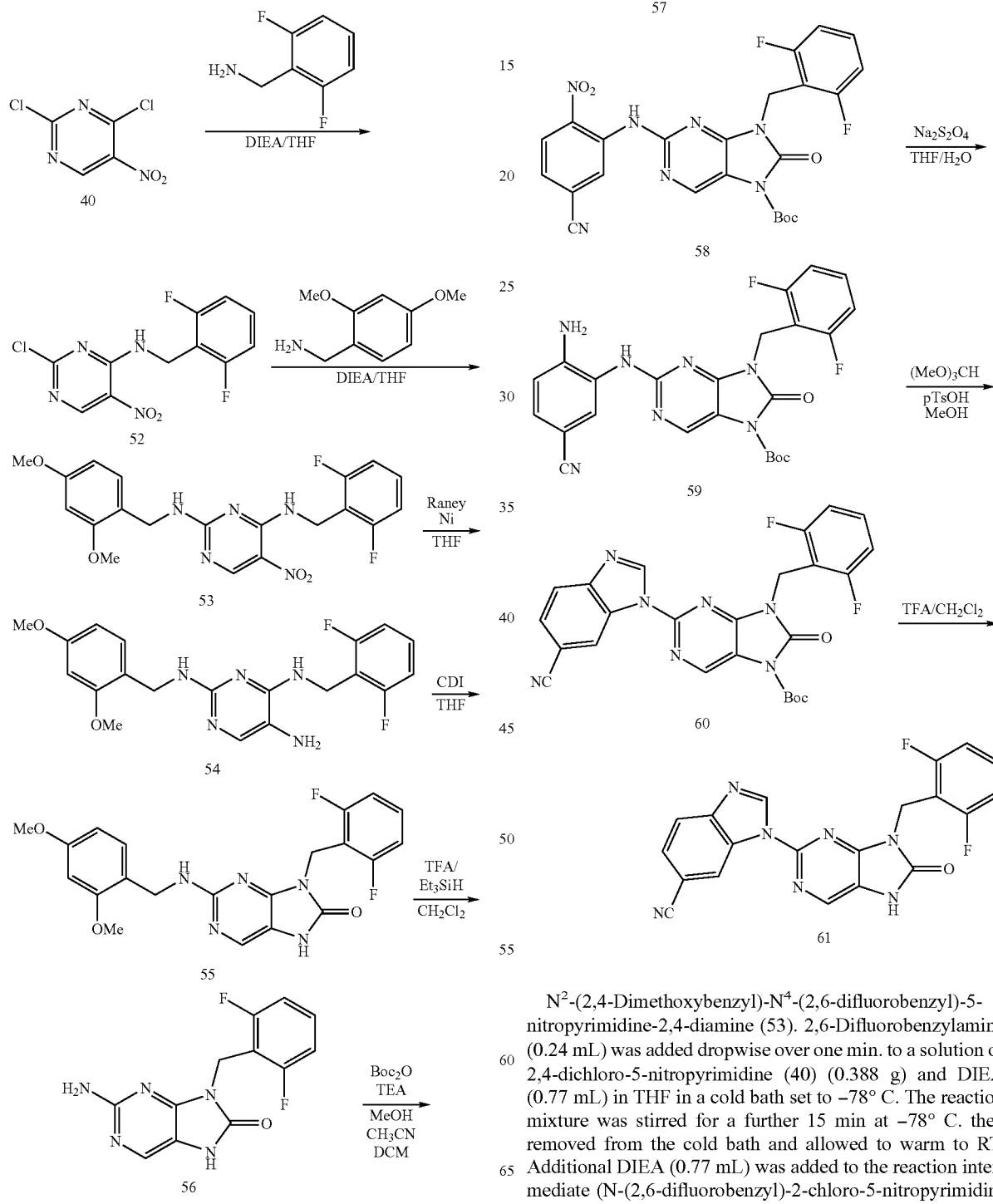

N²-(2,4-Dimethoxybenzyl)-N⁴-(2,6-difluorobenzyl)-5-nitropyrimidine-2,4-diamine (53). 2,6-Difluorobenzylamine (0.24 mL) was added dropwise over one min. to a solution of 2,4-dichloro-5-nitropyrimidine (40) (0.388 g) and DIEA (0.77 mL) in THF in a cold bath set to −78° C. The reaction mixture was stirred for a further 15 min at −78° C. then removed from the cold bath and allowed to warm to RT. Additional DIEA (0.77 mL) was added to the reaction intermediate (N-(2,6-difluorobenzyl)-2-chloro-5-nitropyrimidin-4-amine) (52) followed by the addition of 2,4-dimethoxybenzylamine (0.30 mL) and the resulting mixture was stirred at RT overnight. Purification via column chromatography (eluted with 1 and 2.5% MeOH/DCM) gave $N^2$-(2,4-dimethoxybenzyl)-$N^4$-(2,6-difluorobenzyl)-5-nitropyrimidine-2,4-diamine (53) (0.80 g), MH$^+$=432.

2-(2,4-Dimethoxybenzylamino)-9-(2,6-difluorobenzyl)-7H-purin-8(9H)-one (55). Raney Ni was added to a solution of $N^2$-(2,4-dimethoxybenzyl)-$N^4$-(2,6-difluorobenzyl)-5-nitropyrimidine-2,4-diamine (0.80 g) in THF (50 mL) under argon flush. The suspension was evacuated, charged with hydrogen (balloon) and stirred for 16 hr. The resulting mixture was filtered through a celite plug that was thoroughly rinsed with THF and MeOH to yield $N^2$-(2,4-dimethoxybenzyl)-$N^4$-(2,6-difluorobenzyl)pyrimidine-2,4,5-triamine (54) that was used as such in the next reaction.

Carbonyldiimidazole (0.93 g) was added to a solution of $N^2$-(2,4-dimethoxybenzyl)-$N^4$-(2,6-difluorobenzyl)pyrimidine-2,4,5-triamine (54) in THF (20 mL) and the resultant mixture stirred at RT overnight, then the solvents were removed under reduced pressure and the taken up in EtOAc and washed trice with water. The organics were dried, filtered and evaporated and purified via column chromatography, elution with 2.5 and 4% MeOH/DCM, to yield 2-(2,4-Dimethoxybenzylamino)-9-(2,6-difluorobenzyl)-7H-purin-8(9H)-one (55) (0.58 g), MH$^+$=428.

tert-Butyl 9-(2,6-difluorobenzyl)-2-amino-8-oxo-8,9-dihydropurine-7-carboxylate (57). A 1:1 solution of TFA/DCM (10 mL) was added to 2-(2,4-dimethoxybenzylamino)-9-(2,6-difluorobenzyl)-7H-purin-8(9H)-one (55) (0.58 g) and stirred for 30 min, after which triethylsilane (2 mL) was added and the mixture was stirred an additional 4 hr. The solvents were removed under in vacuo, the residue was taken up in minimal MeOH and triturated with Et$_2$O, to yield the TFA salt of 9-(2,6-difluorobenzyl)-2-amino-7H-purin-8(9H)-one (56) (0.55 g), MH$^+$=278, as a salmon colored solid.

9-(2,6-Difluorobenzyl)-2-amino-7H-purin-8(9H)-one (0.55 g) was dissolved in a mixture of MeOH/ACN/DCM (40 mL), Et$_3$N (2 mL) and di-tert-butyl dicarbonate (0.61 g) were added and the mixture was stirred at RT overnight. The reaction solvents were removed and the crude material was taken up in DCM and washed with H$_2$O, evaporated and purified via column chromatography, elution with 2 and 3% MeOH/DCM gave the titled product (57) (0.36 g), MH$^+$=378, MH$^+$-Boc=278 (major), (M+Na)$^+$=400 and (2M+Na)$^+$=777 were also observed.

tert-Butyl 9-(2,6-difluorobenzyl)-2-(5-cyano-2-nitrophenylamino)-8-oxo-8,9-dihydropurine-7-carboxylate (58). Sodium hydride (88 mg, 95%) was added, under argon flush, to a solution of tert-butyl 9-(2,6-difluorobenzyl)-2-amino-8-oxo-8,9-dihydropurine-7-carboxylate (57) (191 mg) and 3-fluoro-4-nitrobenzonitrile (415 mg) in DMF (5 mL) at −40° C. The reaction mixture was allowed to warm to −20° C. over 3 hr then quenched by the addition of sat. aq. NH$_4$Cl, once at RT the mixture was diluted with EtOAc and separated. The organics were washed with brine (3×), dried, filtered and evaporated, purified via column chromatography, (eluted with DCM and 1 and 2.5% MeOH/DCM) to yield tert-Butyl 9-(2,6-difluorobenzyl)-2-(5-cyano-2-nitrophenylamino)-8-oxo-8,9-dihydropurine-7-carboxylate (58) (288 mg), MH$^+$=524.

tert-Butyl 9-(2,6-difluorobenzyl)-2-(6-cyano-1H-benzo[d]imidazol-1-yl)-8-oxo-8,9-dihydropurine-7-carboxylate (60). A freshly prepared solution of sodium hydrosulfite (tech, 1 g) and sodium bicarbonate (0.5 g) in H$_2$O (10 mL) was added to a solution of the above nitro compound (58) (288 mg) in THF (10 mL). The mixture was stirred vigorously for 5 min., extracted with DCM (3×), the combined organics were washed with brine, dried, filtered and concentrated to yield the intermediate tert-butyl 9-(2,6-difluorobenzyl)-2-(2-amino-5-cyanophenylamino)-8-oxo-8,9-dihydropurine-7-carboxylate (59) that was used as such in the next step.

A catalytic amount of para-toluene sulfonic acid monohydrate was added to a solution of the above amine intermediate and trimethyl orthoformate (3 mL) in MeOH (10 mL). After 1 hr the crude material was adsorbed onto silica gel and purified by column chromatography (eluted with 1 and 2% MeOH/DCM) to yield tert-Butyl 9-(2,6-difluorobenzyl)-2-(6-cyano-1H-benzo[d]imidazol-1-yl)-8-oxo-8,9-dihydropurine-7-carboxylate (60) (164 mg), MH$^+$=504 and MH$^+$-BOC=404.

3-(9-(2,6-Difluorobenzyl)-8-oxo-8,9-dihydro-7H-purin-2-yl)-3H-benzo[d]imidazole-5-carbonitrile (61). A 1:1 solution of TFA/DCM (10 mL) was added to tert-Butyl 9-(2,6-difluorobenzyl)-2-(6-cyano-1H-benzo[d]imidazol-1-yl)-8-oxo-8,9-dihydropurine-7-carboxylate (60) and stirred for 1 hr. The solvents were removed en vacuo and the resulting solid was triturated with Et$_2$O, and suspended in 6N HCl. Removal of solvents and trituration with Et$_2$O of the resulting solid gave the titled compound (61) (68 mg) as a HCl salt, MH$^+$=404, $^1$H NMR (d$_6$-DMSO) δ 11.8 (s, 1H), 9.2 (s, 1H), 8.8 (s, 1H), 8.0 (s, 1H), 7.9 (d, 1H), 7.8 (broad s, 1H), 7.4 (d, 1H), 7.4 (quintet, 1H), 7.1 (m, 2H), 5.2 (s, 2H) ppm, $^{19}$F NMR δ −114.3 (m).

Synthesis of 3-(8-Oxo-9-((R)-5,6,7,8-tetrahydroquinolin-5-yl)-8,9-dihydro-7H-purin-2-yl)-3H-benzo[d]imidazole-5-carbonitrile

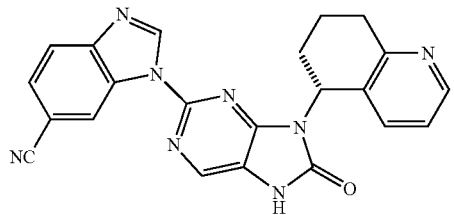

The title compound was synthesized from (R)-5,6,7,8-tetrahydroquinolin-5-amine (obtained via Novozyme 435 resolution (J. Org. Chem., 2003, 68, 3546) in a manner similar to that described in Example 29) via the procedure outlined in Example 20. $^1$H-NMR (300 MHz, CDCl$_3$+5% CD$_3$OD) δ 8.9 (br s, 1H), 8.7 (s, 1H), 8.6 (m, 1H), 8.3 (s, 1H), 7.8 (d, 1H), 7.7 (d, 2H), 7.6 (d, 1H), 7.5 (dd, 1H), 5.9 (dd, 1H), 3.3 (m, 2H), 2.7-2.5 (m, 1H), 2.4-2.2 (m, 2H), 2.1-2.0 (m, 1H); MH$^+$=386409.

Example 21

Synthesis of 3-(8-Oxo-9-(tetrahydro-2H-pyran-4-yl)-8,9-dihydro-7H-purin-2-yl)-3H-benzo[d]imidazole-5-carbonitrile (62)

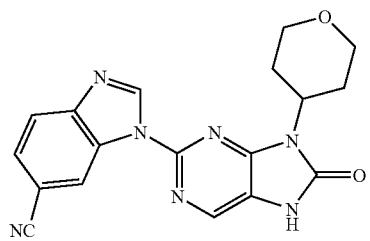

The title compound can be synthesized using the same procedures as described for the synthesis of 3-(9-(2,6-difluorobenzyl)-8-oxo-8,9-dihydro-7H-purin-2-yl)-3H-benzo[d]imidazole-5-carbonitrile (61, Example 20).

$^1$H NMR (d$_6$-DMSO) 11.71 (s, 1H), 9.34 (s, 1H), 8.94 (d, J=1.5 Hz, 1H), 8.38 (s, 1H), 8.00 (d, J=8.1 Hz, 1H), 7.79 (dd, J=8.1, 1.5 Hz, 1H), 4.57 (m, 1H), 4.04 (m, 2H), 3.50 (m, 2H), 2.59 (m, 2H), 1.79 (m, 2H); Mass (MH+) 362.1.

Example 22

Regiospecific synthesis of an oxoimidazopyridine derivative: Synthesis of 3-(2-oxo-3-((R)-1-(pyridin-3-yl)ethyl)-2,3-dihydro-1H-imidazo[4,5-b]pyridin-5-yl)-3H-benzo[d]imidazole-5-carbonitrile

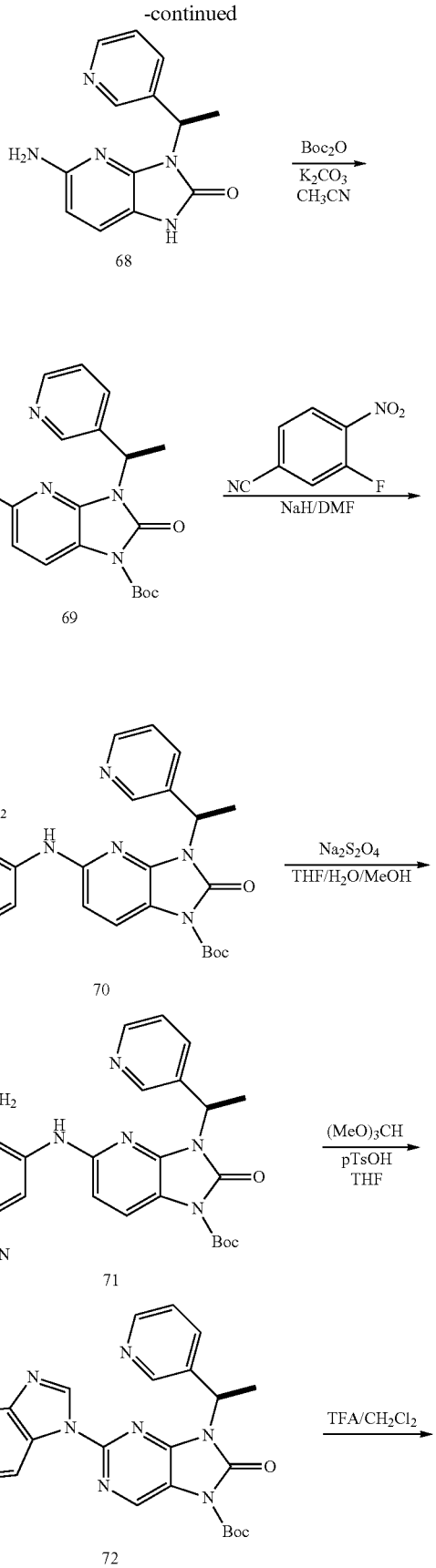

-continued

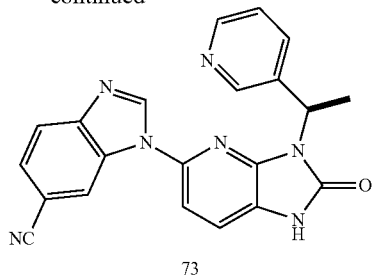

73

(R)—N6-(2,4-Dimethoxybenzyl)-3-nitro-N2-(1-(pyridin-3-yl)ethyl)pyridine-2,6-diamine (64). A solution of 2,6-dichloro-5-nitropyridine (46) (0.5 g) in THF (20 mL) was cooled to 0° C. and treated with 1.6 mL triethylamine followed by (R)-1-pyridin-3-yl-ethylamine (300 μL). The mixture was stirred for 1.5 h, then warmed to RT and stirred another 20 h. 2,4-Dimethoxybenzylamine (0.8 mL) was added and the mixture was heated at 50° C. for four hours. The mixture was diluted with ethyl acetate and washed twice with saturated sodium chloride solution. The organic layer was separated, dried over sodium sulfate, filtered, and concentrated. Column chromatography (50→100% ethyl acetate in hexanes) provided 761 mg of (R)—N6-(2,4-Dimethoxybenzyl)-3-nitro-N2-(1-(pyridin-3-yl)ethyl)pyridine-2,6-diamine (64).

(R)-tert-Butyl 2,4-dimethoxybenzyl(5-nitro-6-(1-(pyridin-3-yl)ethylamino)pyridin-2-yl)carbamate (65). A solution of (R)—N6-(2,4-dimethoxybenzyl)-3-nitro-N2-(1-(pyridin-3-yl)ethyl)pyridine-2,6-diamine (64) (367 mg) in methylene chloride (20 mL) was treated with di-tert-butyl dicarbonate (1.0 g) and 4-dimethylaminopyridine (22 mg). The mixture was stirred for 16 h and concentrated in vacuo. Column chromatography (50→100% ethyl acetate in hexanes) provided 500 mg of (R)-tert-Butyl 2,4-dimethoxybenzyl(5-nitro-6-(1-(pyridin-3-yl)ethylamino)pyridin-2-yl)carbamate (65).

(R)-tert-Butyl 2,4-dimethoxybenzyl(2-oxo-3-(1-(pyridin-3-yl)ethyl)-2,3-dihydro-1H-imidazo[4,5-b]pyridin-5-yl)carbamate (67). A solution of (R)-tert-butyl 2,4-dimethoxybenzyl(5-nitro-6-(1-(pyridin-3-yl)ethylamino)pyridin-2-yl)carbamate (500 mg) in THF (25 mL) was treated with an aqueous solution comprised of 2 g of $Na_2S_2O_4$ and 1 g $NaHCO_3$ in 20 mL of water followed by 1 mL of methanol. The mixture was stirred for 30 minutes, then diluted with ethyl acetate and washed with saturated sodium chloride solution. The organic layer was separated, dried over sodium sulfate, filtered, and concentrated to provide the intermediate (R)-tert-butyl 2,4-dimethoxybenzyl(5-amino-6-(1-(pyridin-3-yl)ethylamino)pyridin-2-yl)carbamate (66). The intermediate was dissolved in THF (50 mL) and treated with 1,1'-carbonyldiimidazole (0.5 g) at 50° C. for 20 h. The mixture was concentrated and purified by column chromatography (2→5% MeOH in methylene chloride) to provide 413 mg of (R)-tert-Butyl 2,4-dimethoxybenzyl(2-oxo-3-(1-(pyridin-3-yl)ethyl)-2,3-dihydro-1H-imidazo[4,5-b]pyridin-5-yl)carbamate (67).

(R)-tert-Butyl 5-amino-2-oxo-3-(1-(pyridin-3-yl)ethyl)-2,3-dihydroimidazo[4,5-b]pyridine-1-carboxylate (69). A solution of (R)-tert-butyl 2,4-dimethoxybenzyl(2-oxo-3-(1-(pyridin-3-yl)ethyl)-2,3-dihydro-1H-imidazo[4,5-b]pyridin-5-yl)carbamate in methylene chloride (15 mL) was treated with TFA (15 mL) and triethylsilane (1.0 mL) for one hour. The mixture was concentrated to provide the intermediate (R)-5-amino-3-(1-(pyridin-3-yl)ethyl)-1H-imidazo[4,5-b]pyridin-2(3H)-one (68), which was dissolved in acetonitrile (50 mL) and stirred vigorously with di-tert-butyl dicarbonate (1.0 g) and potassium carbonate (3.0 g) for 2 h. Methylene chloride (200 mL) and water (100 mL) was added and the organic layer was separated. The aqueous layer was extracted with another 100 mL of methylene chloride. The combined organic layers were separated, dried over sodium sulfate, filtered, and concentrated. Column chromatography (2→3→4% MeOH in methylene chloride) provided 235 mg (R)-tert-Butyl 5-amino-2-oxo-3-(1-(pyridin-3-yl)ethyl)-2,3-dihydroimidazo[4,5-b]pyridine-1-carboxylate (69).

(R)-tert-Butyl 5-(5-cyano-2-nitrophenylamino)-2-oxo-3-(1-(pyridin-3-yl)ethyl)-2,3-dihydroimidazo[4,5-b]pyridine-1-carboxylate (70). A solution of (R)-tert-butyl 5-amino-2-oxo-3-(1-(pyridin-3-yl)ethyl)-2,3-dihydroimidazo[4,5-b]pyridine-1-carboxylate (94 mg) and 3-fluoro-4-nitrobenzonitrile (225 mg) in DMF (6 mL) was cooled to −25° C. and treated with NaH (60% w/w in mineral oil, 75 mg) and slowly allowed to warm to −15° C. The mixture was stirred for four hours between −20° C. and −15° C., then diluted with EtOAc and quenched with saturated ammonium chloride solution. The organic phase was washed three times with brine, separated, dried over sodium sulfate, filtered, and concentrated. Column chromatography (2% MeOH in methylene chloride) provided 100 mg (R)-tert-Butyl 5-(5-cyano-2-nitrophenylamino)-2-oxo-3-(1-(pyridin-3-yl)ethyl)-2,3-dihydroimidazo[4,5-b]pyridine-1-carboxylate (70).

tert-Butyl 5-(6-cyano-1H-benzo[d]imidazol-1-yl)-2-oxo-3-((R)-1-(pyridin-3-yl)ethyl)-2,3-dihydroimidazo[4,5-b]pyridine-1-carboxylate (72). A solution of (R)-tert-butyl 5-(5-cyano-2-nitrophenylamino)-2-oxo-3-(1-(pyridin-3-yl)ethyl)-2,3-dihydroimidazo[4,5-b]pyridine-1-carboxylate (70) (100 mg) in THF (5 mL) was treated with an aqueous solution comprised of 0.5 g of $Na_2S_2O_4$ and 0.25 g $NaHCO_3$ in 5 mL of water. The mixture went quickly from a red color to a slightly yellow color, which indicated reduction of the nitro group. The mixture was diluted with ethyl acetate and washed with saturated sodium chloride solution. The organic layer was separated, dried over sodium sulfate, filtered, and concentrated to provide the intermediate (R)-tert-butyl 5-(2-amino-5-cyanophenylamino)-2-oxo-3-(1-(pyridin-3-yl)ethyl)-2,3-dihydroimidazo[4,5-b]pyridine-1-carboxylate (71). The intermediate was dissolved in THF (5 mL), DMF (1 mL), and trimethylorthoformate (2 mL). The mixture was treated with 10 mg of p-toluenesulfonic acid and stirred for 20 h. The mixture was diluted with ethyl acetate and washed once with saturated sodium bicarbonate and twice with saturated NaCl solution. The organic layer was separated, dried over sodium sulfate, filtered, and concentrated. Column chromatography (2% MeOH in methylene chloride) provided 57 mg tert-Butyl 5-(6-cyano-1H-benzo[d]imidazol-1-yl)-2-oxo-3-((R)-1-(pyridin-3-yl)ethyl)-2,3-dihydroimidazo[4,5-b]pyridine-1-carboxylate (72).

3-(2-oxo-3-((R)-1-(pyridin-3-yl)ethyl)-2,3-dihydro-1H-imidazo[4,5-b]pyridin-5-yl)-3H-benzo[d]imidazole-5-carbonitrile (73). A solution of tert-butyl 5-(6-cyano-1H-benzo[d]imidazol-1-yl)-2-oxo-3-((R)-1-(pyridin-3-yl)ethyl)-2,3-dihydroimidazo[4,5-b]pyridine-1-carboxylate (72) (57 mg) in methylene chloride (1 mL) was treated with TFA (1 mL) for one hour. The mixture was concentrated and the resulting TFA salt was converted to the HCl salt by dissolving it in 5 mL EtOH and adding 0.5 mL of conc. HCl, then concentrating the solution in vacuo. The process was repeated and the resulting residue was dissolved in a minimum amount of methanol and triturated with the addition of ethyl ether. After 3 triturations, 3-(2-oxo-3-((R)-1-(pyridin-3-yl)ethyl)-2,3-dihydro-1H-imidazo[4,5-b]pyridin-5-yl)-3H-benzo[d]imidazole-5-carbonitrile (73) HCl salt (39 mg) was isolated as a tan colored solid:

$^1$H-NMR (CD$_3$OD) δ 9.9 (br s, 1H), 9.2 (s, 1H), 9.0 (m, 2H), 8.5 (s, 1H), 8.3 (m, 1H), 8.2 (m, 1H), 8.1 (d, 1H), 7.9 (d, 1H), 7.8 (d, 1H), 6.3 (q, 1H), 2.3 (d, 3H).

Example 23

Regiospecific synthesis: Synthesis of 9-(2,6-Difluorobenzyl)-2-(6-fluoro-1H-benzo[d]imidazol-1-yl)-9H-purine (78)

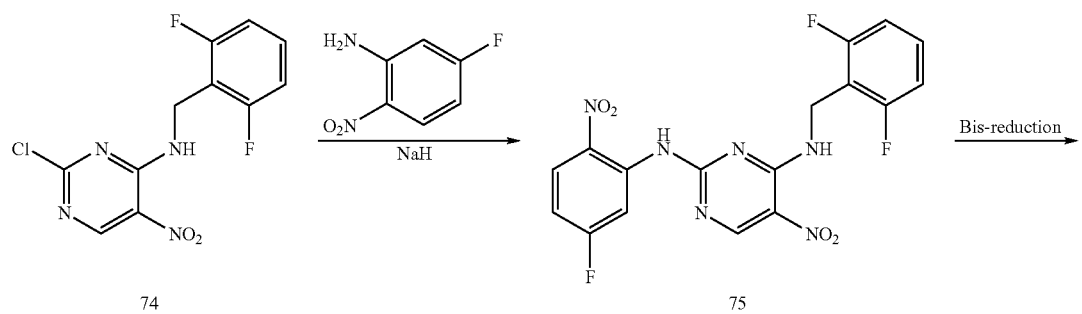

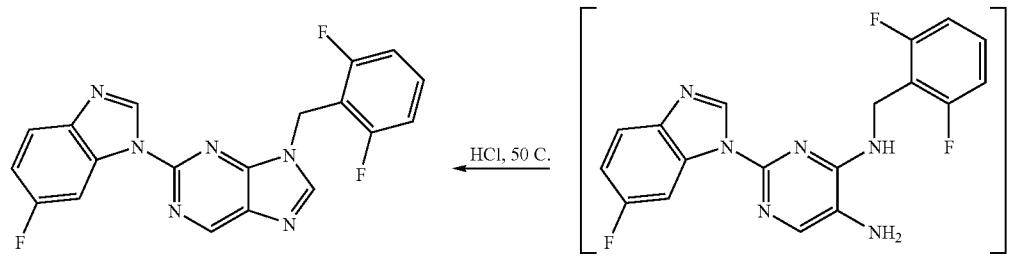

N⁴-(2,6-Difluorobenzyl)-N²-(5-fluoro-2-nitrophenyl)-5-nitropyrimidine-2,4-diamine (75). Under an argon atmosphere, sodium hydride (100 mg) was added to a solution of N-(2,6-difluorobenzyl)-2-chloro-5-nitropyrimidin-4-amine (150 mg) and 5-fluoro-2-nitroaniline (78 mg) in THF (10 mL) at RT. The mixture was stirred for 30 min, quenched via the addition of sat. aq. NH₄Cl, extracted with DCM and purified by preparative HPLC to give a low yield of N⁴-(2,6-difluorobenzyl)-N²-(5-fluoro-2-nitrophenyl)-5-nitropyrimidine-2,4-diamine (75) (24 mg), MH⁺=421.

9-(2,6-Difluorobenzyl)-2-(6-fluoro-1H-benzo[d]imidazol-1-yl)-9H-purine (78). A freshly prepared solution of sodium hydrosulfite (tech, 100 mg) and sodium bicarbonate (50 mg) in H₂O (5 mL) was added to a solution of N⁴-(2,6-difluorobenzyl)-N²-(5-fluoro-2-nitrophenyl)-5-nitropyrimidine-2,4-diamine (75) (24 mg) in THF (5 mL). The mixture was stirred vigorously for 30 min and extracted with DCM (3×). The combined organics were washed with brine, dried, filtered and concentrated to yield the intermediate N⁴-(2,6-difluorobenzyl)-N²-(2-amino-5-fluorophenyl)pyrimidine-2,4,5-triamine (76) for use in the next step. A catalytic amount of para-toluene sulfonic acid monohydrate was added to a solution of the intermediate and trimethyl orthoformate (1 mL) in MeOH (2 mL), after 2 hr conc. HCl (1 mL) was added and the mixture was heated at 50° C. for 4 hr. The reaction solvents were removed and the crude material was purified via preparative HPLC to give 9-(2,6-Difluorobenzyl)-2-(6-fluoro-1H-benzo[d]imidazol-1-yl)-9H-purine (78) as the TFA salt in low yield (0.8 mg) MH⁺=404, ¹H NMR (5% CD₃OD/CDCl₃) δ 9.1 (s, 1H), 9.0 (s, 1H), 8.3 (d, 1H), 8.2 (s, 1H), 7.6 (m, 1H), 7.0 (t, 1H), 6.9 (m, 2H), 5.5 (s, 2H) ppm, ¹⁹F NMR δ −76.6 (s, TFA), −114.5 (m), −117.1 (m).

Example 24

Synthesis of 2-(1H-Benzo[d]imidazol-1-yl)-9-(cis-3-methyl-tetrahydro-2H-pyran-4-yl)-7H-purin-8(9H)-one

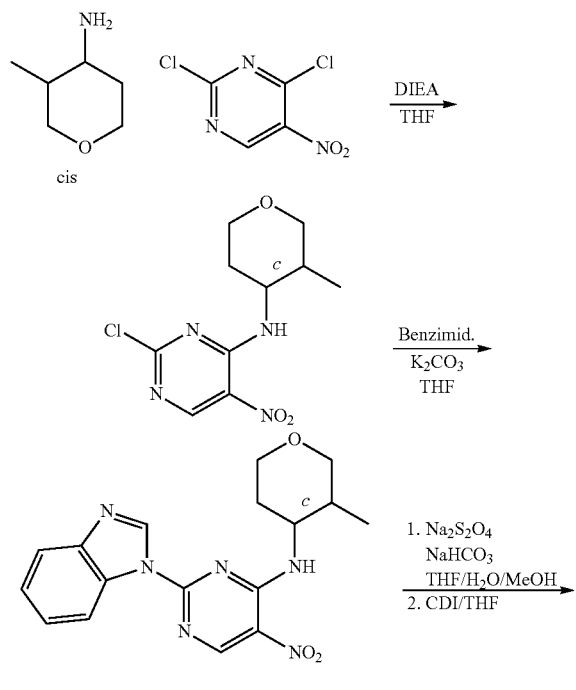

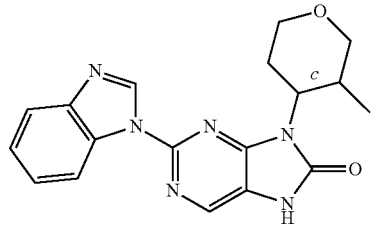

2-Chloro-N-(cis-3-methyl-tetrahydro-2H-pyran-4-yl)-5-nitropyrimidin-4-amine. To a suspension of 0.24 g of the hydrochloride salt of cis-3-methyl-tetrahydro-2H-pyran-4-amine (WO 2004/041161) and DIEA (1.5 mL) in THF (10 mL) at −78° C. was added 2,4-dichloro-5-nitropyrimidine (0.72 g). The mixture was allowed to slowly reach room temperature and stirred for 16 hours. The mixture was diluted with EtOAc and washed 3 times with brine. The organic layer was separated, dried over sodium sulfate, and concentrated in vacuo. Column chromatography (20→40% EtOAc/hexanes) provided 289 mg of the title compound.

2-(1H-Benzo[d]imidazol-1-yl)-N-(cis-3-methyl-tetrahydro-2H-pyran-4-yl)-5-nitropyrimidin-4-amine. To a solution of 2-chloro-N-(cis-3-methyl-tetrahydro-2H-pyran-4-yl)-5-nitropyrimidin-4-amine (115 mg) in acetonitrile (5 mL) was added potassium carbonate (300 mg) and benzimidazole (150 mg). The mixture was stirred at 70° C. for 2.5 hours. After diluting with 70 mL EtOAc, the mixture was washed with brine, dried over sodium sulfate, and concentrated in vacuo. Column chromatography (50→100% EtOAc/hexanes) provided 99 mg of the title compound.

2-(1H-Benzo[d]imidazol-1-yl)-9-(cis-3-methyl-tetrahydro-2H-pyran-4-yl)-7H-purin-8(9H)-one. To a solution of 2-(1H-benzo[d]imidazol-1-yl)-N-(cis-3-methyl-tetrahydro-2H-pyran-4-yl)-5-nitropyrimidin-4-amine (51 mg) in THF (10 mL) was added a solution of sodium hydrosulfite (300 mg) and sodium bicarbonate (150 mg) in water (10 mL). The mixture briefly became blue followed by colorless. Methanol (1 mL) was added to maintain the homogeneity of the solution. The mixture was diluted with 70 mL EtOAc and washed twice with brine. The aqueous washes were extracted with another 50 mL of EtOAc and then the combined organic layers were dried over sodium sulfate and concentrated in vacuo to provide 2-(1H-benzo[d]imidazol-1-yl)-N4-(cis-3-methyl-tetrahydro-2H-pyran-4-yl)pyrimidine-4,5-diamine. The diamine intermediate was dissolved in THF (5 mL) and treated with 1,1'-carbonyldiimidazole (80 mg) at 50° C. for 16 hours. The mixture was diluted with 50 mL EtOAc and washed 3 times with brine. The organic layer was separated, dried over sodium sulfate, and concentrated in vacuo. Column chromatography (2→4% MeOH/DCM) provided 19.3 mg of the title compound. ¹H-NMR (300 MHz, 5% CD₃OD in CDCl₃) δ 8.9 (s, 1H), 8.5 (d, 1H), 8.2 (s, 1H), 7.8 (d, 1H), 7.4 (t, 1H), 7.3 (t, 1H), 4.7 (m, 1H), 4.2 (d(br), 1H), 3.9 (d, 1H), 3.7 (d, 1H), 3.5 (m, 2H), 2.3 (t(br), 1H), 1.8 (d(br), 1H), 1.2 (d, 3H).

Synthesis of 4-(2-(1H-Benzo[d]imidazol-1-yl)-8-oxo-7,8-dihydropurin-9-yl)-1,2,3,4-tetrahydronaphthalene-1-carbonitrile

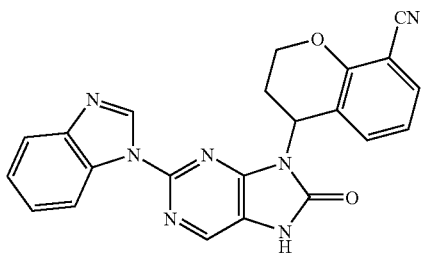

The title compound was synthesized from 4-amino-3,4-dihydro-2H-chromene-8-carbonitrile via the procedure described in Example 24. $^1$H NMR (300 MHz, d$_6$-DMSO) δ 8.87 (s, 1H), 8.57 (s, 1H), 7.70 (m, 3H), 7.31 (m, 3H), 6.94 (t, J=7.8 Hz, 1H), 5.90 (m, 1H), 4.61 (m, 2H), 2.73 (m, 1H), 2.33 (m, 1H); Mass (MH+) 410.1.

Synthesis of cis/trans-4-(2-(1H-Benzo[d]imidazol-1-yl)-8-oxo-7,8-dihydropurin-9-yl)-1,2,3,4-tetrahydronaphthalen-1-yl acetate

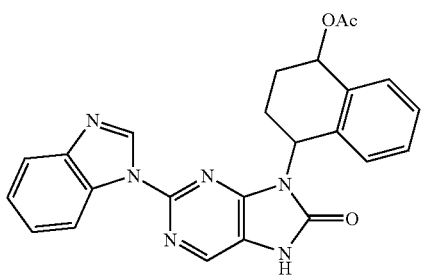

The title compound was synthesized from 4-amino-1,2,3,4-tetrahydronaphthalen-1-yl acetate via the procedure described in Example 24. $^1$H NMR (300 MHz, CDCl$_3$) δ 10.56 (s, 0.66H), 10.48 (s, 0.34H), 8.87 (s, 0.66H), 8.83 (s, 0.34H), 8.30 (s, 0.66H), 8.27 (s, 0.34H), 7.76-7.02 (m, 8H), 6.35 (m, 0.34H), 6.17 (m, 0.66H), 5.93 (s, 0.34H), 5.79 (m, 0.66H), 2.90-2.01 (m, 7H); Mass (MH+) 441.0.

Synthesis of 2-(1H-Benzo[d]imidazol-1-yl)-9-(1-methyl-4,5,6,7-tetrahydro-1H-indol-4-yl)-7H-purin-8(9H)-one

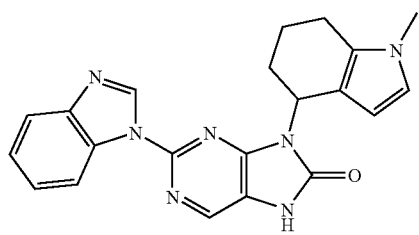

The title compound was synthesized from 1-methyl-4,5,6,7-tetrahydro-1H-indol-4-amine via the procedure described in Example 24. $^1$H NMR (CD$_3$OD) δ 8.90 (s, 1H), 8.25 (s, 1H), 7.88 (m, 1H), 7.68 (m, 1H), 7.32 (m, 2H), 6.51 (d, J=2.7 Hz, 1H), 5.66 (m, 2H), 3.65 (s, 3H), 2.80 (m, 2H), 2.46 (s, 1H), 2.19 (m, 2H), 1.96 (m, 1H); Mass (MH+) 386.0.

Synthesis of 2-(1H-Benzo[d]imidazol-1-yl)-9-(oxepan-4-yl)-7H-purin-8(9H)-one

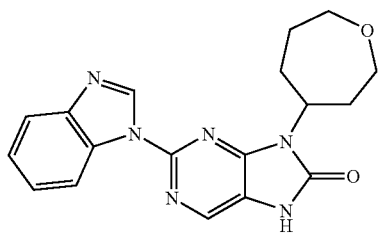

The title compound was synthesized from oxepan-4-amine via the procedure described in Example 24. $^1$H-NMR (CDCl$_3$) δ 9.0 (s, 1H), 8.5 (d, 1H), 8.1 (s, 1H), 7.7 (d, 1H), 7.3 (m, 2H), 4.6 (t, 1H), 3.9 (m, 2H), 3.8 (m, 2H), 2.7 (m, 2H), 2.0 (m, 4H) ppm.

Synthesis of 4-(2-(1H-Benzo[d]imidazol-1-yl)-8-oxo-7,8-dihydropurin-9-yl)chroman-6-carbonitrile

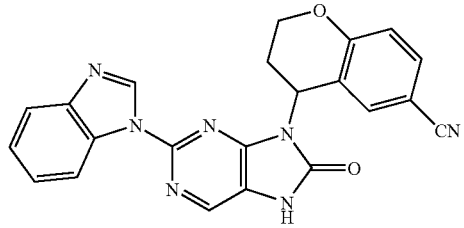

The title compound was synthesized from 4-amino-3,4-dihydro-2H-chromene-6-carbonitrile via the procedure described in Example 24. $^1$H-NMR of TFA salt (300 MHz, CDCl$_3$) δ 9.4 (s, 1H), 9.2 (s, 1H), 8.4 (s, 1H), 8.0 (d, 1H), 7.9 (d, 1H), 7.4-7.6 (m, 3H), 7.1-7.2 (m, 2H), 5.8-6.0 (m, 1H), 4.6-4.7 (m, 1H), 4.4-4.5 (m, 1H), 2.8-3.0 (m, 1H), 2.2-2.4 (m, 1H).

Synthesis of 2-(1H-Benzo[d]imidazol-1-yl)-9-(4-fluoro-2,3-dihydrobenzofuran-3-yl)-7H-purin-8(9H)-one

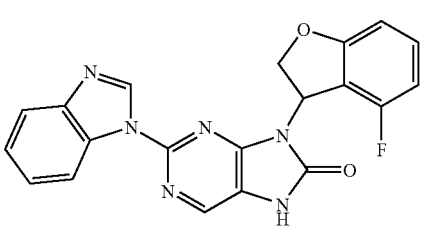

The title compound was synthesized from 4-fluoro-2,3-dihydrobenzofuran-3-amine (prepared in example 37) via the procedure described in Example 24. ¹H-NMR (300 MHz, CDCl₃+5% CD₃OD) δ 8.7 (s, 1H), 8.1-8.2 (m, 1H), 8.1 (s, 1H), 7.6-7.7 (m, 1H), 7.1-7.3 (m, 3H), 6.7 (d, 1H), 6.5 (d, 1H), 6.3-6.4 (m, 1H), 4.8-4.9 (m, 2H).

Synthesis of 2-(6-Fluoro-1H-benzo[d]imidazol-1-yl)-9-(2,3,4,5-tetrahydrobenzo[b]oxepin-5-yl)-7H-purin-8(9H)-one

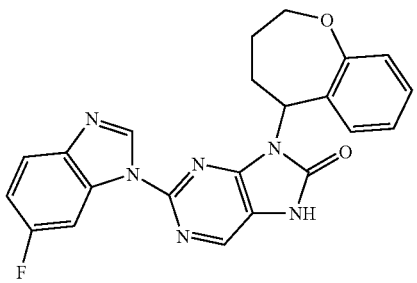

The title compound was synthesized from 2,3,4,5-tetrahydrobenzo[b]oxepin-5-amine (obtained from the corresponding ketone (J. Med. Chem., 2004, 47, 5612) using the same procedures outlined for the 4-aminochromanes) via the procedure described in Example 24. ¹H-NMR (300 MHz, CDCl₃+5% CD₃OD) δ 8.8 (s, 1H), 8.2 (s, 1H), 8.0 (dd, 1H), 7.6-7.7 (m, 1H), 6.95-7.2 (m, 3H), 6.9 (t, 1H), 6.6 (d, 1H), 5.9 (d, 1H), 4.4-4.5 (m, 1H), 3.7-3.9 (m, 1H), 2.8-3.0 (m, 1H), 2.0-2.3 (m, 3H).

Synthesis of 2-(1H-Benzo[d]imidazol-1-yl)-9-(1-(2-chloropyridin-3-yl)ethyl)-7H-purin-8(9H)-one

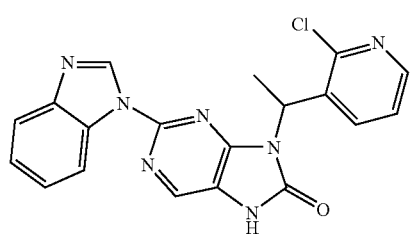

The title compound was synthesized from 3-(α-aminoethyl)-2-chloropyridine via the procedure described in Example 24. ¹H-NMR (CDCl₃) δ 8.8 (s, 1H), 8.4 (d, 1H), 8.3 (d, 1H), 8.2 (d, 1H), 8.1 (s, 1H), 7.7 (d, 1H), 7.3 (m, 3H), 3.4 (m, 1H), 2.0 (d, 3H), ppm.

Synthesis of 2-(1H-Benzo[d]imidazol-1-yl)-9-(5-fluoro-1,2,3,4-tetrahydronaphthalen-1-yl)-7H-purin-8(9H)-one

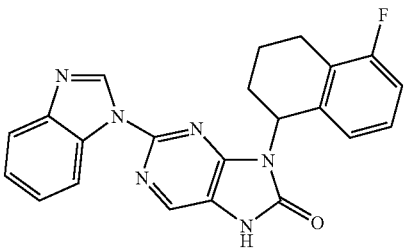

The title compound was synthesized from 5-fluoro-1,2,3,4-tetrahydronaphthalen-1-amine via the procedure described in Example 24. ¹H-NMR (CDCl₃) δ 8.7 (s, 1H), 8.1 (s, 1H), 7.6 (d, 1H), 7.5 (d, 1H), 7.2 (q, 2H), 6.9 (m, 2H), 6.7 (d, 1H), 5.7 (m, 1H), 3.3 (s, 2H), 2.8 (m, 2H), 2.4 (q, 1H), 2.1 (m, 1H), 1.8 (m, 1H), ppm.

Synthesis of 2-(1H-Benzo[d]imidazol-1-yl)-9-(quinolin-3-ylmethyl)-7H-purin-8(9H)-one

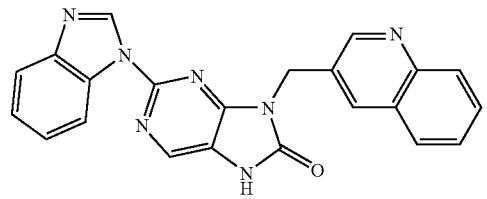

The title compound was synthesized from 3-aminomethylquinoline via the procedure described in Example 24. ¹H-NMR (CDCl₃) δ 9.8 (s, 1H), 9.4 (s, 1H), 8.9 (s, 1H), 8.6 (d, 1H), 8.3 (m, 2H), 8.1 (d, 1H), 7.9 (m, 2H), 7.8 (d, 1H), 7.5 (t, 2H), 5.5 (s, 2H) ppm.

Synthesis of 2-(1H-Benzo[d]imidazol-1-yl)-9-(3-methoxypropyl)-7H-purin-8(9H)-one

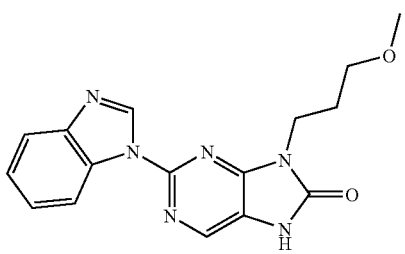

The title compound was synthesized from 3-methoxypropan-1-amine via the procedure described in Example 24. ¹H NMR (CD₃OD) δ 9.71 (s, 1H), 8.81 (d, 1H), 8.30 (s, 1H), 7.83 (d, 1H), 7.57 (m, 2H), 4.15 (t, 2H), 3.50 (t, 2H), 3.28 (s, 3H), 2.13 (m, 2H); MS (MH⁺) 325.2.

Synthesis of 9-(Tetrahydro-2H-pyran-4-yl)-2-(6-(trifluoromethyl)-1H-benzo[d]imidazol-1-yl)-7H-purin-8(9H)-one

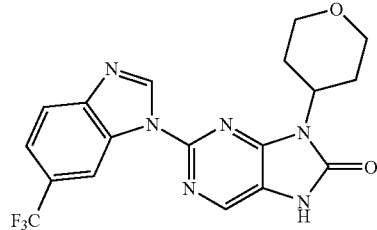

The title compound was synthesized from 3-methoxypropan-1-amine via the procedure described in Example 24. $^1$H NMR (CD$_3$OD+CHCl$_3$) δ 9.49 (s, 1H), 9.04 (s, 1H), 8.33 (s, 1H), 7.94 (d, 1H), 7.72 (m, 1H), 4.67 (m, 1H), 4.17 (m, 2H), 3.61 (m, 2H), 2.81 (m, 2H), 1.85 (m, 2H); MS (MH$^+$) 405.1.

Synthesis of 2-(5,6-Difluoro-1H-benzo[d]imidazol-1-yl)-9-(pyridin-3-ylmethyl)-7H-purin-8(9H)-one

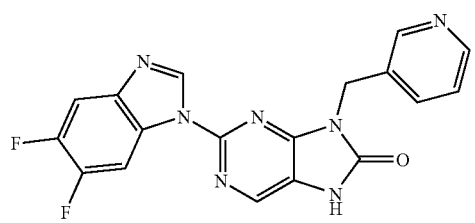

The title compound was synthesized from 5,6-difluoro-1H-benzo[d]imidazole (Example 4) via the procedure described in Example 24. $^1$H-NMR (300 MHz, CD$_3$OD) δ 9.2 (s, 1H), 9.0 (br, 1H), 8.7 (br, 1H), 8.6 (d, 1H), 8.4 (dd, 1H), 8.3 (s, 1H), 7.9 (dd, 1H), 7.6 (m, 2H), 5.4 (s, 2H).

Synthesis of 2-(6-Chloro-5-fluoro-1H-benzo[d]imidazol-1-yl)-9-(1-(pyridin-3-yl)ethyl)-7H-purin-8(9H)-one

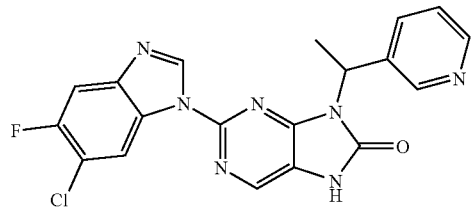

The title compound was synthesized from 6-chloro-5-fluorobenzimidazole via the procedure described in Example 24. $^1$H-NMR (300 MHz, CD$_3$OD) δ 9.2 (bs, 1H), 9.0 (m, 1H), 8.9-8.5 (m, 2H), 8.4 (m, 2H), 7.9 (m, 2H), 7.7 (m, 1H), 6.2 (q, 1H), 2.2 (d, 3H).

Synthesis of 2-(5,6-Dimethoxy-1H-benzo[d]imidazol-1-yl)-9-(pyridin-3-ylmethyl)-7H-purin-8(9H)-one

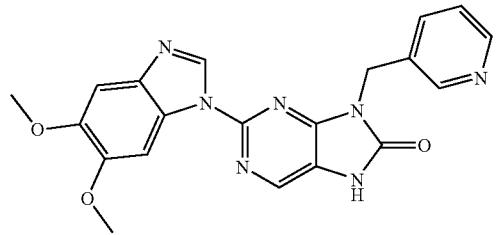

The title compound was synthesized from 5,6-dimethoxy-1H-benzo[d]imidazole via the procedure described in Example 24. $^1$H-NMR (300 MHz, CDCl$_3$) δ 8.6 (s, 1H), 8.5 (S, 1H), 8.4 (S, 1H), 8.0 (s, 1H), 7.9 (s, 1H), 7.5 (d, 1H), 7.3 (d, 1H), 6.9 (t, 1H), 4.8 (s, 2H), 3.7 (s, 6H).

Procedure for the synthesis of 2-(1H-Benzo[d]imidazol-1-yl)-9-(8-fluoroisochroman-4-yl)-7H-purin-8(9H)-one

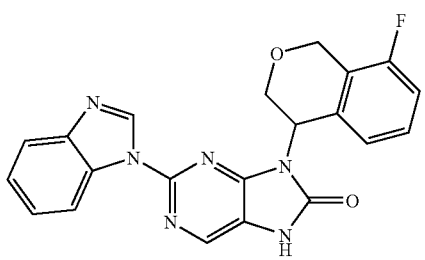

8-Fluoro-3,4-dihydro-1H-isochromen-4-amine

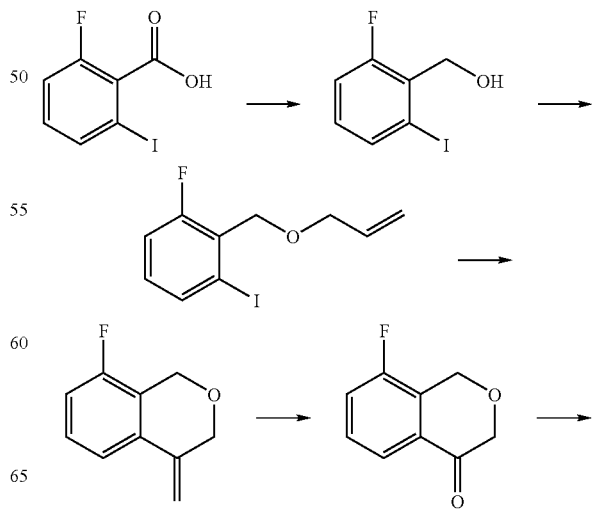

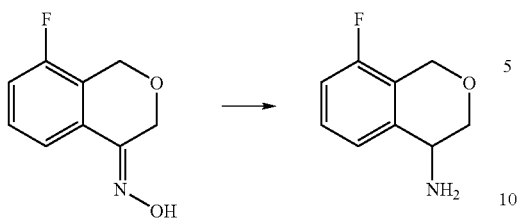

(2-Fluoro-6-iodophenyl)methanol. To a stirred solution of 2-fluoro-6-iodobenzoic acid (10 mmol) in THF (6.5 mL) and trimethylborate (3.25 mL) was added borane dimethylsulfide (12 mmol) slowly, maintaining the internal temperature at 20-25° C. Stirring was continued for an additional 16 h at room temperature and then methanol (1.44 mL) was added cautiously. The resulted solution was evaporated in vacuo to offer 2.5 g of the title compound as a pale yellow oil.

2-(Allyloxymethyl)-1-fluoro-3-iodobenzene. To a solution of (2-fluoro-6-iodophenyl)methanol (10 mmol) in 50 mL of THF was added NaH (12 mmol) in small portions at room temperature. After the addition, allylbromide (12 mmol) was added slowly via syringe. The reaction mixture was stirred 16 hours at room temperature. The resulting white heterogeneous mixture was quenched with water and then diluted with 100 mL of Et$_2$O, followed by washing with water and brine. The organic layer was dried over MgSO$_4$ and then concentrated to dryness in vacuo to offer 2.8 g of the title compound.

8-Fluoro-4-methylene-3,4-dihydro-1H-isochromene. 2-(Allyloxymethyl)-1-fluoro-3-iodobenzene (1 g) was dissolved in 20 mL of CH$_3$CN and 2.4 mL of Et$_3$N. The reaction solution was vacuum degassed three times, followed by the addition of Pd(OAc)$_2$ (37.6 mg) and PPh$_3$ (89.8 mg). The resulting mixture was heated at 80° C. for 16 hours. The reaction mixture was cooled to room temperature and diluted with Et$_2$O. The organic layer was washed with 1N HCl, 10% aqueous NaHCO$_3$, brine, and then dried over Na$_2$SO$_4$. After filtration, the filtrate was concentrated to dryness to offer a brown oil, which was purified by flash chromatography to offer 200 mg of the title compound.

8-Fluoro-1H-isochromen-4(3H)-one. 8-Fluoro-4-methylene-3,4-dihydro-1H-isochromene (400 mg) was dissolved in a solution of 1:1 MeOH/DCM (50 mL) and 1 mL of pyridine added. The mixture was chilled to −78° C. and ozone was bubbled through the mixture for 40 min. The reaction monitored by TLC. The mixture was purged with nitrogen at −78° C. for 10 min and then treated with PPh$_3$. After concentration, the resulting residue was purified by preparative TLC to offer 300 mg of the title compound.

8-Fluoro-3,4-dihydro-1H-isochromen-4-amine. The title compound was prepared from 8-fluoro-1H-isochromen-4 (3H)-one via the procedure described in Example 29. $^1$H-NMR (300 MHz, CD$_3$OD) δ 7.4 (m, 1H), 7.3 (d, 1), 7.2 (m, 1H), 5.0 (d, 1H), 4.7 (d, 1H), 4.4 (s, 1H), 4.2 (d, 1H) 3.9 (d, 1H) ppm.

2-(1H-Benzo[d]imidazol-1-yl)-9-(8-fluoroisochroman-4-yl)-7H-purin-8(9H)-one. The title compound was synthesized from 8-fluoroisochroman-4-amine via the procedure described in Example 24. $^1$H-NMR (300 MHz, CDCl$_3$) δ 8.7 (bs, 1H), 8.2 (s, 1H), 7.6 (m, 2H), 7.3-6.9 (m, 4H), 6.8 (d, 1H), 5.8 (t, 1H), 5.0 (s, 2H), 4.2 (m, 2H).

Example 25

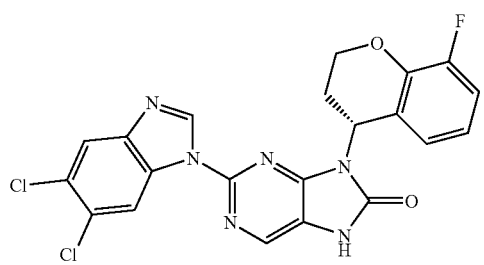

2-(5,6-Dichloro-1H-benzo[d]imidazol-1-yl)-9-((R)-8-fluorochroman-4-yl)-7H-purin-8(9H)-one. A solution of (R)-2-chloro-N-(8-fluorochroman-4-yl)-5-nitropyrimidin-4-amine in acetonitrile was treated with 5,6-dichlorobenzimidazole and potassium carbonate. The mixture was stirred at reflux for 6 hours, cooled to room temperature, diluted with 150 mL of EtOAc, and washed twice with 30 mL portions of water. The organic layer was separated, dried with magnesium sulfate, filtered, and concentrated in vacuo. Purification by column chromatography (2% MeOH/DCM) gave the intermediate nitropyrimidinamine. The title compound was synthesized from the intermediate nitropyrimidinamine via the procedures described in Example 24. $^1$H-NMR (300 MHz, CDCl$_3$) δ 8.7 (s, 1H), 8.3 (s, 1H), 8.2 (s, 1H), 7.8 (t, 1H), 7.0 (t, 1H), 6.6 (m, 2H), 5.9 (t, 1H), 4.6 (m, 1H), 4.4 (m, 1H), 3.0 (m, 1H), 2.3 (m, 1H).

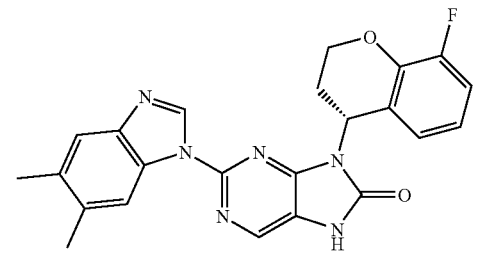

2-(5,6-Dimethyl-1H-benzo[d]imidazol-1-yl)-9-((R)-8-fluorochroman-4-yl)-7H-purin-8(9H)-one. The title compound was synthesized from 5,6-dichlorobenzimidazole via the procedures described in Example 25. $^1$H-NMR (300 MHz, CDCl$_3$) δ 9.6 (s, 1H), 8.8 (s, 1H), 8.3 (s, 1H), 8.0 (s, 1H), 7.6 (s, 1H), 7.0 (t, 1H), 6.7 (m, 1H), 5.9 (t, 1H), 4.7 (m, 1H), 4.5 (m, 1H), 3.2 (m, 2H), 2.4 (d, 6H).

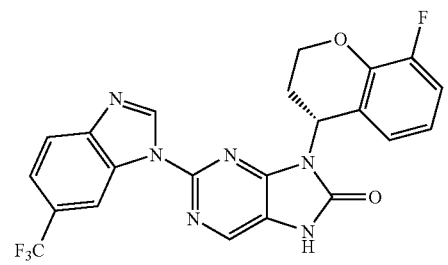

-continued

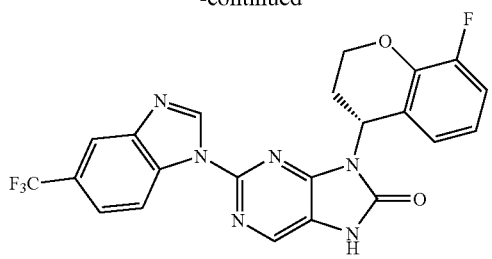

9-((R)-8-Fluorochroman-4-yl)-2-(6-(trifluoromethyl)-1H-benzo[d]imidazol-1-yl)-7H-purin-8(9H)-one and 9-((R)-8-fluorochroman-4-yl)-2-(5-(trifluoromethyl)-1H-benzo[d]imidazol-1-yl)-7H-purin-8(9H)-one. The title compound was synthesized from 5-trifluoromethylbenzimidazole (US 2004/0087601) via the procedures described in Example 25. Purification by column chromatography (2% MeOH/DCM) eluted the 6-trifluoromethyl isomer first ($^1$H-NMR (300 MHz, CDCl$_3$) δ 8.8 (d, 2H), 8.4 (s, 1H), 7.9 (d, 1H), 7.6 (d, 2H), 7.0 (t, 1H), 6.7 (m, 2H), 5.9 (t, 1H), 4.7 (m, 1H), 4.4 (m, 1H), 3.0 (m, 1H), 2.4 (m, 1H).) followed by the 5-trifluoromethyl isomer ($^1$H-NMR (300 MHz, CDCl$_3$) δ 9.0 (s, 1H), 8.4 (s, 1H), 8.1 (s, 1H), 8.0 (d, 1H), 7.6 (d, 2H), 7.0 (m, 1H), 6.8 (m, 2H), 5.9 (t, 1H), 4.7 (m, 1H), 4.4 (m, 1H), 2.9 (m, 1H), 2.4 (m, 1H).

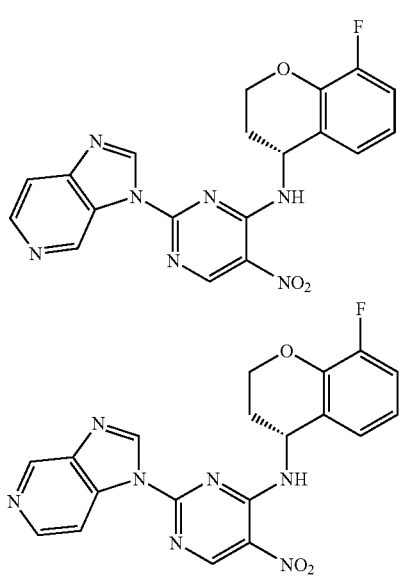

N—((R)-8-Fluorochroman-4-yl)-2-(3H-imidazo[4,5-c]pyridin-3-yl)-5-nitropyrimidin-4-amine and N—((R)-8-fluorochroman-4-yl)-2-(1H-imidazo[4,5-c]pyridin-1-yl)-5-nitropyrimidin-4-amine. The title compound was synthesized from 5-azabenzimidazole via the procedure described in Example 25. Purification by column chromatography (1% MeOH/DCM) provided N—((R)-8-fluorochroman-4-yl)-2-(3H-imidazo[4,5-c]pyridin-3-yl)-5-nitropyrimidin-4-amine as the first eluting isomer: ($^1$H-NMR (300 MHz, CDCl$_3$) δ 9.8 (s, 1H), 9.4 (s, 1H), 9.2 (s, 1H), 8.9 (d, 1H), 8.6 (d, 1H), 7.8 (d, 1H), 7.1 (m, 2H), 6.9 (m, 1H), 5.8 (q, 1H), 4.6 (m, 1H), 4.4 (m, 1H), 2.6 (m, 1H), 2.4 (m, 1H).). N—((R)-8-Fluorochroman-4-yl)-2-(1H-imidazo[4,5-c]pyridin-1-yl)-5-nitropyrimidin-4-amine eluted second: ($^1$H-NMR (300 MHz, CDCl$_3$) δ 9.4 (s, 1H), 9.2 (s, 1H), 9.1 (s, 1H), 8.9 (d, 1H), 8.6 (d, 1H), 8.4 (d, 1H), 7.1 (m, 2H), 6.9 (m, 1H), 5.7 (q, 1H), 4.5 (m, 1H), 4.4 (m, 1H), 2.6 (m, 1H), 2.4 (m, 1H).).

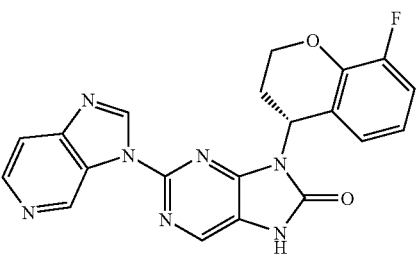

9-((R)-8-fluorochroman-4-yl)-2-(3H-imidazo[4,5-c]pyridin-3-yl)-7H-purin-8(9H)-one. The title compound was synthesized from N—((R)-8-fluorochroman-4-yl)-2-(3H-imidazo[4,5-c]pyridin-3-yl)-5-nitropyrimidin-4-amine via the procedures described in Example 24. $^1$H-NMR (300 MHz, CDCl$_3$) δ 9.8 (s, 1H), 9.4 (s, 1H), 8.6 (d, 1H), 8.3 (m, 2H), 7.0 (t, 1H), 6.7 (m, 2H), 5.9 (t, 1H), 4.6 (m, 1H), 4.4 (m, 1H), 2.8 (m, 1H), 2.4 (m, 1H).

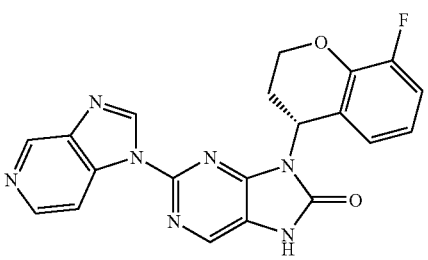

9-((R)-8-fluorochroman-4-yl)-2-(1H-imidazo[4,5-c]pyridin-1-yl)-7H-purin-8(9H)-one. The title compound was synthesized from N—((R)-8-fluorochroman-4-yl)-2-(1H-imidazo[4,5-c]pyridin-1-yl)-5-nitropyrimidin-4-amine via the procedures described in Example 24. $^1$H-NMR (300 MHz, CDCl$_3$) δ 9.3 (d, 2H), 8.4 (d, 1H), 8.3 (d, 2H), 7.0 (t, 1H), 6.7 (m, 2H), 5.9 (t, 1H), 4.6 (m, 1H), 4.4 (m, 1H), 2.8 (m, 1H), 2.4 (m, 1H).

Synthesis of 2-(5,6-Difluoro-1H-benzo[d]imidazol-1-yl)-9-((R)-8-fluorochroman-4-yl)-7H-purin-8(9H)-one

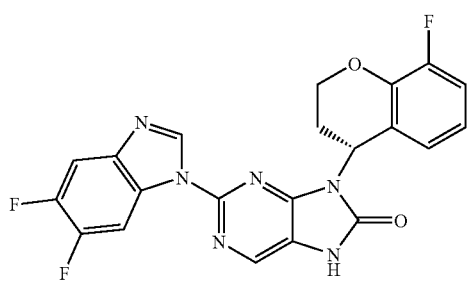

The title compound was synthesized from 5,6-difluoro-1H-benzo[d]imidazole (Example 4) via the procedure described in Example 25. $^1$H-NMR (CDCl$_3$) δ 9.2 (s, 1H), 8.8

(s, 1H), 8.3 (s, 1H), 7.8 (t, 1H), 7.6 (t, 1H), 7.1 (t, 1H), 6.8 (m, 1H), 5.9 (t, 1H), 4.7 (m, 1H), 4.4 (m, 1H), 3.6 (s, 3H), 2.9 (m, 1H), 2.4 (m, 1H) ppm.

Synthesis of 9-(R)-Chroman-4-yl-2-(6-methane-sulfonyl-benzoimidazol-1-yl)-7,9-dihydro-purin-8-one and 9-(R)-Chroman-4-yl-2-(5-methanesulfonyl-benzoimidazol-1-yl)-7,9-dihydro-purin-8-one

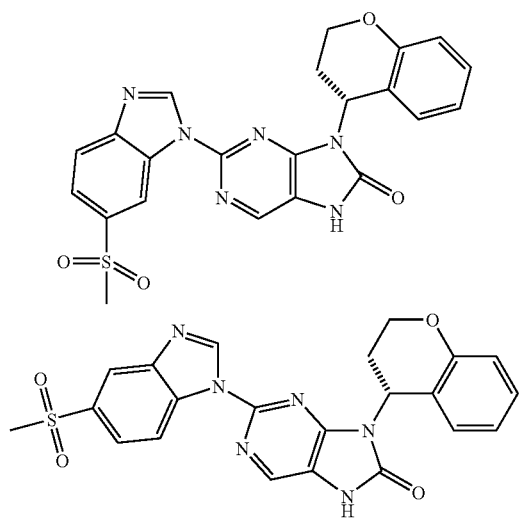

The title compounds were synthesized from 5-methylsulfonylbenzimidazole (prepared as per examples 4 and 5) via the procedure described in Example 25. Purification by column chromatography (2% MeOH/DCM) provided 9-(R)-chroman-4-yl-2-(6-methanesulfonyl-benzoimidazol-1-yl)-7,9-dihydro-purin-8-one as the first eluting isomer: $^1$H-NMR (CDCl$_3$) δ 9.2 (s, 1H), 8.8 (s, 1H), 8.3 (s, 1H), 7.9 (d, 2H), 7.2 (t, 1H), 7.0 (d, 1H), 6.9 (d, 1H), 6.8 (t, 1H), 5.9 (t, 1H), 4.6 (m, 1H), 4.4 (t, 1H), 3.1 (s, 3H), 2.9 (m, 1H), 2.4 (m, 1H) ppm, and 9-(R)-Chroman-4-yl-2-(5-methanesulfonyl-benzoimidazol-1-yl)-7,9-dihydro-purin-8-one as the second eluting isomer $^1$H-NMR (CDCl$_3$) δ 8.9 (s, 1H), 8.4 (s, 1H), 8.3 (s, 1H), 8.0 (d, 1H), 7.8 (d, 1H), 7.2 (m, 1H), 7.1 (d, 1H), 6.9 (d, 1H), 6.8 (t, 1H), 5.9 (t, 1H), 4.5 (m, 1H), 4.4 (t, 1H), 3.1 (s, 3H), 2.9 (m, 1H), 2.4 (m, 1H) ppm.

Synthesis of 9-((R)-8-Fluorochroman-4-yl)-2-(7H-purin-7-yl)-7H-purin-8(9H)-one

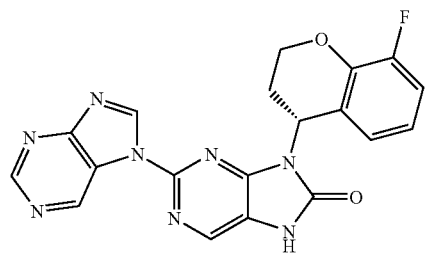

The title compound was synthesized from 7H-purine via the procedure described in Example 25. $^1$H-NMR (CDCl$_3$) δ 9.4 (s, 1H), 9.2 (s, 1H), 9.1 (s, 1H), 8.3 (s, 1H), 7.8 (s, 1H), 7.0 (m, 1H), 6.8 (d, 2H), 5.9 (t, 1H), 4.6 (m, 1H), 4.4 (m, 1H), 2.9 (m, 1H), 2.4 (m, 1H) ppm.

Synthesis of 2-(1H-Benzo[d][1,2,3]triazol-1-yl)-9-((R)-8-fluorochroman-4-yl)-7H-purin-8(9H)-one

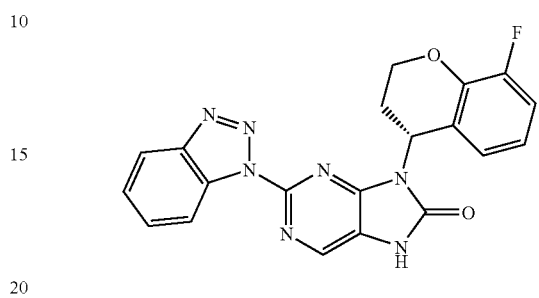

The title compound was synthesized from 1H-benzo[d][1,2,3]triazole via the procedure described in Example 25. $^1$H-NMR (5% CD$_3$OD in CDCl$_3$) δ 8.4 (br s, 1H), 8.0 (d, 1H), 7.5-7.3 (m, 3H), 7.0-6.9 (m, 1H), 6.7 (m, 2H), 5.9 (dd, 1H), 4.5 (dt, 1H), 4.3 (td, 1H), 2.9-2.8 (m, 1H), 2.4-2.2 (m, 1H) ppm.

Example 26

Synthesis of 3-(9-((R)-6,8-difluorochroman-4-yl)-8-oxo-8,9-dihydro-7H-purin-2-yl)-3H-benzo[d]imidazole-5-carbonitrile

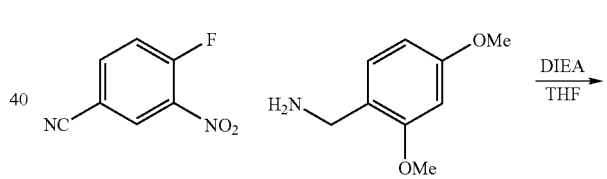

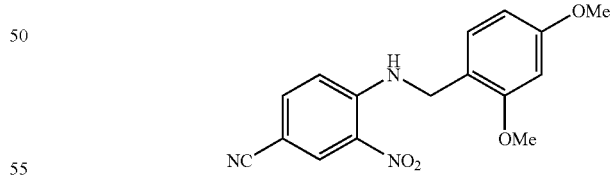

4-(2,4-dimethoxybenzylamino)-3-nitrobenzonitrile. A solution of 4-fluoro-3-nitrobenzonitrile (5.0 g) in THF (100 mL) was treated with DIEA (6.3 mL) and 2,4-dimethoxybenzylamine (5.0 mL), and then stirred for 24 h. The solvent was evaporated and the crude mixture was dissolved in EtOAc (100 mL). The solution was washed once with 1 M HCl and twice with saturated aqueous NaCl (100 mL each). The organic layer was separated, dried over Na$_2$SO$_4$, filtered, and concentrated in vacuo. Column chromatography (20% EtOAc/DCM) provided 9.25 g of the title compound.

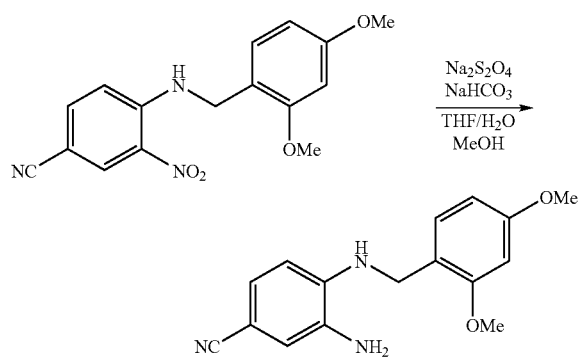

4-(2,4-dimethoxybenzylamino)-3-aminobenzonitrile. A solution of 4-(2,4-dimethoxybenzylamino)-3-nitrobenzonitrile (4.54 g) in THF (400 mL) was treated with a solution of sodium hydrosulfite (20 g) and sodium bicarbonate (10 g) in distilled water (350 mL). Enough methanol was immediately added (50 mL) to maintain a homogeneous solution. After 15 minutes, EtOAc (500 mL) and saturated aqueous NaCl (500 mL) were added and the organic layer was separated. The aqueous layer was extracted again with 400 mL EtOAc. The combined organic layers were washed with saturated aqueous NaCl (500 mL) and separated. The organic phase was dried over $Na_2SO_4$, filtered, and concentrated in vacuo to provide 4.33 g of the title compound.

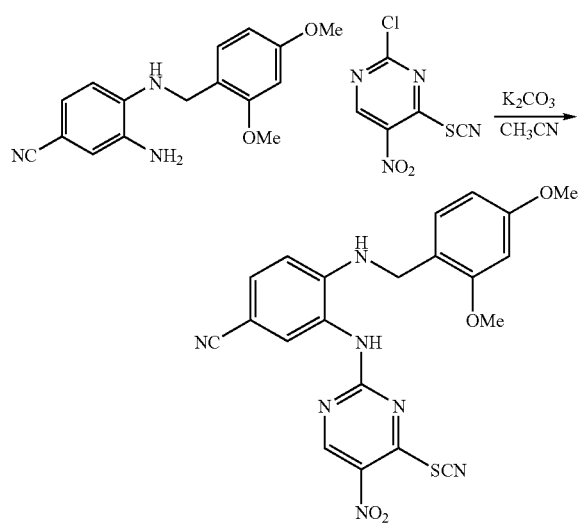

4-(2,4-dimethoxybenzylamino)-3-(5-nitro-4-thiocyanatopyrimidin-2-ylamino)benzonitrile. A solution of 4-(2,4-dimethoxybenzylamino)-3-aminobenzonitrile (3.9 g) in acetonitrile (100 mL) was cooled to 0° C. and treated with potassium carbonate (6.3 g) followed by a solution containing 3 g of 2-chloro-5-nitro-4-thiocyanatopyrimidine (WO 2003/032994) in acetonitrile (50 mL). The mixture was stirred for 30 minutes at 0° C. and 30 minutes at room temperature resulting in the formation of a precipitate. The mixture was quenched at 0° C. by the addition of 4% acetic acid (150 mL) and filtered. The precipitate was swirled in 100 mL acetonitrile and filtered again. The precipitate was washed with acetonitrile, which resulted in the slow dissolution of product into the filtrate. After air-drying, 1.5 g of the title compound remained as the precipitate cake. The filtrate was extracted with EtOAc, dried over $Na_2SO_4$, filtered, and concentrated in vacuo. Column chromatography (0→20% EtOAc/DCM) and recrystallization from acetonitrile provided 0.415 g of additional title compound.

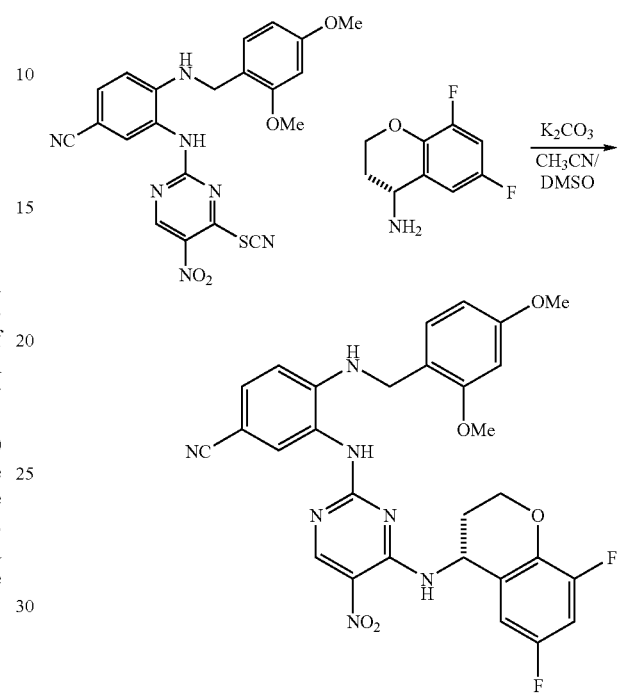

(R)-4-(2,4-dimethoxybenzylamino)-3-(4-(6,8-difluorochroman-4-ylamino)-5-nitropyrimidin-2-ylamino)benzonitrile. A partial suspension of 4-(2,4-dimethoxybenzylamino)-3-(5-nitro-4-thiocyanatopyrimidin-2-ylamino)benzonitrile (415 mg) in 40 mL of acetonitrile was treated with a solution of (R)-6,8-difluorochroman-4-amine HCl salt (320 mg) in DMSO (10 mL) followed by potassium carbonate (1.0 g). The mixture was stirred for 24 hours, and then diluted with EtOAc (200 mL). The mixture was washed once with saturated aqueous ammonium chloride (200 mL) and 3 times with saturated aqueous NaCl (200 mL each). The organic layer was separated, dried over $Na_2SO_4$, filtered, and concentrated in vacuo. Column chromatography (20→40% EtOAc/hexanes) provided 358 mg of the title compound.

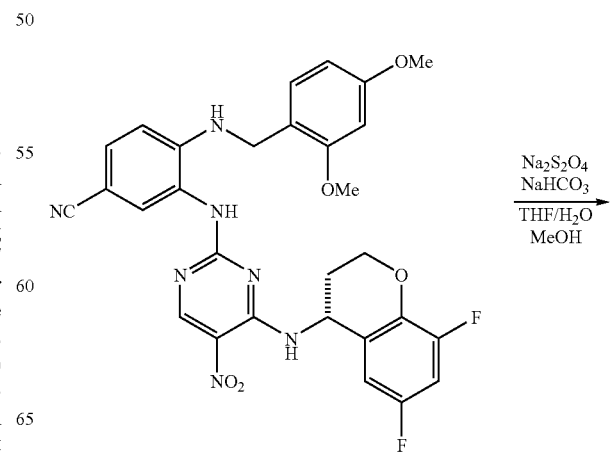

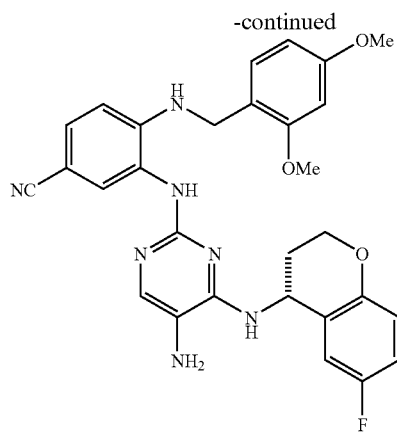

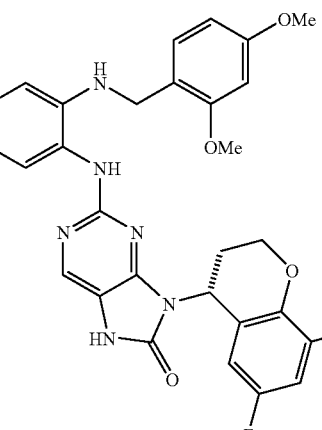

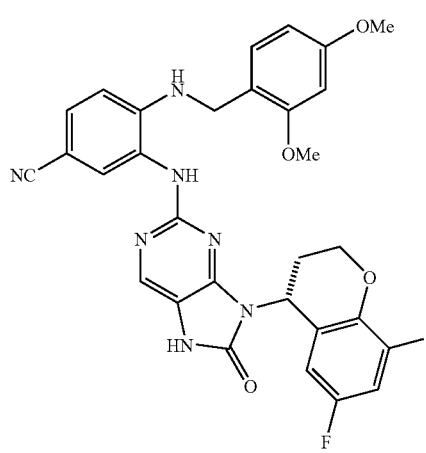

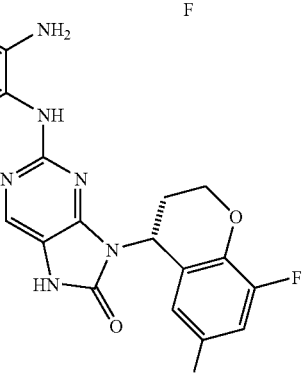

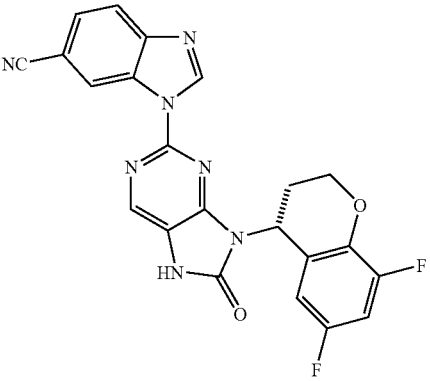

(R)-4-(2,4-dimethoxybenzylamino)-3-(9-(6,8-difluorochroman-4-yl)-8-oxo-8,9-dihydro-7H-purin-2-ylamino)benzonitrile. A solution of (R)-4-(2,4-dimethoxybenzylamino)-3-(4-(6,8-difluorochroman-4-ylamino)-5-nitropyrimidin-2-ylamino)benzonitrile (358 mg) in THF (25 mL) was treated with a solution of sodium hydrosulfite (1.5 g) and sodium bicarbonate (1.5 g) in 20 mL of distilled water. Methanol (5 mL) was added to maintain a homogeneous solution. After 15 minutes, the mixture was diluted with EtOAc (100 mL) and washed with saturated aqueous NaCl (2×100 mL). The organic layer was separated, dried over $Na_2SO_4$, filtered, and concentrated in vacuo to provide the intermediate (R)-4-(2,4-dimethoxybenzylamino)-3-(5-amino-4-(6,8-difluorochroman-4-ylamino)pyrimidin-2-ylamino)benzonitrile. The intermediate was dissolved in THF (5 mL) and treated with carbonyldiimidazole (0.55 g) for 16 hours. The mixture was diluted with EtOAc (100 mL) and washed twice with saturated aqueous NaCl (2×100 mL). The organic layer was separated, dried over $Na_2SO_4$, filtered, and concentrated in vacuo. Column chromatography (2→3% MeOH/DCM) provided 230 mg of the title compound.

3-(9-((R)-6,8-difluorochroman-4-yl)-8-oxo-8,9-dihydro-7H-purin-2-yl)-3H-benzo[d]imidazole-5-carbonitrile. A solution of (R)-4-(2,4-dimethoxybenzylamino)-3-(9-(6,8-difluorochroman-4-yl)-8-oxo-8,9-dihydro-7H-purin-2-ylamino)benzonitrile (230 mg) in DCM (5 mL) was treated with TFA (5 mL) and triethylsilane (1 mL) for 16 h. The mixture was concentrated in vacuo to provide the intermediate (R)-4-amino-3-(9-(6,8-difluorochroman-4-yl)-8-oxo-8,9-dihydro-7H-purin-2-ylamino)benzonitrile. The intermediate was dissolved in 5 mL THF and treated with 3 mL trimethylorthoformate followed by p-toluenesulfonic acid (3 mg). After 1 hour, the mixture was diluted with EtOAc (100 mL) and washed once with saturated aqueous sodium bicarbonate (100 mL). The organic layer was separated, dried over $Na_2SO_4$, filtered, and concentrated in vacuo. Column chromatography (50→100% EtOAc/hexanes) provided 78 mg of the title compound. $^1$H-NMR (300 MHz, 5% $CD_3OD$ in $CDCl_3$) δ 8.8 (s, 1H), 8.7 (s, 1H), 8.2 (s, 1H), 7.8 (d, 1H), 7.6

(dd, 1H), 6.8 (td, 1H), 6.4 (dd, 1H), 5.8 (dd, 1H), 4.6 (m, 1H), 4.4 (td, 1H), 2.9 (m, 1H), 2.3 (m, 1H).

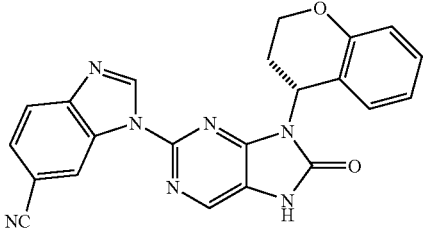

3-(9-((R)-chroman-4-yl)-8-oxo-8,9-dihydro-7H-purin-2-yl)-3H-benzo[d]imidazole-5-carbonitrile. The title compound was synthesized from (R)-chroman-4-amine via the procedures described in Example 26. $^1$H-NMR (300 MHz, 5% CD$_3$OD in CDCl$_3$) δ 8.8 (s, 1H), 8.5 (s, 1H), 8.2 (s, 1H), 7.8 (d, 1H), 7.5 (dd, 1H), 7.1 (m, 2H), 6.8 (d, 1H), 6.7 (td, 1H), 5.8 (dd, 1H), 4.5 (m, 1H), 4.3 (td, 1H), 2.8 (m, 1H), 2.3 (m, 1H).

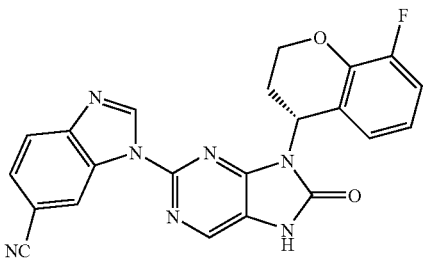

3-[9-(8-Fluoro-chroman-4-yl)-8-oxo-8,9-dihydro-7H-purin-2-yl]-3H-benzoimidazole-5-carbonitrile. The title compound was synthesized from (R)-8-fluorochroman-4-amine via the procedures described in Example 26. $^1$H-NMR (300 MHz, CDCl$_3$) δ 8.8 (s, 1H), 8.6 (s, 1H), 8.2 (s, 1H), 7.8 (d, 1H), 7.6 (d, 1H), 7.0 (t, 1H), 6.6 (m, 2H), 5.8 (t, 1H), 4.6 (m, 1H), 4.4 (m, 1H), 2.8 (m, 1H), 2.4 (m, 1H).

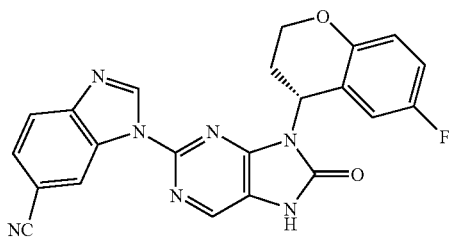

3-(9-((R)-6-fluorochroman-4-yl)-8-oxo-8,9-dihydro-7H-purin-2-yl)-3H-benzo[d]imidazole-5-carbonitrile. The title compound was synthesized from (R)-6-fluorochroman-4-amine via the procedures described in Example 26. $^1$H NMR (300 MHz, CDCl$_3$+5% CD$_3$OD): δ 8.86 (s, 1H), 8.41 (s, 1H), 8.18 (s, 1H), 7.72 (d, 1H), 7.51 (d, 1H), 7.0-7.1 (m, 1H), 6.8-6.9 (m, 1H), 6.49 (dd, 1H), 5.76 (br t, 1H), 4.4-4.5 (m, 1H), 4.24 (br t, 1H), 2.7-2.9 (m, 1H), 2.2-2.3 (m, 1H). Conditions for introduction of the chromanyl amine were improved as described below:

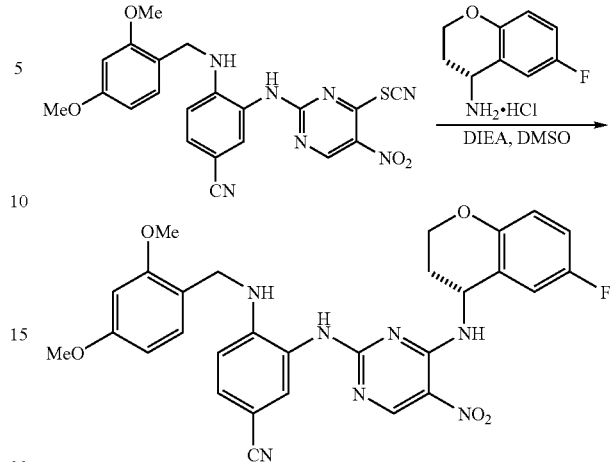

(R)-4-(2,4-dimethoxybenzylamino)-3-(4-(6-fluorochroman-4-ylamino)-5-nitropyrimidin-2-ylamino)benzonitrile.

A solution of 4-(2,4-dimethoxybenzylamino)-3-(5-nitro-4-thiocyanatopyrimidin-2-ylamino)benzonitrile (139 mg) in anhydrous DMSO (3 mL) was added to solution of (R)-6-fluorochroman-4-amine hydrochloride (79 mg) in anhydrous DMSO (3 mL) and DIEA (0.21 mL), the resulting dark red solution was stirred at RT under an atmosphere of Ar over which time the solution lighten to yellow. Upon completion of the reaction, the mixture was cooled to 0° C. with an ice bath, and water (25 mL) was added (exotherm). The resulting yellow solid was collected via filtration, washed with additional water, air dried, then dissolved in CH$_2$Cl$_2$, the organic solution was dried (MgSO$_4$), filtered and evaporated to yield the titled compound (quant.), NMR CDCl$_3$ $^1$H δ 9.0 (s, 1H), 8.6 (d, 1H), 7.7 (br s, 1H), 7.4 (dd, 1H), 7.1 (d, 1H), 7.0-6.8 (m, 4H), 6.5-6.4 (m, 2H), 5.2 (br s, 1H), 4.3 (s, 2H), 4.2 (br s, 2H), 3.8 (s, 6H), 2.2 (br s, 1H), 1.8 (br s, 1H); $^{19}$F δ −123 ppm; MH$^+$=572.

This material was taken on using the same procedures outlined in Example 26 to give 3-(9-((R)-6-fluorochroman-4-yl)-8-oxo-8,9-dihydro-7H-purin-2-yl)-3H-benzo[d]imidazole-5-carbonitrile.

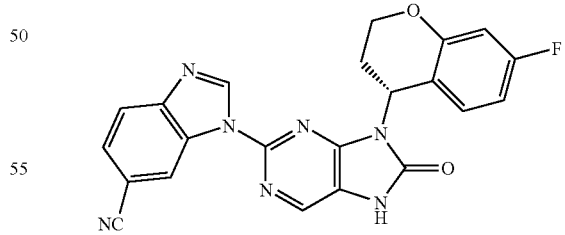

3-(9-((R)-7-fluorochroman-4-yl)-8-oxo-8,9-dihydro-7H-purin-2-yl)-3H-benzo[d]imidazole-5-carbonitrile. The title compound was synthesized from (R)-7-fluorochroman-4-amine via the procedures described in Example 26. $^1$H NMR (300 MHz, CDCl$_3$+5% CD$_3$OD): δ 8.86 (s, 1H), 8.58 (s, 1H), 8.19 (s, 1H), 7.79 (d, 1H), 7.56 (d, 1H), 6.7-6.9 (m, 2H), 6.4-6.5 (m, 1H), 5.78 (br t, 1H), 4.5-4.6 (m, 1H), 4.32 (br t, 1H), 2.7-2.9 (m, 1H), 2.2-2.4 (m, 1H).

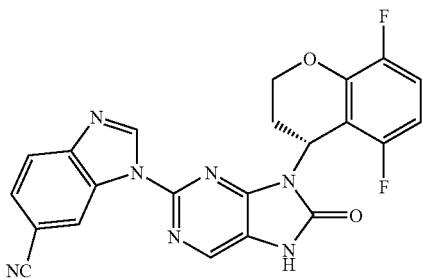

3-[9-(5,8-Difluoro-chroman-4-yl)-8-oxo-8,9-dihydro-7H-purin-2-yl]-3H-benzoimidazole-5-carbonitrile. The title compound was synthesized from (R)-5,8-difluorochroman-4-amine via the procedures described in Example 26. $^1$H-NMR (300 MHz, CDCl$_3$) δ 8.8 (s, 1H), 8.7 (s, 1H), 8.2 (s, 1H), 7.8 (d, 1H), 7.6 (d, 1H), 7.0 (m, 1H), 6.4 (m, 1H), 5.9 (t, 1H), 4.6 (m, 1H), 4.4 (m, 1H), 2.5 (m, 2H).

Synthesis of 3-(8-Oxo-9-((R)-5,6,7,8-tetrahydroquinoxalin-5-yl)-8,9-dihydro-7H-purin-2-yl)-3H-benzo[d]imidazole-5-carbonitrile

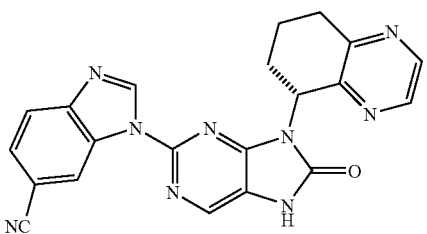

The title compound was synthesized from (R)-5,6,7,8-tetrahydroquinoxalin-5-amine (example 34) via the procedure described in Example 26. $^1$H-NMR (300 MHz, CDCl$_3$) δ 9.8 (br, 1H), 8.9 (s, 1H), 8.6 (s, 1H), 8.4 (s, 1H), 8.3 (s, 1H), 8.2 (s, 1H), 7.9 (d, 1H), 7.6 (d, 2H), 5.9 (dd, 2H), 3.2-3.5 (m, 2H), 2.8 (q, 1H), 2.3-2.5 (m, 2H), 2.1 (m, 1H).

Synthesis of 3-(9-Oxepan-4-yl-8-oxo-8,9-dihydro-7H-purin-2-yl)-3H-benzoimidazole-5-carbonitrile

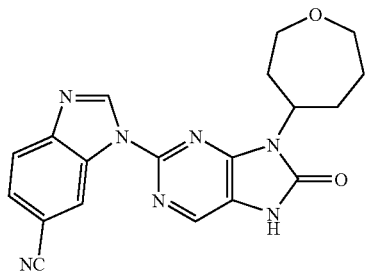

The title compound was synthesized from oxepan-4-amine (obtained from oxepan-4-one (Chemische Berichte, 1958, 91, 1589) via oxime reduction as per example 29) via the procedure described in Example 26. $^1$H-NMR (CDCl$_3$) δ 9.2 (s, 1H), 9.0 (s, 1H), 8.2 (s, 1H), 7.9 (d, 1H), 7.6 (d, 1H), 4.7 (t, 1H), 3.8 (m, 6H), 2.7 (m, 2H), 2.0 (m, 2H) ppm.

Synthesis of 3-(8-Oxo-9-(4,5,6,7-tetrahydrobenzofuran-4-yl)-8,9-dihydro-7H-purin-2-yl)-3H-benzo[d]imidazole-5-carbonitrile

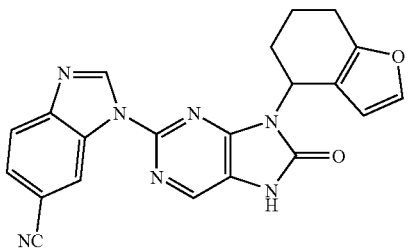

The title compound was synthesized from 4,5,6,7-tetrahydrobenzofuran-4-amine (obtained via reductive amination of 6,7-dihydrobenzofuran-4(5H)-one as per example 33) via the procedure described in Example 26 $^1$H-NMR (CDCl$_3$) δ 9.0 (s, 1H), 8.3 (s, 1H), 8.2 (s, 1H), 7.9 (d, 1H), 7.6 (d, 1H), 7.3 (s, 1H), 6.0 (s, 1H), 5.6 (t, 1H), 3.0 (m, 1H), 2.8 (d, 2H), 2.3 (m, 3H), 2.0 (m, 1H) ppm.

Synthesis of 2-(1H-Benzo[d]imidazol-1-yl)-9-(4,5,6,7-tetrahydrobenzo[b]thiophen-4-yl)-7H-purin-8(9H)-one

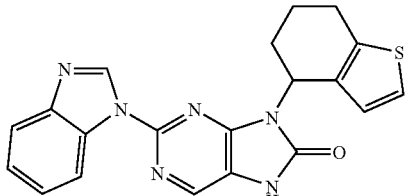

The title compound was synthesized from 4,5,6,7-tetrahydrobenzo[b]thiophen-4-amine (obtained via reductive amination of 6,7-dihydrobenzo[b]thiophen-4(5H)-one as per example 33) via the procedure described in Example 26 $^1$H-NMR (5% CD$_3$OD in CDCl$_3$) δ 9.2 (s, 1H), 8.2 (s, 1H), 7.8-7.7 (m, 2H), 7.4 (m, 2H), 7.0 (d, 1H), 6.6 (d, 1H), 5.7 (dd, 1H), 3.0 (br s, 2H), 2.4-2.0 (m, 4H) ppm.

Synthesis of 9-((R)-8-Fluorochroman-4-yl)-2-(5-methyl-1H-benzo[d]imidazol-1-yl)-7H-purin-8(9H)-one

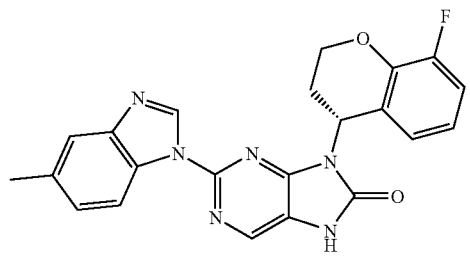

The title compound was synthesized from (R)-8-fluoro-chroman-4-amine and 4-fluoro-3-nitrotoluene via the procedures described in Example 26. $^1$H-NMR (CDCl$_3$) δ 9.0 (s, 1H), 8.2 (s, 1H), 7.6 (d, 1H), 7.5 (s, 1H), 7.1 (d, 1H), 6.9 (m, 2H), 5.8 (t, 1H), 4.6 (m, 1H), 4.4 (m, 1H), 2.8 (m, 1H), 2.4 (s, 3H), 2.3 (m, 1H) ppm.

Example 27

Synthesis of 2-(6-fluoro-1H-benzo[d]imidazol-1-yl)-9-((R)-8-fluoro-chroman-4-yl)-7H-purin-8(9H)-one

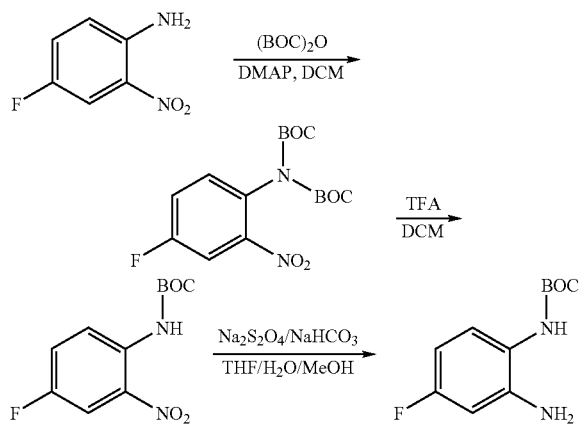

4-Fluoro-2-nitro-phenyl di-tert-butyl imidodicarbonate. A catalytic amount of DMAP was added to a mixture of 4-fluoro-2-nitrobenzenamine (0.78 g) and di-tert-butyl dicarbonate (2.18 g) in DCM (20 mL) and stirred at room temperature for 15 hr. The mixture was diluted with H$_2$O and twice extracted with DCM, the combined organics were dried, filtered and evaporated to yield the bis-BOC material (quant). $^1$H-NMR (300 MHz, CDCl$_3$) δ 7.8 (dd, 1H), 7.3 (m, 2H), 1.4 (s, 18H).

tert-Butyl 4-fluoro-2-nitrophenylcarbamate. (procedure: Connell, R. D.; Rein, T.; Akermark, B.; Helquist, P. J. J. Org. Chem. 1988, 53, 3845) To a stirred solution of the Bis-BOC material in DCM (20 mL) was added TFA (0.58 mL). After 3 hr the reaction was quenched with aq. NaHCO$_3$ (5 mL), brine was added, the mixture separated and extracted with additional DCM. The combined organics were evaporated, purified via column chromatography (eluted with 7.5% EtOAc/Hex) to give the titled product (1.12 g). $^1$H-NMR (300 MHz, CDCl$_3$) δ 9.5 (br 1H), 8.5 (dd, 1H), 7.9 (dd, 1H), 7.3 (m, 1H), 1.5 (s, 9H).

tert-Butyl 2-amino-4-fluorophenylcarbamate. To a solution of tert-butyl 4-fluoro-2-nitrophenylcarbamate (0.34 g) in THF (30 mL) was added a premixed solution of sodium hydrosulfite (2 g) and sodium bicarbonate (1 g) in water (50 mL). MeOH (10 mL) was also added to aid solution of the mixture, which was stirred at room temperature for 30 min, when sodium chloride was added to saturate the solution. The resultant mixture was extracted with EtOAc (2×). The combined organics were dried, filtered and evaporated to yield the titled compound (quant) that was used as such for the next step. $^1$H-NMR (300 MHz, CDCl$_3$) δ 7.5 (dd, 1H), 6.6 (dd, 1H), 6.5 (m, 1H), 6.4 (br 1H), 4.7 (br 2H), 1.5 (s, 9H); MH$^+$=227 (minor) 127 (-BOC), 171 (-tBu).

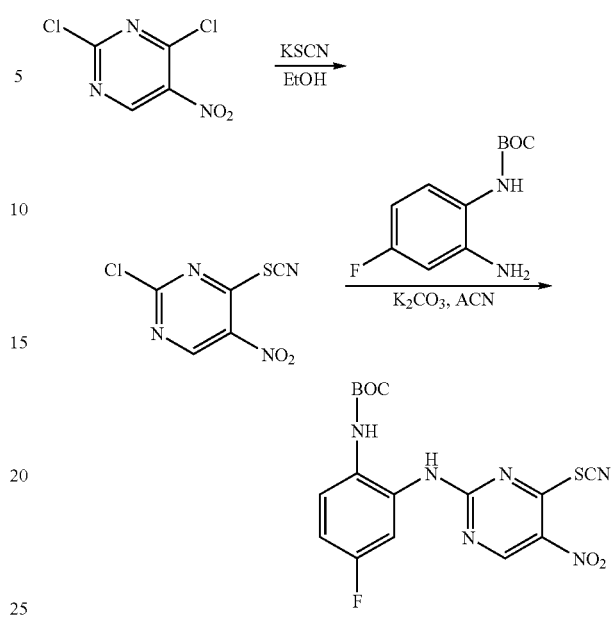

2-Chloro-5-nitro-4-thiocyanatopyrimidine. (compound known, e.g. WO 2003/032994) Potassium thiocyanate (0.97 g, 10 mM) was added to a solution of 2,4-dichloro-5-nitropyrimidine (1.94 g 10, mM) in EtOH (40 mL) cooled to 0° C. via an ice bath. The solution was stirred at 0° C. for 30 min, then the bath was removed and the resulting suspension allowed to come to RT over 60 min, when water (100 mL) was added. The precipitate was collected via filtration, washed with ice cold water, dissolved with DCM, dried (MgSO$_4$), filtered and evaporated to yield the titled compound (1.7 g). $^1$H-NMR (300 MHz, CDCl$_3$) δ 9.4 (s, 1H).

tert-Butyl 4-fluoro-2-(5-nitro-4-thiocyanatopyrimidin-2-ylamino)phenylcarbamate. Potassium carbonate (207 mg) was added to a stirred solution of 2-chloro-5-nitro-4-thiocyanatopyrimidine (108 mg) and tert-butyl 4-fluoro-2-nitrophenylcarbamate (113 mg) in ACN (5 mL) and stirred for 15 hr. The solution was diluted with brine and extracted with EtOAc (2×). The combined organics were evaporated and purified via column chromatography, elution with 30% EtOAc/Hex gave the titled compound (144 mg, 71% yield). $^1$H-NMR (300 MHz, DMSO-d6) δ 10.5 (br s, 1H), 9.3 (br s, 1H), 8.9 (br s, 1H), 7.7-7.4 (m, 2H), 7.1 (br s, 1H), 1.5 (s, 9H), 1.5 (s, 9H); MH$^+$=407, 307 (-BOC), 351 (-tBu).

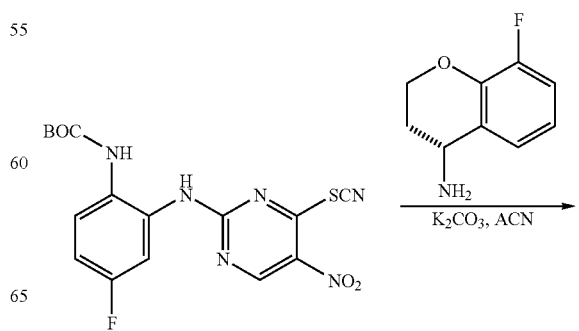

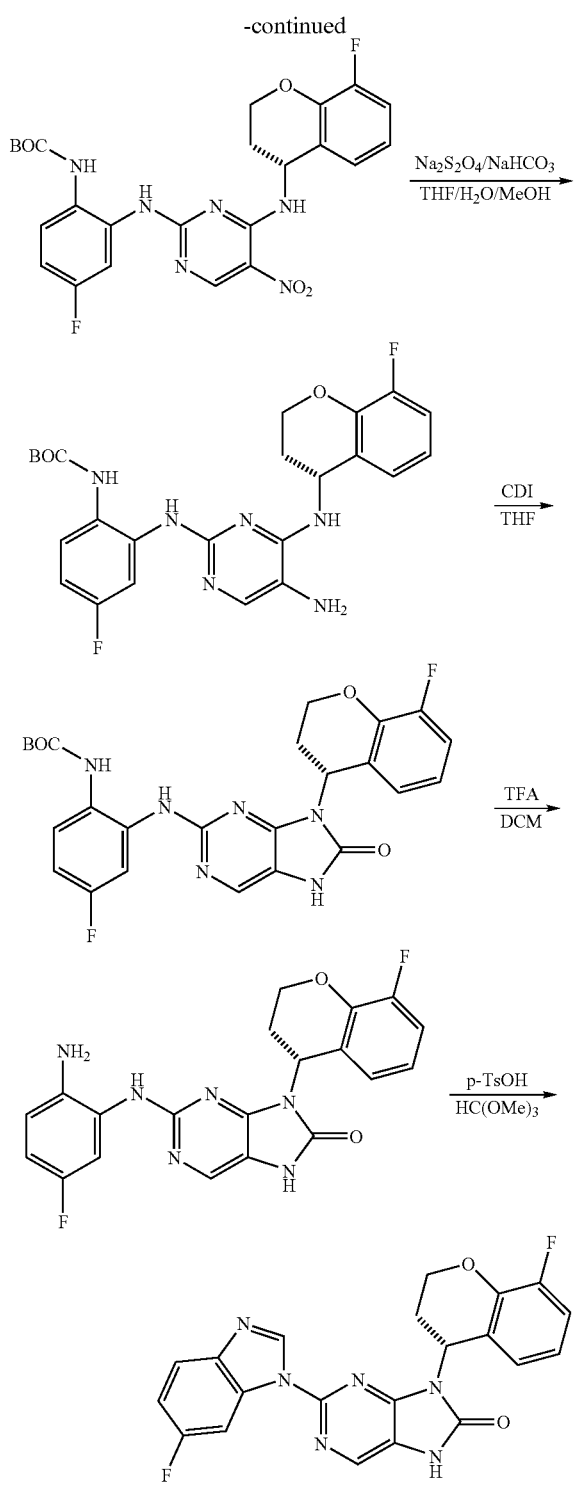

tional EtOAc, the combined organics were evaporated and purified via column chromatography, elution with 20-30% EtOAc/H gave the titled product in 83% yield. ¹H-NMR (300 MHz, CDCl₃) δ 9.1 (s, 1H), 8.7 (m, 1H), 8.2 (br s, 1H), 7.7 (m, 1H), 7.3 (m, 1H), 7.3-6.8 (m, 4H), 6.5 (s, 1H), 5.5 (br s, 1H), 4.4 (m 2H), 2.4 (m, 1H), 2.2 (m, 1H), 1.5 (s, 9H); MH⁺=515, 459 (-tBu).

(R)-tert-Butyl 4-fluoro-2-(9-(8-fluorochroman-4-yl)-8-oxo-8,9-dihydro-7H-purin-2-ylamino)phenylcarbamate. To a solution of (R)-tert-butyl 4-fluoro-2-(4-(8-fluorochroman-4-ylamino)-5-nitropyrimidin-2-ylamino)phenylcarbamate (141 mg) in THF (20 mL) was added a premixed solution of sodium hydrosulfite (0.6 g) and sodium bicarbonate (0.3 g) in water (50 mL). MeOH (5 mL) was also added to aid solution of the mixture, which was stirred at room temperature for 30 min, when sodium chloride was added to saturate the solution. The resultant mixture was extracted with EtOAc (2×), the combined organics were dried, filtered and evaporated to yield (R)-tert-butyl 2-(5-amino-4-(8-fluorochroman-4-ylamino)pyrimidin-2-ylamino)-4-fluorophenylcarbamate that was used as such for the next step, MH⁺=485.

To a stirred solution of the above material in THF (5 mL) was added CDI (131 mg). After 15 hr brine and EtOAc were added and the mixture was separated. The aq. layer was washed with additional EtOAc and the combined organics were evaporated and purified by column chromatography (eluted 3% MeOH/DCM) to yield titled product (86 mg, 62% yield for two steps). ¹H-NMR (300 MHz, 5% CD₃OD in CDCl₃) δ 7.9 (s, 1H), 7.4 (dd, 1H), 7.3 (m, 1H), 6.9 (dd, 1H), 6.7-6.5 (m, 3H), 5.7 (dd, 1H), 4.6 (m 1H), 4.3 (td, 1H), 2.9 (m, 1H), 2.2 (m, 1H), 1.5 (s, 9H); MH⁺=511, 411 (-BOC), 455 (-tBu).

2-(6-Fluoro-1H-benzo[d]imidazol-1-yl)-9-((R)-8-fluorochroman-4-yl)-7H-purin-8(9H)-one. A freshly prepared solution of 30% TFA/DCM (5 mL) was added to (R)-tert-butyl 4-fluoro-2-(9-(8-fluorochroman-4-yl)-8-oxo-8,9-dihydro-7H-purin-2-ylamino)phenylcarbamate and the solution was stirred at room temperature for 60 min then the solvents were removed in vacuo to yield (R)-2-(2-amino-5-fluorophenylamino)-9-(8-fluorochroman-4-yl)-7H-purin-8(9H)-one that was used as such MH⁺=411.

To the above di-amine was added MeOH (2 mL), trimethylorthoformate (2 mL) and p-TsOH (cat). The mixture was stirred at RT for 60 min then the solvents were reduced and the resultant material partitioned between DCM and brine and separated. The crude product was purified via column chromatography (eluted with 4% MeOH/DCM) to yield the titled compound (46 mg). ¹H-NMR (300 MHz, 5% CD₃OD in CDCl₃) δ 8.7 (s, 1H), 8.1 (s, 1H), 7.5 (m, 2H), 6.9 (m, 2H), 6.6 (m, 2H), 5.8 (dd, 1H), 4.6 (m 1H), 4.3 (td, 1H), 2.8 (m, 1H), 2.3 (m, 1H); MH⁺=421.

(R)-tert-Butyl 4-fluoro-2-(4-(8-fluorochroman-4-ylamino)-5-nitropyrimidin-2-ylamino)phenylcarbamate. A solution of the (R)-8-fluorochroman-4-amine hydrochloride (104 mg) in DMSO (2 mL) and potassium carbonate (141 mg) were added to a stirred solution of tert-butyl 4-fluoro-2-(5-nitro-4-thiocyanatopyrimidin-2-ylamino)phenylcarbamate (140 mg) in ACN (10 mL). The mixture was stirred for 15 hr at room temperature then partitioned between brine and EtOAc and separated. The aq. layer was washed with addi-

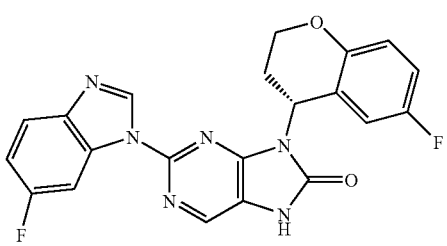

2-(6-Fluoro-1H-benzo[d]imidazol-1-yl)-9-((R)-6-fluorochroman-4-yl)-7H-purin-8(9H)-one. The title compound was synthesized from (R)-6-fluorochroman-4-amine via the procedures described in Example 27. $^1$H NMR (300 MHz, CDCl$_3$+5% CD$_3$OD): δ 8.72 (s, 1H), 8.16 (s, 1H), 7.5-7.7 (m, 2H), 6.9-7.0 (m, 2H), 6.8-6.9 (m, 1H), 6.54 (dd, 1H), 5.78 (br t, 1H), 4.4-4.5 (m, 1H), 4.26 (m, 1H), 2.7-2.8 (m, 1H), 2.2-2.3 (m, 1H).

Synthesis of 2-(6-Chloro-1H-benzo[d]imidazol-1-yl)-9-(tetrahydro-2H-pyran-4-yl)-7H-purin-8(9H)-one

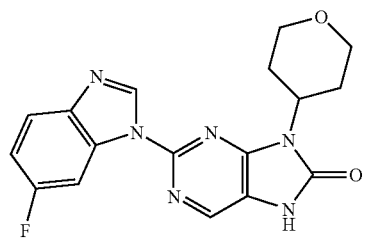

2-(6-Fluoro-1H-benzo[d]imidazol-1-yl)-9-(tetrahydro-2H-pyran-4-yl)-7H-purin-8(9H)-one. The title compound was synthesized from 4-aminotetrahydropyran via the procedures described in Example 27. $^1$H NMR (d$_6$-DMSO) δ 11.65 (s, 1H), 9.13 (s, 1H), 8.34 (s, 1H), 8.28 (m, 1H), 7.82 (m, 1H), 7.25 (td, J=9.0, 2.4 Hz, 1H), 4.56 (m, 1H), 4.03 (dd, J=11.1, 3.9 Hz, 2H), 3.50 (t, J=11.1 Hz, 2H), 2.59 (m, 2H), 1.78 (m, 2H).

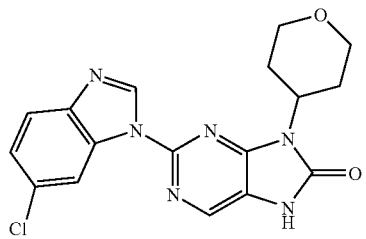

The title compound was synthesized from 4-aminotetrahydropyran and 4-chloro-2-nitrobenzenamine via the procedures described in Example 27 $^1$H NMR (CD$_3$OD+CHCl$_3$) δ 9.15 (s, 1H), 8.67 (d, 1H), 8.27 (s, 1H), 7.70 (d, 1H), 7.37 (dd, 1H), 4.64 (m, 1H), 4.18 (m, 2H), 3.61 (m, 2H), 2.81 (m, 2H), 1.85 (m, 2H); MS (MH$^+$) 371.1.

Procedure for the synthesis of 2-(1H-Benzo[d]imidazol-1-yl)-9-(3,4-dihydro-2H-pyrano[2,3-b]pyridin-4-yl)-7H-purin-8(9H)-one

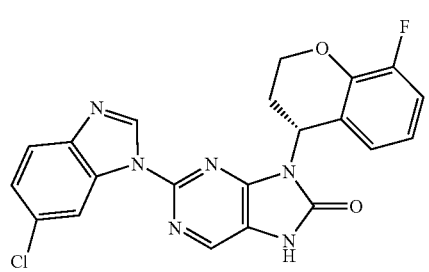

2-(6-Chloro-1H-benzo[d]imidazol-1-yl)-9-((R)-8-fluorochroman-4-yl)-7H-purin-8(9H)-one. The title compound was synthesized from (R)-8-fluorochroman-4-amine and 4-chloro-2-nitrobenzenamine via the procedures described in Example 27. $^1$H NMR (300 MHz, CDCl$_3$+5% CD$_3$OD): δ 8.7 (s, 1H), 8.2 (s, 1H), 8.1 (s, 1H), 7.6 (d, 1H), 7.2 (dd, 1H), 6.9 (td, 1H), 6.7-6.5 (m, 2H). 5.8 (dd, 1H), 4.6 (m 1H), 4.4 (td, 1H), 2.9 (m, 1H), 2.3 (m, 1H).

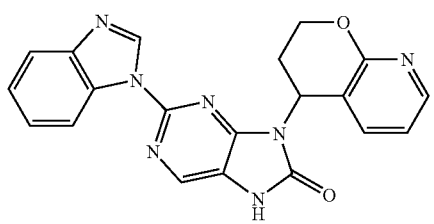

Synthesis of 3,4-dihydro-2H-pyrano[2,3-b]pyridin-4-amine

Synthesis of 2-(6-Fluoro-1H-benzo[d]imidazol-1-yl)-9-(pyrazin-2-ylmethyl)-7H-purin-8(9H)-one

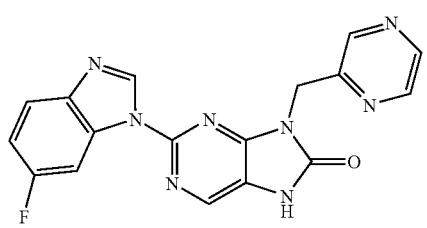

The title compound was synthesized from pyrazin-2-yl-methanamine via the procedure described in Example 27. $^1$H-NMR (300 MHz, CDCl$_3$+5% CD$_3$OD) δ 8.9 (br, 1H), 8.7 (s, 1H), 8.5 (s, 1H), 8.5 (s, 1H) 8.2 (s, 1H), 8.2 (dd, 1H), 7.7 (dd, 1H), 7.0 (td, 1H), 5.3 (s, 2H).

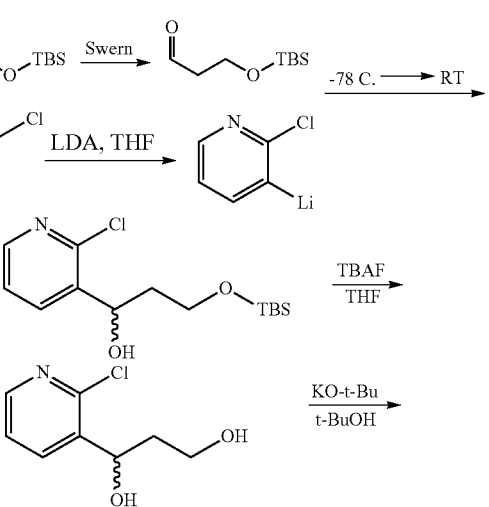

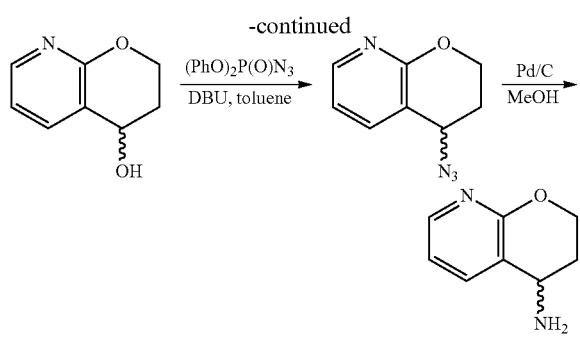

3-(tert-Butyldimethylsilyloxy)-1-(2-chloropyridin-3-yl)propan-1-ol. (Prepared similarly to literature procedure, Murtiashaw, C. W., et. al. *J. Org. Chem.*, 1992, 57, 1930-1933). A solution of 3-(tert-butyldimethylsilyloxy)propanal (2.3 g, prepared from 3-(tert-butyldimethylsilyloxy)propan-1-ol via Swern oxidation as per Li, X.; Lantrip, D.; Fuchs, P. L. *J. Am. Chem. Soc.*, 2003, 125, 14262-14263, Supporting information) in THF (10 mL) was slowly added via double ended needle to a solution of 2-chloro-3-lithiopyridine (prepared in turn from freshly prepared LDA (11.4 mM) and 2-chloropyridine (11.4 mM) (as per Gribble, G. W.; Saulnier, M. G. *Tet. Lett.* 1980, 21, 4137-4140) in THF (25 mL) at −78° C. The resulting mixture was allowed to slowly warm to RT over 15 hr, quenched via the addition of sat. NH$_4$Cl (2 mL) and solvents reduced in vacuo. The resultant slurry was taken up in EtOAc, washed with brine, and purified via column chromatography (eluted with 15, 20 and 25% EtOAc/Hex) to yield the titled product (1.0 g), NMR CDCl$_3$ $^1$H δ 8.3 (dd, 1H), 8.0 (dd, 1H), 7.3 (dd, 1H), 5.2 (d, 1H), 4.5 (m, 1H), 4.0-3.8 (m, 2H), 2.1 (m, 1H), 1.8 (m, 1H) 0.9 (s, 9H), 0.1 (s, 6H); MH$^+$=302/304.

1-(2-Chloropyridin-3-yl)propane-1,3-diol. A solution of tetrabutylammonium fluoride in THF (1M, 3.3 mL) was added to a solution of 3-(tert-butyldimethylsilyloxy)-1-(2-chloropyridin-3-yl)propan-1-ol in THF (5 mL) and stirred for 60 min, then silica gel was added and the solvent were removed under reduced pressure. The entire flask contents were added to a column, that was prepared and eluted with 75% ETOAC/Hex, to yield that titled product (0.49 g), NMR CD$_3$OD $^1$H δ 8.3 (dd, 1H), 8.0 (dd, 1H), 7.4 (dd, 1H), 5.1 (dd, 1H), 3.8 (m, 2H), 2.0 (m, 1H), 1.8 (m, 1H); MH$^+$=188/190.

3,4-Dihydro-2H-pyrano[2,3-b]pyridin-4-ol. Potassium tert-butoxide (0.88 g) was added to a solution of 1-(2-chloropyridin-3-yl)propane-1,3-diol (0.49 g) in tert-butanol and the solution was heated at reflux for 3 hr, allowed to cool to RT, quenched via the addition al of sat. NH$_4$Cl (2 mL), solvents reduced then silica gel added and remaining solvents removed in vacuo. The material was added to a silica gel column that was eluted with EtOAc and 1% MeOH/EtOAc to yield the titled product (0.35 g) NMR CDCl$_3$ $^1$H δ 8.1 (dd, 1H), 7.7 (dd, 1H), 6.9 (dd, 1H), 4.9 (dd, 1H), 4.5 (m, 2H), 2.1 (m, 2H); MH$^+$=152.

4-Azido-3,4-dihydro-2H-pyrano[2,3-b]pyridine. (Prep ref: Phompson, A. S. et. al. *J. Org. Chem.*, 1993, 58, 5886-5888). Diphenyl phosphoryl azide (0.81 mL) was added to a suspension of 3,4-dihydro-2H-pyrano[2,3-b]pyridin-4-ol (0.37 g) in dry toluene (10 mL) then the mixture was cooled to 0° C. under an Ar atmosphere. Neat DBU (0.56 mL) was added and the resultant biphasic mixture was stirred at 0° C. for 2 hr and then at RT for 15 hr. The biphasic solution was diluted with sat. NaHCO$_3$ and extracted with DCM (2×). The combined organics were concentrated and purified by silica gel chromatography using 10, 25 and 50% EtOAc/Hex elutants to afford the titled product (0.31 g) NMR CDCl$_3$ $^1$H δ 8.2 (dd, 1H), 7.6 (dd, 1H), 7.0 (dd, 1H), 4.7 (dd, 1H), 4.4 (m, 2H), 2.2 (m, 1H), 2.1 (m, 1H); MH$^+$=177.

3,4-Dihydro-2H-pyrano[2,3-b]pyridin-4-amine. A catalytic amount of Pd/C (9 mg) was added to a solution of 4-azido-3,4-dihydro-2H-pyrano[2,3-b]pyridine (88 mg) in MeOH (5 mL). The flask closed with a septum, evacuated under house vacuum and hydrogen added via balloon. The resulting suspension was stirred at RT for 60 min, when the H$_2$ balloon was removed, the mixture evacuated and filtered through a plug of celite, that was thoroughly rinsed with MeOH. Removal of the solvents gave the titled compound (73 mg), NMR CDCl$_3$ $^1$H δ 8.1 (dd, 1H), 7.7 (dd, 1H), 6.9 (dd, 1H), 4.5-4.3 (m, 2H), 4.1 (dd, 1H), 2.2 (m, 1H), 1.9 (m, 1H), 1.6 (br s, 2H); MH$^+$=151.

2-(1H-Benzo[d]imidazol-1-yl)-9-(3,4-dihydro-2H-pyrano[2,3-b]pyridin-4-yl)-7H-purin-8(9H)-one. The titled compound was prepared in the same manner described in Example 19 from 3,4-dihydro-2H-pyrano[2,3-b]pyridin-4-amine. $^1$H NMR (CDCl$_3$+5% CD$_3$OD) δ 8.8 (s, 1H), 8.2 (s, 1H), 8.1 (m, 1H), 7.7 (m, 2H), 7.3 (m, 2H), 6.8 (dd, 2H), 5.9 (dd, 1H), 4.7 (m 1H), 4.5 (td, 1H), 2.9 (m, 1H), 2.3 (m, 1H); MH$^+$=386.

Example 28

Synthesis of 2-(5-Fluoro-1H-benzo[d]imidazol-1-yl)-9-((R)-8-fluorochroman-4-yl)-7H-purin-8(9H)-one

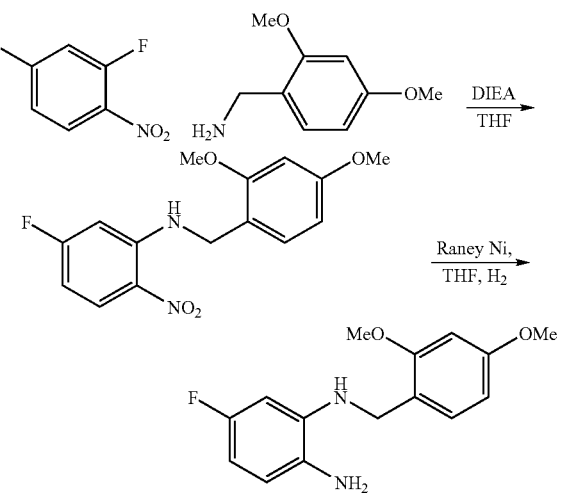

N-(2,4-Dimethoxybenzyl)-5-fluoro-2-nitrobenzenamine. A solution of 2,4-difluoro-1-nitrobenzene (1.1 mL), 2,4-dimethoxy benzylamine (1.5 mL) and DIEA (5.2 mL), in THF (40 mL) was heated at 60° C. for 60 min, allowed to cool to RT, partitioned between EtOAc and H$_2$O, separated, dried (MgSO$_4$), filtered and evaporated to yield the titled product as a yellow solid (3.14 g). $^1$H-NMR (300 MHz, CDCl$_3$) δ 8.5 (br s, 1H), 7.2 (dd, 1H), 7.2 (d, 1H), 6.6-6.4 (m, 3H), 6.3 (m, 1H), 4.3 (d, 2H), 3.9 (s, 3H), 3.8 (s, 3H).

N$^1$-(2,4-Dimethoxybenzyl)-5-fluorobenzene-1,2-diamine. Under a flush of Ar, a catalytic amount of a Raney Ni solution in water was added to a solution of N-(2,4-dimethoxybenzyl)-5-fluoro-2-nitrobenzenamine (0.5 g) in THF (20 mL). The flask was closed with a septum, evacuated under house vacuum and hydrogen added via balloon. The resulting suspension was stirred at RT for 16 hr, when the H₂ balloon was removed, mixture evacuated and filtered through a plug of celite, that was thoroughly rinsed with THF and MeOH, to yield the titled diamine that was used as such.

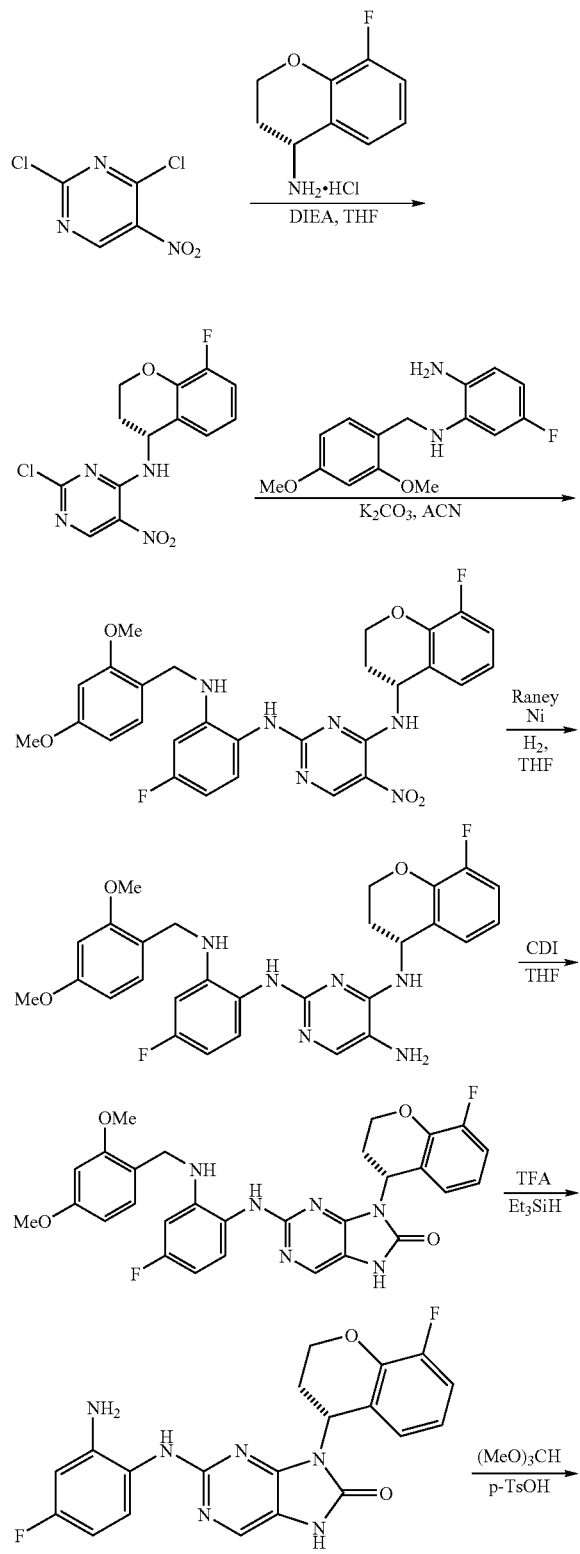

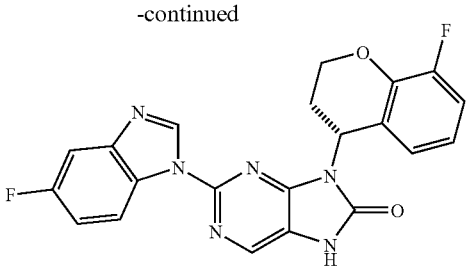

(R)-2-Chloro-N-(8-fluorochroman-4-yl)-5-nitropyrimidin-4-amine. A solution of (R)-8-fluorochroman-4-amine hydrochloride (1.02 g) and DIEA (2.6 mL) in DCM (10 mL) was slowly added to a solution of 2,4-dichloro-5-nitropyrimidine (0.97 g) THF (25 mL) at −78° C. The reaction mixture was stirred for 30 min at −78° C. then allowed to warm to RT overnight. The reaction was quenched with the addition of sat. NH₄Cl (1 mL), the solvent volume was reduced in vacuo, and the resulting mixture partition between EtOAc and water then separated. The crude material was purified via column chromatography, elution with 30% EtOAc/Hex gave the titled product (1.43 g). ¹H-NMR (300 MHz, CDCl₃) δ 9.1 (s, 1H), 8.6 (br d, 1H), 7.1-6.8 (m, 3H), 5.6 (dd, 1H), 4.4 (m 1H), 4.3 (m, 1H), 2.4 (m, 1H), 2.2 (m, 1H).

(R)—N²-(2-(2,4-Dimethoxybenzylamino)-4-fluorophenyl)-N⁴-(8-fluorochroman-4-yl)-5-nitropyrimidine-2,4-diamine. A mixture of (R)-2-chloro-N-(8-fluorochroman-4-yl)-5-nitropyrimidin-4-amine (32 mg), N¹-(2,4-dimethoxybenzyl)-5-fluorobenzene-1,2-diamine (28 mg) and KCO₃ (41 mg) in ACN was heated at 65° C. for 3 hr, cooled to RT, diluted with brine and extracted with EtOAc (2×). The combined organics were evaporated, and purified by column chromatography (eluted with 30% EtOAc/Hex) to yield the titled product (21 mg). ¹H-NMR (300 MHz, CDCl₃) δ 9.0 (s, 1H), 8.6 (br d, 1H), 7.2-6.8 (m, 6H), 6.5-6.3 (m, 4H), 4.4-4.2 (m, 4H), 3.8 (s, 6H), 2.3-2.2 (m, 2H).

(R)-2-(2-(2,4-Dimethoxybenzylamino)-4-fluorophenylamino)-9-(8-fluorochroman-4-yl)-7H-purin-8(9H)-one. Under an Ar atmosphere, a catalytic amount of a Raney Ni solution in water was added to a solution of (R)—N²-(2-(2,4-dimethoxybenzylamino)-4-fluorophenyl)-N⁴-(8-fluorochroman-4-yl)-5-nitropyrimidine-2,4-diamine (21 mg) in THF. The flask was closed with a septum, evacuated under house vacuum and hydrogen added via balloon. The resulting suspension was stirred at RT for 2 hr, when the H₂ balloon was removed, the mixture evacuated and filtered through a plug of celite, that was thoroughly rinsed with THF and MeOH, to yield (R)—N²-(2-(2,4-dimethoxybenzylamino)-4-fluorophenyl)-N⁴-(8-fluorochroman-4-yl)pyrimidine-2,4,5-triamine that was used directly.

To a stirred solution of the above material in THF (5 mL) was added CDI (12 mg). After 18 hr brine and EtOAc were added and the mixture was separated. The organic layer was evaporated and purified by column chromatography (eluted 4% MeOH/DCM) to yield titled product (14 mg). ¹H NMR (300 MHz, CDCl₃+5% CD₃OD): δ 7.8 (s, 1H), 7.3 (s, 1H), 7.1 (d, 1H), 6.9 (m, 2H), 6.7-6.2 (m, 6H), 5.7 (dd, 1H), 4.5 (m 1H), 4.2 (m, 1H), 4.1 (s, 2H), 3.8 (s, 3H), 3.7 (s, 3H), 2.8 (m, 1H), 2.2 (m, 1H).

2-(5-Fluoro-1H-benzo[d]imidazol-1-yl)-9-((R)-8-fluorochroman-4-yl)-7H-purin-8(9H)-one A mixture of (R)-2-(2-(2,4-dimethoxybenzylamino)-4-fluorophenylamino)-9-(8-fluorochroman-4-yl)-7H-purin-8(9H)-one (14 mg) and TFA (1 mL) was stirred for 60 min when triethyl silane (0.5 mL) was added. The resulting solution was stirred at RT for 16 hr, then the solvents were reduced in vacuo to yield (R)-2-(2-amino-4-fluorophenylamino)-9-(8-fluorochroman-4-yl)-7H-purin-8(9H)-one that was used as such.

A catalytic amount of p-TsOH was added to a solution of the above amine in trimethylorthoformate (2 mL). The mixture was stirred at RT for 15 hr then the solvents were reduced and the resultant material partitioned between DCM and brine and separated. The crude product was purified via column chromatography (eluted with 5% MeOH/DCM) to yield the titled compound (9 mg). $^1$H-NMR (300 MHz, CDCl$_3$) δ 10.0 (s, 1H), 8.9 (s, 1H), 8.3 (s, 1H), 7.8 (dd, 1H), 7.4 (d, 1H), 7.1 (m, 2H), 6.8 (m, 2H), 5.9 (dd, 1H), 4.7 (m 1H), 4.4 (td, 1H), 2.9 (m, 1H), 2.4 (m, 1H).

Synthesis of 2-(6-fluoro-1H-benzo[d]imidazol-1-yl)-9-((R)-8-fluorochroman-4-yl)-7H-purin-8(9H)-one

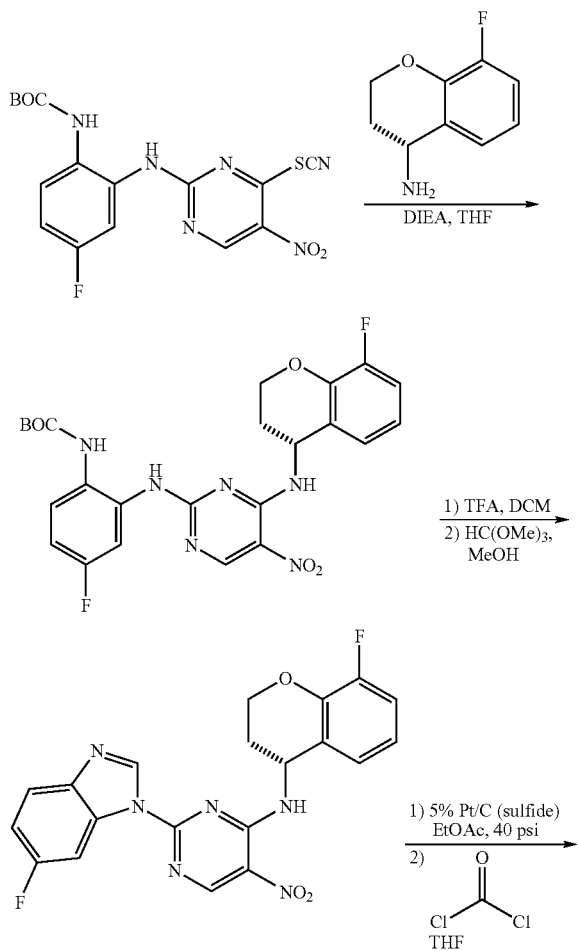

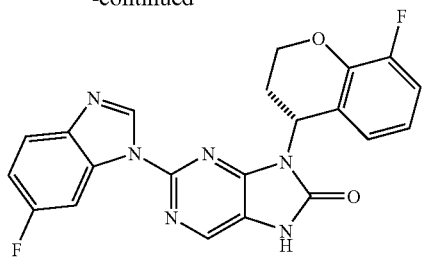

(R)-tert-Butyl 4-fluoro-2-(4-(8-fluorochroman-4-ylamino)-5-nitropyrimidin-2-ylamino)phenylcarbamate. tert-Butyl 4-fluoro-2-(5-nitro-4-thiocyanatopyrimidin-2-ylamino)phenylcarbamate (2.0 g) was added to a solution of (R)-8-fluorochroman-4-amine hydrochloride (1.1 gram) and N,N-diisopropylethylamine (2.2 mL) in THF (anhydrous, 50 mL). The mixture was stirred for 6 hr at room temperature then partitioned between water and EtOAc and separated. The aq. layer was washed with additional EtOAc and the combined organics were dried over Na$_2$SO$_4$ and concentrated in vacuo to give the title product in 94% yield. MH$^+$=515, 459 (-tBu).

2-(6-Fluoro-1H-benzo[d]imidazol-1-yl)-N—((R)-8-fluorochroman-4-yl)-5-nitropyrimidin-4-amine. A freshly prepared solution of 30% TFA/DCM (100 mL) was added to (R)-tert-butyl 4-fluoro-2-(4-(8-fluorochroman-4-ylamino)-5-nitropyrimidin-2-ylamino)phenylcarbamate and the solution was stirred at room temperature for 60 min. The solvents were removed in vacuo to yield (R)—N2-(2-amino-5-fluorophenyl)-N4-(8-fluorochroman-4-yl)-5-nitropyrimidine-2,4-diamine that was carried on without further purification. MH$^+$=415.

To the above diamine was added MeOH (50 mL) and trimethylorthoformate (50 mL). The mixture was stirred for 30 minutes at room temperature, and the solvents were removed in vacuo to yield crude 2-(6-fluoro-1H-benzo[d]imidazol-1-yl)-N—((R)-8-fluorochroman-4-yl)-5-nitropyrimidin-4-amine in 94% yield (2 steps). MH$^+$=425.

2-(6-Fluoro-1H-benzo[d]imidazol-1-yl)-9-((R)-8-fluorochroman-4-yl)-7H-purin-8(9H)-one. To a solution of the 2-(6-fluoro-1H-benzo[d]imidazol-1-yl)-N—((R)-8-fluorochroman-4-yl)-5-nitropyrimidin-4-amine in EtOAc (20 mL) was added 5 mol % of Platinum, 5% on activated carbon power, sulfide, 0.5% S (as sulfide) (45.6 mg). The mixture was sparged with argon, transferred to the Parr hydrogenation apparatus, then subjected to a purge/fill sequence with hydrogen (repeated 5×). The mixture was hydrogenated for 18 hr at 40 psi. Filtration through a pad of Celite and concentration of the filtrate gave crude 2-(6-fluoro-1H-benzo[d]imidazol-1-yl)N$^4$—((R)-8-fluorochroman-4-yl)pyrimidine-4,5-diamine that was carried on without further purification. MH$^+$=425.

To a solution of the above diamine in THF (50 mL) was added dropwise 20% phosgene solution in toluene at room temperature. A light brown precipitate formed immediately. Stirring was maintained for an additional 30 min at room temperature and the solvents were removed in vacuo to yield the titled compound. The crude product was crystallized from hot EtOAc to yield 1.10 g (53%, 2 steps) of the title compound as off white solid. Treatment with 5 mL methanol and 5 mL of HCl (conc. aq) gave 1.25 g of the hydrochloride salt as off white solid. $^1$H-NMR (300 MHz, CD$_3$OD) δ 10.0 (s, 1H), 8.4 (s, 1H), 7.9-7.8 (m, 2H), 7.5 (td, 1H), 7.0-6.9 (m, 1H), 6.7-6.6

(m, 2H), 5.9 (dd, 1H), 4.6 (dt, 1H), 4.4 (td, 1H), 2.9-2.8 (m, 1H), 2.4-2.3 (m, 1H); MH⁺=421.

Example 29

Synthesis and Resolution of 8-Fluorochroman-4-amine

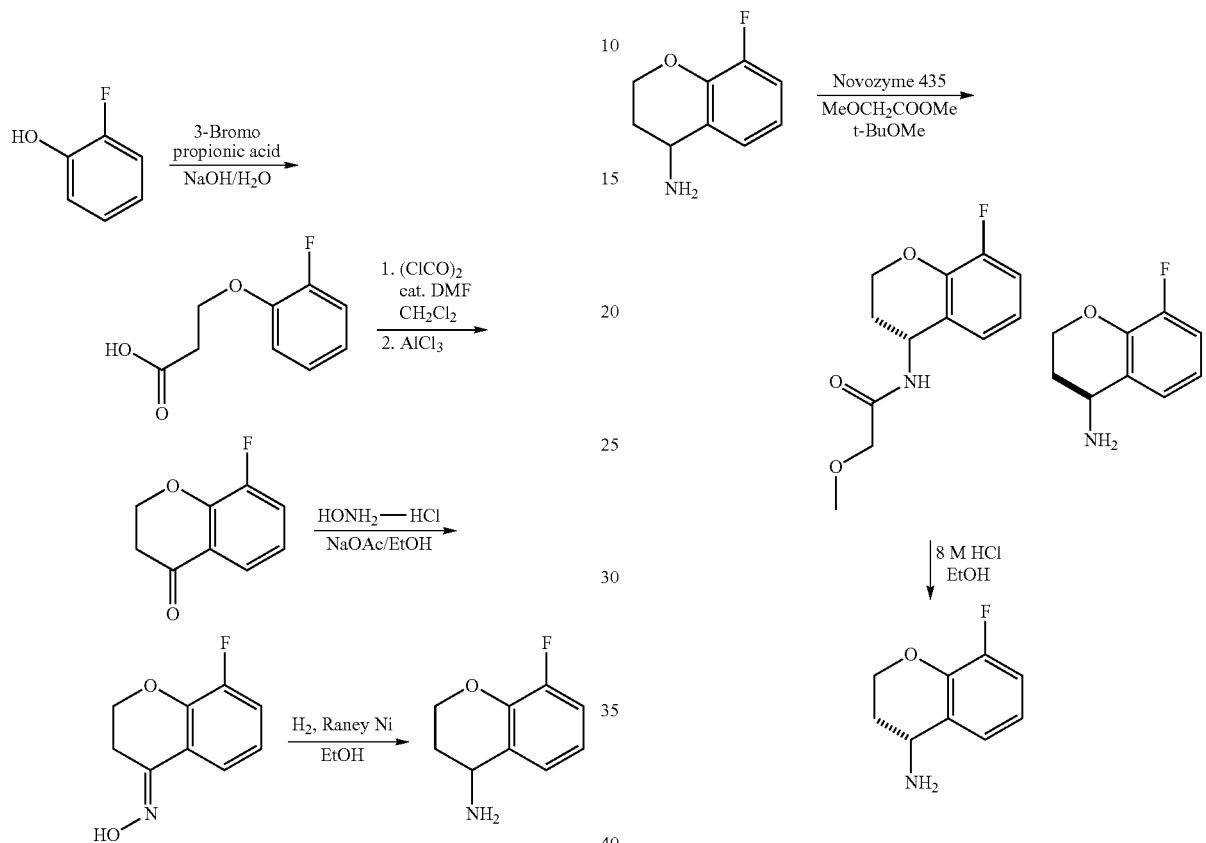

3-(2-Fluorophenoxy)propanoic acid. A mixture of 2-fluorophenol (15 g), 3-bromopropanoic acid (20 g) and NaOH (11 g) was refluxed in 50 mL of water. The solution was cooled to room temperature and acidified to pH 2 with 3 M HCl. The resulting precipitate was isolated by filtration to yield 9.27 g of title compound as a white solid. The filtrate was extracted 3 times with EtOAc to yield 2.5 g of less pure compound.

8-Fluorochroman-4-one. Oxalyl chloride (8.79 mL) and 1 drop of DMF were added to an ice cold solution of 3-(2-fluorophenoxy)propanoic acid (9.27 g) in DCM (50 mL). The solution was stirred at 0° C. for 2 hours, then aluminum chloride (7.39 g, 55.42 mM) was added and the solution was stirred for 16 hours at room temperature. The mixture was poured onto ice water, and extracted three times with DCM. The combined organics were washed with 0.5M NaOH and brine, then dried, evaporated, and purified by column chromatography (eluting with 20% EtOAc/Hex) to give of the title compound (8.20 g, 98%).

8-Fluorochroman-4-amine. A round bottom flask was charged with 8-fluorochroman-4-one (8.2 g), hydroxylamine hydrochloride (3.78 g) and sodium acetate (4.46 g). A reflux condenser was added, the flask was purged with argon, dry EtOH (20 mL) was added, and the mixture was stirred at reflux for 18 hours. The solution was cooled to room temperature, diluted with EtOAc, and washed with water. The organic phase was dried, and evaporated to give the intermediate 8-fluorochroman-4-one oxime, which was reduced with Raney Nickel in EtOH at 50 PSI to yield the titled amine (4.69 g, 57%).

Resolution of 8-fluorochroman-4-amine. (Procedure based on US published application 2004/0157739). A mixture of 8-fluorochroman-4-amine (3.40 g), methyl 2-methoxyacetate (2.44 g) and Novozyme 435 (Aldrich, 0.68 g) in anhydrous tert-butyl methyl ether (75 mL) was heated at reflux under argon for 2 hours (at which time the ratio of acylated to unacylated product was 1:1 by HPLC). The solid that formed upon cooling was collected via filtration and dissolved in EtOAc. The mixture was filtered to remove the biocatalyst and washed once with 0.5M HCl to remove any lingering (S)-amine. The solvent was evaporated and the product was recrystallized from tert-butyl methyl ether to yield (R)—N-(8-fluorochroman-4-yl)-2-methoxyacetamide (0.78 g). The reaction solvent and recrystallization mother liquor was washed 3 times with 0.5 M HCl and concentrated to yield additional (R)—N-(8-fluorochroman-4-yl)-2-methoxyacetamide (0.83 g). The combined acidic aqueous layers were made basic by NaOH and extracted with DCM to yield (S)-8-fluorochroman-4-amine (1.6 g). A solution of (R)—N-(8-fluorochroman-4-yl)-2-methoxyacetamide (0.78 g) in 8M HCl in EtOH (50 mL) was heated at reflux for 4 hours. The solvents were removed from the cooled reaction mixture, the resulting solid was taken up in 50 mL of 0.5M NaOH, salted

Example 30

Chroman-4-amine, 5-fluorochroman-4-amine, 6-fluorochroman-4-amine, 6-chlorochroman-4-amine, 6-methylchroman-4-amine, 6-methoxychroman-4-amine, 7-fluorochroman-4-amine, 5,8-difluorochroman-4-amine, and 6,8-difluorochroman-4-amine

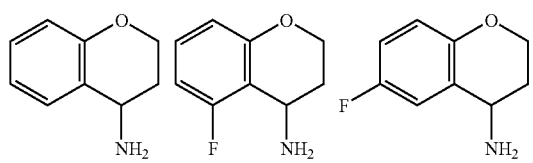

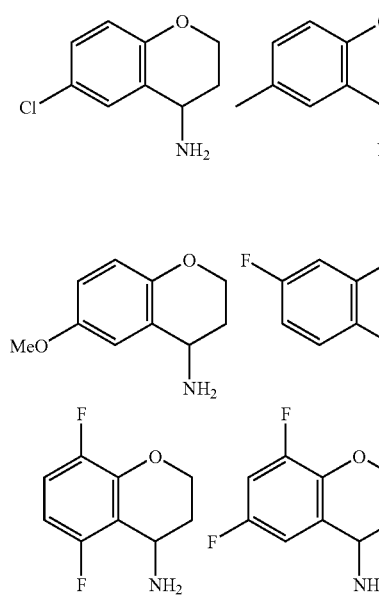

These amines were prepared via procedures described in Example 29 for the synthesis of 8-fluorochroman-4-amine. The corresponding chroman-4-ones were commercially available as advanced intermediates for the synthesis of chroman-4-amine, 6-fluorochroman-4-amine, 6-chlorochroman-4-amine, 6-methylchroman-4-amine, and 6-methoxychroman-4-amine. For the synthesis of 5-fluorochroman-4-amine, the intermediate 5-fluorochroman-4-one was obtained using procedures from GB 2355264, which also provided 7-fluorochroman-4-one. 7-Fluorochroman-4-one could be used in the synthesis of 7-fluorochroman-4-amine. Chroman-4-amine, 5-fluorochroman-4-amine, 6-fluorochroman-4-amine, 7-fluorochroman-4-amine, 5,8-difluorochroman-4-amine, and 6,8-difluorochroman-4-amine were resolved via the procedure described in Example 29 for the resolution of 8-fluorochroman-4-amine.

Example 31

1-Methyl-4,5,6,7-tetrahydro-1H-indol-4-amine

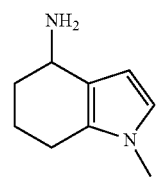

The title compound was obtained from 1-methyl-6,7-dihydro-1H-indol-4(5H)-one (Heterocycles (1984), 22, 2313) via the procedure described in Example 29 that were used to obtain 8-fluorochroman-4-amine from 8-fluorochroman-4-one.

Example 32

Synthesis of 5,6-Difluorochroman-4-amine

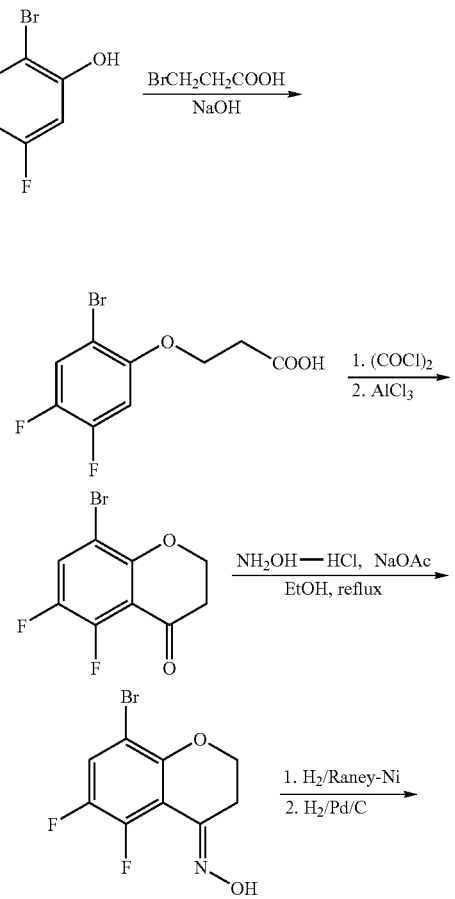

-continued

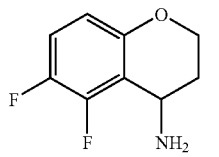

3-(2-Bromo-4,5-difluorophenoxy)propanoic acid. A solution of 1.68 g of NaOH (42 mmol) in 5 mL of water was added slowly to the suspension of 2.29 mL (20 mmol) 2-bromo-4,5-difluorophenol and 3.07 g (20 mmol) 3-bromopropionic acid. The mixture was heated at 100° C. in an oil bath for 5 hours, and then allowed to cool to room temperature. Water was added to completely dissolve any solid material and the reaction mixture was made acidic with concentrated HCl. The product was extracted into ether (3 times), and the combined organic layers was dried over $Na_2SO_4$ and evaporated to give 3.7 g (66%) of the title compound as a light brown solid. $^1$H NMR (300 MHz, $CDCl_3$): δ 7.4 (t, 1H), 6.8 (q, 1H), 4.3 (t, 2H), 2.9 (t, 2H).

8-Bromo-5,6-difluoro-2,3-dihydrochromen-4-one. Oxalyl chloride (1.7 mL, 20 mmol) was added to the solution of 2.8 g (10 mmol) of 3-(2-bromo-4,5-difluorophenoxy)-propanoic acid in 40 mL of anhydrous DCM followed by a drop of DMF. After 1.5 hours, a drying tube was attached and the solution was cooled in an ice-water bath. $AlCl_3$ (1.5 g, 11 mmol) was added and the dark red solution was allowed to slowly reach room temperature while being stirred for 16 hours. The mixture was poured into ice and the organic layer was separated. The aqueous layer was extracted with DCM twice. The combined organic layers were washed with 0.5 N NaOH and brine, then dried over $Na_2SO_4$ and concentrated. Column chromatography of this residue with hexane and EtOAc provided 1.9 g of the title compound as an off-white solid (73%). $^1$H NMR (300 MHz, $CDCl_3$): δ 7.6 (t, 1H), 4.65 (t, 2H), 2.85 (t, 2H).

8-Bromo-5,6-difluoro-2,3-dihydrochromen-4-one oxime. To a solution of 8-bromo-5,6-difluoro-2,3-dihydrochromen-4-one (7.2 mmol) in 40 mL of ethanol was added hydroxylamine hydrochloride (0.55 g, 7.9 mmol) and sodium acetate (0.65 g, 7.9 mmol). This mixture heated at reflux for 20 hrs. The mixture was cooled, diluted with EtOAc, washed with water and brine, and then dried over $Na_2SO_4$. Concentration of the solvent provided the title compound as a white solid (1.9 g). $^1$H NMR (300 MHz, 10% $CD_3OD$ in $CDCl_3$): δ 7.3 (t, 1H), 4.2 (t, 2H), 2.9 (t, 2H).

5,6-Difluoro-3,4-dihydro-2H-chromen-4-amine. Raney-Ni (5 mL slurry in water) was added to a solution of 8-bromo-5,6-difluoro-2,3-dihydrochromen-4-one oxime (1.9 g) in 200 mL MeOH. The mixture was hydrogenated at 50 psi for 24 hrs to provide 8-bromo-5,6-difluoro-3,4-dihydro-2H-chromen-4-amine. Pd/C (0.3 g) was added to the mixture and hydrogenation was resumed at 50 psi for 4 hours. The title compound was obtained after filtration and concentration in vacuo. $^1$H NMR (300 MHz, 10% $CD_3OD$ in $CDCl_3$): δ 7.15 (q, 1H), 6.6 (m, 1H), 4.6 (bm, 1H), 4.25 (bm, 2H), 2.2-2.4 (m, 2H).

Example 33

Synthesis of 4-Amino-3,4-dihydro-2H-chromene-8-carbonitrile

4-Amino-3,4-dihydro-2H-chromene-8-carbonitrile. A mixture of 260 mg of 4-oxo-3,4-dihydro-2H-chromene-8-carbonitrile (made from 2-hydroxybenzonitrile via the procedure described in Example 29), ammonium acetate (1.2 g), and 3 A molecular sieves (1.5 g) in 10 mL of methanol was stirred for 5 days. The mixture was filtered through celite and the filtrate concentrated in vacuo. The crude residue was treated with 100 mL of 1 M HCl and extracted with ethyl ether (3×100 mL). The aqueous layer was made basic to pH 10 with saturated NaOH and extracted with DCM (3×100 mL). The combined DCM layers were washed with brine, dried over magnesium sulfate, and concentrated in vacuo to provide 150 mg of the title compound.

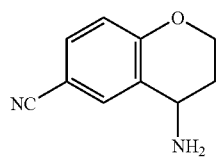

4-Amino-3,4-dihydro-2H-chromene-6-carbonitrile. The title compound was made from 6-cyano-4-chromanone (Syntech) via the same procedure that was described in Example 33.

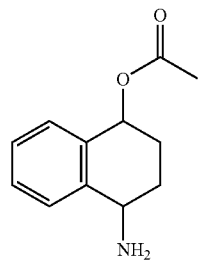

4-Amino-1,2,3,4-tetrahydronaphthalen-1-yl acetate. The title compound was made from 4-oxo-1,2,3,4-tetrahydronaphthalen-1-yl acetate (Tetrahedron: Asymmetry 2001, 12, 2283) via the same procedure that was described in Example 33.

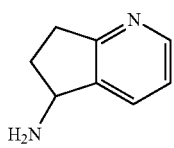

6,7-Dihydro-5H-cyclopenta[b]pyridin-5-amine. The title compound was made as described in WO 03/045924.

Example 34

Synthesis of (R)-5,6,7,8-Tetrahydroquinoxalin-5-amine

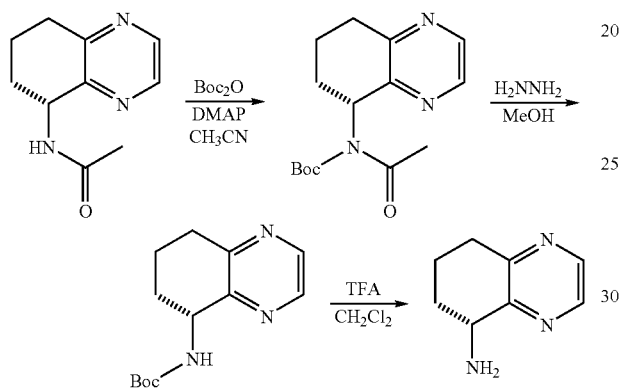

(R)-tert-Butyl acetyl(5,6,7,8-tetrahydroquinoxalin-5-yl)carbamate. A solution containing 483 mg of (R)—N-(5,6,7,8-tetrahydroquinoxalin-5-yl)acetamide (J. Org. Chem. (2003), 68, 3546) in acetonitrile (20 mL) was treated with Boc$_2$O (3 g) and DMAP (5 mg). The mixture was heated at 60° C. for 1.5 h and then concentrated in vacuo. Column chromatography (50% EtOAc/hexanes) provided 293 mg of the title compound.

(R)-tert-Butyl 5,6,7,8-tetrahydroquinoxalin-5-ylcarbamate. A solution of (R)-tert-butyl acetyl(5,6,7,8-tetrahydroquinoxalin-5-yl)carbamate (293 mg) in methanol (10 mL) was treated with hydrazine hydrate (0.5 mL) for 1.5 h. The mixture was diluted with EtOAc and washed twice with saturated aqueous sodium chloride. The organic layer was separated, dried with sodium sulfate, and concentrated in vacuo to provide 238 mg of the title compound.

2,3-dihydrobenzofuran-3-amine. To the solution of benzofuran-3(2H)-one oxime (1.0 g, obtained from commercially available benzofuran-3(2H)-one via the procedure outlined for the synthesis of 4-fluorobenzofuran-3(2H)-one oxime from 4-fluorobenzofuran-3(2H)-one) in 50 mL MeOH, 10% Palladium on active carbon (0.1 g) was added. The mixture was evacuated then filled with H$_2$ three times. Finally the oxime was reduced under a H$_2$ balloon for 24 hours. The mixture was filtered through a pad of celite, and the cake was washed with MeOH twice. After removing the solvents under vacuum, 0.99 g brown-yellow residue was obtained as the desired amine. $^1$H NMR (300 MHz, CDCl$_3$): δ 7.32 (d, 1H), 7.19 (t, 1H), 6.94 (t, 1H), 6.82 (d, 1H), 4.5-4.7 (m, 1H), 4.64 (s, 1H), 4.1-4.2 (m, 1H).

(R)-5,6,7,8-Tetrahydroquinoxalin-5-amine. A solution of (R)-tert-butyl 5,6,7,8-tetrahydroquinoxalin-5-ylcarbamate (238 mg) in 10 ml of 1:1 TFA/DCM was stirred for 30 minutes. The mixture was concentrated in vacuo to provide the title compound as the TFA salt.

Example 35

Synthesis of 2-(1H-Benzo[d]imidazol-1-yl)-9-(4,5,6,7-tetrahydro-1H-indol-4-yl)-7H-purin-8(9H)-one

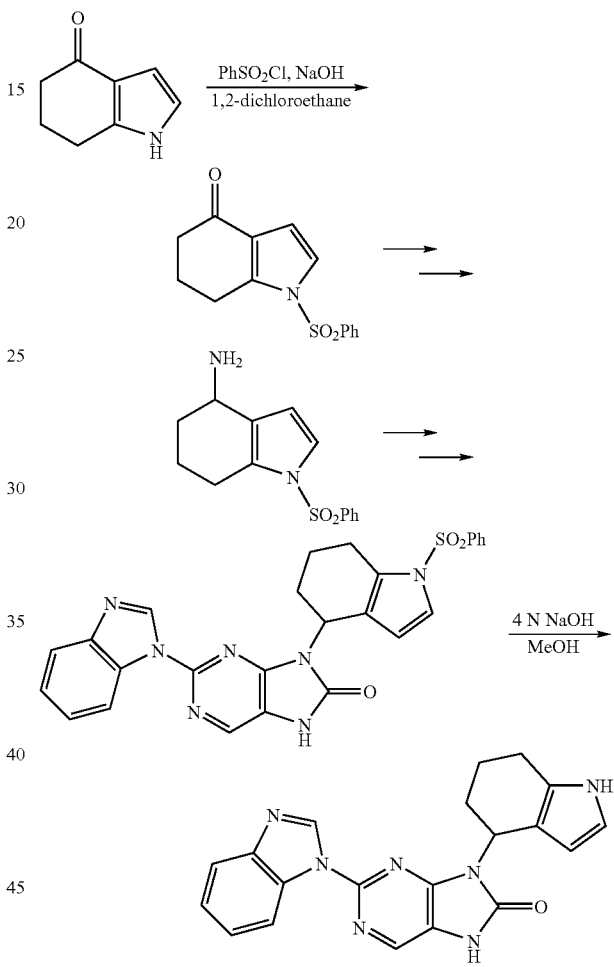

1-(Phenylsulfonyl)-4-oxo-4,5,6,7-tetrahydroindole. To a suspension of NaOH (4.44 g) in 1,2-dichloroethane (250 mL) was added 4-oxo-4,5,6,7-tetrahydroindole (5.0 g). The mixture was then cooled to 0° C. and stirred for 30 min, following which a solution of phenylsulfonyl chloride (5.7 mL) in 1,2-dichloroethane (50 mL) was added dropwise over a period of 30 min. After 30 min of stirring, the reaction mixture was allowed to come to room temperature and stirred overnight. The reaction was quenched by pouring onto distilled water (100 mL). The organic layer was separated, and the aqueous layer was extracted with dichloromethane (3×50 mL). The combined organic extract was washed with distilled water to neutrality, dried over MgSO$_4$, and concentrated in vacuo to afford 7.0 g of the title compound.

1-(Phenylsulfonyl)-4,5,6,7-tetrahydro-1H-indol-4-amine. The title compound was obtained from 1-(phenylsulfonyl)-4-oxo-4,5,6,7-tetrahydroindole via the procedure described in Example 29 that was used to obtain 8-fluorochroman-4-amine from 8-fluorochroman-4-one.

2-(1H-Benzo[d]imidazol-1-yl)-9-(1-(phenylsulfonyl)-4,5,6,7-tetrahydro-1H-indol-4-yl)-7H-purin-8(9H)-one. The title compound was obtained from 1-(phenylsulfonyl)-4,5,6,7-tetrahydro-1H-indol-4-amine via the procedures described in Example 24.

2-(1H-benzo[d]imidazol-1-yl)-9-(4,5,6,7-tetrahydro-1H-indol-4-yl)-7H-purin-8(9H)-one. To a solution of 2-(1H-benzo[d]imidazol-1-yl)-9-(1-(phenylsulfonyl)-4,5,6,7-tetrahydro-1H-indol-4-yl)-7H-purin-8(9H)-one (50 mg) in MeOH (1 mL) was added 4 N NaOH (1 mL), and the mixture was refluxed overnight and cooled. Volatiles were removed under reduced pressure, and the resultant neutralized with 4 N HCl. The white precipitate was filtered, washed with a small amount of water, and dried in vacuo to afford 36 mg of the title compound. $^1$H NMR (d$_6$-DMSO) δ 11.6 (s, 1H), 10.7 (s, 1H), 8.86 (s, 1H), 8.27 (s, 1H), 7.69 (d, J=7.8 Hz, 1H), 7.58 (d, J=8.1 Hz, 1H), 7.33 (m, 2H), 6.53 (t, J=2.4 Hz, 1H), 5.64 (t, J=2.4 Hz, 1H), 5.54 (m, 1H), 2.72 (m, 2H), 2.30 (m, 1H), 2.07 (m, 2H), 1.84 (m, 1H).

Examples 36 and 37

(Dihydrobenzofurans): 2-(1H-benzo[d]imidazol-1-yl)-9-(2,3-dihydrobenzofuran-3-yl)-7H-purin-8(9H)-one and 2-(1H-benzo[d]imidazol-1-yl)-9-(4-fluoro-2,3-dihydrobenzofuran-3-yl)-7H-purin-8(9H)-one

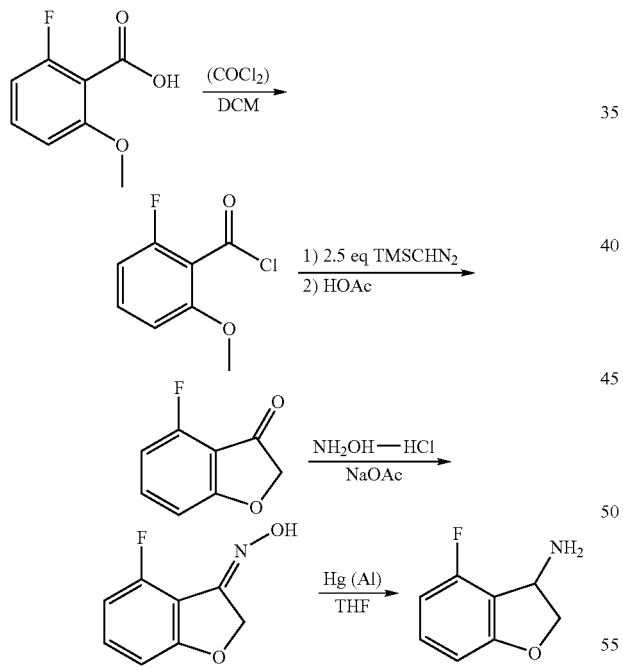

2-fluoro-6-methoxybenzoyl chloride. Oxalyl chloride (0.56 mL, 6.4 mmol) was added to the solution of 1.0 g (5.9 mmol) 2-fluoro-6-methoxybenzoic acid in 5 mL anhydrous CH$_2$Cl$_2$. Then a drop of DMF was added. After one hour, when the slow bubbling was ceased, volatiles were removed under reduced pressure to afford 1.1 g (95%) acid chloride as pale-yellow liquid. $^1$H NMR (300 MHz, CDCl$_3$): δ 7.45 (q, 1H), 6.7-6.8 (m, 2H), 3.9 (s, 3H).

4-fluorobenzofuran-3(2H)-one. The yellow (trimethylsilyl)diazomethane ether solution (2.0 M, 3.7 mL) was added to 0.57 g (3.0 mmol) above acid chloride with stirring. After 3 hours, solvent was evaporated. The yellow residue was dissolved in 3 mL acetic acid (strong gas and heat evolution, used a water bath to cool the flask for a minute), and stirred for 15 min at room temperature. The solvents were removed under vacuum, and the red residue was taken into 2 mL CH$_2$Cl$_2$, washed with water twice, then brine, and dried over Na$_2$SO$_4$. This crude product was purified by column chromatography (eluting with 10% EtOAc in hexanes) to give 0.24 g (53%) 4-fluorobenzofuran-3(2H)-one as white solid. $^1$H NMR (300 MHz, CDCl$_3$): δ 7.58 (m, 1H), 6.92 (br d, 1H), 6.71 (t, 1H), 4.65 (s, 2H).

(Z)-4-fluorobenzofuran-3(2H)-one oxime. The above ketone (0.70 g, 4.6 mmol) was dissolved in 5 ml ethyl alcohol, and then added 0.64 g (9.2 mmol) hydroxylamine hydrochloride and 0.75 g (9.2 mmol) sodium acetate. This suspension was brought to reflux for 1 hr. The mixture was cooled to room temperature and added 4 mL water to dissolve the excess reagents. Suction filtration, and then wash the solid cake with small amount of cold water provided 0.48 g (63%) desired oxime as white needle crystals. $^1$H NMR (300 MHz, CDCl$_3$): δ 8.38 (s, 1H), 7.38 (q, 1H), 6.6-6.8 (m, 2H), 5.21 (s, 2H).

4-fluoro-2,3-dihydrobenzofuran-3-amine. The above oxime (0.48 g) was dissolved in 40 mL anhydrous THF under Argon. Fresh prepared aluminum amalgam (by dipping 1 g polished aluminum foil sequentially in 2% HgCl$_2$ aqueous solution, water, and finally THF) was added quickly and the mixture was refluxed for 24 hours under Argon. Shinny mercury beads appeared at the bottom of the flask. The mixture was allowed to cool to room temperature and filtered through a pad of celite. Flask and solid cake were washed with THF three times, then methanol three times. The combined filtrate was rotary evaporated to give 0.41 g yellow solid as a mixture of approximately (determined by NMR) 20% desired amine with 80% starting oxime. This mixture was used for next step without purification. $^1$H NMR (300 MHz, CDCl$_3$): δ 7.18 (q, 1H), 6.5-6.7 (m, 2H), 4.8-4.9 (m, 1H), 4.69 (t, 1H), 4.2-4.3 (m, 1H).

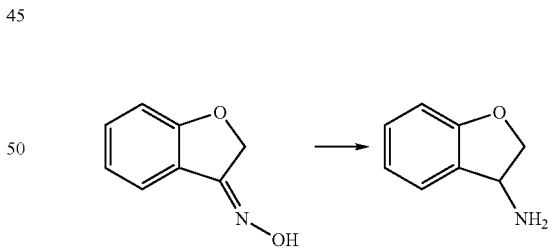

2,3-dihydrobenzofuran-3-amine. To the solution of benzofuran-3(2H)-one oxime (1.0 g, obtained from commercially available benzofuran-3(2H)-one via the procedure outlined for the synthesis of 4-fluorobenzofuran-3(2H)-one oxime from 4-fluorobenzofuran-3(2H)-one) in 50 mL MeOH, 10% Palladium on active carbon (0.1 g) was added. The mixture was evacuated then filled with H$_2$ three times. Finally the oxime was reduced under a H$_2$ balloon for 24 hours. The mixture was filtered through a pad of celite, and the cake was washed with MeOH twice. After removing the solvents under vacuum, 0.99 g brown-yellow residue was obtained as the desired amine. ¹H NMR (300 MHz, CDCl₃): δ 7.32 (d, 1H), 7.19 (t, 1H), 6.94 (t, 1H), 6.82 (d, 1H), 4.5-4.7 (m, 1H), 4.64 (s, 1H), 4.1-4.2 (m, 1H).

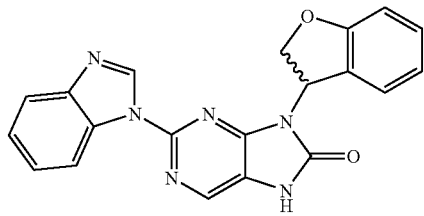

The above racemic 2-(1H-benzo[d]imidazol-1-yl)-9-(2,3-dihydrobenzofuran-3-yl)-7H-purin-8(9H)-one can be separated on chiral CHIRALCEL OD-H column (Cellulose tris (3,5-dimethylphenylcarbamate) on a 5 μM silica-gel substrate) eluting with 85:15 hexanes:ethanol (both with 0.1% diethylamine). One enantiomer has a retention time of 25 min, the other one 33.5 min.

Synthesis of 2-(1H-Benzo[d]imidazol-1-yl)-9-(trans-4-hydroxycyclohexyl)-7H-purin-8(9H)-one

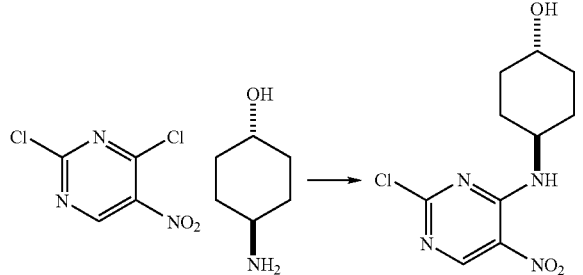

Trans-4-(2-Chloro-5nitropyrimidin-4-ylamino)cyclohexanol. A solution of 2,4-dicloro-5-nitropyrimidine (930 mg) in DCM (40 mL) was treated with DIEA (0.9 mL) and trans-4-aminocyclohexanol (345 mg) at −78° C. for 6 hours. The mixture was allowed to slowly warm to room temperature and stirred for 12 more hours. The solvent was evaporated and the crude mixture was purified by silica gel chromatography (DCM:EtOAc 70:30) to provide 630 mg of the title compound.

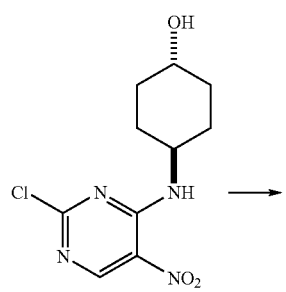

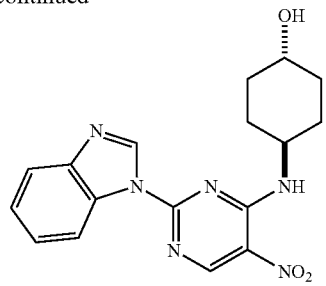

Trans-4-(2-(1H-Benzo[d]imidazol-1-yl)-5-nitropyrimidin-4-ylamino)cyclohexanol. A mixture of trans-4-(2-chloro-5nitropyrimidin-4-ylamino)cyclohexanol (310 mg), benzimidazole (390 mg), and potassium carbonate (0.5 g) was heated in acetonitrile at 60° C. for 2 hours. The mixture was concentrated onto silicon gel and purified by column chromatography (DCM:EtOAc:MeOH 70:22:8) to give 350 mg of the title compound.

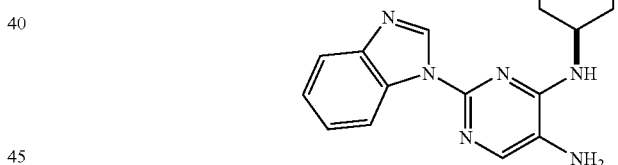

Trans-4-(5-Amino-2-(1H-benzo[d]imidazol-1-yl)pyrimidin-4-ylamino)cyclohexanol. A solution of trans-4-(2-(1H-benzo[d]imidazol-1-yl)-5-nitropyrimidin-4-ylamino)cyclohexanol (162 mg) in THF (20 ml) was treated with a solution of sodium hydrosulfite (500 mg) and NaHCO3 (500 mg) in 20 mL of water and stirred for 25 minutes. The mixture was diluted with 200 mL EtOAc and washed twice with saturated sodium chloride. The organic phase was dried over Na₂SO₄, filtered, and concentrated in vacuo to provide 150 mg of the title compound.

Trans-4-(2-(1H-Benzo[d]imidazol-1-yl)-8-oxo-7,8-dihydropurin-9-yl)cyclohexyl 1H-imidazole-1-carboxylate. A solution of trans-4-(5-amino-2-(1H-benzo[d]imidazol-1-yl) pyrimidin-4-ylamino)cyclohexanol (150 mg) in DCM (15 mL) was treated with carbonyldiimidazole (250 mg) overnight. The mixture was diluted with 100 mL of DCM and washed with brine once, then twice with water. The organic layer was dried over Na₂SO₄, filtered, and concentrated in vacuo. Column chromatography purification (DCM:EtOAc; MeOH 70:22:8) provided 30 mg of the title compound.

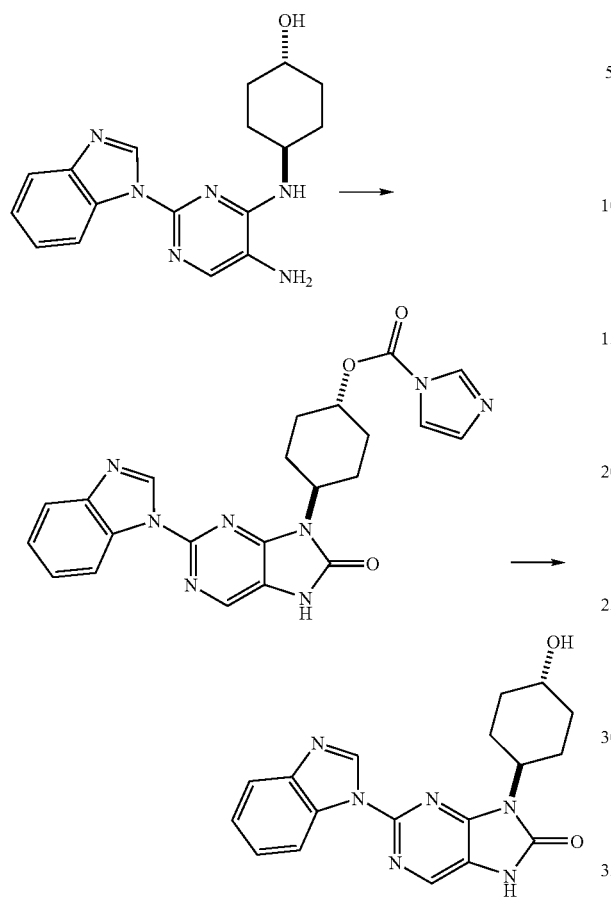

2-(1H-Benzo[d]imidazol-1-yl)-9-(trans-4-hydroxycyclohexyl)-7H-purin-8(9H)-one. trans-4-(2-(1H-benzo[d]imidazol-1-yl)-8-oxo-7,8-dihydropurin-9-yl)cyclohexyl 1H-imidazole-1-carboxylate (30 mg) was dissolved in DMSO (6 mL) and treated with 1N HCl (5 ml) at 50° C. for 3 hours. The mixture was diluted with EtOAc and washed with brine three times. The organic layer was dried over Na₂SO₄, filtered, and concentrated in vacuo to obtain 16 mg of the title compound. ¹H-NMR (300 MHz, CDCl₃) δ 10.0 (s, 1H), 8.9 (dd, 1H), 8.2 (s, 1H), 7.9 (dd, 1H), 7.6 (dd, 2H), 4.4 (m, 1H), 4.1 (s, 1H), 2.9 (m, 2H), 2.0 (m, 2H), 1.6 (m, 4H).

Synthesis of 2-(1H-Benzo[d]imidazol-1-yl)-9-(4-oxocyclohexyl)-7H-purin-8(9H)-one

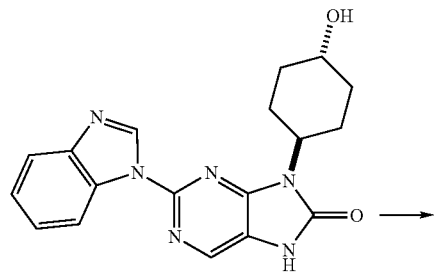

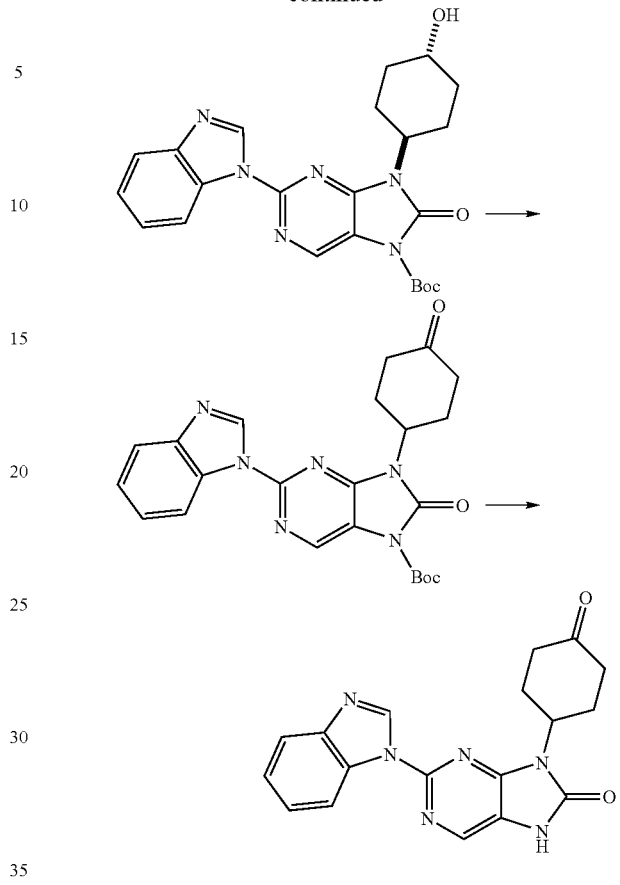

tert-Butyl 2-(1H-benzo[d]imidazol-1-yl)-9-(trans-4-hydroxycyclohexyl)-8-oxo-8,9-dihydropurine-7-carboxylate. Crude 2-(1H-benzo[d]imidazol-1-yl)-9-(trans-4-hydroxycyclohexyl)-7H-purin-8(9H)-one (16 mg) was dissolved in DCM and treated with Boc₂O (150 mg) and Et₃N (1 ml). The mixture was stirred for 2 hours, then diluted with DCM and washed 3 times with brine. The organic layer was dried over Na₂SO₄, filtered, and concentrated in vacuo. Chromatography column (DCM:EtOAc:MeOH, 70:25:5) provided 17 mg of the title compound. A pure sample of the starting material, 2-(1H-benzo[d]imidazol-1-yl)-9-(trans-4-hydroxycyclohexyl)-7H-purin-8(9H)-one, could be obtained by deprotection of the title compound with 1:1 TFA/DCM for one hour, and then treating the resulting material with 10% methanolic HCl for another hour followed by concentration in vacuo.

2-(1H-Benzo[d]imidazol-1-yl)-9-(4-oxocyclohexyl)-7H-purin-8(9H)-one. A solution of oxalyl chloride (6.4 mg) in DCM (0.5 ml) was cooled to −60° C. and treated with a solution of DMSO (8 mg) in DCM (0.5 ml). The reaction mixture was stirred for 2 minutes, then treated with a solution of tert-butyl 2-(1H-benzo[d]imidazol-1-yl)-9-(trans-4-hydroxycyclohexyl)-8-oxo-8,9-dihydropurine-7-carboxylate (4 mg) in DCM (0.5 ml). After 15 minutes, triethylamine (0.4 mL) was added and the mixture was stirred at room temperature for 30 minutes. The mixture was diluted with 10 mL DCM and washed with 15 mL of water. The organic layer was dried over Na₂SO₄, filtered, and concentrated in vacuo. The residue was purified by column chromatography to provide 2.3 mg of tert-butyl 2-(1H-benzo[d]imidazol-1-yl)-8-oxo-9-(4-oxocyclohexyl)-8,9-dihydropurine-7-carboxylate, which was deprotected with TFA/DCM (6 ml, 1:1) for 1 h. The mixture was concentrated and the residue was triturated with ethyl ether to provide 1.8 mg of the title compound. ¹H-NMR (300 MHz, CDCl₃) δ 9.0 (s, 1H), 8.5 (dd, 1H), 8.4 (s, 1H), 7.9 (dd, 1H), 7.4 (m, 2H), 4.9 (m, 1H), 3.0 (m, 2H), 2.6 (m, 4H), 2.3 (m, 2H).

Synthesis of 2-(6-Fluoro-1H-benzo[d]imidazol-1-yl)-9-(trans-4-hydroxycyclohexyl)-7H-purin-8(9H)-one

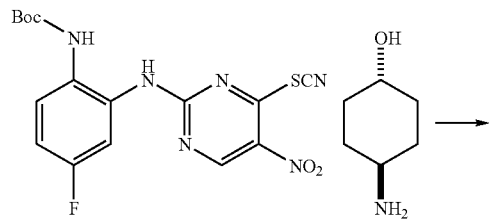

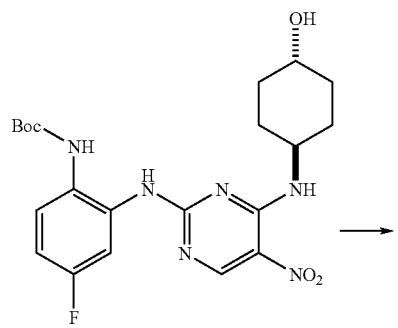

tert-Butyl 4-fluoro-2-(4-(trans-4-hydroxycyclohexylamino)-5-nitropyrimidin-2-ylamino)phenylcarbamate. Potassium carbonate (105 mg) was added to a stirred mixture of tert-butyl 4-fluoro-2-(5-nitro-4-thiocyanatopyrimidin-2-ylamino)phenyl-carbamate (101 mg) in acetonitrile (5 ml) followed by the addition of trans-4-hydroxycyclohexylamine (44 mg). The reaction mixture was stirred for 16 hours, then diluted with DCM and washed with water and brine. The organic layer was dried over Na₂SO₄, filtered, and concentrated in vacuo to provide 110 mg of the title compound.

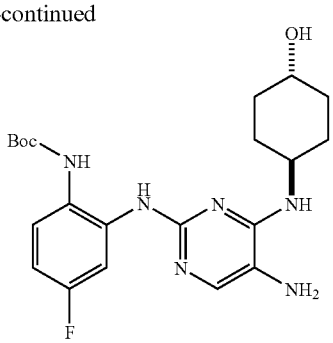

tert-Butyl 2-(5-amino-4-(trans-4-hydroxycyclohexylamino)pyrimidin-2-ylamino)-4-fluorophenylcarbamate. A solution of tert-butyl 4-fluoro-2-(4-(trans-4-hydroxycyclohexylamino)-5-nitropyrimidin-2-ylamino)phenylcarbamate (110 mg) in THF (30 mL) was treated with a mixture containing sodium hydrosulfite (600 mg in 20 ml H2O) and sodium bicarbonate (10 ml, saturated). The resulting mixture was stirred for 5 minutes during which the color changed from yellow to almost colorless. Saturated sodium chloride was added and the mixture was extracted with EtOAc twice. The combined organic layers were washed with saturated sodium chloride and separated. The organic phase was dried over Na₂SO₄, filtered, and concentrated in vacuo to provide 111 mg of the title compound.

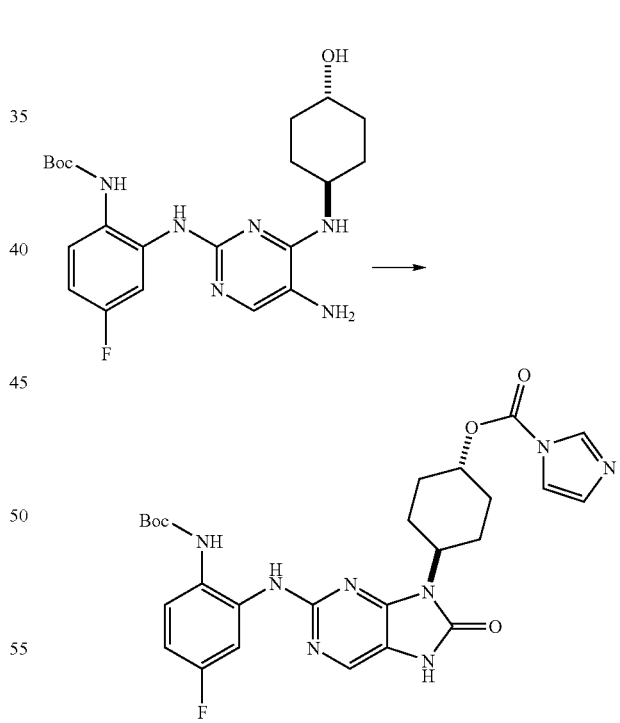

Trans-4-(2-(2-(tert-Butoxycarbonyl)-5-fluorophenylamino)-8-oxo-7,8-dihydropurin-9-yl)cyclohexyl 1H-imidazole-1-carboxylate. A solution of tert-butyl 2-(5-amino-4-(trans-4-hydroxycyclohexylamino)pyrimidin-2-ylamino)-4-fluorophenylcarbamate (111 mg) in DCM (10 mL) was treated with carbonyldiimidazole overnight. The reaction mixture was diluted with DCM (10 ml) and washed with water. The organic layer was dried over Na₂SO₄, filtered, and

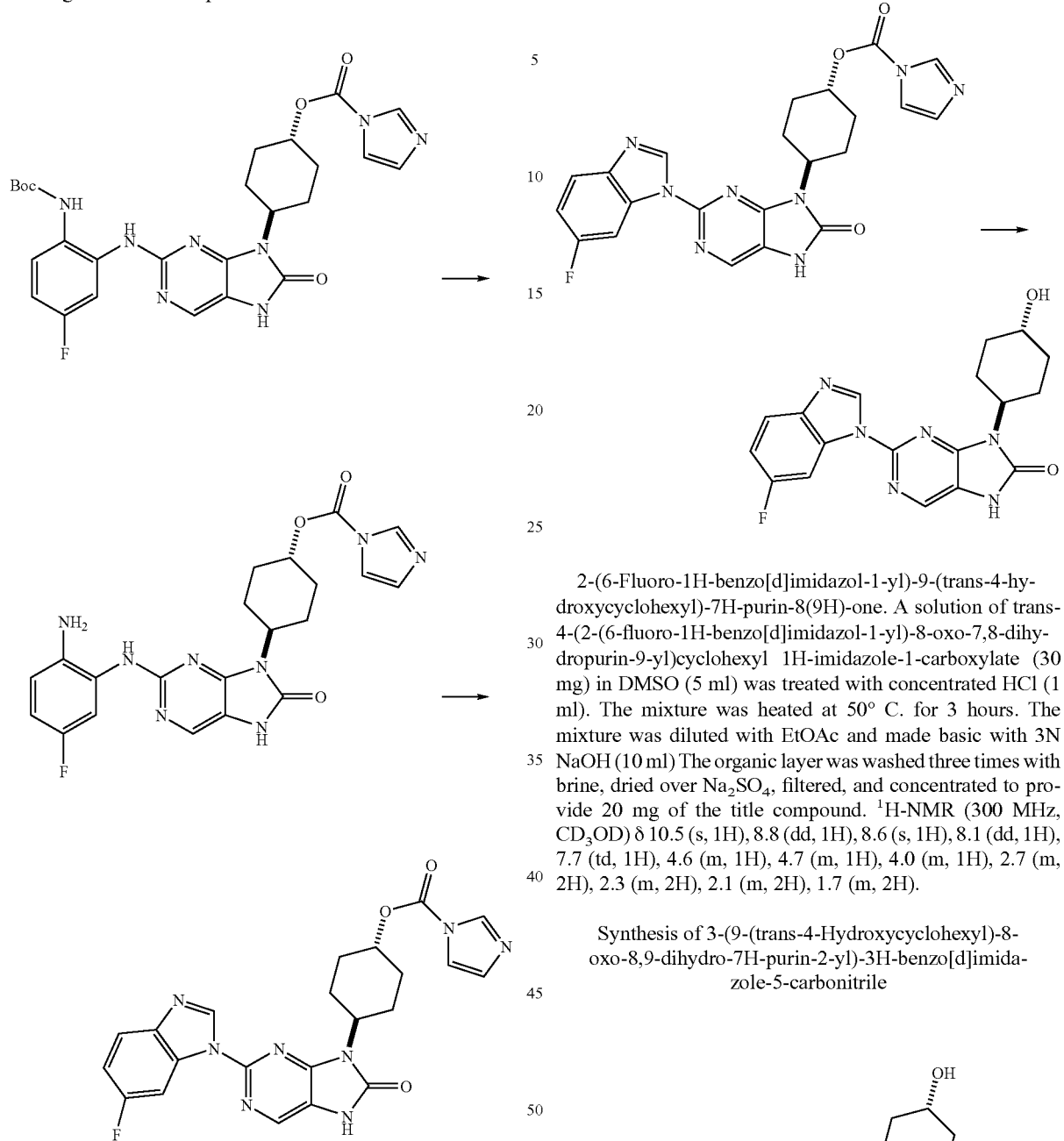

2-(6-Fluoro-1H-benzo[d]imidazol-1-yl)-9-(trans-4-hydroxycyclohexyl)-7H-purin-8(9H)-one. A solution of trans-4-(2-(6-fluoro-1H-benzo[d]imidazol-1-yl)-8-oxo-7,8-dihydropurin-9-yl)cyclohexyl 1H-imidazole-1-carboxylate (30 mg) in DMSO (5 ml) was treated with concentrated HCl (1 ml). The mixture was heated at 50° C. for 3 hours. The mixture was diluted with EtOAc and made basic with 3N NaOH (10 ml) The organic layer was washed three times with brine, dried over Na$_2$SO$_4$, filtered, and concentrated to provide 20 mg of the title compound. $^1$H-NMR (300 MHz, CD$_3$OD) δ 10.5 (s, 1H), 8.8 (dd, 1H), 8.6 (s, 1H), 8.1 (dd, 1H), 7.7 (td, 1H), 4.6 (m, 1H), 4.7 (m, 1H), 4.0 (m, 1H), 2.7 (m, 2H), 2.3 (m, 2H), 2.1 (m, 2H), 1.7 (m, 2H).

Synthesis of 3-(9-(trans-4-Hydroxycyclohexyl)-8-oxo-8,9-dihydro-7H-purin-2-yl)-3H-benzo[d]imidazole-5-carbonitrile Trans-4-(2-(6-Fluoro-1H-benzo[d]imidazol-1-yl)-8-oxo-7,8-dihydropurin-9-yl)cyclohexyl 1H-imidazole-1-carboxylate. A solution of trans-4-(2-(2-(tert-butoxycarbonyl)-5-fluorophenylamino)-8-oxo-7,8-dihydropurin-9-yl)cyclohexyl 1H-imidazole-1-carboxylate (100 mg) in TFA/DCM (18 ml, 1:1) was stirred for 1 hour. The mixture was concentrated in vacuo to provide 95 mg of material. This material was dissolved in THF (30 ml) and treated with CH(OCH$_3$)$_3$ (1 ml) followed by p-toluenesulfonic acid (5 mg). The mixture was stirred for 3 h, diluted with EtOAc (100 ml) and washed three times with brine. The organic layer was dried over Na$_2$SO$_4$ and the solvent was concentrated to provide 22 mg of the title compound.

concentrated in vacuo. Silica gel chromatography provided 100 mg of the title compound.

The title compound could be obtained from 4-(2,4-dimethoxybenzylamino)-3-(4,5-diaminopyrimidin-2-ylamino)benzonitrile using the same procedures outlined for the synthesis of 2-(6-fluoro-1H-benzo[d]imidazol-1-yl)-9-(trans-4-hydroxycyclohexyl)-7H-purin-8(9H)-one from tert-butyl 4-fluoro-2-(5-nitro-4-thiocyanatopyrimidin-2-ylamino)phenylcarbamate. $^1$H-NMR (300 MHz, CD$_3$OD) δ

9.8 (s, 1H), 9.1 (s, 1H), 8.3 (s, 1H), 8.0 (d, 1H), 7.8 (d, 1H), 4.4 (m, 1H), 3.8 (m, 1H), 2.5 (q, 2H), 2.2 (d, 2H), 1.9 (d, 2H), 1.5 (q, 2H).

Synthesis of 2-(6-Fluoro-1H-benzo[d]imidazol-1-yl)-9-(4-oxocyclohexyl)-7H-purin-8(9H)-one

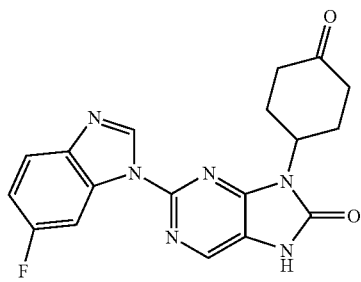

The title compound could be obtained from 2-(6-fluoro-1H-benzo[d]imidazol-1-yl)-9-(trans-4-hydroxycyclohexyl)-7H-purin-8(9H)-one using the same procedure outlined for the synthesis of 2-(1H-benzo[d]imidazol-1-yl)-9-(4-oxocyclohexyl)-7H-purin-8(9H)-one from 2-(1H-benzo[d]imidazol-1-yl)-9-(trans-4-hydroxycyclohexyl)-7H-purin-8(9H)-one. $^1$H-NMR (300 MHz, CDCl$_3$) δ 8.8 (s, 1H), 9.2 (s, 1H), 9.1 (s, 1H), 7.6 (dd, 1H), 7.8 (dd, 1H), 4.8 (m, 1H), 2.8 (m, 2H), 2.5 (m, 4H), 2.1 (m, 2H).

Synthesis of 3-(8-Oxo-9-(4-oxocyclohexyl)-8,9-dihydro-7H-purin-2-yl)-3H-benzo[d]imidazole-5-carbonitrile

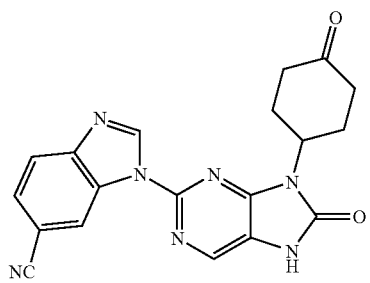

The title compound could be obtained from 3-(9-(trans-4-hydroxycyclohexyl)-8-oxo-8,9-dihydro-7H-purin-2-yl)-3H-benzo[d]imidazole-5-carbonitrile using the same procedures outlined for the synthesis of 2-(1H-benzo[d]imidazol-1-yl)-9-(4-oxocyclohexyl)-7H-purin-8(9H)-one from 2-(1H-benzo[d]imidazol-1-yl)-9-(trans-4-hydroxycyclohexyl)-7H-purin-8(9H)-one. $^1$H-NMR (300 MHz, CD$_3$OD) δ 9.3 (s, 1H), 9.2 (s, 1H), 8.5 (s, 1H), 8.1 (d, 1H), 7.8 (d, 1H), 4.6 (m, 1H), 2.9 (m, 2H), 2.6 (m, 4H), 2.2 (m, 2H).

Synthesis of 3-(9-(3-Hydroxycyclohexyl)-8-oxo-8,9-dihydro-7H-purin-2-yl)-3H-benzo[d]imidazole-5-carbonitrile The title compound could be obtained from 4-(2,4-dimethoxybenzylamino)-3-(4,5-diaminopyrimidin-2-ylamino)benzonitrile and 3-hydroxycyclohexylamine using the same procedures outlined for the synthesis of 2-(6-fluoro-1H-benzo[d]imidazol-1-yl)-9-(trans-4-hydroxycyclohexyl)-7H-purin-8(9H)-one from tert-butyl 4-fluoro-2-(5-nitro-4-thiocyanatopyrimidin-2-ylamino)phenylcarbamate.
$^1$H-NMR (300 MHz, CD$_3$OD) δ 9.4 (s, 1H), 9.2 (s, 1H), 8.4 (s, 1H), 8.1 (d, 1H), 7.9 (d, 1H), 4.6 (m, 1H), 3.9 (m, 1H), 2.5 (m, 2H), 2.2 (m, 2H), 2.1 (m, 2H), 1.6 (m, 2H).

Synthesis of 3-(8-Oxo-9-(3-oxocyclohexyl)-8,9-dihydro-7H-purin-2-yl)-3H-benzo[d]imidazole-5-carbonitrile The title compound could be obtained from 3-(9-(3-hydroxycyclohexyl)-8-oxo-8,9-dihydro-7H-purin-2-yl)-3H-benzo[d]imidazole-5-carbonitrile using the same procedures outlined for the synthesis of 2-(1H-benzo[d]imidazol-1-yl)-9-(4-oxocyclohexyl)-7H-purin-8(9H)-one from 2-(1H-benzo[d]imidazol-1-yl)-9-(trans-4-hydroxycyclohexyl)-7H-purin-8(9H)-one. 1H-NMR (300 MHz, CD$_3$OD) δ 9.2 (s, 1H), 8.6 (s, 1H), 8.5 (s, 1H), 8.1 (d, 1H), 7.9 (d, 1H), 5.0 (m, 1H), 3.8 (m, 1H), 3.7 (m, 1H), 2.9 (m, 2H), 2.6 (m, 2H), 2.3 (m, 2H).

Synthesis of 2-(6-Fluoro-1H-benzo[d]imidazol-1-yl)-9-(trans-4-methoxycyclohexyl)-7H-purin-8(9H)-one A solution of 2-(6-fluoro-1H-benzo[d]imidazol-1-yl)-9-(trans-4-hydroxycyclohexyl)-7H-purin-8(9H)-one (112 mg) in DCM was treated with excess Boc$_2$O and triethylamine until TLC analysis indicated that the starting material had been consumed (4 hours). The mixture was washed with brine, dried over Na$_2$SO$_4$, and concentrated. The resulting residue was dissolved in THF, treated with excess iodomethane, and then NaH (10 equivalents). The mixture was stirred for 6 hours and quenched by the addition of saturated ammonium chloride. The intermediate was extracted with EtOAc, dried, and concentrated. Silica gel chromatography (70:25:5 DCM:EtOAc:MeOH) provided pure tert-butyl 2-(6-fluoro-1H-benzo[d]imidazol-1-yl)-9-(trans-4-methoxycyclohexyl)-8-oxo-8,9-dihydropurine-7-carboxylate, which was deprotected in 1:1 TFA/DCM for 16 hours and concentrated in vacuo to obtain the title compound. The HCl salt was obtained by treating a methanolic solution (10 mL) with 0.5 mL of concentrated HCl followed by solvent evaporation. $^1$H-NMR (300 MHz, CDCl$_3$) δ 9.0 (s, 1H), 8.3 (dd, 1H), 8.1 (s, 1H), 7.6 (dd, 1H), 7.1 (td, 1H), 4.4 (m, 1H), 3.8 (m, 1H), 2.5 (m, 2H), 2.1 (m, 2H), 1.9 (m, 2H), 1.5 (m, 2H).

Synthesis of trans-Methyl 4-(2-(6-fluoro-1H-benzo[d]imidazol-1-yl)-8-oxo-7,8-dihydropurin-9-yl)cyclohexanecarboxylate

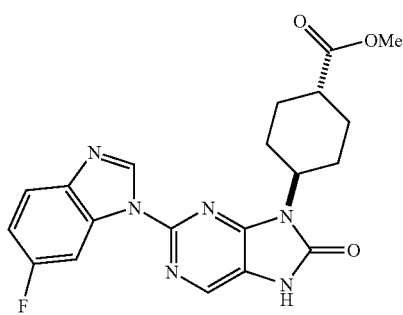

The title compound was obtained from tert-butyl 4-fluoro-2-(5-nitro-4-thiocyanatopyrimidine-2-ylamino)phenylcarbamate and methyl trans-4-aminocyclohexanecarboxylate using procedures outline in Example 27. $^1$H-NMR (300 MHz, CDCl$_3$) δ 9.0 (s, 1H), 8.4 (s, 1H), 8.3 (dd, 1H), 7.8 (dd, 1H), 7.2 (td, 1H), 4.5 (m, 1H), 2.6 (m, 3H), 2.3 (m, 2H), 2.0 (m, 2H), 1.7 (m, 2H).

Synthesis of trans-4-(2-(6-Fluoro-1H-benzo[d]imidazol-1-yl)-8-oxo-7,8-dihydropurin-9-yl)cyclohexanecarboxylic acid

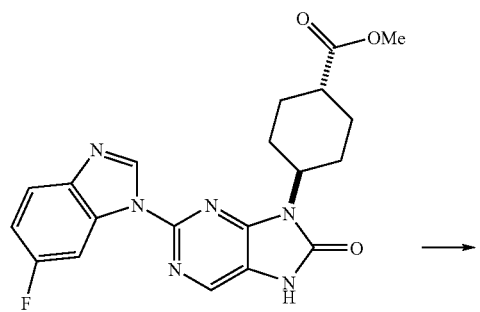

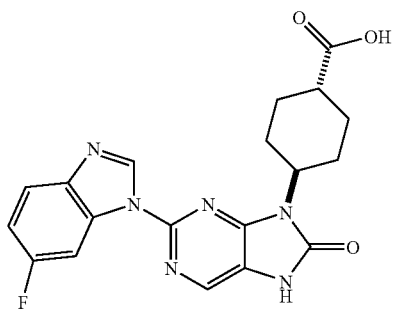

A solution of trans-methyl 4-(2-(6-fluoro-1H-benzo[d]imidazol-1-yl)-8-oxo-7,8-dihydropurin-9-yl)cyclohexanecarboxylate (5 mg) in THF was treated with an aqueous solution of KOH (35 mg) in 2 mL of water. The mixture was heated at 50° C. for 12 hours. The mixture was acidified with TFA and concentrated. Silica gel chromatography (60:30:10 DCM:EtOAc:MeOH) provided 4.3 mg of the title compound. $^1$H-NMR (300 MHz, CDCl$_3$) δ 9.0 (s, 1H), 8.3 (dd, 1H), 8.1 (s, 1H), 7.7 (dd, 1H), 7.1 (td, 1H), 4.3 (m, 1H), 2.4 (m, 3H), 2.2 (m, 2H), 1.9 (m, 2H), 1.6 (m, 2H).

Synthesis of 2-(6-Fluoro-1H-benzo[d]imidazol-1-yl)-9-(trans-4-(hydroxymethyl)cyclohexyl)-7H-purin-8(9H)-one

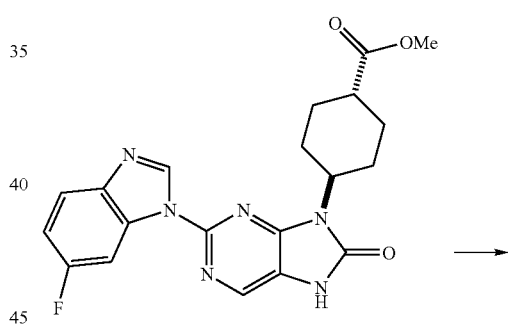

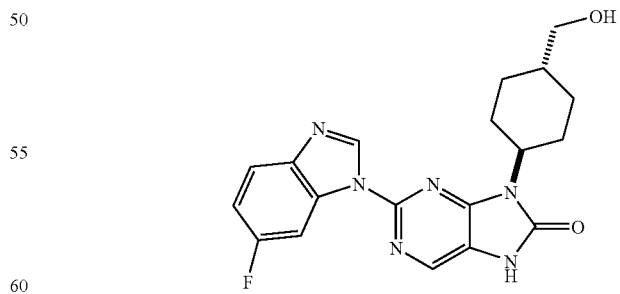

A solution of trans-methyl 4-(2-(6-fluoro-1H-benzo[d]imidazol-1-yl)-8-oxo-7,8-dihydropurin-9-yl)cyclohexanecarboxylate (6 mg) in DCM was treated with 10 equivalents of a 1 M THF solution of LiAlH$_4$ at −10° C. The mixture was stirred at −10° C. for 12 hours and 0° C. for 2 more hours. The mixture was quenched with aqueous sodium bicarbonate and extracted with EtOAc. Silica gel chromatography provided 3.0 mg of the title compound. $^1$H-NMR (300 MHz, CDCl$_3$) δ 9.0 (s, 1H), 8.3 (dd, 1H), 8.1 (s, 1H), 7.7 (dd, 1H), 7.1 (td, 1H), 4.3 (m, 1H), 3.3 (d, 2H), 2.4 (m, 2H), 1.9 (m, 4H), 1.6 (m, 2H).

Synthesis of trans-4-(2-(6-Fluoro-1H-benzo[d]imidazol-1-yl)-8-oxo-7,8-dihydropurin-9-yl)cyclohexanecarboxamide

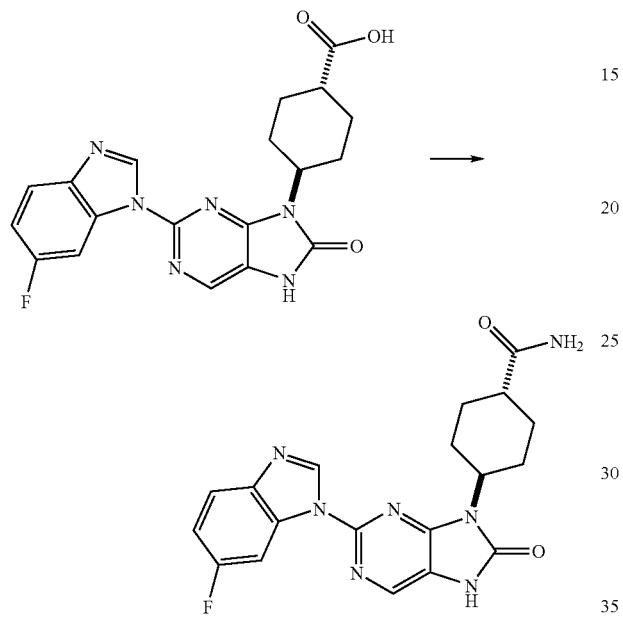

A suspension of trans-4-(2-(6-fluoro-1H-benzo[d]imidazol-1-yl)-8-oxo-7,8-dihydropurin-9-yl)cyclohexanecarboxylic acid (10 mg) in DCM was treated with 6 drops of DMF followed by 3 equivalents of oxalyl chloride. The mixture was stirred for 45 minutes, then it was sparged with an ammonia balloon for 10 minutes. The mixture was concentrated and purified by HPLC to provide 1.7 mg of the title compound. $^1$H-NMR (300 MHz, CD$_3$OD) δ 9.1 (s, 1H), 8.3 (dd, 1H), 8.2 (s, 1H) 7.7 (dd, 1H), 7.1 (td, 1H), 4.4 (m, 1H), 2.5 (m, 2H), 2.4 (m, 1H), 2.1 (m, 2H), 1.9 (m, 2H), 1.7 (m, 2H).

Synthesis of trans-4-(2-(6-Fluoro-1H-benzo[d]imidazol-1-yl)-8-oxo-7,8-dihydropurin-9-yl)-N-methylcyclohexanecarboxamide

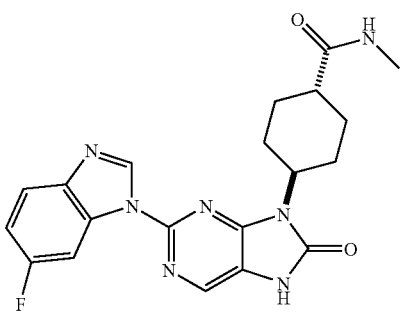

The title compound could be obtained from trans-4-(2-(6-fluoro-1H-benzo[d]imidazol-1-yl)-8-oxo-7,8-dihydropurin-9-yl)cyclohexane-carboxylic acid and 2 M methylamine in THF using the same procedure outlined for the synthesis of trans-4-(2-(6-fluoro-1H-benzo[d]imidazol-1-yl)-8-oxo-7,8-dihydropurin-9-yl)cyclohexanecarboxamide. $^1$H-NMR (300 MHz, CDCl$_3$ with 5% CD$_3$OD) δ 9.0 (s, 1H), 8.3 (dd, 1H), 8.2 (s, 1H), 7.7 (dd, 1H), 7.1 (td, 1H), 4.4 (m, 1H), 2.8 (s, 3H) 2.5 (m, 2H), 2.3 (m, 1H), 2.1 (m, 2H), 2.0 (m, 2H), 1.8 (m, 2H).

Synthesis of 9-(8-oxa-bicyclo[3.2.1]octan-3-yl)-2-(6-fluoro-1H-benzo[d]imidazol-1-yl)-7H-purin-8(9H)-one

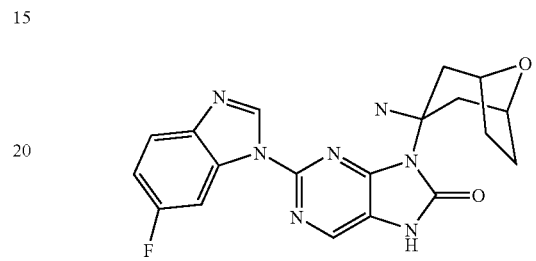

The title compound was obtained from tert-butyl 4-fluoro-2-(5-nitro-4-thiocyanatopyrimidine-2-ylamino)phenylcarbamate and 8-oxa-bicyclo[3.2.1]octan-3-amine (WO 2004/041161) using procedures outlined in Example 27. $^1$H-NMR (300 MHz, CDCl$_3$) δ 9.4 (bs, 1H), 9.0 (s, 1H), 8.4 (dd, 1H), 8.3 (s, 1H), 7.8 (dd, 1H), 7.1 (td, 1H), 4.9 (m, 1H), 4.6 (m, 2H), 2.9 (m, 2H), 2.2 (m, 2H), 2.0 (m, 2H), 1.8 (m, 2H).

Synthesis of (+/−)-2-(6-Fluoro-1H-benzo[d]imidazol-1-yl)-9-(trans-2-phenyl-tetrahydro-2H-pyran-4-yl)-7H-purin-8(9H)-one

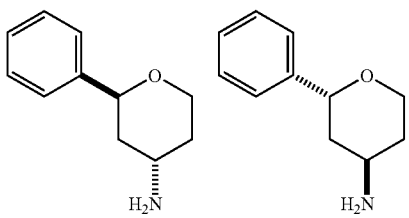

Trans-2-Phenyl-tetrahydro-2H-pyran-4-amine. Sulfuric acid (80%, 16.5 g) was added dropwise at 0° C. to a mixture of but-3-en-1-ol (13.6 g) and benzaldehyde (10 g). After the addition the mixture was stirred at room temperature for 16 hours. The mixture was poured into ice water, made basic (pH 8-10) with 1 N NaOH, extracted with EtOAc, dried, and concentrated. Silica gel chromatography provided 9 g of cis-2-phenyl-tetrahydro-2H-pyran-4-ol.

A solution of cis-2-phenyltetrahydro-2H-pyran-4-ol (1 g) in DCM (20 mL) was cooled in an ice-salt water bath and treated with DIEA (2.2 g) and methanesulfonyl chloride (0.7 g) for 2 hours. The mixture was diluted with DCM (50 mL) and washed with water and brine. The organic layer was dried and concentrated. Preparative TLC provided 0.9 g of cis-2-phenyl-tetrahydro-2H-pyran-4-yl methanesulfonate.

A solution of cis-2-phenyl-tetrahydro-2H-pyran-4-yl methanesulfonate (0.8 g) in DMF (10 mL) was treated with sodium azide (0.8 g) and heated at 100° C. for 4 hours. The mixture was diluted with DCM (50 mL) and washed with water and brine. The organic layer was dried and concentrated. Preparative TLC provided 0.5 g of trans-4-azido-2-phenyl-tetrahydro-2H-pyran.

The title compound was obtained via catalytic hydrogenation (Pd—C, H$_2$) of trans-4-azido-2-phenyl-tetrahydro-2H-pyran.

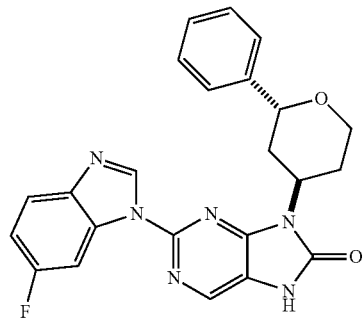

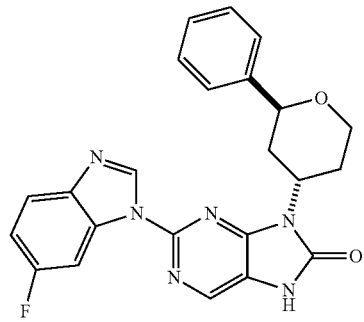

(+/−)-2-(6-Fluoro-1H-benzo[d]imidazol-1-yl)-9-(trans-2-phenyl-tetrahydro-2H-pyran-4-yl)-7H-purin-8(9H)-one. The title compound was obtained from tert-butyl 4-fluoro-2-(5-nitro-4-thiocyanatopyrimidine-2-ylamino)phenylcarbamate and trans-2-phenyl-tetrahydro-2H-pyran-4-amine using procedures outlined in Example 27. $^1$H-NMR (300 MHz, CDCl$_3$ with 5% CD$_3$OD) δ 9.0 (s, 1H), 8.2 (dd, 1H), 8.1 (s, 1H), 7.6 (dd, 1H), 7.4 (d, 2H), 7.3 (t, 2H), 7.2 (t, 1H), 7.0 (td, 1H), 5.2 (br s, 1H), 4.7 (m, 1H), 3.9-3.8 (m, 1H), 3.7 (td, 1H), 3.1-2.8 (m, 2H), 2.4 (br d, 1H), 1.7 (br d, 1H).

Synthesis of 3-(9-(2,2-Dimethylchroman-4-yl)-8-oxo-8,9-dihydro-7H-purin-2-yl)-3H-benzo[d]imidazole-5-carbonitrile 2,2-Dimethylchroman-4-amine. A solution of 2'-hydroxyacetophenone (5.0 mL), acetone (4.7 mL), and pyrrolidine (5.4 mL) in 150 mL of methanol was stirred for 66 hours. The mixture was concentrated and treated with aqueous HCl (pH<1). The acidic layer was extracted twice with ethyl ether, which was dried and concentrated to provide 2,2-dimethylchroman-4-one. The 2,2-dimethylchroman-4-one was dissolved in 300 mL of methanol and treated with ammonium acetate (65 g) and sodium cyanoborohydride (2.5 g) for 24 hours. The resulting mixture was concentrated to 100 mL and diluted with 300 mL water. Concentrated HCl was carefully added until the pH was less than 1 and the acidic mixture was extracted with ethyl ether. The acidic phase was made basic with KOH and then extracted twice with ethyl ether. The basic extracts were dried and concentrated to provide the title compound.

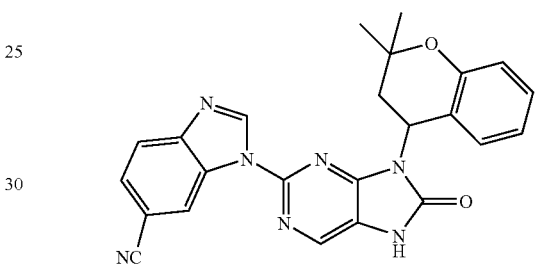

3-(9-(2,2-Dimethylchroman-4-yl)-8-oxo-8,9-dihydro-7H-purin-2-yl)-3H-benzo[d]imidazole-5-carbonitrile. The title compound was obtained from 4-(2,4-dimethoxybenzylamino)-3-(4,5-diaminopyrimidin-2-ylamino)benzonitrile and 2,2-dimethylchroman-4-amine using procedures outlined in Example 26. $^1$H-NMR (300 MHz, CDCl$_3$) δ 9.6 (s, 1H), 9.0 (s, 1H), 8.5 (bs, 1H), 8.3 (s, 1H), 7.8 (d, 1H), 7.6 (dd, 1H), 7.2 (m, 2H), 6.8 (d, 1H), 6.7 (td, 1H), 5.9 (dd, 1H), 2.9 (t, 1H), 2.2 (dd, 1H), 1.6 (s, 3H), 1.5 (s, 3H).

Synthesis of 2-(6-Fluoro-1H-benzo[d]imidazol-1-yl)-9-(1,2,3,4-tetrahydroquinolin-6-yl)-7H-purin-8(9H)-one

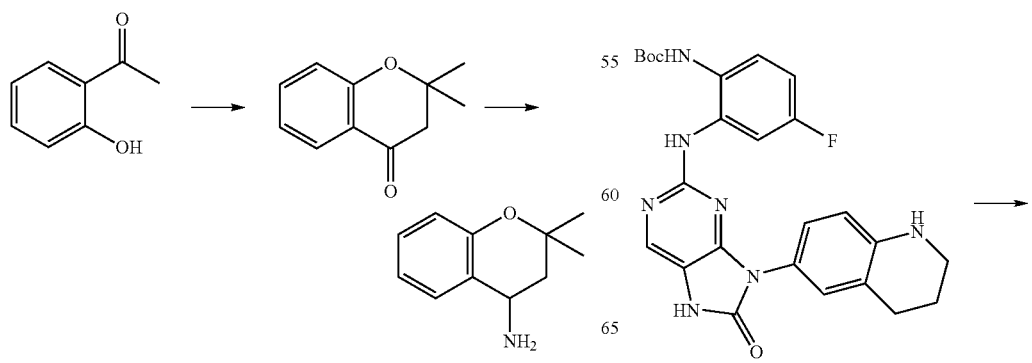

-continued

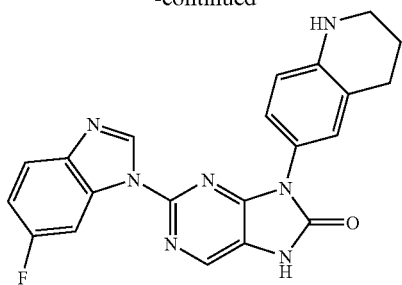

A solution of tert-butyl 4-fluoro-2-(8-oxo-9-(1,2,3,4-tetrahydroquinolin-6-yl)-8,9-dihydro-7H-purin-2-ylamino) phenylcarbamate (obtained from tert-butyl 4-fluoro-2-(5-nitro-4-thiocyanatopyrimidine-2-ylamino)phenylcarbamate and 1,2,3,4-tetrahydroquinolin-6-amine (*J. Org. Chem.* (2002), 67, 7890) using procedures outlined in Example 27) was stirred for 45 minutes in 1:1 TFA/DCM and concentrated to afford 2-(2-amino-5-fluorophenylamino)-9-(1,2,3,4-tetrahydroquinolin-6-yl)-7H-purin-8(9H)-one. The 2-(2-amino-5-fluorophenylamino)-9-(1,2,3,4-tetrahydroquinolin-6-yl)-7H-purin-8(9H)-one was stirred for 15 minutes in trimethylorthoformate and concentrated to afford 6-(2-(6-fluoro-1H-benzo[d]imidazol-1-yl)-8-oxo-7,8-dihydropurin-9-yl)-3,4-dihydroquinoline-1(2H)-carbaldehyde, which was purified by silica gel chromatography (2→5% MeOH in DCM). This material was deformylated by refluxing for 1 hour in 11:2 1 M HCl:MeOH to provide the title compound as the HCl salt. $^1$H-NMR (300 MHz, CD$_3$OD) δ 10.0 (s, 1H), 8.4 (s, 1H), 8.4 (dd, 1H), 7.8 (dd, 1H), 7.8 (s, 1H), 7.8 (d, 1H), 7.5 (d, 1H), 7.4 (td, 1H), 3.6 (dd, 2H), 3.1 (t, 2H), 2.2 (m, 2H).

Synthesis of 2-(6-Fluoro-1H-benzo[d]imidazol-1-yl)-9-(5,6,7,8-tetrahydroquinolin-6-yl)-7H-purin-8(9H)-one

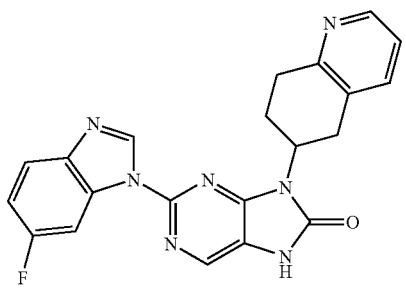

The title compound was obtained from tert-butyl 4-fluoro-2-(5-nitro-4-thiocyanatopyrimidine-2-ylamino)phenylcarbamate and 5,6,7,8-tetrahydroquinolin-6-amine (*J. Org. Chem.* (2002), 67, 7890) using procedures outlined in Example 27. $^1$H-NMR (300 MHz, CD$_3$OD) δ 9.3 (s, 1H), 8.6 (d, 1H), 8.5 (dd, 1H), 8.1 (dd, 1H), 7.9 (dd, 1H), 7.4 (td, 1H), 5.2 (m, 1H), 4.2 (dd, 1H), 3.6 (m, 3H), 3.2 (m, 1H), 2.6 (m, 1H).

Synthesis of 2-(1H-Benzo[d]imidazol-1-yl)-9-(tetrahydro-1-oxido-2H-thiopyran-4-yl)-7H-purin-8(9H)-one

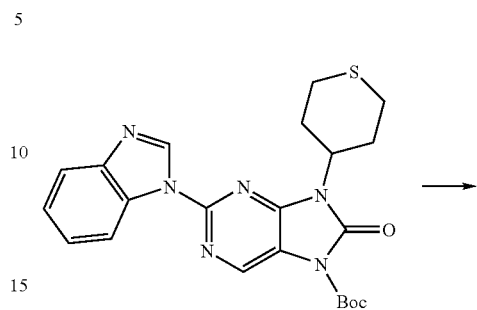

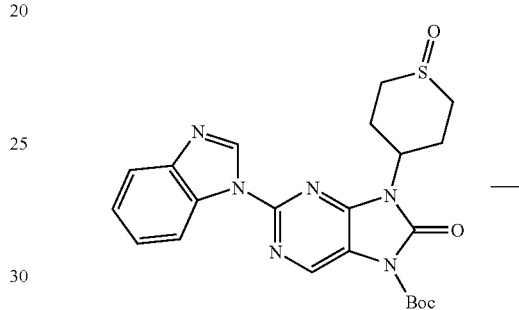

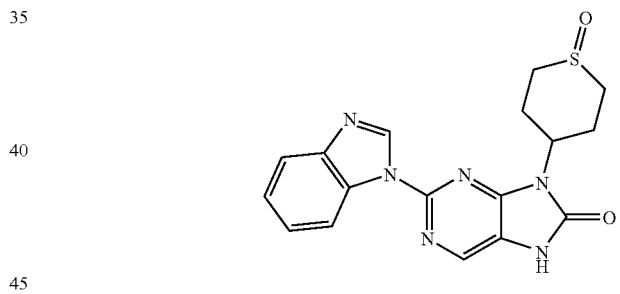

A solution of tert-butyl 2-(1H-benzo[d]imidazol-1-yl)-8-oxo-9-(tetrahydro-2H-thiopyran-4-yl)-8,9-dihydropurine-7-carboxylate (8 mg, obtained from tetrahydrothiopyran-4-ylamine using procedures outlined in Example 16 followed by protection using the procedure outline for the synthesis of tert-butyl 2-(1H-benzo[d]imidazol-1-yl)-9-(trans-4-hydroxycyclohexyl)-8-oxo-8,9-dihydropurine-7-carboxylate) in MeOH/H$_2$O (10 ml, 1:1) was treated with KIO$_4$ (50 mg) and stirred for 3 hours. The reaction mixture was diluted with 10 ml of saturated NaHCO$_3$ and extracted 3 times with DCM. The organic layers were dried over Na$_2$SO$_4$, filtered, and concentrated in vacuo. Chromatography column purification (DCM:EtOAc:MeOH 75:25:5) provided 5.6 mg of tert-butyl 2-(1H-benzo[d]imidazol-1-yl)-8-oxo-9-(tetrahydro-1-oxido-2H-thiopyran-4-yl)-8,9-dihydropurine-7-carboxylate. This material was treated with TFA/DCM (6 ml, 1:1) for 1 hour and concentrated. Trituration with Et$_2$O provided 3.3 mg of the title compound. $^1$H NMR (300 MHz CDCl$_3$) δ 9.1 (br, 1H), 8.5 (m, 1H), 8.2 (s, 1H), 7.8 (m, 1H), 7.4 (m, 2H), 4.6 (m, 1H), 3.6 (m, 2H), 2.9 (m, 4H), 2.2 (m, 2H).

Synthesis of 2-(1H-Benzo[d]imidazol-1-yl)-9-(tetrahydro-1,1-dioxido-2H-thiopyran-4-yl)-7H-purin-8(9H)-one

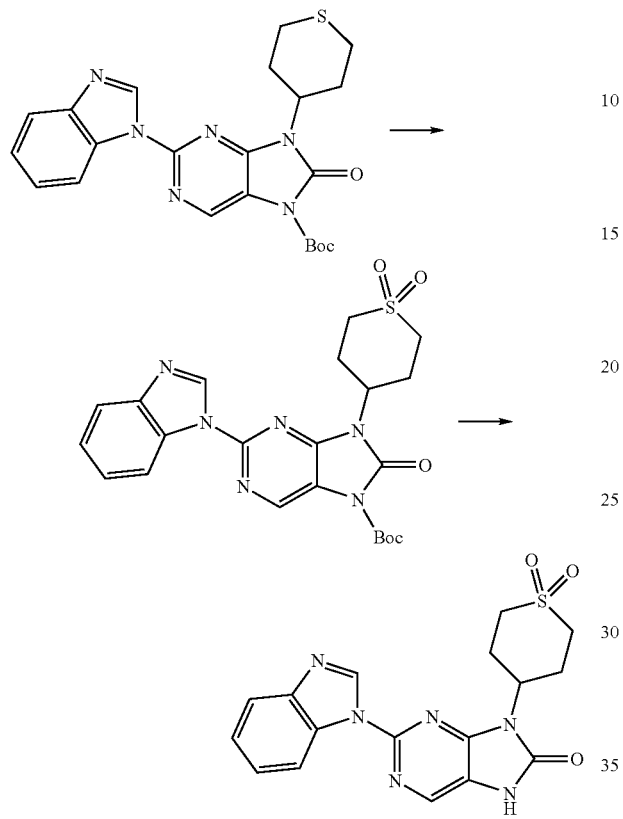

A solution of tert-butyl 2-(1H-benzo[d]imidazol-1-yl)-8-oxo-9-(tetrahydro-2H-thiopyran-4-yl)-8,9-dihydropurine-7-carboxylate (8 mg) in DCM (10 ml) was treated with MCPBA (13 mg) and stirred for 16 hours. The mixture was washed 3 times with brine. The organic layer was dried over Na$_2$SO$_4$, filtered, and concentrated in vacuo. Chromatography column purification (DCM:EtOAc;MeOH 75:25:5) provided 2.2 mg of tert-butyl 2-(1H-benzo[d]imidazol-1-yl)-8-oxo-9-(tetrahydro-1,1-dioxido-2H-thiopyran-4-yl)-8,9-dihydropurine-7-carboxylate. This material was treated with TFA/DCM (6 ml, 1:1) for 1 hour and concentrated. Trituration with Et$_2$O provided 1.3 mg of the title compound. $^1$H NMR (300 MHz, CDCl$_3$) δ 9.2 (br, 1H), 8.7 (d, 1H), 7.8 (d, 1H), 7.5 (t, 1H), 7.4 (t, 1H), 4.6 (m, 1H), 3.0-3.5 (m, 6H), 2.2 (m, 2H).

Synthesis of 2-(1H-Benzo[d]imidazol-1-yl)-9-(thiochroman-4-yl)-7H-purin-8(9H)-one

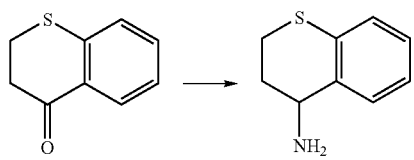

Thiochroman-4-amine. To a solution of thiochroman-4-one (1.6 g) in EtOH (100 ml) was added NH$_4$OAc (8.2 g), the mixture was heated at 50° C. for 35 minutes then cooled to room temperature and treated with Na(CN)BH$_4$ (0.96 g). The mixture was stirred at room temperature for 64 hours and the reaction solvent was removed in vacuo. The residue was dissolved in EtOAc and washed 4 times with 4N HCl. The combined aqueous washes were made basic with 3N NaOH, then extracted 5 times with EtOAc. The combined organic layers were dried over Na$_2$SO$_4$ and concentrated to provide 1.4 g of the title compound.

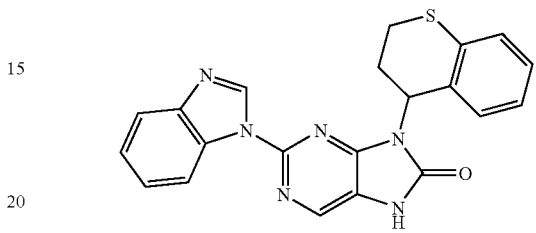

2-(1H-Benzo[d]imidazol-1-yl)-9-(thiochroman-4-yl)-7H-purin-8(9H)-one. The title compound was synthesized from thiochroman-4-amine using the procedures outlined in Example 16. $^1$H NMR (300 MHz, CD$_3$OD) δ 9.1 (s, 1H), 8.5 (s, 1H), 8.3 (m, 1H), 7.8 (m, 1H), 7.4 (m, 3H), 7.3 (m, 1H), 7.0-7.2 (m, 2H), 6.0 (m, 1H), 3.4 (m, 2H), 3.1 (m, 1H), 2.6 (m, 1H).

Synthesis of 2-(6-Fluoro-1H-benzo[d]imidazol-1-yl)-9-((R)-4-oxo-1,2,3,4-tetrahydronaphthalen-1-yl)-7H-purin-8(9H)-one, 2-(6-Fluoro-1H-benzo[d]imidazol-1-yl)-9-((1R,4R)-4-hydroxy-1,2,3,4-tetrahydronaphthalen-1-yl)-7H-purin-8(9H)-one, and 2-(6-fluoro-1H-benzo[d]imidazol-1-yl)-9-((1R,4S)-4-hydroxy-1,2,3,4-tetrahydronaphthalen-1-yl)-7H-purin-8(9H)-one

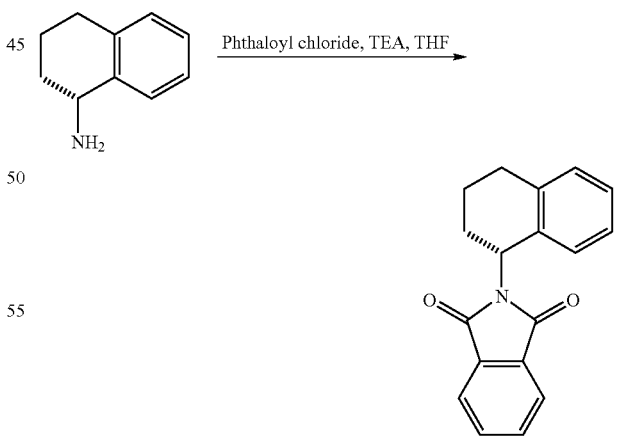

(R)-2-(1,2,3,4-Tetrahydronaphthalen-1-yl)isoindoline-1,3-dione. To a solution of (R)-1,2,3,4-tetrahydro-1-naphthylamine (6.0 g) in THF (150 mL) at 0° C. was added TEA (18.5 mL) and phthaloyl chloride (8.2 g), and the resultant mixture was stirred at room temperature overnight and 70° C. for 3 h.

The mixture was diluted with CH$_2$Cl$_2$, washed with saturated NaHCO$_3$, dried over MgSO$_4$, and concentrated in vacuo. The resulting crude was chromatographed on silica gel (EtOAc/hexane, 5/95 to 30/70) to afford 8.2 g of the title compound.

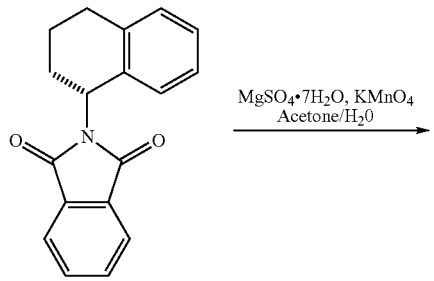

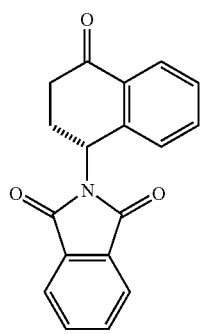

(R)-2-(4-Oxo-1,2,3,4-tetrahydronaphthalen-1-yl)isoindoline-1,3-dione. To a solution of (R)-2-(1,2,3,4-tetrahydronaphthalen-1-yl)isoindoline-1,3-dione (3.9 g) in acetone (60 mL) at 0° C. was added MgSO$_4$.7H$_2$O (11.5 g) and water (20 mL). Then KMnO$_4$ (11.5 g) was added portionwise over the period of 2 h and stirring continued at room temperature overnight. The brown solid was filtered off and the filtrate treated with saturated sodium metabisulfite, filtered, and extracted with CH$_2$Cl$_2$. The combined organic layer was washed with distilled water and saturated brine, dried over MgSO$_4$, and concentrated in vacuo. The resultant was chromatographed on silica gel (EtOAc/hexane, 25/75) to afford 0.14 g of the title compound.

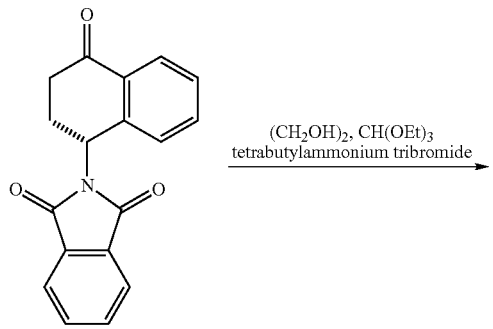

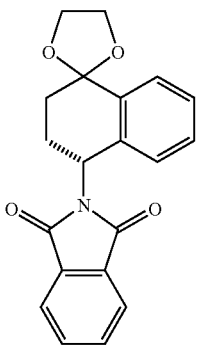

1,3-Dioxolane of (R)-2-(4-oxo-1,2,3,4-Tetrahydronaphthalen-1-yl)isoindoline-1,3-dione. To the mixture of (R)-2-(4-oxo-1,2,3,4-tetrahydronaphthalen-1-yl)isoindoline-1,3-dione (138 mg), triethyl orthoformate (0.3 mL), and 1,2-ethanediol (1.5 mL) was added tetrabutylammonium tribromide (12 mg). The reaction mixture was stirred at room temperature overnight and heated at 90° C. for 3 h. After cooling, the mixture was diluted with CH$_2$Cl$_2$, washed with saturated NaHCO$_3$, water, and brine, dried over MgSO$_4$, and concentrated in vacuo. The residue was purified by PTLC (EtOAc/hexane, 1/2) to afford 150 mg of the title compound.

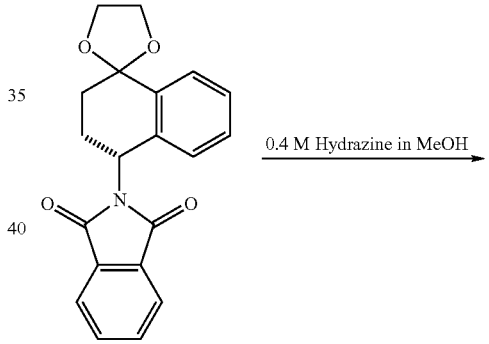

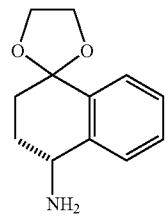

1,3-Dioxolane of (R)-4-amino-3,4-dihydronaphthalen-1 (2H)-one. A solution of 1,3-dioxolane of (R)-2-(4-oxo-1,2,3,4-tetrahydronaphthalen-1-yl)isoindoline-1,3-dione (145 mg) in 0.4 M methanolic hydrazine (40 mL) was stirred at room temperature overnight. The solvent and excess hydrazine were evaporated and a small amount of CH$_2$Cl$_2$ was added to the residue. The white solid was filtered off and the filtrate concentrated in vacuo to afford 85 mg of the title compound.

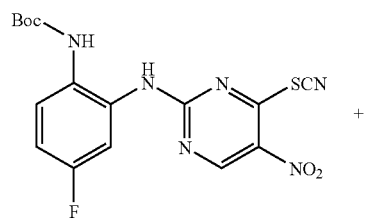

+

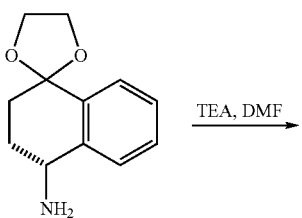

TEA, DMF →

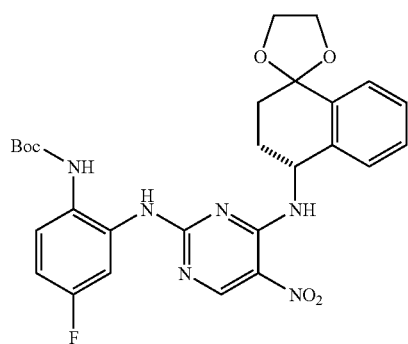

1,3-Dioxolane of (R)-tert-butyl 4-fluoro-2-(5-nitro-4-(4-oxo-1,2,3,4-tetrahydronaphthalen-1-ylamino)pyrimidin-2-ylamino)phenylcarbamate. A solution of tert-butyl 4 fluoro-2-(5-nitro-4-thiocyanatopyrimidin-2-ylamino) phenylcarbamate (170 mg), 1,3-Dioxolane of (R)-4-amino-3,4-dihydronaphthalen-1(2H)-one (85 mg), and TEA (0.2 mL) in DMF (5 mL) was stirred at room temperature overnight. The reaction mixture was diluted with EtOAc, washed with saturated brine, dried over MgSO₄, and concentrated in vacuo. The residue was purified by PTLC (EtOAc/hexane, 50/50) to afford 150 mg of the title compound.

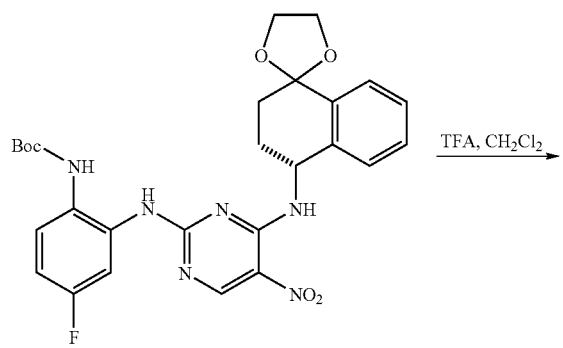

TFA, CH₂Cl₂ →

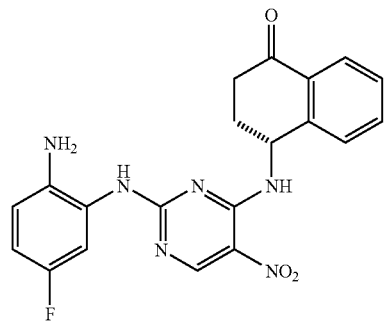

(R)-4-(2-(2-Amino-5-fluorophenylamino)-5-nitropyrimidin-4-ylamino)-3,4-dihydronaphthalen-1(2H)-one. A solution of 1,3-dioxolane of (R)-tert-butyl 4-fluoro-2-(5-nitro-4-(4-oxo-1,2,3,4-tetrahydronaphthalen-1-ylamino)pyrimidin-2-ylamino)phenylcarbamate (145 mg) and TFA (2.5 mL) in CH₂Cl₂ (5 mL) was stirred at room temperature for 1 h. Volatiles were removed in vacuo and the crude (120 mg) was subjected to the next step without further purification.

CH(OMe)₃
MeOH/THF →

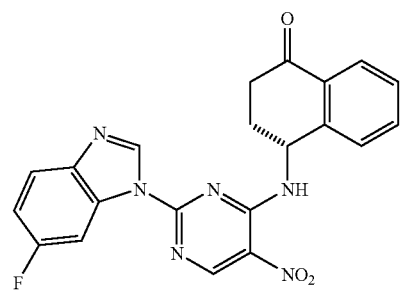

(4R)-4-(2-(6-Fluoro-1H-benzo[d]imidazol-1-yl)-5-nitro-pyrimidin-4-ylamino)-3,4-dihydronaphthalen-1(2H)-one. A solution of (R)-4-(2-(2-amino-5-fluorophenylamino)-5-nitropyrimidin-4-ylamino)-3,4-dihydronaphthalen-1(2H)-one (120 mg) and CH(OMe)₃ (2.5 mL) in MeOH/THF (2.5 mL/10 mL) was stirred at room temperature overnight. Volatiles were removed in vacuo and the residue was purified by PTLC (EtOAc) to afford 80 mg of the title compound.

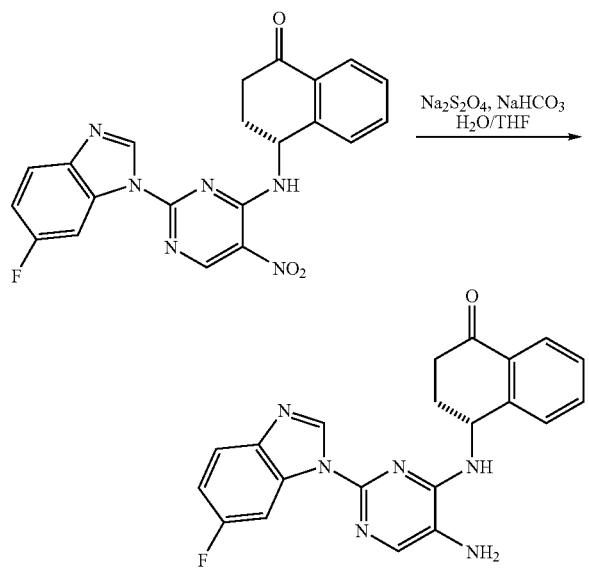

(4R)-4-(5-Amino-2-(6-fluoro-1H-benzo[d]imidazol-1-yl)pyrimidin-4-ylamino)-3,4-dihydronaphthalen-1(2H)-one.

To the solution of (4R)-4-(2-(6-fluoro-1H-benzo[d]imidazol-1-yl)-5-nitropyrimidin-4-ylamino)-3,4-dihydronaphthalen-1(2H)-one (80 mg) in THF (10 mL) was added $Na_2S_2O_4$ (480 mg) and $NaHCO_3$ (240 mg) in $H_2O$ (10 mL), and stirring continued at room temperature for 1.5 h. The reaction mixture was diluted with $CH_2Cl_2$, washed with saturated brine, dried over $MgSO_4$, and concentrated in vacuo. The crude (32 mg) was subjected to the next step without further purification.

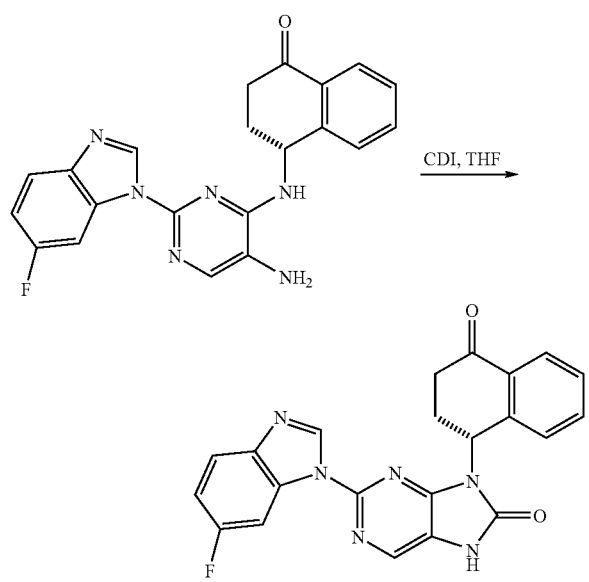

2-(6-Fluoro-1H-benzo[d]imidazol-1-yl)-9-((R)-4-oxo-1,2,3,4-tetrahydronaphthalen-1-yl)-7H-purin-8(9H)-one. A solution of (4R)-4-(5-amino-2-(6-fluoro-1H-benzo[d]imidazol-1-yl)pyrimidin-4-ylamino)-3,4-dihydronaphthalen-1(2H)-one (32 mg) and CDI (100 mg) in THF (6 mL) was stirred at room temperature overnight and refluxed for 2.5 h. Volatiles were removed in vacuo and the residue was purified by preparative HPLC to afford 9 mg of the title compound as the TFA salt. $^1$H NMR (CD$_3$OD) δ 9.20 (s, 1H), 8.36 (s, 1H), 8.20 (m, 1H), 7.68 (m, 1H), 7.58-7.47 (m, 3H), 7.20-7.14 (m, 2H), 6.10 (m, 1H), 3.09-2.93 (m, 3H), 2.49 (m, 1H); MS (MH$^+$) 415.1.

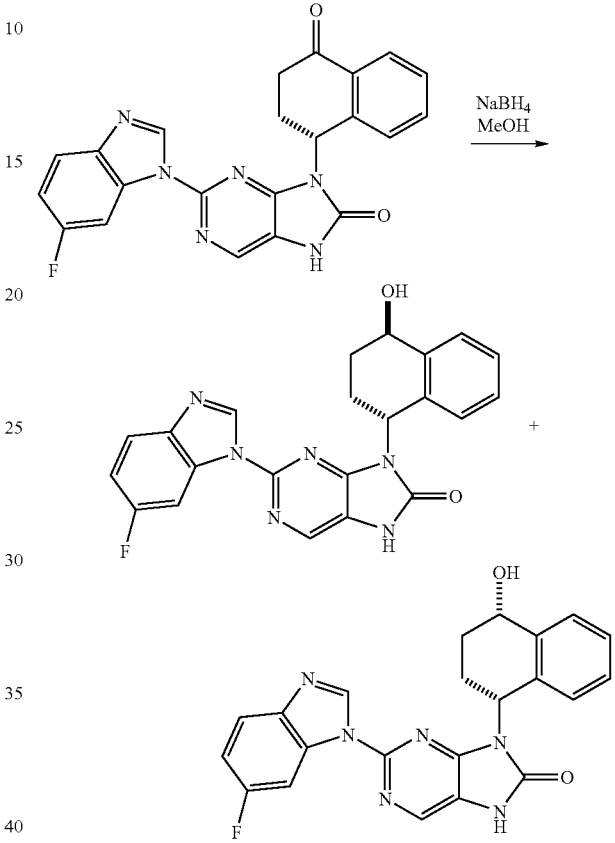

2-(6-Fluoro-1H-benzo[d]imidazol-1-yl)-9-((1R,4R)-4-hydroxy-1,2,3,4-tetrahydronaphthalen-1-yl)-7H-purin-8(9H)-one and 2-(6-fluoro-1H-benzo[d]imidazol-1-yl)-9-((1R,4S)-4-hydroxy-1,2,3,4-tetrahydronaphthalen-1-yl)-7H-purin-8(9H)-one. To a solution of 2-(6-fluoro-1H-benzo[d]imidazol-1-yl)-9-((R)-4-oxo-1,2,3,4-tetrahydronaphthalen-1-yl)-7H-purin-8(9H)-one (6 mg) in MeOH (2.5 mL) at 0° C. was added NaBH$_4$ (4.5 mg), and stirring continued at 0° C. for 3 h. The reaction was quenched by the addition of saturated NH$_4$Cl and extracted with CH$_2$Cl$_2$. The combined organic extracts were dried over MgSO$_4$ and concentrated in vacuo. The residue was purified by preparative HPLC to afford the title compounds as the TFA salts. 2-(6-fluoro-1H-benzo[d]imidazol-1-yl)-9-((1R,4R)-4-hydroxy-1,2,3,4-tetrahydronaphthalen-1-yl)-7H-purin-8(9H)-one. 3 mg, $R_f$=0.28 (MeOH/DCM, 5/95); $^1$H NMR (CD$_3$OD) δ 8.97 (s, 1H), 8.30 (s, 1H), 7.80 (d, 1H), 7.66 (dd, 1H), 7.56 (dd, 1H), 7.30 (t, 1H), 7.13 (m, 2H), 6.95 (d, 1H), 5.85 (dd, 1H), 5.11 (dd, 1H), 2.63 (m, 1H), 2.43 (m, 1H), 2.32 (m, 1H), 1.94 (m, 1H); MS (MH$^+$) 417.0. 2-(6-fluoro-1H-benzo[d]imidazol-1-yl)-9-((1R,4S)-4-hydroxy-1,2,3,4-tetrahydronaphthalen-1-yl)-7H-purin-8(9H)-one. 2 mg, $R_f$=0.33 (MeOH/DCM, 5/95); $^1$H NMR (CD$_3$OD) δ 9.01 (s, 1H), 8.33 (s, 1H), 8.00 (m, 1H), 7.67-6.94 (m, 6H), 5.72 (m, 1H), 4.91 (m, 1H), 2.99 (m, 1H), 2.42-2.05 (m, 3H); MS (MH+) 417.0.

Preparation of (1R,4R)-4-(tert-butyldiphenylsilyloxy)-1,2,3,4-tetrahydronaphthalen-1-amine

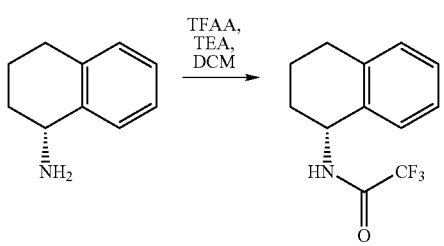

(R)-2,2,2-Trifluoro-N-(1,2,3,4-tetrahydronaphthalen-1-yl)acetamide. A 250 ml round bottom flask was charged with of (R)-1,2,3,4-tetrahydronaphthalen-1-amine (5 g, 34 mM), then purged with argon when DCM (50 ml) was added, and the solution was cooled to 0° C. Triethylamine (9.5 mL) was added by syringe followed be trifluoroacetic anhydride (7.1 mL) of was added over 5 min by syringe. The solution was then stirred overnight, slowly warming to room temp. The mixture was diluted with DCM and washed with water, 1 N HCl, and brine. The organic layer was dried over MgSO$_4$ and concentrated in vacuo, and purified by column chromatography (eluting with 1:1 DCM/Hex), to give 6.6 g (80%) of the titled compound. $^1$H-NMR (300 MHz, CDCl$_3$) ☐ 7.2 (m, 3H), 7.1 (t, 1H), 6.5 (broad s, 1H), 5.2 (q, 1H), 2.8 (q, 2H), 2.1 (m 1H), 1.9 (m, 3H) ppm.

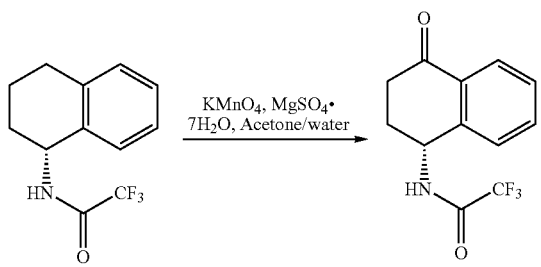

(R)-2,2,2-Trifluoro-N-(4-oxo-1,2,3,4-tetrahydronaphthalen-1-yl)acetamide. To a solution of (R)-2,2,2-trifluoro-N-(1,2,3,4-tetrahydronaphthalen-1-yl)acetamide (1 g) in acetone (30 mL) at 0° C. was added a solution of MgSO$_4$.7H$_2$O (2.0 g) in water (15 mL). After 5 min of stirring, KMnO$_4$ (2 g) was added in small portions over 1 hr. The mixture was then stirred overnight, slowly warming to room temp. Celite was added and the mixture was filtered. The filtrate was treated with saturated sodium metabisulfite and filtered. The filtrate was extracted with DCM several times. The combined organic extracts were washed with distilled water and brine, dried over MgSO$_4$ and concentrated in vacuo to afford 0.96 g (91%) of the title compound, whose purity was good enough to use crude. $^1$H-NMR (300 MHz, CDCl$_3$) ☐ 8.2 (d, 1H), 7.7 (t, 1H), 7.6 (t, 1H), 7.5 (d, 1H), 6.8 (broad s, 1H), 5.5 (m, 1H), 2.9 (m, 2H), 2.6 (m 1H), 2.4 (m, 1H) ppm.

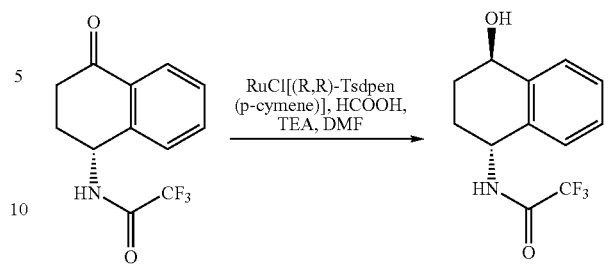

2,2,2-Trifluoro-N-((1R,4R)-4-hydroxy-1,2,3,4-tetrahydronaphthalen-1-yl)acetamide. (R)-2,2,2-Trifluoro-N-(4-oxo-1,2,3,4-tetrahydronaphthalen-1-yl)acetamide (0.5 g), RuCl[(R,R)-Tsdpen(p-cymene)] and DMF (25 mL) were added to a flask that was purged with argon (catalyst prepared using procedure from Org Syn, Vol 82, pg 10-17, note 5). Triethylamine and HCOOH were added and the reaction mixture was stirred at 50° C. overnight. Further addition of catalyst (0.06 g), TEA (0.4 mL) and HCOOH (0.12 mL) were required to drive the reaction to completion after continued heating at 50° C. for an additional 6-8 hr. The reaction mixture was cooled to room temp, diluted with 150 mL EtOAc, and washed with 20 mL distilled water. The organic phase was dried over MgSO$_4$ and concentrated in vacuo, and purified by column chromatography (eluting with 1% MeOH/DCM), to give 0.417 g (83%) of the titled compound. $^1$H-NMR (300 MHz, CDCl$_3$) ☐ 7.5 (d, 1H), 7.3 (m, 2H), 7.2 (d, 1H), 6.4 (broad s, 1H), 5.3 (q, 1H), 4.8 (d, 1H), 2.4 (m, 1H), 2.2 (m 1H), 1.8 (m, 2H) ppm.

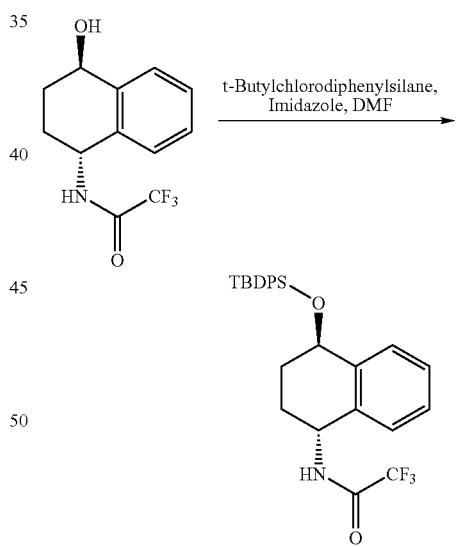

N-((1R,4R)-4-(tert-butyldiphenylsilyloxy)-1,2,3,4-tetrahydronaphthalen-1-yl)-2,2,2-trifluoroacetamide. tert-Butylchlorodiphenylsilane (4.4 mL) was added to a stirred solution of 2,2,2-trifluoro-N-((1R,4R)-4-hydroxy-1,2,3,4-tetrahydronaphthalen-1-yl)acetamide (2.2 g) and imidazole (1.7 g) in DMF (35 mL). The reaction mixture was stirred at room temp overnight. The reaction mixture was diluted with EtOAc (150 mL), and washed with distilled water (20 mL). The organic phase was dried over MgSO4 and concentrated in vacuo and purified by column chromatography (eluting with 1:1 DCM/Hex), to give 4.0 g (95%) of the titled compound.

¹H-NMR (300 MHz, CDCl₃) □ 7.7 (d, 2H), 7.6 (d, 2H), 7.4 (m, 6H), 7.2 (m, 4H), 6.3 (broad s, 1H), 5.2 (q, 1H), 4.8 (t, 1H), 2.4 (m, 1H), 1.8 (m, 2H), 1.6 (m, 1H) ppm.

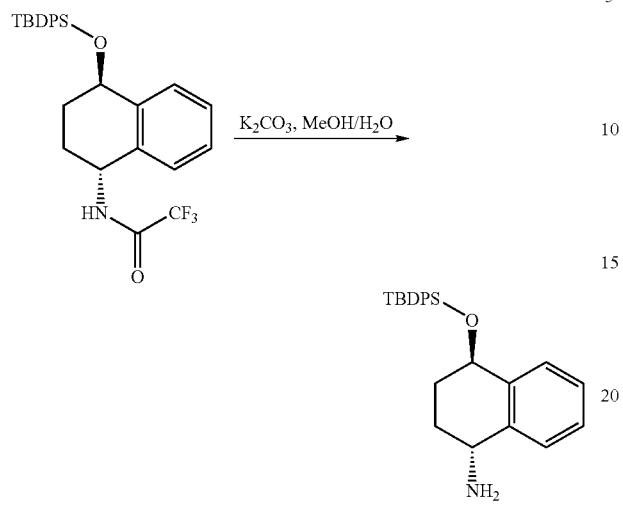

(1R,4R)-4-(tert-Butyldiphenylsilyloxy)-1,2,3,4-tetrahydronaphthalen-1-amine. Potassium carbonate (8.3 g) in water (16 mL) was added to a solution of N-((1R,4R)-4-(tert-butyldiphenylsilyloxy)-1,2,3,4-tetrahydronaphthalen-1-yl)-2,2,2-trifluoroacetamide (4 g) in MeOH (160 mL). The reaction mixture was stirred at room temp overnight then diluted with EtOAc (150 mL), and after separation, the aqueous phase was extracted several times with EtOAc. The organic phase was dried over MgSO₄ and concentrated in vacuo to afford 3.1 g of the title compound, whose purity was good enough to use crude. ¹H-NMR (300 MHz, CDCl3) □ 7.7 (d, 2H), 7.6 (d, 2H), 7.4 (m, 7H), 7.2 (m, 3H), 4.8 (t, 1H), 4.2 (t, 1H), 3.8 (broad s, 2H), 2.4 (m, 1H), 1.8 (m, 2H), 1.6 (m, 1H) ppm.

Preparation of substituted systems: preparation of (1R,4R)-4-(tert-butyldiphenylsilyloxy)-7-fluoro-1,2,3,4-tetrahydronaphthalen-1-amine

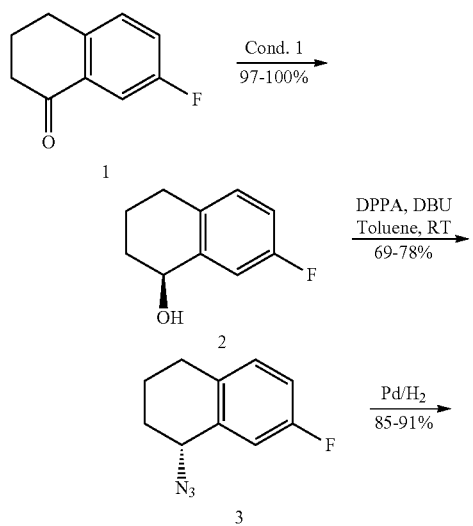

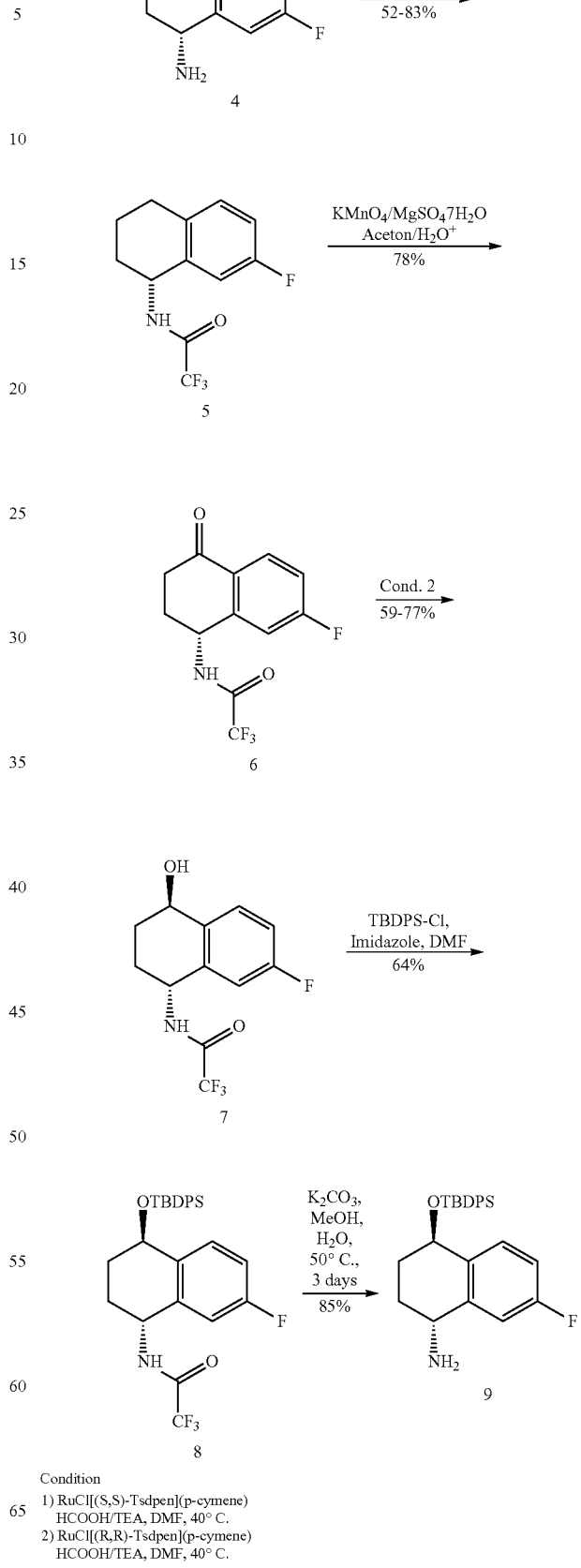

Condition
1) RuCl[(S,S)-Tsdpen](p-cymene) HCOOH/TEA, DMF, 40° C.
2) RuCl[(R,R)-Tsdpen](p-cymene) HCOOH/TEA, DMF, 40° C.

Synthesis of (S)-7-Fluoro-1,2,3,4-tetrahydronaphthalen-1-ol

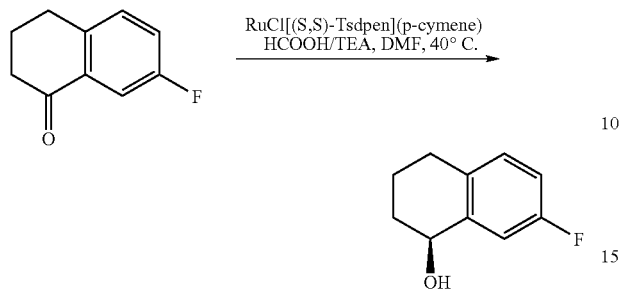

To an ice bath-cooled triethylamine (37.6 mL, 270.5 mmol, 7.4 equiv.) was added drop-wise formic acid (10.4 mL, 270.5 mmol, 7.4 equiv). The reaction solution was stirred at RT for 20 min. 7-Fluoro-3,4-dihydronaphthalen-1(2H)-one (6.0 g, 36.6 mmol, 1 equiv.) and Noyori(S,S) catalyst (560 mg, 2.5 mol %, prepared according to lit. 1, were added. Most was dissolved. DMF (10 mL) was added to make the reaction homogeneous. The reaction turned to dark red and was stirred at 40° C. overnight. TLC was checked and showed no more starting material. The solvents were removed by evaporation. The residue was mixed with water (100 mL) and stirred for 30 min to result a red solid, which was collected on funnel and washed with water and small amount of cold EtOH, then was dried in vacuo overnight. A red solid product (10.1 g, 100%) was obtained. $^1$H NMR (400 MHz, DMSO-d6) δ 7.16 (dd, 1H), 7.08 (t, 1H), 6.86-6.97 (m, 1H), 5.25 (d, 1H), 4.53 (q, 1H), 2.58-2.67 (m, 2H), 1.82-1.90 (m, 2H), 1.59-1.70 (m, 2H).

Synthesis of (R)-1-azido-7-fluoro-1,2,3,4-tetrahydronaphthalene

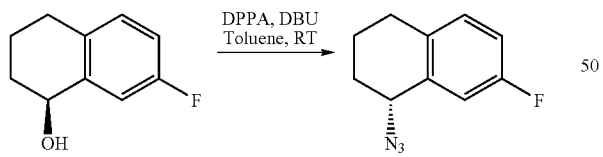

DBU (27.1 mL, 180.5 mmol, 3 equiv.) was added to a solution of (S)-7-Fluoro-1,2,3,4-tetrahydronaphthalen-1-ol (10 g, 60.2 mmol, 1 equiv.) in toluene (300 mL). The resulted dark red solution was cooled in ice bath. Diphenylphosphoryl azide (38.6 mL, 180.6 mmol, 3 equiv) was added drop-wise within 30 min. The reaction solution was slowly brought to RT and stirred overnight. TLC was checked and showed no more SM. The reaction was diluted with methylene chloride (200 mL). The methylene chloride layer was washed with saturated NaHCO$_3$, brine, water, saturated NH$_4$Cl, and brine. The organic layer was separated and dried (Na$_2$SO$_4$), evaporated under reduced pressure to give a dark-red syrup which was purified on ISCO (80 g column, 0-2% EtOAc-hexane) to give a colorless oil product (7.9 g, 70%). $^1$H NMR (400 MHz, CDCl$_3$) δ 7.07-7.11 (m, 1H), 7.02 (dd, 1H), 6.91-6.96 (m, 1H), 4.51 (t, 1H), 2.69-2.86 (m, 2H), 1.76-2.05 (m, 4H).

Synthesis of (R)-7-fluoro-1,2,3,4-tetrahydronaphthalen-1-amine

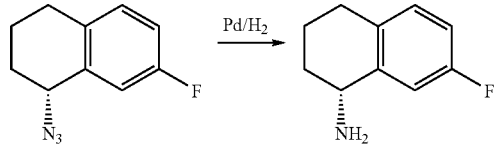

(R)-1-azido-7-fluoro-1,2,3,4-tetrahydronaphthalene (4.85 g) was dissolved in methanol (70 mL) and mixed with Pd/C (10%, wet, 485 mg), applied to Parr apparatus under H$_2$ (35 psi) overnight. The catalyst was removed by filtration and washed twice with MeOH. The filtrate and washings were combined and evaporated under reduced pressure to give a yellow oil product (3.82 g, 91%). $^1$H NMR (400 MHz, DMSO-d6) δ 7.28 (dd, 1H), 7.06 (t, 1H), 6.91 (m, 1H), 3.74-3.76 (m, 1H), 2.60-2.72 (m, 2H), 2.10 (broad, 2H), 1.80-1.90 (m, 2H), 1.45-1.67 (m, 2H). $^{19}$F NMR (400 MHz, DMSO-d6) δ −117.6.

Synthesis of (R)-2,2,2-trifluoro-N-(7-fluoro-1,2,3,4-tetrahydronaphthalen-1-yl)acetamide

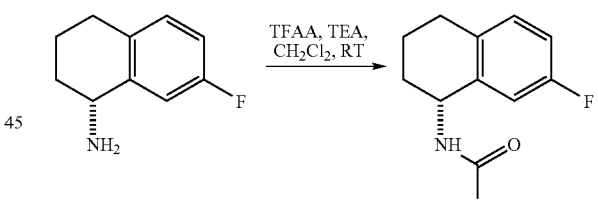

(R)-7-fluoro-1,2,3,4-tetrahydronaphthalen-1-amine (6.13 g, 37.1 mmol, 1 equiv) was dissolved in methylene chloride (80 mL) containing triethylamine (10.3 mL, 2 equiv) and cooled in ice bath. Trifluoroacetic anhydride (7.6 mL, 55.7 mmol, 1.5 equiv) was added dropwise within 20 min. The reaction solution was stirred at RT under argon for 16 h. The reaction was diluted with dichloromethane (20 mL) and washed with saturated NaHCO$_3$, brine and dried (Na$_2$SO$_4$). Solvents were removed by evaporation. The residue was purified on ISCO (0-20% EtOAc-hexane) to give a white solid product (7.85 g, 81%). $^1$H NMR (400 MHz, DMSO-d6) δ 9.83 (s, 1H), 7.15-7.20 (m, 1H), 7.04 (m, 1H), 6.88 (dd, 1H), 4.99-5.02 (m, 1H), 2.69-2.79 (m, 2H), 1.70-1.99 (m, 4H).

Synthesis of (R)-2,2,2-trifluoro-N-(7-fluoro-4-oxo-1,2,3,4-tetrahydronaphthalen-1-yl)acetamide

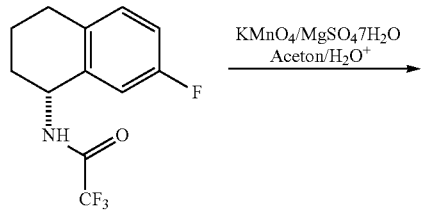

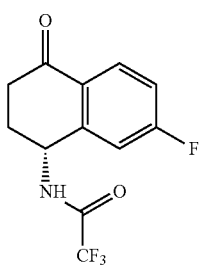

To a solution of (R)-2,2,2-trifluoro-N-(7-fluoro-1,2,3,4-tetrahydronaphthalen-1-yl)acetamide (3.51 g, 13.4 mmol, 1 equiv) in acetone (217 mL) was added magnesium sulfate heptahydrate (9.92 g, 40.3 mmol, 3 equiv) with water (167 mL). The mixture was stirred in ice bath. Potassium permangnate (6.37 g, 40.3 mmol, 3 equiv) was added in portions within 1 hour period. After addition, the reaction mixture was stirred at RT for 16 h. The resulting black solid was filtered off and washed with acetone. The combined filtrate and washings were diluted with $CH_2Cl_2$ (200 mL). The aqueous phase was separated and washed with $CH_2Cl_2$. The $CH_2Cl_2$ solution was washed with saturated $Na_2S_2O_7$ solution (150 mL). The resulting black solid was filtered off The filtrate was evaporated to remove organic solvents. The concentrate was diluted with $CH_2Cl_2$ (400 mL). The aqueous phase was separated and washed with CH2Cl2. The combined $CH_2Cl_2$ phase was concentrated to give a white solid product (3.54 g, 96%). $^1H$ NMR (400 MHz, DMSO-d6) δ 10.00 (s, 1H), 8.00 (q, 1H), 7.30-7.36 (m, 1H), 7.15 (dd, 1H), 5.32-5.38 (m, 1H), 2.60-2.85 (m, 2H), 2.16-2.30 (m, 2H).

Synthesis of 2,2,2-Trifluoro-N-((1R,4R)-7-fluoro-4-hydroxy-1,2,3,4-tetrahydronaphthalen-1-yl) acetamide

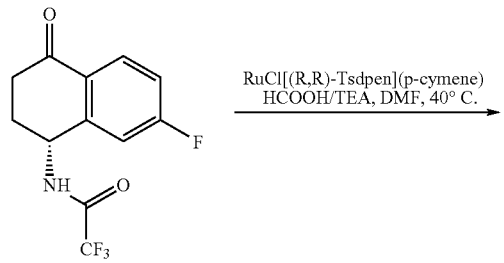

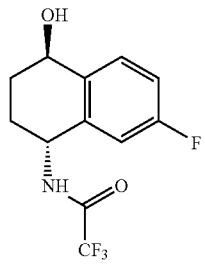

To ice bath-cooled triethylamine (13.3 mL, 95.2 mmol, 7.4 equiv.) was added dropwise formic acid (3.65 mL, 95.2 mmol, 7.4 equiv.). The reaction solution was stirred at RT for 20 min. A solution of (R)-2,2,2-trifluoro-N-(7-fluoro-4-oxo-1,2,3,4-tetrahydronaphthalen-1-yl)acetamide (3.54 g, 12.9 mmol, 1 equiv) in DMF (10 ml) and Noyori catalyst (R,R form) (204.3 mg, 2.5 mol %) were added and stirred at RT overnight. TLC was checked and found only small amount of product formed. The reaction solution was stirred at 40° C. for 16 h. TLC showed reaction completed. The solvents were evaporated off The residue was treated with $CH_2Cl_2$ to result a white solid precipitate, which was collected on funnel and washed with small amount of $CH_2Cl_2$ (2.15 g). The filtrate gave additional 0.58 g of product after chromatography (ISCO, 30-40% EtOAc-hexane). Total: 2.73 g (77%). $^1H$ NMR (400 MHz, DMSO-d6) δ 9.83 (s, 1H), 7.52 (q, 1H), 7.13 (m, 1H), 6.85 (dd, 1H), 5.36 (d, 1H), 5.05 (m, 1H), 4.55-4.62 (m, 1H), 2.06-2.14 (m, 2H), 1.64-1.80 (m, 2H).

Synthesis of N-((1R,4R)-4-(tert-butyldiphenylsilyloxy)-7-fluoro-1,2,3,4-tetrahydronaphthalen-1-yl)-2,2,2-trifluoroacetamide

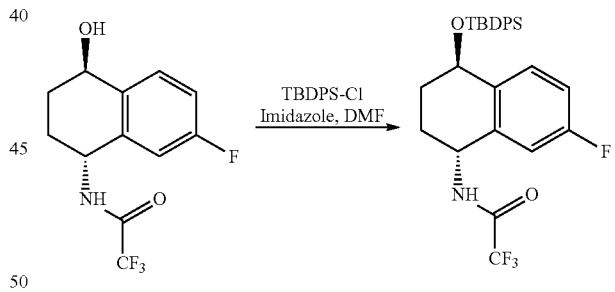

2,2,2-Trifluoro-N-((1R,4R)-7-fluoro-4-hydroxy-1,2,3,4-tetrahydronaphthalen-1-yl)acetamide (2.71 g, 9.78 mmol, 1 equiv) and imidazole (1.33 g, 19.56 mmol, 2 equiv) were dissolved in anhydrous DMF (40 mL) and cooled in ice bath. Tert-Butyldiphenylsilyl chloride (3.25 mL, 12.71, 1.3 equiv) was added dropwise. The reaction solution was stirred at RT for 16 h. The DMF was removed by evaporation. The residue was dissolved in EtOAc (200 mL) and washed with water, brine and dried ($Na_2SO_4$). The organic phase was evaporated to dryness to give an oil residue, which was purified by ISCO (40 g column, EtOAc-hexane 10-50%) to give a white solid product (2.16 g, TLC: pure) and a mixture (3.0 g). $^1H$ NMR (400 MHz, DMSO-d6) δ 9.11 (s, 1H), 7.26-7.30 (q, 1H), 7.09 (m, 1H), 6.98 (dd, 1H), 5.07-5.14 (m, 1H), 4.77-4.80 (m, 1H), 2.06-2.15 (m, 1H), 1.74-1.92 (m, 2H), 1.56-1.669 m, 1H), 1.03 (s, 9H).

Synthesis of (1R,4R)-4-(tert-butyldiphenylsilyloxy)-7-fluoro-1,2,3,4-tetrahydronaphthalen-1-amine

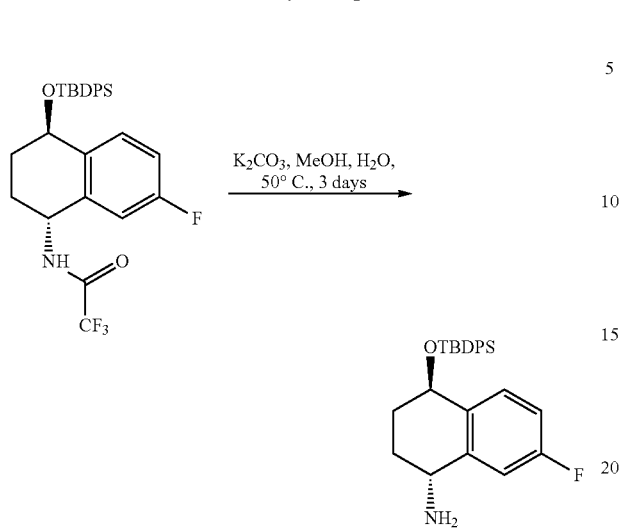

A mixture of N-((1R,4R)-4-(tert-butyldiphenylsilyloxy)-7-fluoro-1,2,3,4-tetrahydronaphthalen-1-yl)-2,2,2-trifluoroacetamide (2.16 g, 4.19 mmol, 1 equiv) and $K_2CO_3$ (4.06 g, 29.3 mmol, 7 equiv) in MeOH (166 mL) plus water (16.7 mL) was stirred at 50° for 3 days. TLC showed no more SM. The solvents were evaporated off The residue was dissolved in EtOAc (100 mL) and washed with water, brine and dried ($Na_2SO_4$). Evaporation of EtOAc solution gave an oil crude which was purified by ISCO (40 g column, MeOH-DCM 0-20%) to give a colorless oil product (1.5 g). A mixture from (8) was treated by the same method as above to give a colorless oil product (2.3 g). Total: 3.8 g (yield from 7 to 9: 91%). MS (ESI): 420.4; $^1$H NMR (400 MHz, DMSO-d6) δ 7.60-7.85 (m, 4H), 7.42-7.45 (m, 6H), 7.27-7.33 (dd, 1H), 7.17-7.22 (m, 1H), 6.92-6.97 (t, 1H), 4.75 (m, 1H), 3.77-3.84 (m, 1H), 3.33 (broad, 1H), 2.00-2.09 (m, 1H), 1.82-1.90 (m, 1H), 1.63-1.73 (m, 1H), 1.27-1.39 (m, 1H), 1.02 (s, 9H); 19F NMR (400 MHz, DMSO-d6) δ −115.3.

Synthesis of (1R,4R)-4-(tert-butyldiphenylsilyloxy)-5,7-difluoro-1,2,3,4-tetrahydronaphthalen-1-amine

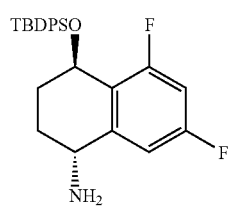

The title compound was synthesized in the same manner as (1R,4R)-4-(tert-butyldiphenylsilyloxy)-7-fluoro-1,2,3,4-tetrahydronaphthalen-1-amine. $^1$H-NMR (300 MHz, $CD_3OD$) □ 7.7 (d, 2H), 7.5 (d, 2H), 7.2-7.4 (m, 6H), 6.8 (d, 1H), 6.5 (t, 1H), 4.9 (m, 1H), 4.1 (m, 1H), 2.5 (m, 1H), 1.8 (m, 2H), 1.6 (m, 1H), 1.0 (s, 9H) ppm.

The above method is generally applicable to stereo-controlled synthesis of protected 4-hydroxytetrahydronapthalen-1-amines:

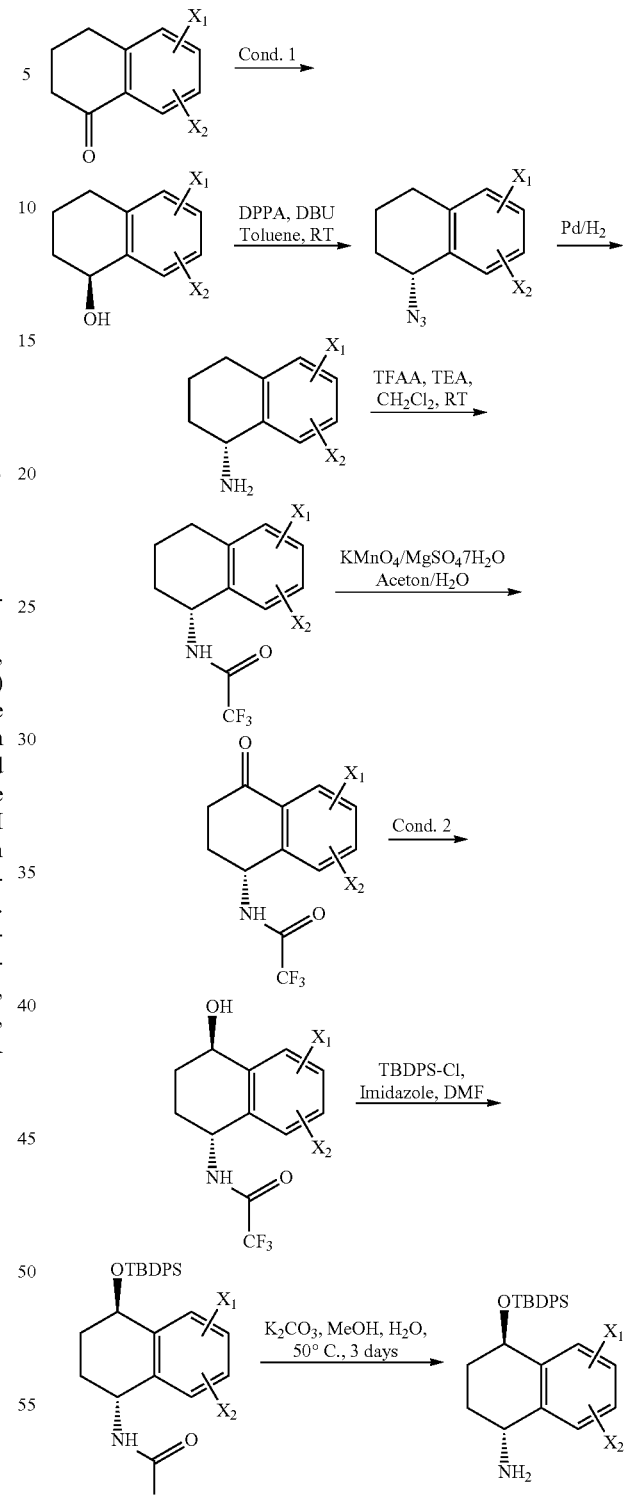

Condition
1) RuCl[(S,S)-Tsdpen](p-cymene) HCOOH/TEA, DMF, 40° C.
2) RuCl[(R,R)-Tsdpen](p-cymene) HCOOH/TEA, DMF, 40° C.

wherein $X_1$ and $X_2$ may be substituents such as hydrogen, lower alkyl, halogen, nitrile, trifluoromethyl, lower alkoxy, carboxy, carboxamide, and the like.

Synthesis of 1-(5-nitro-4-thiocyanatopyrimidin-2-yl)benzimidazole

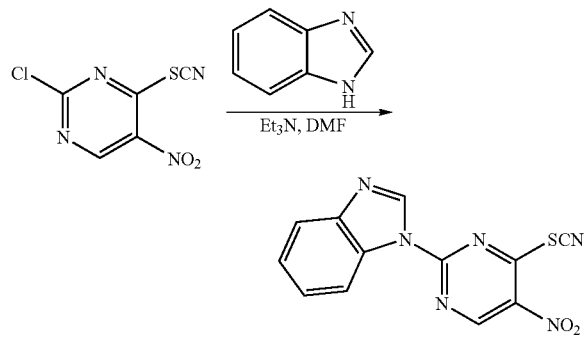

A mixture of 2-chloro-5-nitro-4-thiocyanatopyrimidine (5.0 g, 23 mmol, WO 2003/032994) and benzimidazole (2.72 g, 23 mmol) in 200 mL of DMF was cooled to 0 C and Et₃N (2.33 g, 23 mmol) was added. The ice-bath was removed and the contents were stirred for 3 h at RT. The reaction mixture was diluted with water and filtered. The solid was washed with water, followed by ice-cold methanol and dried in vacuo to provide 3.1 g of 1-(5-nitro-4-thiocyanatopyrimidin-2-yl)benzimidazole. $^1$H NMR (300 MHz, DMSO-d6) □□ 9.70 (s, 1H), 9.15 (s, 1H), 8.90-8.80 (m, 1H), 7.95-7.80 (m, 1H), 7.55-7.35 (m, 2H).

Preparation of 6-fluoro-1-(5-nitro-4-thiocyanatopyrimidin-2-yl)-1H-benzo[d]imidazole: Synthesis of tert-butyl 2-amino-4-fluorophenylcarbamate

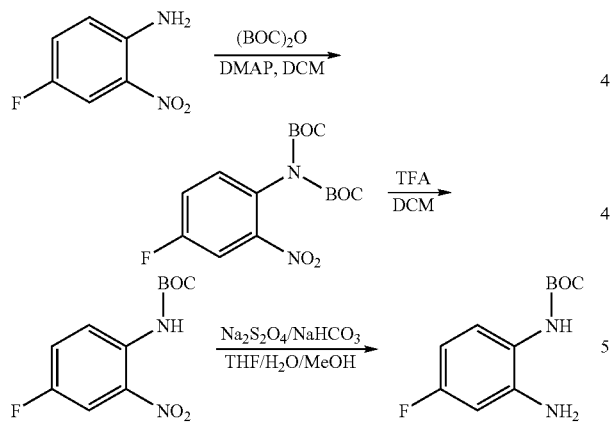

4-Fluoro-2-nitro-phenyl di-tert-butyl imidodicarbonate. A catalytic amount of DMAP was added to a mixture of 4-fluoro-2-nitrobenzenamine (0.78 g) and di-tert-butyl dicarbonate (2.18 g) in DCM (20 mL) and stirred at room temperature for 15 hr. The mixture was diluted with H₂O and twice extracted with DCM, the combined organics were dried, filtered and evaporated to yield the bis-BOC material (quant), $^1$H-NMR (300 MHz, CDCl₃) δ 7.8 (dd, 1H), 7.3 (m, 2H), 1.4 (s, 18H); 19F δ −109 ppm that was used as such in the next step.

tert-Butyl 4-fluoro-2-nitrophenylcarbamate. (procedure: Connell, R. D.; Rein, T.; Akermark, B.; Helquist, P. J. J. Org. Chem. 1988, 53, 3845) To a stirred solution of the Bis-BOC material in DCM (20 mL) was added TFA (0.58 mL). After 3 hr the reaction was quenched with aq. NaHCO₃ (5 mL), brine was added, the mixture separated and extracted with additional DCM. The combined organics were evaporated, purified via column chromatography (eluted with 7.5% EtOAc/Hex) to give the titled product (1.12 g), 1H-NMR (300 MHz, CDCl₃) δ 9.5 (br 1H), 8.5 (dd, 1H), 7.9 (dd, 1H), 7.3 (m, 1H), 1.5 (s, 9H); 19F δ −119 ppm.

tert-Butyl 2-amino-4-fluorophenylcarbamate. To a solution of tert-butyl 4-fluoro-2-nitrophenylcarbamate (0.34 g) in THF (30 mL) was added a premixed solution of sodium hydrosulfite (2 g) and sodium bicarbonate (1 g) in water (50 mL). MeOH (10 mL) was also added to aid solution of the mixture, which was stirred at room temperature for 30 min, when sodium chloride was added to saturate the solution. The resultant mixture was extracted with EtOAc (2×). The combined organics were dried, filtered and evaporated to yield the titled compound (quant) that was used as such for the next step. $^1$H-NMR (300 MHz, CDCl₃) δ 7.5 (dd, 1H), 6.6 (dd, 1H), 6.5 (m, 1H), 6.4 (br 1H), 4.7 (br 2H), 1.5 (s, 9H); 19F δ −119 ppm; MH+=227 (minor) 127 (-BOC), 171 (-tBu).

Synthesis of 6-fluoro-1-(5-nitro-4-thiocyanatopyrimidin-2-yl)-1H-benzo[d]imidazole

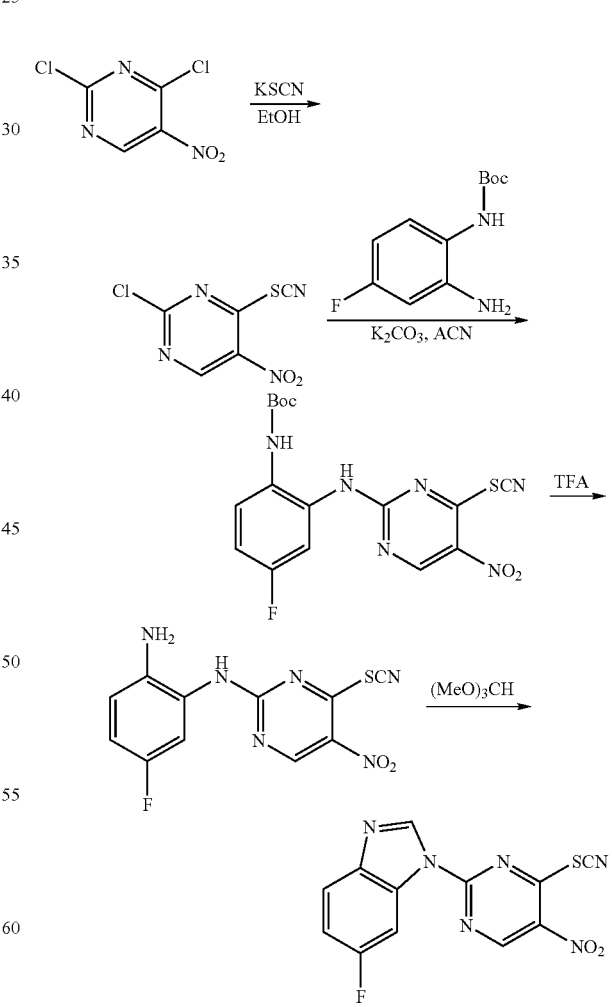

2-Chloro-5-nitro-4-thiocyanatopyrimidine. (compound known, e.g. WO 2003/032994) Potassium thiocyanate (0.97 g, 10 mM) was added to a solution of 2,4-dichloro-5-nitropyrimidine (1.94 g 10, mM) in EtOH (40 mL) cooled to 0° C. via an ice bath. The solution was stirred at 0° C. for 30 min, then the bath was removed and the resulting suspension allowed to come to RT over 60 min, when water (100 mL) was added. The precipitate was collected via filtration, washed with ice cold water, dissolved with DCM, dried (MgSO$_4$), filtered and evaporated to yield the titled compound (1.7 g). NMR CDCl$_3$ 1H δ 9.4 (s, 1H) ppm.

tert-Butyl 4-fluoro-2-(5-nitro-4-thiocyanatopyrimidin-2-ylamino)phenylcarbamate. Potassium carbonate (207 mg) was added to a stirred solution of 2-chloro-5-nitro-4-thiocyanatopyrimidine (108 mg) and tert-butyl 4-fluoro-2-nitrophenylcarbamate (113 mg) in ACN (5 mL) and stirred for 15 hr. The solution was diluted with brine and extracted with EtOAc (2×). The combined organics were evaporated and purified via column chromatography, elution with 30% EtOAc/Hex gave the titled compound (144 mg, 71% yield) $^1$H-NMR (300 MHz, DMSO-d6) δ 10.5 (br s, 1H), 9.3 (br s, 1H), 8.9 (br s, 1H), 7.7-7.4 (m, 2H), 7.1 (br s, 1H), 1.5 (s, 9H), 1.5 (s, 9H) ppm; MH+=407, 307 (-BOC), 351 (-tBu).

6-Fluoro-1-(5-nitro-4-thiocyanatopyrimidin-2-yl)-1H-benzo[d]imidazole tert-Butyl 4-fluoro-2-(5-nitro-4-thiocyanatopyrimidin-2-ylamino)phenylcarbamate (4.06 g) was dissolved in 30% TFA/DCM (50 mL) and stirred until no starting material remained (90 min). The reaction solvents were removed, to yield crude 5-fluoro-N1-(5-nitro-4-thiocyanatopyrimidin-2-yl)benzene-1,2-diamine (MH+=306) as a TFA salt that was used immediately as such in the next step. Trimethyl ortho formate (15 mL) and MeOH (100 mL) were added to the above diamine and the solution was stirred for 16 hrs. The resulting orange ppt was collected via filtration, washed with MeOH and dried under reduced pressure to yield the titled compound (2.62 g), $^1$H-NMR (400 MHz, d6-DMSO) δ 9.2 (s, 1H), 9.1 (s, 1H), 8.5 (dd, 1H), 7.8 (dd, 1H), 7.3 (dd, 1H) ppm; MH+=317.

Some similar thiocyanatopyrimidines, such as tert-butyl 4-chloro-2-(5-nitro-4-thiocyanatopyrimidin-2-ylamino)phenylcarbamate, tert-butyl 2-(5-nitro-4-thiocyanatopyrimidin-2-ylamino)-4-(trifluoromethoxy)phenylcarbamate, and tert-butyl 2-(5-nitro-4-thiocyanatopyrimidin-2-ylamino)-4-(trifluoromethyl)phenylcarbamate, were prepared via procedures described above for the synthesis of tert-butyl 4-fluoro-2-(5-nitro-4-thiocyanatopyrimidin-2-ylamino)phenylcarbamate, from corresponding 4-chloro-2-nitrobenzenamine, 2-nitro-4-(trifluoromethyl)benzenamine and 2-nitro-4-(trifluoromethoxy)benzenamine.

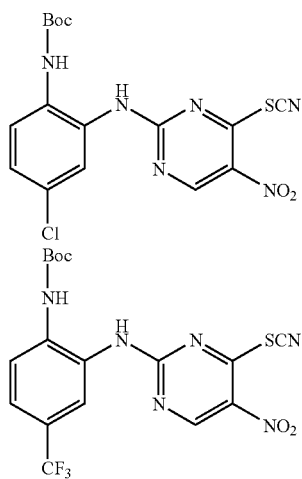

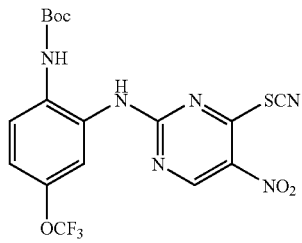

Preparation of 3-(5-nitro-4-thiocyanatopyrimidin-2-yl)-3H-benzo[d]imidazole-5-carbonitrile

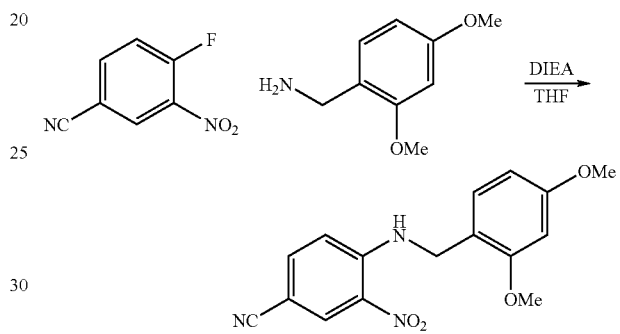

4-(2,4-Dimethoxybenzylamino)-3-nitrobenzonitrile. A solution of 4-fluoro-3-nitrobenzonitrile (5.0 g) in THF (100 mL) was treated with DIEA (6.3 mL) and 2,4-dimethoxybenzylamine (5.0 mL), and then stirred for 24 h. The solvent was evaporated and the crude mixture was dissolved in EtOAc (100 mL). The solution was washed once with 1 M HCl and twice with saturated aqueous NaCl (100 mL each). The organic layer was separated, dried over Na$_2$SO$_4$, filtered, and concentrated in vacuo. Column chromatography (20% EtOAc/DCM) provided 9.25 g of the title compound.

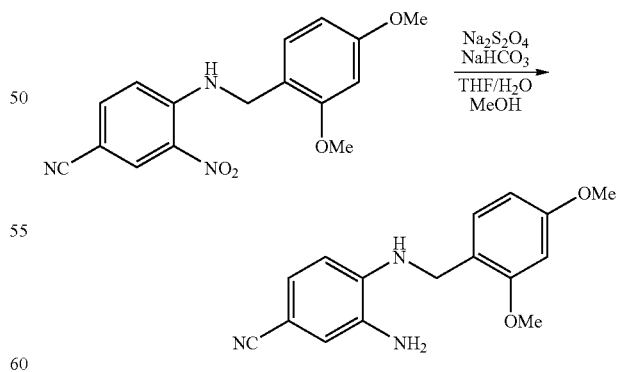

4-(2,4-Dimethoxybenzylamino)-3-aminobenzonitrile. A solution of 4-(2,4-dimethoxybenzylamino)-3-nitrobenzonitrile (4.54 g) in THF (400 mL) was treated with a solution of sodium hydrosulfite (20 g) and sodium bicarbonate (10 g) in distilled water (350 mL). Enough methanol was immediately added (50 mL) to maintain a homogeneous solution. After 15 minutes, EtOAc (500 mL) and saturated aqueous NaCl (500 mL) were added and the organic layer was separated. The aqueous layer was extracted again with 400 mL EtOAc. The combined organic layers were washed with saturated aqueous NaCl (500 mL) and separated. The organic phase was dried over Na$_2$SO$_4$, filtered, and concentrated in vacuo to provide 4.33 g of the title compound.

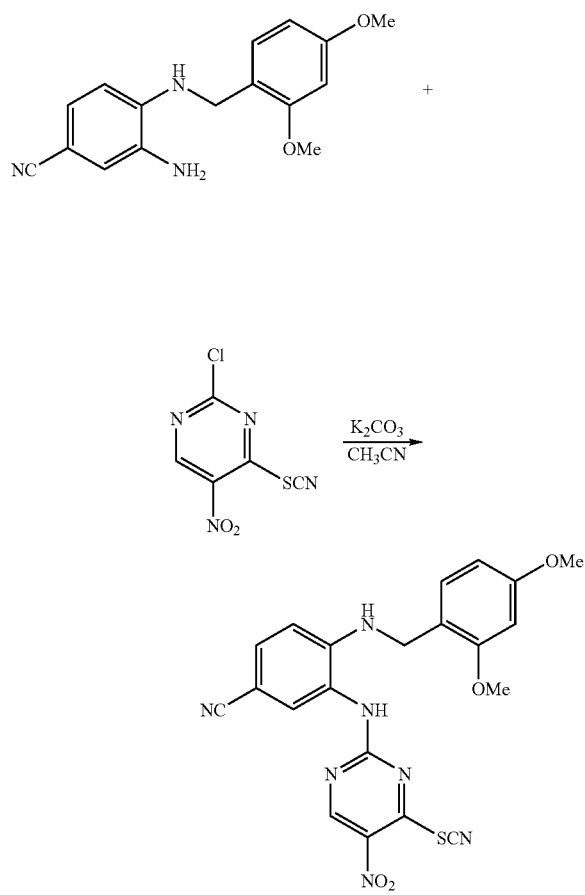

4-(2,4-Dimethoxybenzylamino)-3-(5-nitro-4-thiocyanatopyrimidin-2-ylamino)benzonitrile. A solution of 4-(2,4-dimethoxybenzylamino)-3-aminobenzonitrile (3.9 g) in acetonitrile (100 mL) was cooled to 0° C. and treated with potassium carbonate (6.3 g) followed by a solution containing 3 g of 2-chloro-5-nitro-4-thiocyanatopyrimidine (WO 2003/032994) in acetonitrile (50 mL). The mixture was stirred for 30 minutes at 0° C. and 30 minutes at room temperature resulting in the formation of a precipitate. The mixture was quenched at 0° C. by the addition of 4% acetic acid (150 mL) and filtered. The precipitate was swirled in 100 mL acetonitrile and filtered again. The precipitate was washed with acetonitrile, which resulted in the slow dissolution of product into the filtrate. After air-drying, 1.5 g of the title compound remained as the precipitate cake. The filtrate was extracted with EtOAc, dried over Na$_2$SO$_4$, filtered, and concentrated in vacuo. Column chromatography (0→20% EtOAc/DCM) and recrystallization from acetonitrile provided 0.415 g of additional title compound.

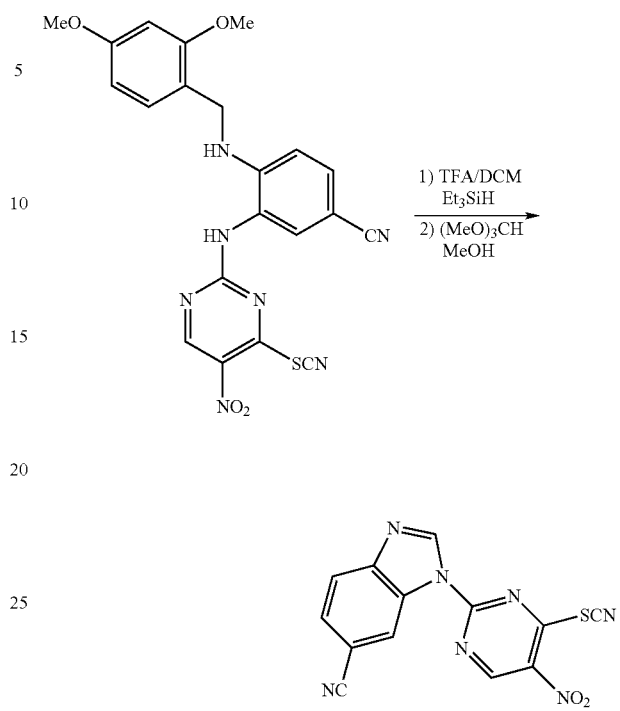

3-(5-Nitro-4-thiocyanatopyrimidin-2-yl)-3H-benzo[d]imidazole-5-carbonitrile. To a solution of 0.58 g (1.25 mmol) 4-(2,4-dimethoxybenzylamino)-3-(5-nitro-4-thiocyanatopyrimidin-2-ylamino)benzonitrile in 10 mL 30% (v/v) TFA in DCM was added 0.01 mL of triethylsilane. The mixture was stirred for 0.5 hr, LCMS indicated the completion of deprotection. A red residue was obtained after removing the volatiles on rotary evaporator, and was suspended (majority dissolved) in 10 mL 1:1 trimethyl orthoformate:MeOH. The resulting mixture was stirred for 2 hrs at room temperature. Yellow solids were precipitated. Desired product (0.38 g, ~95% overall yield) was obtained after suction filtration and washing with cold MeOH twice. $^1$H-NMR (300 MHz, CDCl$_3$+10% CD$_3$OD) δ 9.5 (s, 1H), 9.2 (s, 1H), 9.1 (s, 1H), 7.9 (d, 1H), 7.7 (d, 1H) ppm; MS (ESI), m/z 324 ([M+H]+).

Preparation of 3-(9-((1R,4R)-4-hydroxy-1,2,3,4-tetrahydronaphthalen-1-yl)-7H-8-oxo-8,9-dihydro-7H-purin-2-yl)-3H-benzo[d]imidazole-5-carbonitrile

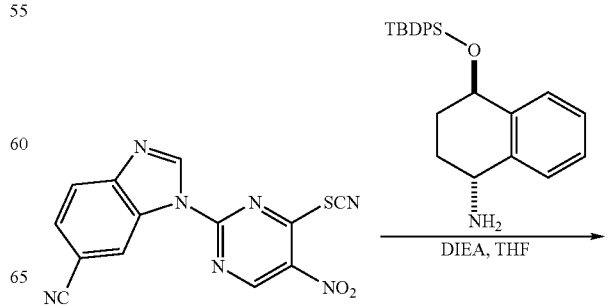

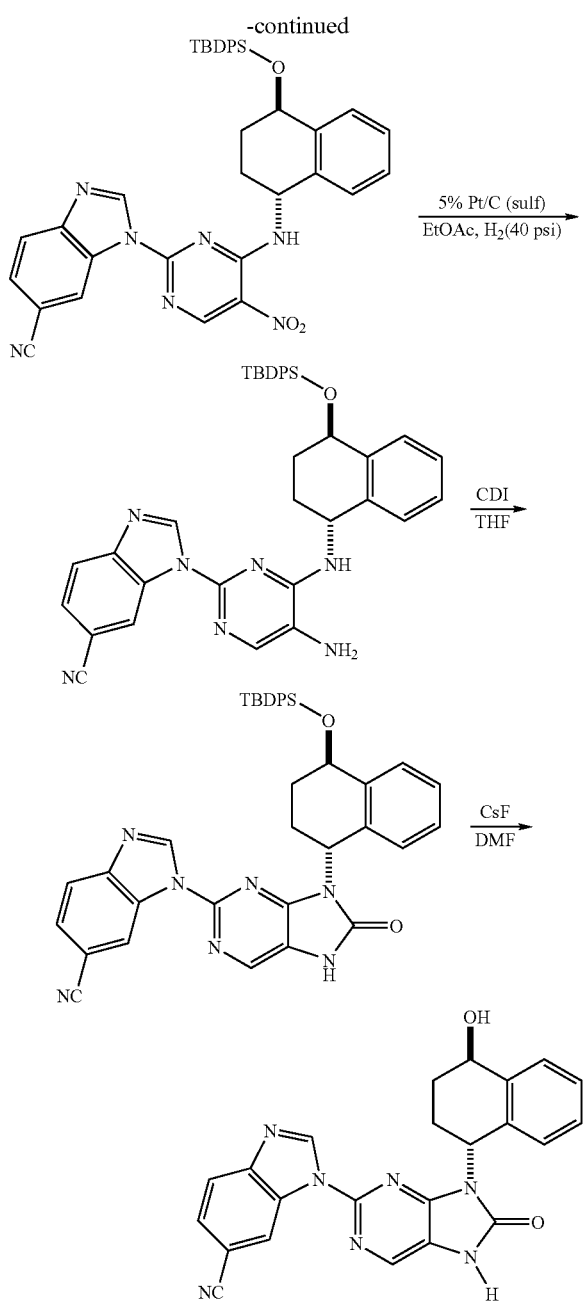

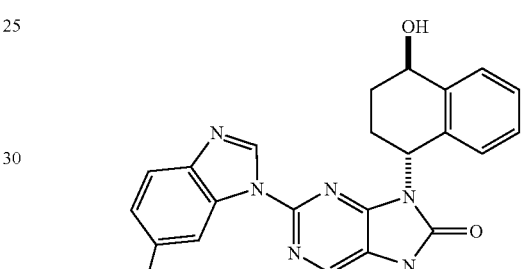

3-(4-((1R,4R)-4-(tert-butyldiphenylsilyloxy)-1,2,3,4-tetrahydronaphthalen-1-ylamino)-5-nitropyrimidin-2-yl)-3H-benzo[d]imidazole-5-carbonitrile. A solution of (1R,4R)-4-(tert-butyldiphenylsilyloxy)-1,2,3,4-tetrahydronaphthalen-1-amine (4.0 g) and DIEA (5.3 mL) in anhydrous THF (20 mL) were added via syringe over 1 min to 6-cyano-1-(5-nitro-4-thiocyanatopyrimidin-2-yl)-1H-benzo[d]imidazole (3.43 g, 10.601 mM) in THF at 0° C. The resulting solution was allowed to warm slowly to RT overnight, then partitioned between water and DCM. Column purification (1% MeOH/DCM) gave the titled product (5.21 g), MH+=666.

3-(9-((1R,4R)-4-(tert-butyldiphenylsilyloxy)-1,2,3,4-tetrahydronaphthalen-1-yl)-8-oxo-8,9-dihydro-7H-purin-2-yl)-3H-benzo[d]imidazole-5-carbonitrile. Under a flush of Ar, 0.52 g of 5% Pt/C (sulfided) was added to a solution of 3-(4-((1R,4R)-4-(tert-butyldiphenylsilyloxy)-1,2,3,4-tetrahydronaphthalen-1-ylamino)-5-nitropyrimidin-2-yl)-3H-benzo[d]imidazole-5-carbonitrile (5.2 g) in 3:1 EtOAc/MeOH (30 mL), in a Parr hydrogenation vessel. The mixture was then evacuated under vacuum/filled with hydrogen 3 times. The resulting suspension was stirred at RT for 15 hr under 40 psi of hydrogen. The mixture was then evacuated, air was slowly let in, and then it was filtered through a plug of celite, that was thoroughly rinsed with EtOAc and MeOH. Evaporation of the solvents under vacuum afforded 3-(5-amino-4-((1R,4R)-4-(tert-butyldiphenylsilyloxy)-1,2,3,4-tetrahydronaphthalen-1-ylamino)pyrimidin-2-yl)-3H-benzo[d]imidazole-5-carbonitrile (MH+=636) that was used as such. The above diamine was dissolved in anhydrous THF and treated with an excess of 1,1'-carbonyldiimidazole (3+ eq.) and stirred under an Ar atmosphere for 15 hr. Upon completion of the reaction the mixture was partition between water and DCM, separated and solvents removed under reduced pressure. Purification via column chromatography (elution with 1% MeOH/DCM) yielded the titled product (4.43 g), MH+=662.

3-(9-((1R,4R)-4-hydroxy-1,2,3,4-tetrahydronaphthalen-1-yl)-8-oxo-8,9-7H-purin-2-yl)-3H-benzo[d]imidazole-5-carbonitrile. A mixture of 3-(9-((1R,4R)-4-(tert-butyldiphenylsilyloxy)-1,2,3,4-tetrahydronaphthalen-1-yl)-8-oxo-8,9-dihydro-7H-purin-2-yl)-3H-benzo[d]imidazole-5-carbonitrile (0.18 g) and CsF (xs, 60 mg) in DMF were stirred and heated at 55° C. for 15 hr at which time LC analysis indicated no SM remained. The cooled mixture was treated with water and extracted twice with DCM. The combined organics were concentrated and purified via column chromatography (elution with 1 and 2% MeOH/DCM) to yield the titled product (100 mg). $^1$H-NMR (300 MHz, CDCl$_3$) δ 9.1 (m, 2H), 8.4 (d, 2H), 8.1 (d, 1H), 8.0 (d, 1H), 7.7 (d, 1H), 7.4 (t, 1H), 7.2 (t, 1H), 7.0 (d, 1H), 6.1 (dd, 1H), 5.5 (dd, 1H), 2.8-2.4 (m, 4H), 2.2 (q, 1H), 1.5 (bs, 1H) ppm; MH+=424.

Synthesis of substituted hydroxytetralins

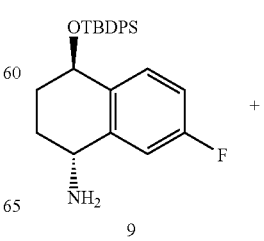

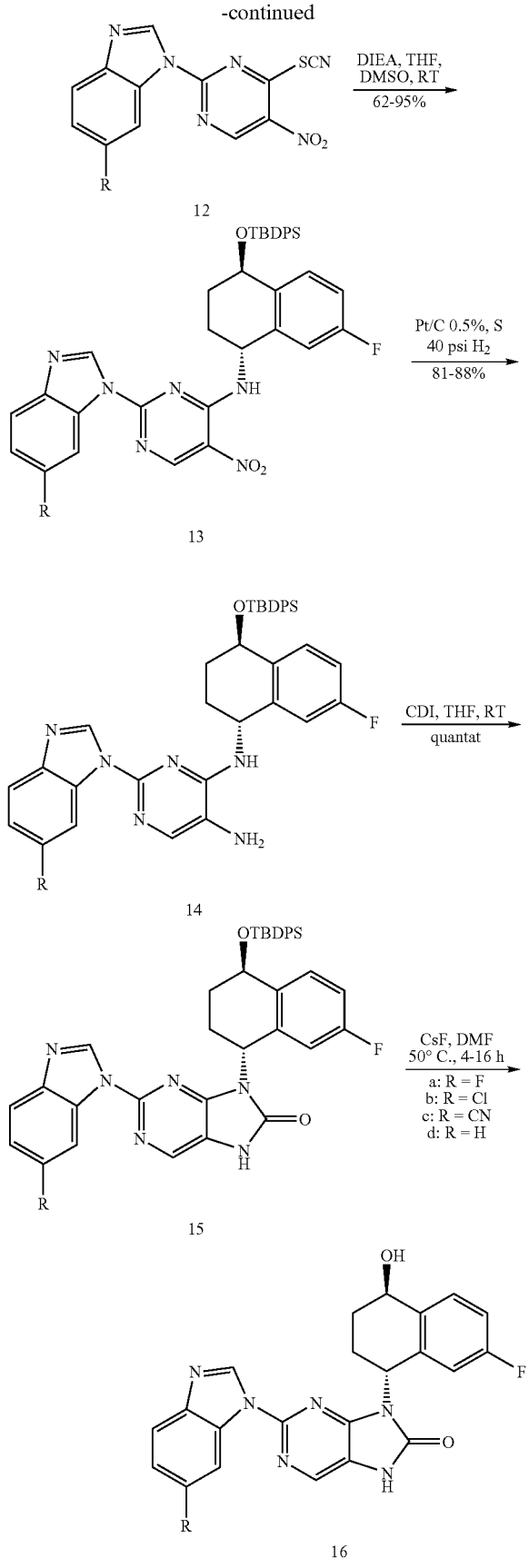

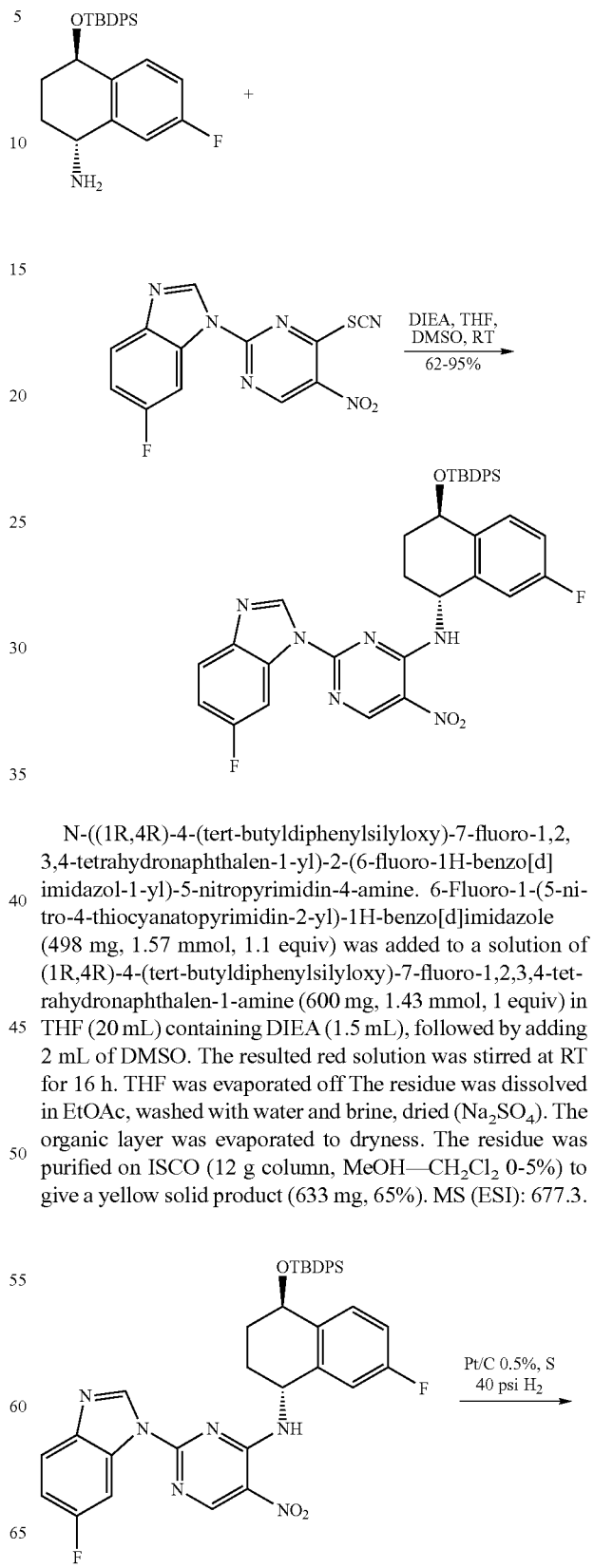

Method for synthesis of 16a, R=F The synthesis of 16b-d is analogous to 16a.

N-((1R,4R)-4-(tert-butyldiphenylsilyloxy)-7-fluoro-1,2,3,4-tetrahydronaphthalen-1-yl)-2-(6-fluoro-1H-benzo[d]imidazol-1-yl)-5-nitropyrimidin-4-amine. 6-Fluoro-1-(5-nitro-4-thiocyanatopyrimidin-2-yl)-1H-benzo[d]imidazole (498 mg, 1.57 mmol, 1.1 equiv) was added to a solution of (1R,4R)-4-(tert-butyldiphenylsilyloxy)-7-fluoro-1,2,3,4-tetrahydronaphthalen-1-amine (600 mg, 1.43 mmol, 1 equiv) in THF (20 mL) containing DIEA (1.5 mL), followed by adding 2 mL of DMSO. The resulted red solution was stirred at RT for 16 h. THF was evaporated off The residue was dissolved in EtOAc, washed with water and brine, dried (Na$_2$SO$_4$). The organic layer was evaporated to dryness. The residue was purified on ISCO (12 g column, MeOH—CH$_2$Cl$_2$ 0-5%) to give a yellow solid product (633 mg, 65%). MS (ESI): 677.3.

-continued

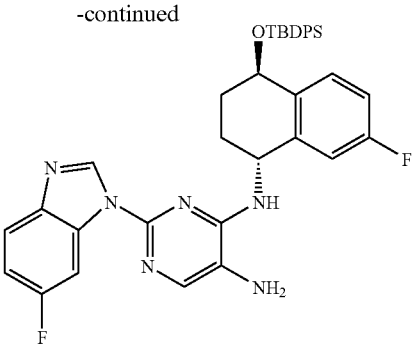

N4-((1R,4R)-4-(tert-butyldiphenylsilyloxy)-7-fluoro-1,2,3,4-tetrahydronaphthalen-1-yl)-2-(6-fluoro-1H-benzo[d]imidazol-1-yl)pyrimidine-4,5-diamine. N-((1R,4R)-4-(tert-butyldiphenylsilyloxy)-7-fluoro-1,2,3,4-tetrahydronaphthalen-1-yl)-2-(6-fluoro-1H-benzo[d]imidazol-1-yl)-5-nitropyrimidin-4-amine (633 mg, 0.975 mmol) was dissolved in EtOAc (25 mL) and MeOH (25 mL), and mixed with platinum on carbon, sulfided (10%, wet) (127 mg, 20% w/w). The reaction mixture was applied to Parr apparatus under H2 (40 psi) for 5 h. TLC showed the reaction completed. The catalyst was filtered off and washed with MeOH. The filtrate and washings were combined and evaporated to dryness to give a white solid product (498 mg, 82%). MS (ESI): 647.5; $^1$H NMR (400 MHz, DMSO-d6) δ 8.95 (s, 1H), 8.18 (dd, 1H), 7.63-7.76 (m, 6H), 7.41-7.53 (m, 6H), 7.25-7.30 (m, 1H), 7.02-7.22 (m, 3H), 5.57-5.65 (m, 1H), 4.92 (broad, 2H), 4.87-4.91 (m, 1H), 2.28-2.38 (m, 1H), 1.86-1.98 (m, 2H), 1.72-1.82 (m, 1H), 1.02 (s, 9H).

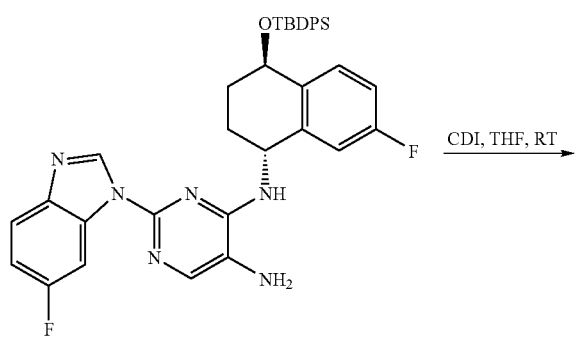

9-((1R,4R)-4-(tert-butyldiphenylsilyloxy)-7-fluoro-1,2,3,4-tetrahydronaphthalen-1-yl)-2-(6-fluoro-1H-benzo[d]imidazol-1-yl)-7H-purin-8(9H)-one. N4-((1R,4R)-4-(tert-butyldiphenylsilyloxy)-7-fluoro-1,2,3,4-tetrahydronaphthalen-1-yl)-2-(6-fluoro-1H-benzo[d]imidazol-1-yl)pyrimidine-4,5-diamine (490 mg, 0.751 mmol, 1 equiv) was dissolved in anhydrous THF (15 mL) and CDI (737 mg, 4.54 mmol, 7 equiv) was added. The reaction was stirred at RT under argon overnight. The solvent was removed by evaporation. The residue was dissolved in EtOAc (30 mL) and washed with saturated NaHCO₃, water and brine, dried (Na₂SO₄). The organic layer was evaporated to dryness. The residue was applied to ISCO (12 g column, MeOH—CH₂Cl₂ 0-2%) to give a white solid product (420 mg, 82%). MS (ESI): 673.3

Synthesis of 2-(6-fluoro-1H-benzo[d]imidazol-1-yl)-9-((1R,4R)-7-fluoro-4-hydroxy-1,2,3,4-tetrahydronaphthalen-1-yl)-7H-purin-8(9H)-one

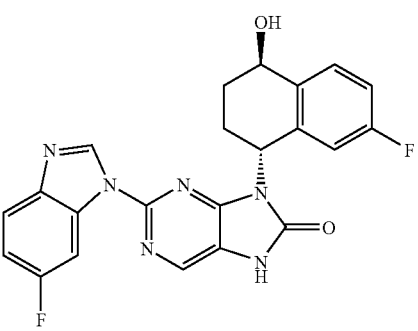

9-((1R,4R)-4-(tert-butyldiphenylsilyloxy)-7-fluoro-1,2,3,4-tetrahydronaphthalen-1-yl)-2-(6-fluoro-1H-benzo[d]imidazol-1-yl)-7H-purin-8(9H)-one. (156 mg, 0.232 mmol, 1 equiv) and cesium fluoride (141 mg, 0.92 mmol, 4 equiv) were added to DMF (5 mL). The reaction mixture was stirred at 50° C. for 24 h. DMF was removed by evaporation. The residue was treated with 3 mL MeOH. The solid was filtered off and washed with MeOH. The combined filtrate and washing were applied to HPLC (Varian ProStar, Sunfire C18 column, 19×100 mm, ACN-H2O gradient elution) to give a white solid product (67.8 mg, 68%). $^1$H NMR (400 MHz, DMSO-d6) δ 8.87 (s, 1H), 8.28 (s, 1H), 7.72 (q, 2H), 7.52 (dd, 1H), 7.07-7.17 (m, 2H), 6.77 (dd, 1H), 5.68 (q, 1H), 5.55 (d, 1H), 4.83-4.92 (m, 1H), 2.42-2.47 (m, 1H), 2.23-2.33 (m, 1H), 2.10-2.18 (m, 1H), 1.78-1.89 (m, 1H); $^{19}$F NMR (400 MHz, DMSO-d6) δ −115.7, −117.2; LC-MS: M+H=435.2, RT=5.13 min.

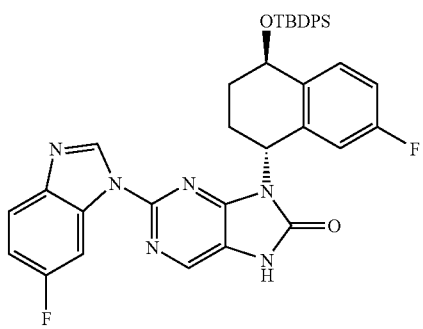 → CDI, THF, RT

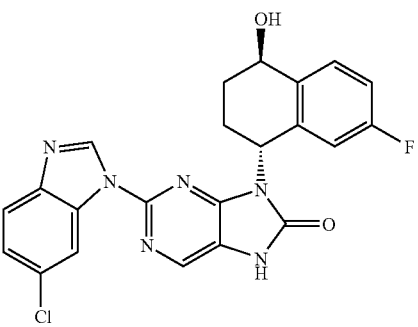

2-(6-Chloro-1H-benzo[d]imidazol-1-yl)-9-((1R,4R)-7-fluoro-4-hydroxy-1,2,3,4-tetrahydronaphthalen-1-yl)-7H-purin-8(9H)-one. $^1$H NMR (400 MHz, MeOD): δ 8.89 (s, 1H), 8.28 (s, 1H), 8.03 (d, 1H), 7.79 (t, 1H), 7.63 (d, 1H), 7.30 (dd, 1H), 7.02 (t, 1H), 6.65 (dd, 1H), 5.78-5.84 (m, 1H), 5.17-5.23 (m, 1H), 2.64-2.74 (m, 1H), 2.43-2.50 (m, 1H), 2.24-2.33 (m, 1H), 1.88-1.99 (m, 1H); $^{19}$F NMR (MeOD): δ −116.8; LC-MS: 451.0, 452.9, RT=5.47 min.

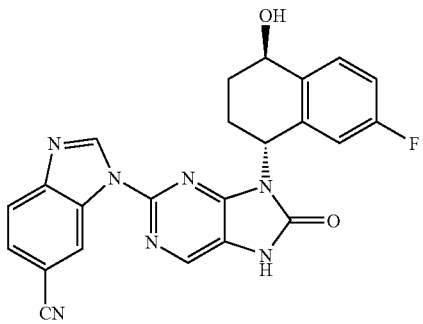

3-(9-((1R,4R)-7-Fluoro-4-hydroxy-1,2,3,4-tetrahydronaphthalen-1-yl)-8-oxo-8,9-dihydro-7H-purin-2-yl)-3H-benzo[d]imidazole-5-carbonitrile. $^1$H NMR (400 MHz, MeOD): δ 9.07 (d, 1H), 8.34 (d, 1H), 8.26 (s, 1H), 7.89 (q, 1H), 7.83 (dd, 1H), 7.63 (dt, 1H), 7.05 (dt, 1H), 6.70 (dd, 1H), 5.84 (q, 1H), 5.13 (m, 1H), 2.56-2.63 (m, 1H), 2.43-2.46 (m, 1H), 2.28-2.33 (m, 1H), 1.90-1.99 (m, 1H); 19F NMR (400 MHz, MeOD): δ −116.7; LC-MS: M+H=442.0, RT=5.23 min.

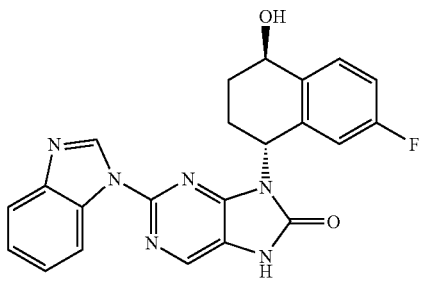

2-(1H-benzo[d]imidazol-1-yl)-9-((1R,4R)-7-fluoro-4-hydroxy-1,2,3,4-tetrahydronaphthalen-1-yl)-7H-purin-8(9H)-one. $^1$H NMR (400 MHz, DMSO-d6): δ 8.86 (s, 1H), 8.31 (s, 1H), 7.79 (q, 1H), 7.70 (d, 1H), 7.62 (d, 1H), 7.28 (t, 1H), 7.20 (t, 1H), 7.13 (t, 1H), 6.84 (dd, 1H), 5.66-5.73 (m, 1H), 5.64 (broad, 1H), 4.80-4.87 (m, 1H), 2.37-2.48 (m, 1H), 2.20-2.30 (m, 1H), 2.11-2.19 (m, 1H), 1.78-1.90 (m, 1H); $^{19}$F NMR (DMSO-d6): δ −115.8; LC-MS: M+H=417.3, RT=4.60 min.

By routes analogous to the syntheses above, using (1R, 4R)-4-(tert-butyldiphenylsilyloxy)-5,7-difluoro-1,2,3,4-tetrahydronaphthalen-1-amine the compounds below have been prepared:

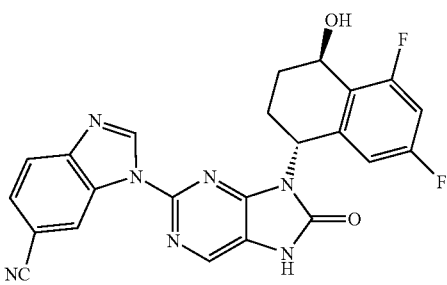

3-(9-((1R,4R)-5,7-difluoro-4-hydroxy-1,2,3,4-tetrahydronaphthalen-1-yl)-8-oxo-8,9-dihydro-7H-purin-2-yl)-3H-benzo[d]imidazole-5-carbonitrile. $^1$H-NMR (300 MHz, CD3OD) □ 8.7 (s, 1H), 8.5 (s, 1H), 8.2 (s, 1H), 7.7 (d, 1H), 7.5 (d, 1H), 6.9 (t, 1H), 6.7 (d, 1H), 5.8 (m, 1H), 5.3 (m, 1H), 2.3-2.6 (m, 3H), 2.1 (m, 1H) ppm, MS (ESI), m/z 460.0 ([M+H]+).

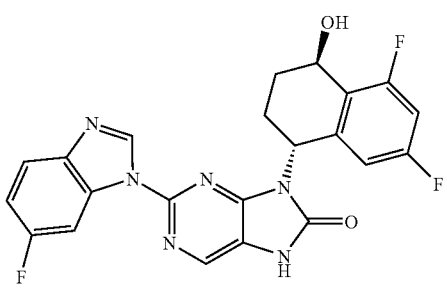

9-((1R,4R)-5,7-difluoro-4-hydroxy-1,2,3,4-tetrahydronaphthalen-1-yl)-2-(6-fluoro-1H-benzo[d]imidazol-1-yl)-7H-purin-8(9H)-one. $^1$H-NMR (300 MHz, CD$_3$OD) □ 8.7 (s, 1H), 8.2 (s, 1H), 7.8 (m, 2H), 7.1 (t, 1H), 6.9 (t, 1H), 6.7 (d, 1H), 5.8 (m, 1H), 5.3 (m, 1H), 2.3-2.6 (m, 3H), 2.0 (m, 1H) ppm, $^{19}$F-NMR (300 MHz, CD$_3$OD) □ −112.7, −113.5, −118.5 ppm, MS (ESI), m/z 453.2 ([M+H]+).

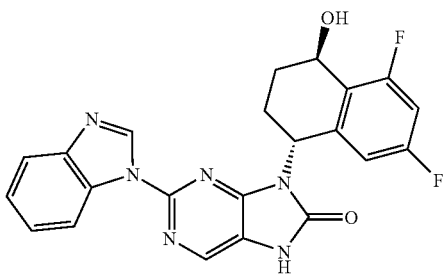

2-(1H-benzo[d]imidazol-1-yl)-9-((1R,4R)-5,7-difluoro-4-hydroxy-1,2,3,4-tetrahydronaphthalen-1-yl)-7H-purin-8(9H)-one. $^1$H-NMR (300 MHz, CD$_3$OD) □ 8.8 (s, 1H), 8.2 (s, 1H), 7.8 (m, 1H), 7.6 (m, 1H), 7.3 (m, 2H), 7.0 (t, 1H), 6.7 (d, 1H), 5.8 (m, 1H), 5.3 (m, 1H), 2.3-2.5 (m, 3H, 2.0 (m, 1H) ppm, MS (ESI), m/z 435.2 ([M+H]+).

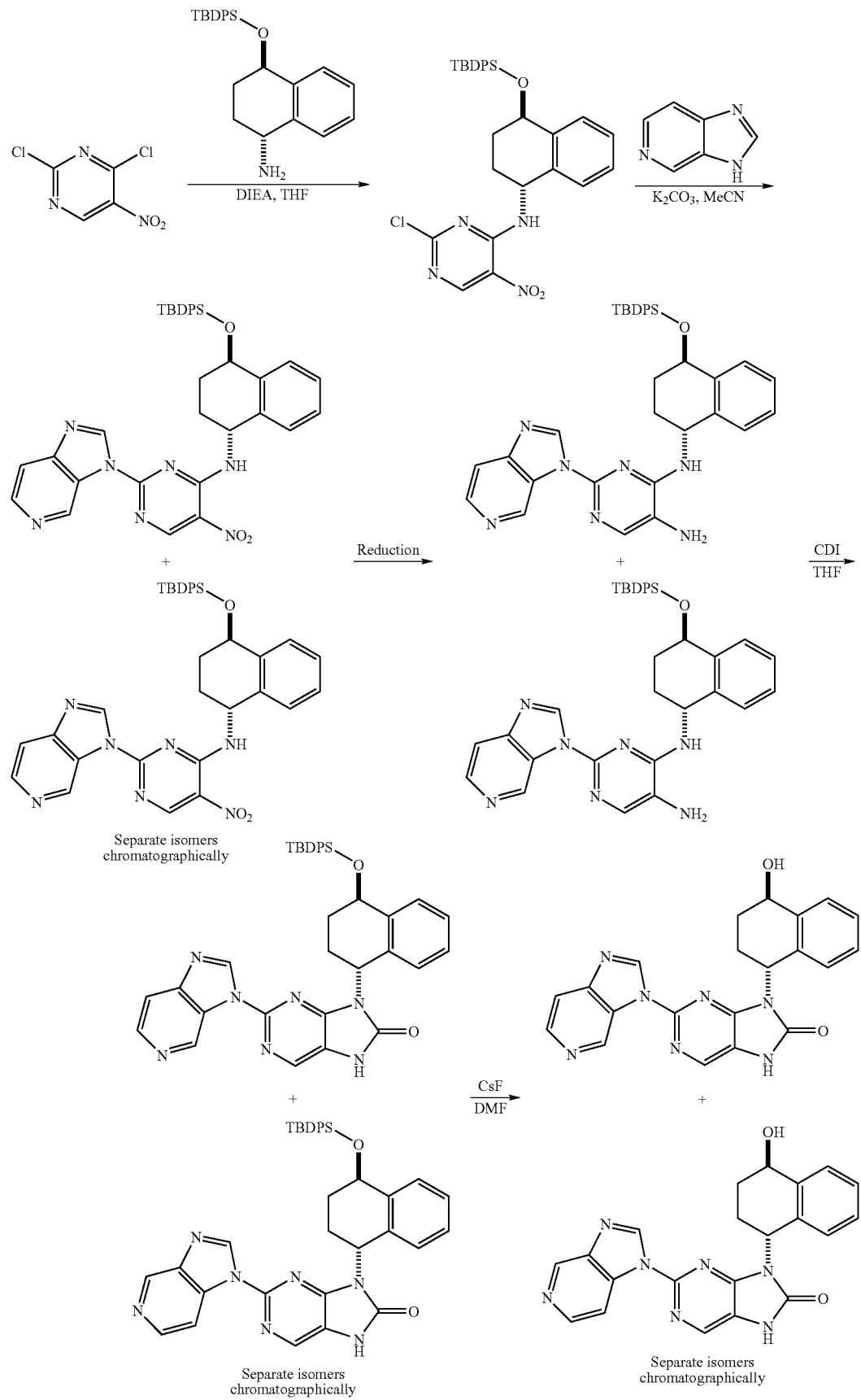

N-((1R,4R)-4-(tert-Butyldiphenylsilyloxy)-1,2,3,4-tetrahydronaphthalen-1-yl)-2-chloro-5-nitropyrimidin-4-amine. A solution of (1R,4R)-4-(tert-butyldiphenylsilyloxy)-1,2,3,4-tetrahydronaphthalen-1-amine (1 equiv.) in THF would be slowly added to mixture of 2,4-dichloro-5-nitropyrimidine and appropriate base, usually DIEA (3-5 equiv.), in THF at −78° C. After the addition was complete the cooling bath would be removed and the reaction would be allowed to warm to RT overnight. Isolation and purification of the above compound would be accomplished via an aqueous/ethyl acetate separation and chromatography on silica gel.

N-((1R,4R)-4-(tert-Butyldiphenylsilyloxy)-1,2,3,4-tetrahydronaphthalen-1-yl)-2-(3H-imidazo[4,5-c]pyridin-3-yl)-5-nitropyrimidin-4-amine and N-((1R,4R)-4-(tert-butyldiphenylsilyloxy)-1,2,3,4-tetrahydronaphthalen-1-yl)-2-(1H-imidazo[4,5-c]pyridin-3-yl)-5-nitropyrimidin-4-amine. A suspension of N-((1R,4R)-4-(tert-butyldiphenylsilyloxy)-1,2,3,4-tetrahydronaphthalen-1-yl)-2-chloro-5-nitropyrimidin-4-amine, 5-azabenzimidazole (1 equiv.) and potassium carbonate (3-5 equiv.) in a polar solvent, usually ACN, would be heated at reflux until the reaction is complete. After the reaction had cooled to RT, the mixture would be diluted with water then extracted with ethyl acetate. The isolated material would be a mixture of the 5- and 6-aza compounds which would be attempted to be separated at this stage via column chromatography.

$N^4$-((1R,4R)-4-(tert-Butyldiphenylsilyloxy)-1,2,3,4-tetrahydronaphthalen-1-yl)-2-(3H-imidazo[4,5-c]pyridin-3-yl)pyrimidine-4,5-diamine and isomer if present. The nitro group of the above compound(s) may be easily reduced via a variety of methods, but usually via catalytic Raney Ni in THF under one atmosphere of $H_2$. After the reaction has been determined to be complete (2-15 hr), the mixture would be filtered to remove the catalyst, solvents removed and the crude material taken on as is to the next step.

9-((1R,4R)-4-(tert-Butyldiphenylsilyloxy)-1,2,3,4-tetrahydronaphthalen-1-yl)-2-(3H-imidazo[4,5-c]pyridin-3-yl)-7H-purin-8(9H)-one. The cyclization is usually accomplished via the addition of 1,1'-carbonyldiimidazole (3-5 equiv.) to a solution of the above diamine in THF. An aqueous/DCM extraction upon completion of the reaction followed by silica gel purification (and separation of isomers if not previously achieved) will yield the titled compound.

Preparation of 9-((1R,4R)-4-hydroxy-1,2,3,4-tetrahydronaphthalen-1-yl)-2-(3H-imidazo[4,5-c]pyridin-3-yl)-7H-purin-8(9H)-one. Removal of this silicon protecting group is usually accomplished via CsF (2-xs equiv.) in DMF heated (40-60° C.) for 6 to 15 hr. The cooled reaction would be partitioned between $H_2O$ and DCM, separated then purified via column chromatography to yield the titled product (and separation of isomers if not previously achieved).

Jak3 Kinase Assay

Human Jak3 cDNA was amplified by PCR. A fragment encoding the catalytic domain of Jak3 (508aa to 1124aa) was ligated with GST at 5' end. This fused GST-Jak3 DNA fragment was cloned into the EcoRI site of the donor plasmid pFastBac 1 (Life Technologies #10359-016). The transformation, transposition, and transfection of insect cells (Sf9) were performed according to the manufacture's instructions. The cell lysate containing recombinant GST-Jak3 was used in the kinase assay. Anti-GST antibody (10 μg/ml, Sigma #G1417) was coated onto a 384-well plate at 4° C. overnight. Cell lysate containing GST-Jak3 (1:100 dilution) was added to the anti-GST coated plates, and GST-Jak3 was captured by immobilized anti-GST antibody. Testing compounds and substrate mix (50 mM HEPES, pH 7, 0.5 mM $Na_3VO_4$, 25 mM $MgCl_2$, 1 mM DTT, 0.005% BSA, 1 μM ATP, and 4.5 μg/ml biotinyl poly-Glu,Ala,Tyr) were added to the plate to initiate the reaction. After a 60-min incubation, the reaction was stopped by 4 mM EDTA, and phosphorylation of biotinyl poly-Glu,Ala,Tyr was detected using 17 μg/ml Cy5-streptavidin (Amersham, #PA92005) and 2.7 μg/ml Europium-conjugated anti-phosphotyrosine antibody (PerkinElmer #AD0069) using homogeneous time-resolved fluorescence (HTRF) technology.

Jak3 Cellular Assay

The mouse F7 pre-B lymphocyte cell line was used for the cellular Jak3 assay. Human IL-2Rβc cDNA is stably expressed in F7 cells (Kawahara et al., 1995). F7 cells were maintained in RPMI 1640 medium supplemented with 10% fetal bovine serum plus IL-3. Cells (30,000 cells/well) in serum-free medium were seeded in 96-well plates for the cell proliferation assay. Testing compounds were added to cells, followed by the addition of IL-2 (final 20 ng/ml). After a 24-h incubation, the number of viable cells was determined by the CellTiter-Glo Luminescent Cell Viability Assay kit (Promega, #G7573) according to the manufacturer's instructions.

The results of testing of representative species are shown below. The compounds in Table 1 exhibited $IC_{50}$ less than 100 nM. The compounds in Table 2 exhibited $IC_{50}$ between 101 nM and 1 μM. The compounds in Table 3 exhibited $IC_{50}$ between 1 μM and 10 μM.

TABLE 1

| Synthesis Example | Reference No. | |
|---|---|---|
| Example 20 | 101 | 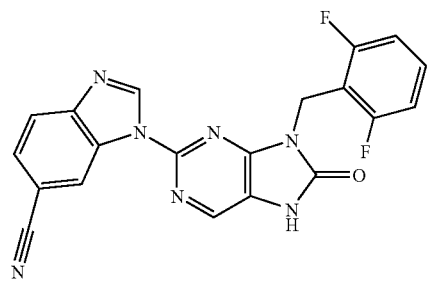 |

TABLE 1-continued

| Synthesis Example | Reference No. |
|---|---|
| Example 22 | 102 |
| | 103 |
| | 104 |
| | 105 |
| | 106 |

TABLE 1-continued
| Synthesis Example | Reference No. | |
|---|---|---|
| | 107 | 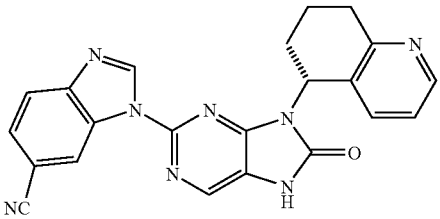 |
| | 108 | 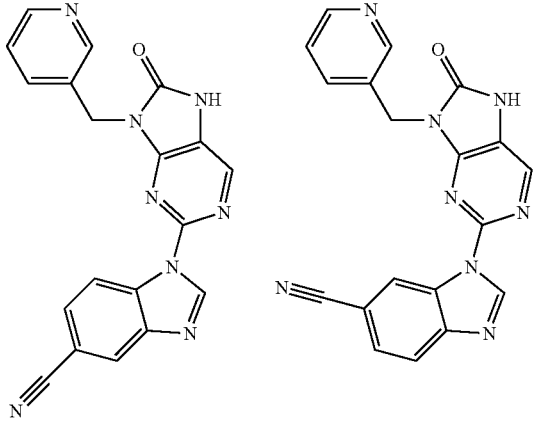 |
| | 109 | 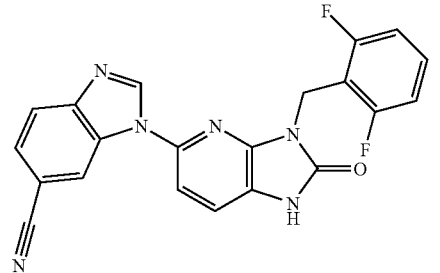 |
| | 110 | 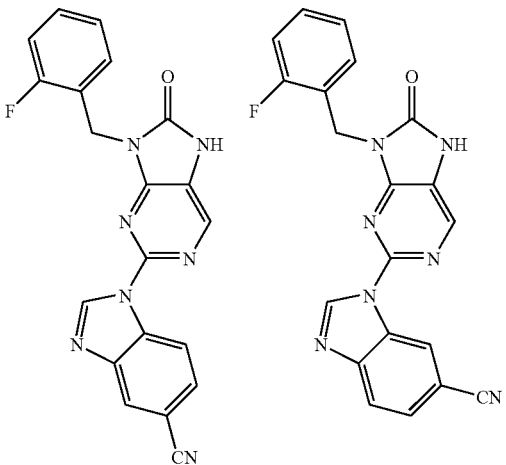 |

TABLE 1-continued
| Synthesis Example | Reference No. | |
|---|---|---|
| | 111 | 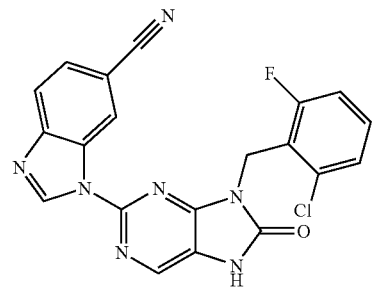 |
| | 112 | 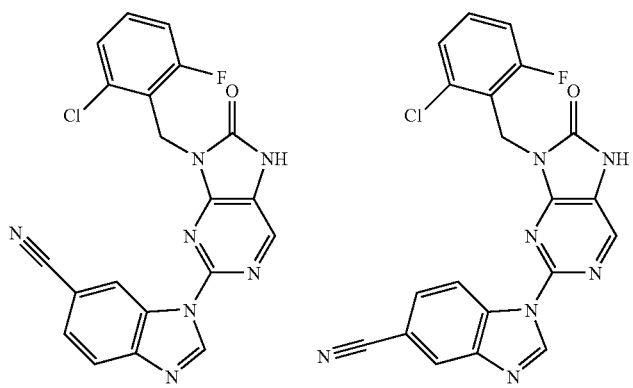 |
| | 113 | 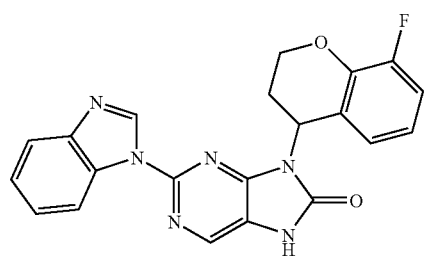 |
| Example 16 | 114 | 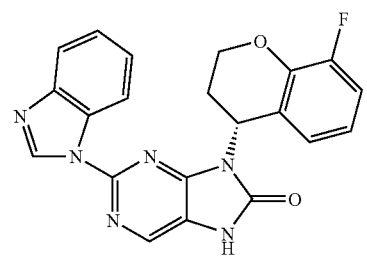 |
| | 115 | 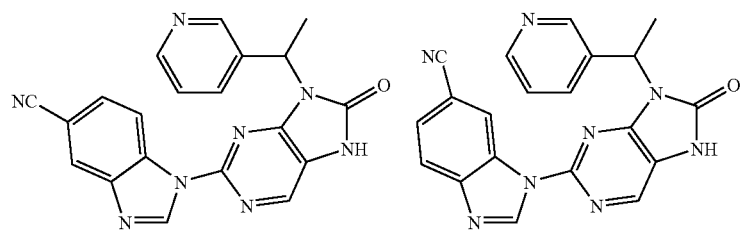 |

TABLE 1-continued
| Synthesis Example | Reference No. |
|---|---|
| | 116 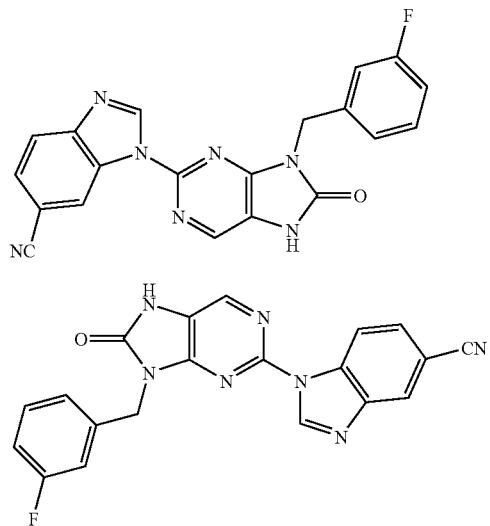 |
| | 117 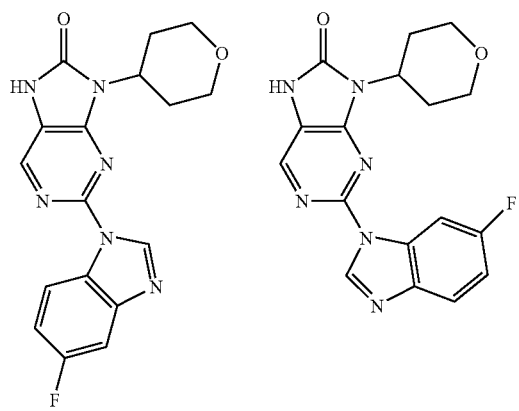 |
| | 118 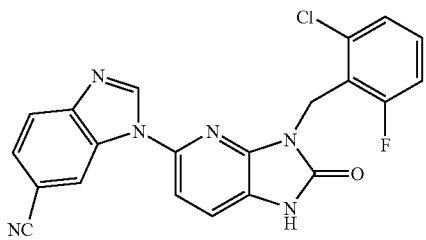 |
| | 119 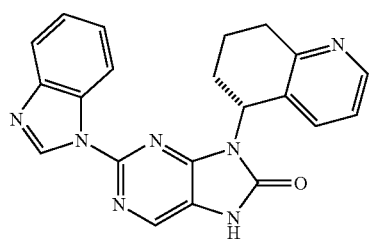 |

TABLE 1-continued
| Synthesis Example | Reference No. | |
|---|---|---|
| | 120 | 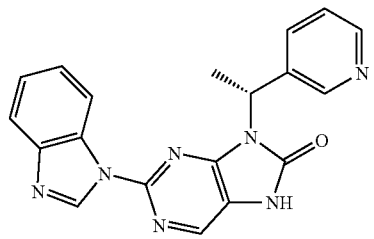 |
| | 121 | 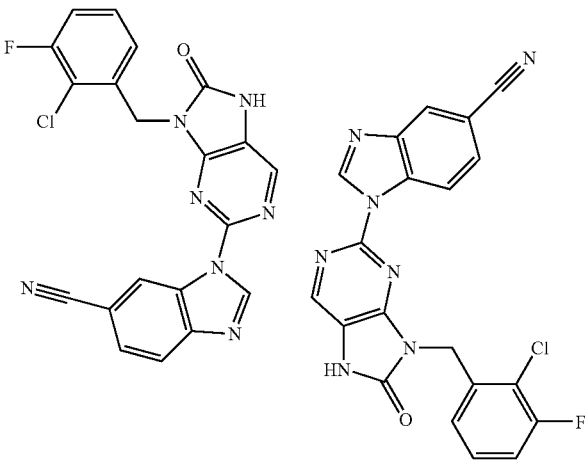 |
| | 122 | 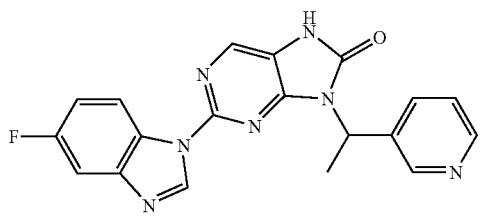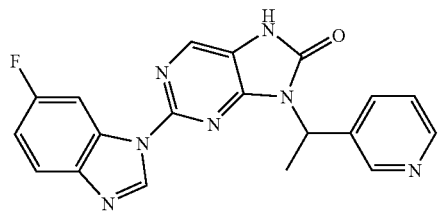 |

TABLE 1-continued
| Synthesis Example | Reference No. | |
|---|---|---|
| | 123 | 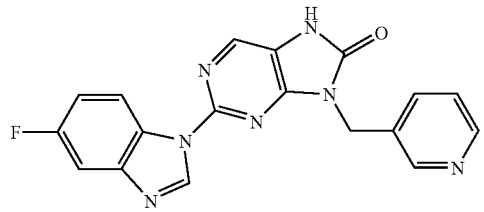 |
| | | 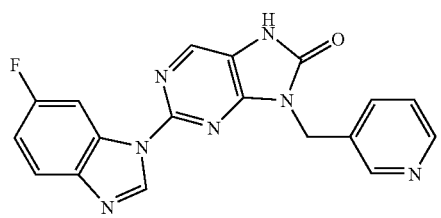 |
| Example 15 | 124 | 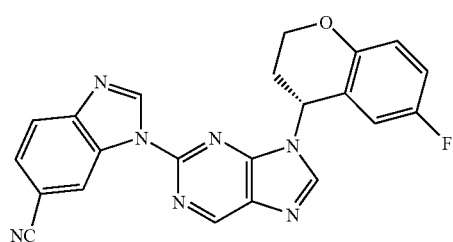 |
| | 125 | 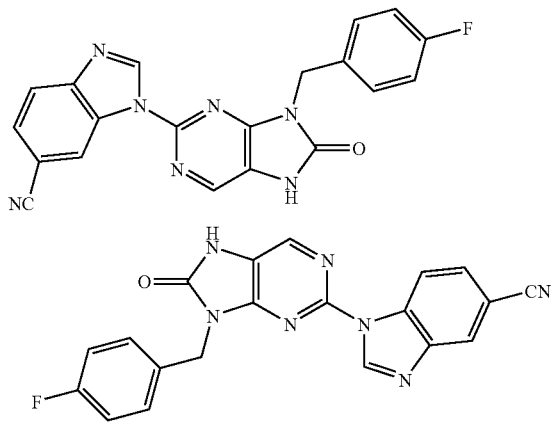 |
| | 402 | 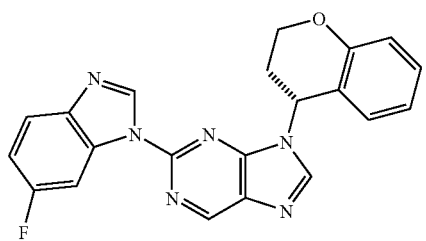 |

TABLE 1-continued

| Synthesis Example | Reference No. |
|---|---|
| Example 23 | 126 |
| | 127 |
| | 128 |
| | 129 |
| | 130 |

TABLE 1-continued
| Synthesis Example | Reference No. | |
|---|---|---|
| | 131 | 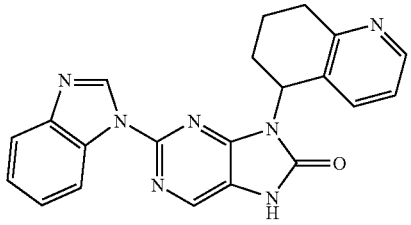 |
| | 132 | 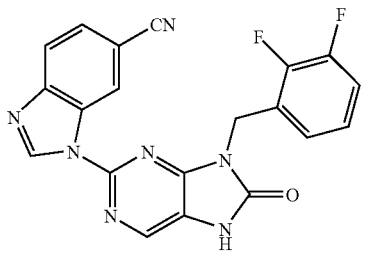 |
| | 133 | 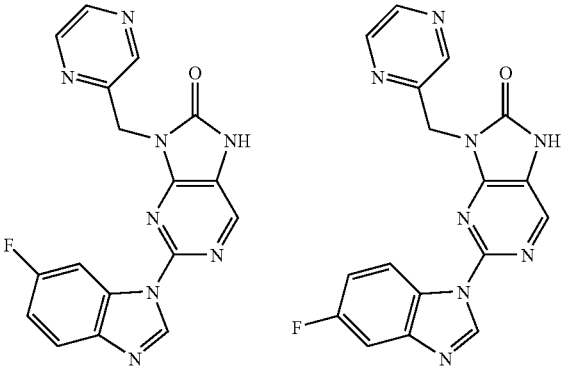 |
| Example 21 | 134 | 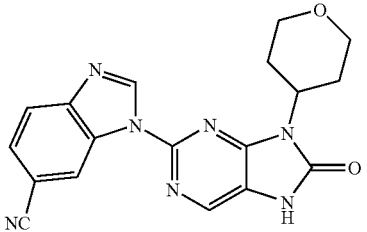 |
| | 135 | 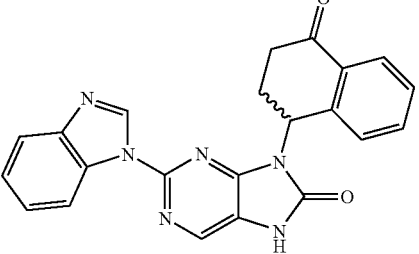 |

TABLE 1-continued
| Synthesis Example | Reference No. | |
|---|---|---|
| | 136 | 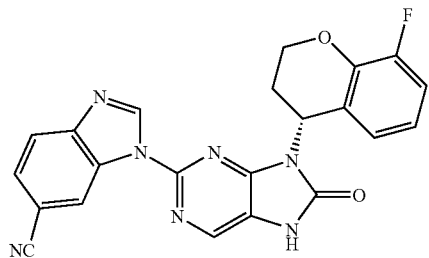 |
| | 137 | 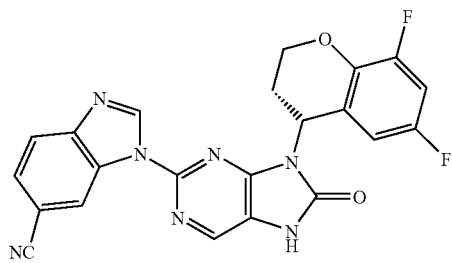 |
| | 138 | 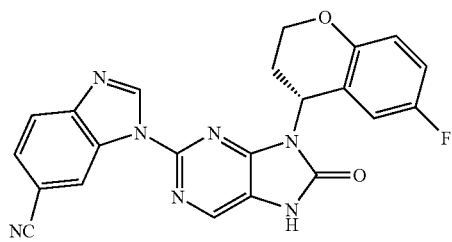 |
| | 139 | 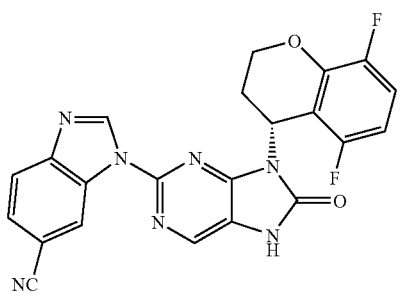 |
| Example 26 | 140 | 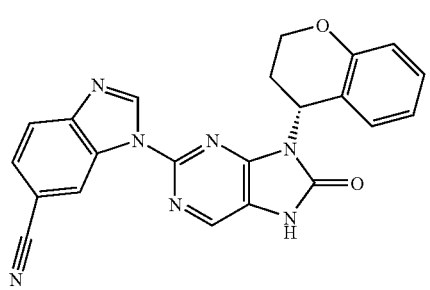 |

TABLE 1-continued
| Synthesis Example | Reference No. | |
|---|---|---|
| | 141 | 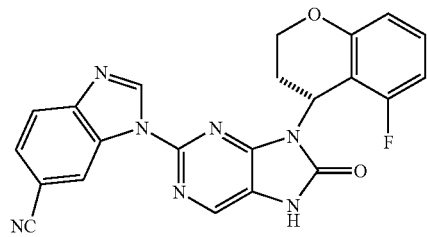 |
| | 404 | 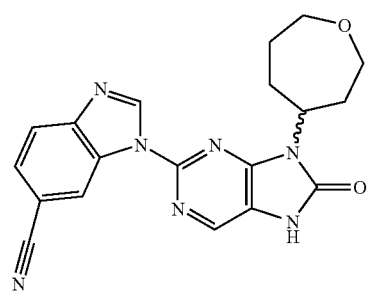 |
| | 405 | 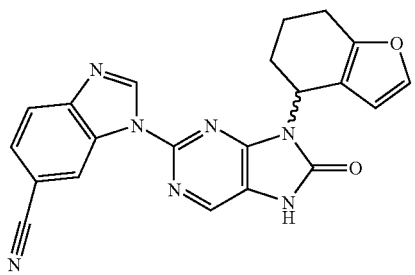 |
| Example 28 | 142 | 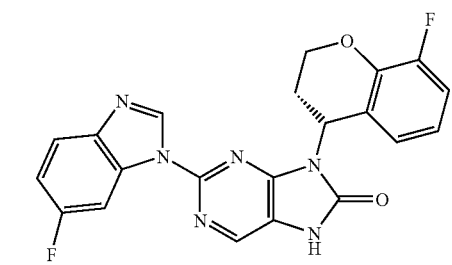 |
| | 143 | 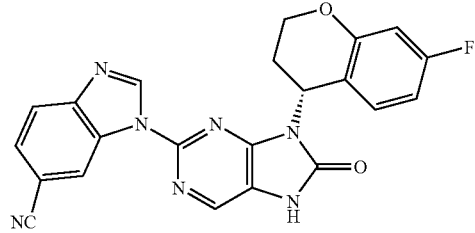 |

TABLE 1-continued
| Synthesis Example | Reference No. | |
|---|---|---|
| | 144 | 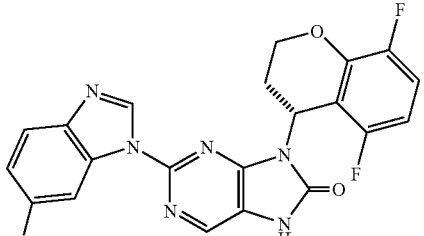 |
| | 145 | 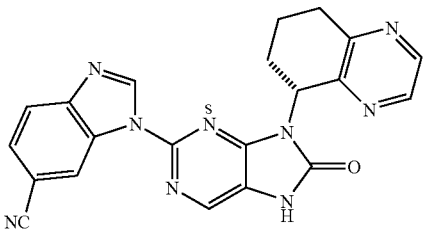 |
| | 146 | 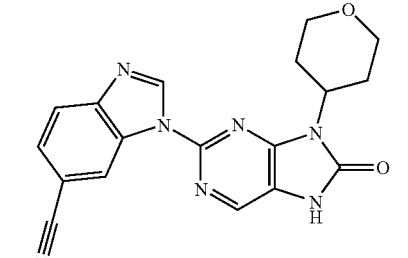 |
| | 147 | 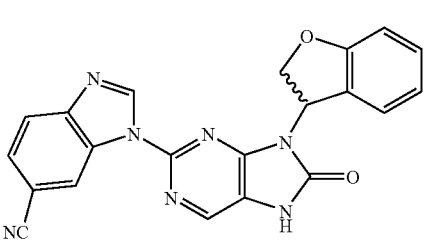 |
| | 148 | 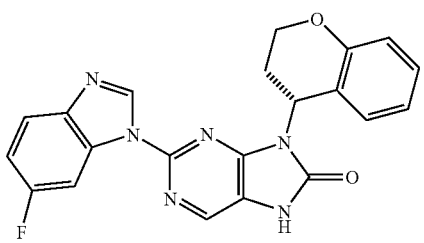 |
| | 149 | 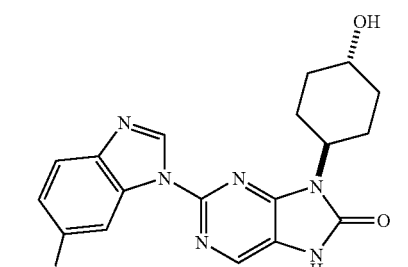 |

TABLE 1-continued
| Synthesis Example | Reference No. | |
|---|---|---|
| | 150 | 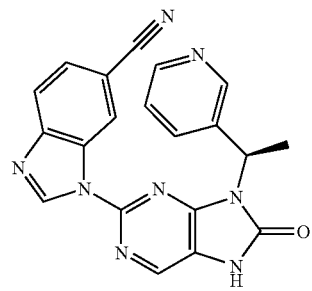 |
| | 151 | 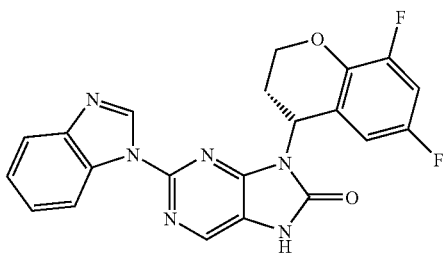 |
| | 152 | 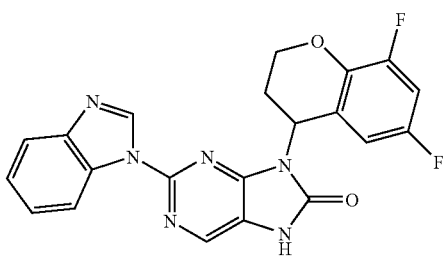 |
| Example 27 | 153 | 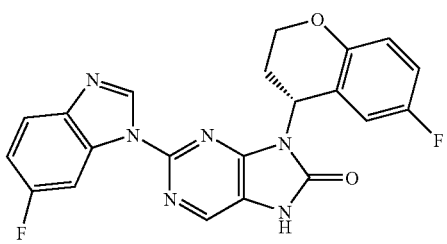 |
| | 154 | 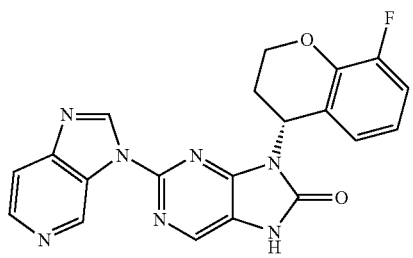 |

TABLE 1-continued
| Synthesis Example | Reference No. | |
|---|---|---|
| | 155 | 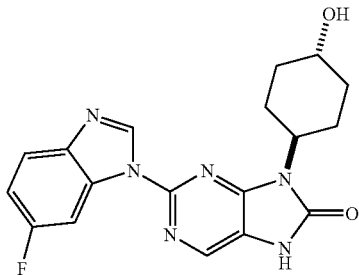 |
| | 156 | 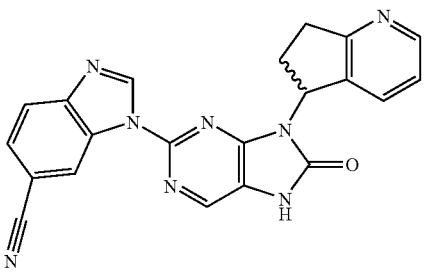 |
| | 157 | 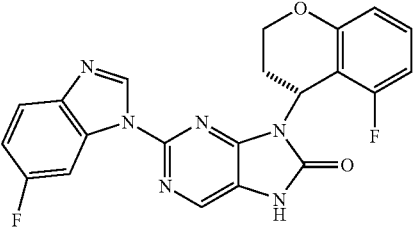 |
| | 158 | 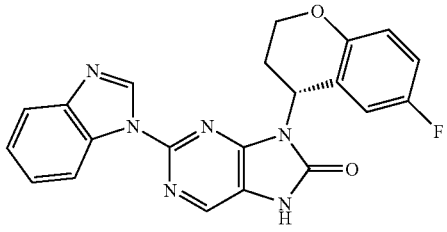 |
| | 159 | 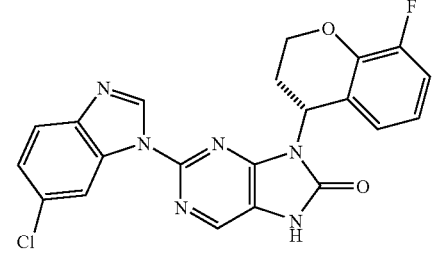 |
| | 160 | 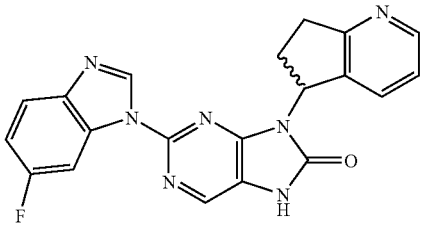 |

TABLE 1-continued
| Synthesis Example | Reference No. | |
|---|---|---|
| | 161 | 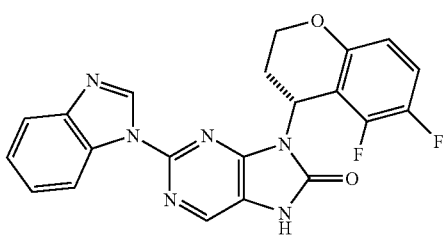 |
| | 162 | 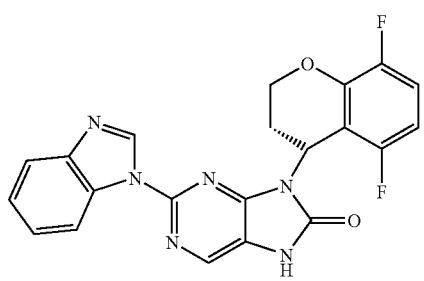 |
| | 163 | 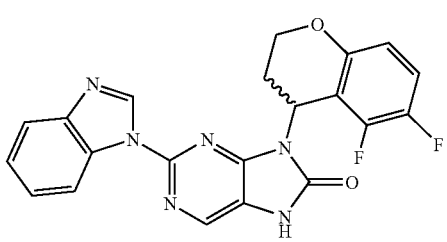 |
| | 164 | 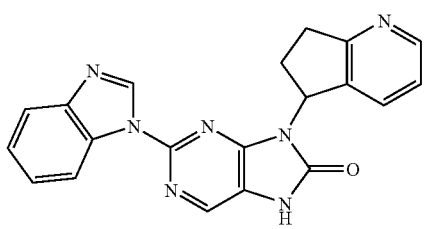 |
| | 165 | 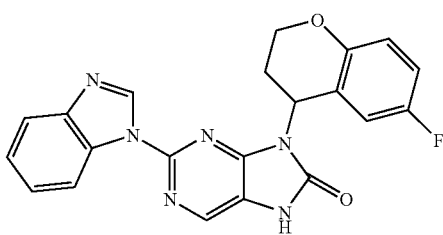 |
| | 166 | 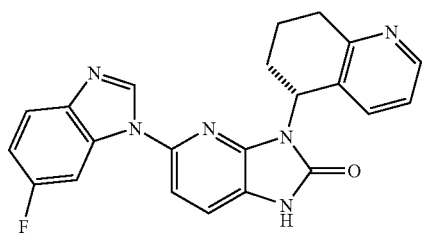 |

TABLE 1-continued
| Synthesis Example | Reference No. | |
|---|---|---|
| | 167 | 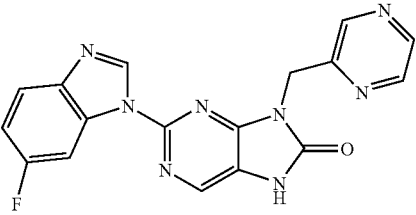 |
| | 168 | 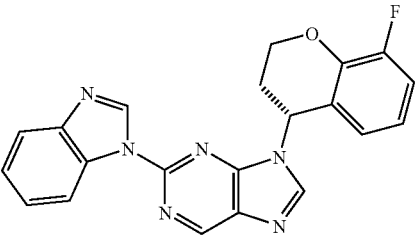 |
| | 169 | 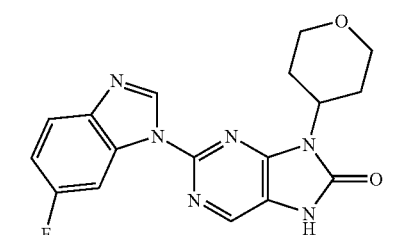 |
| | 170 | 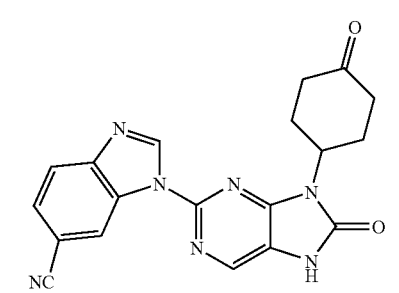 |
| | 171 | 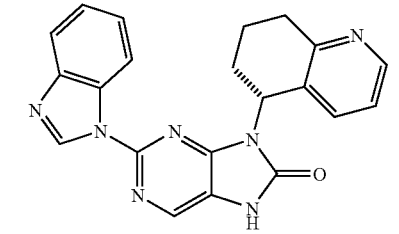 |
| | 172 | 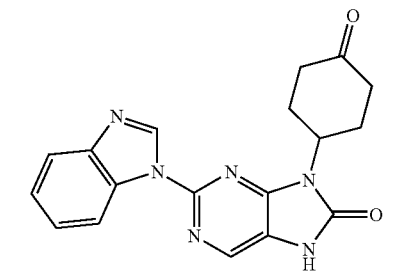 |

TABLE 1-continued

| Synthesis Example | Reference No. |
|---|---|
| | 173 |
| | 174 |
| | 175 |
| | 176 |
| | 177 |
| | 178 |

TABLE 1-continued
| Synthesis Example | Reference No. | |
|---|---|---|
| | 179 | 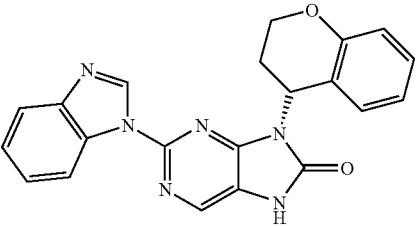 |
| | 180 | 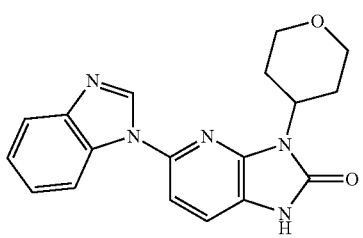 |
| | 407 | 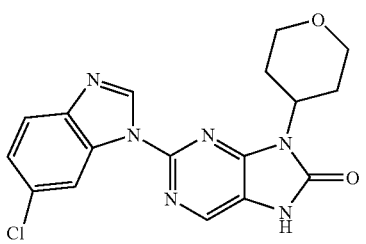 |
| | 411 | 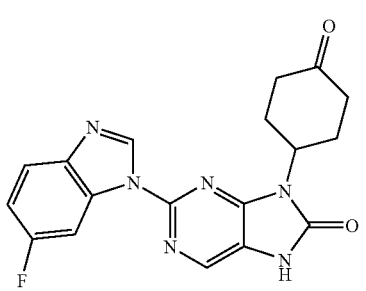 |
| | 412 | 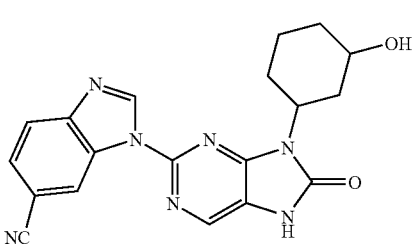 |
| | 414 | 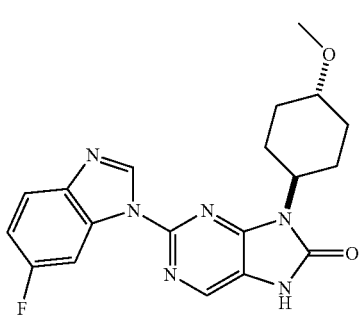 |

TABLE 1-continued
| Synthesis Example | Reference No. | |
|---|---|---|
| | 417 | 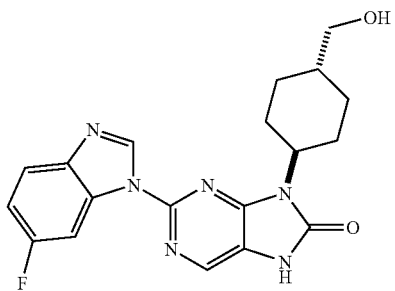 |
| | 418 | 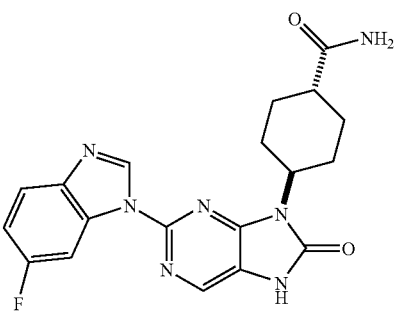 |
| | 420 | 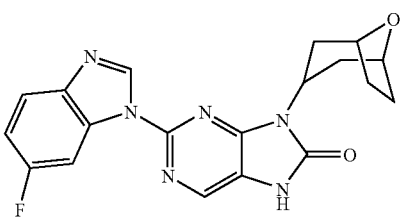 |
| | 426 | 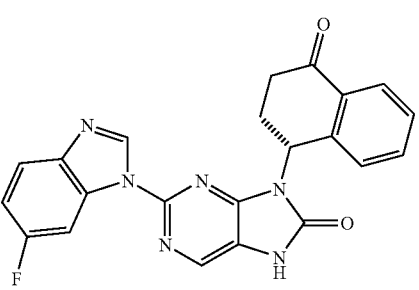 |
| | 425 | 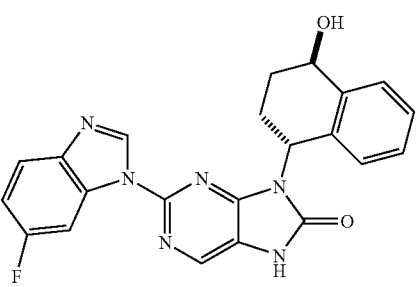 |

TABLE 1-continued

| Synthesis Example | Reference No. | |
|---|---|---|
| | 427 | (structure) |
| Example 36 | 181 | (structure) |
| | 182 | (structure) |
| | 183 | (structure) |
| | 406 | (structure) |
| | 428 | (structure) |

TABLE 1-continued
| Synthesis Example | Reference No. | |
|---|---|---|
| | 429 | 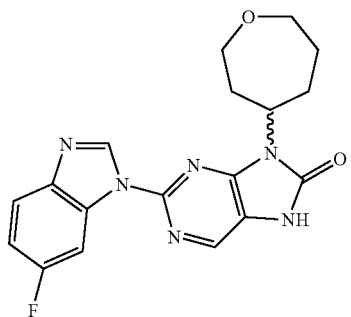 |
| | 430 | 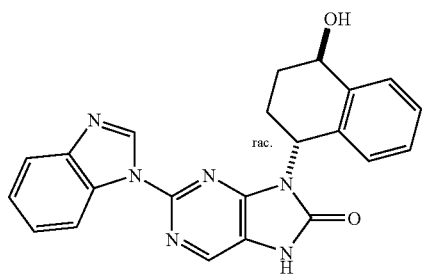 |
| | 431 | 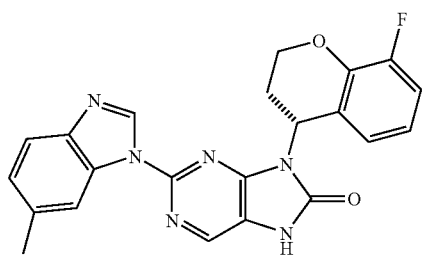 |
| | 432 | 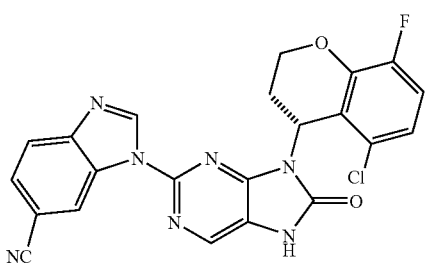 |
| | 433 | 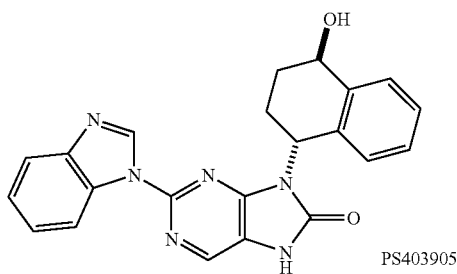 |

TABLE 1-continued
| Synthesis Example | Reference No. | |
|---|---|---|
| | 434 | 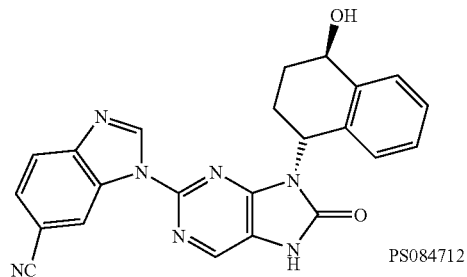 PS084712 |
| | 435 | 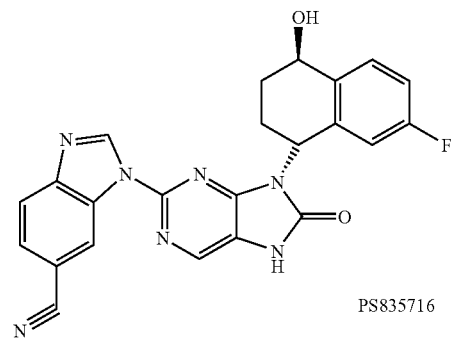 PS835716 |
| | 436 | 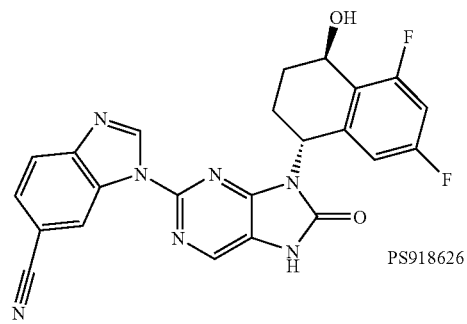 PS918626 |
| | 437 | 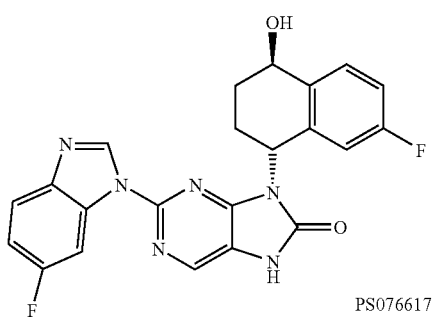 PS076617 |

TABLE 1-continued
| Synthesis Example | Reference No. | |
|---|---|---|
| | 438 | 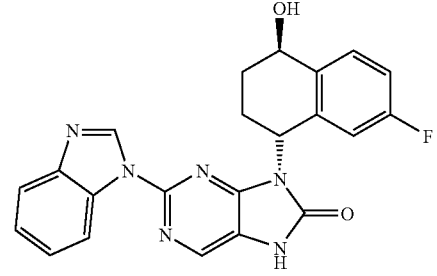 PS593667 |
| | 439 | 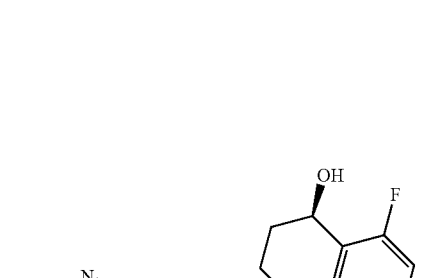 PS920827 |
| | 440 | 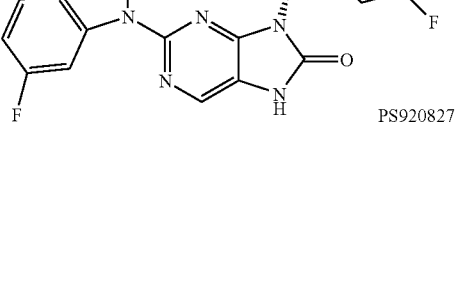 PS637249 |
| | 441 | 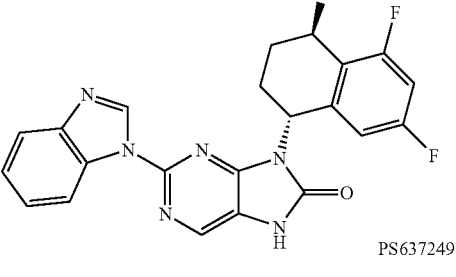 PS210826 |

TABLE 2
| Synthesis Example | Reference No. | |
|---|---|---|
| | 201 | 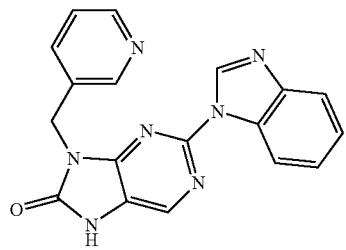 |
| | 202 | 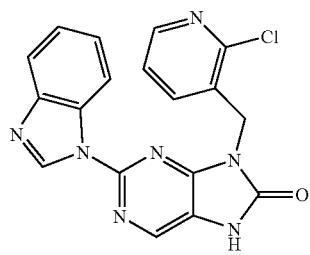 |
| | 203 | 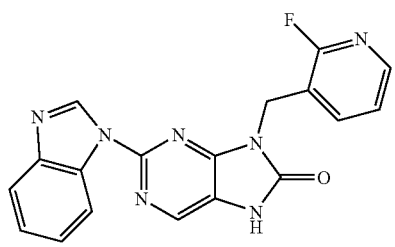 |
| | 204 | 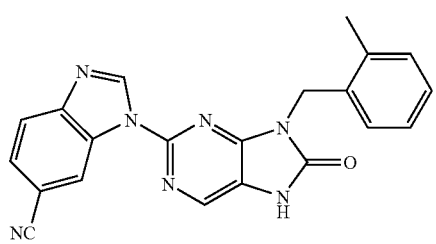 |
| | | 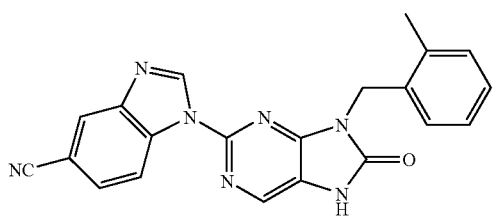 |

TABLE 2-continued
| Synthesis Example | Reference No. |
|---|---|
| | 205 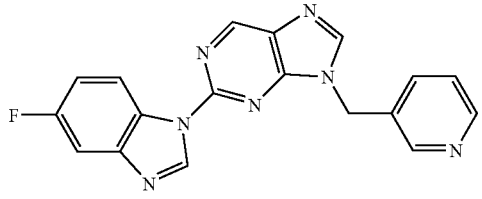 |
| | 206 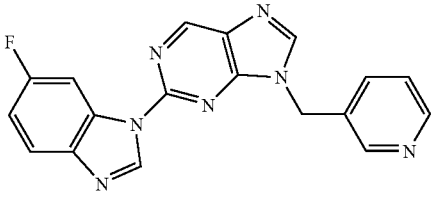 |
| | 207 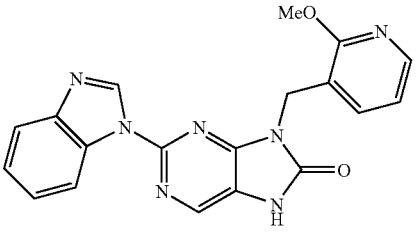 |
| | 208 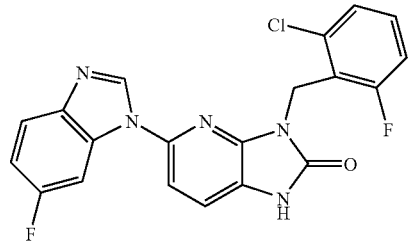 |
| | 209 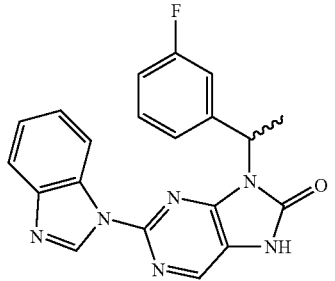 |

TABLE 2-continued
| Synthesis Example | Reference No. | |
|---|---|---|
| | 210 | 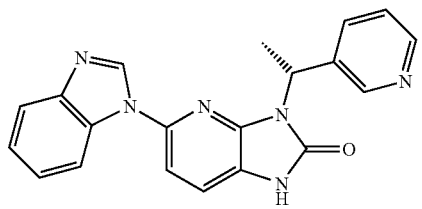 |
| | 211 | 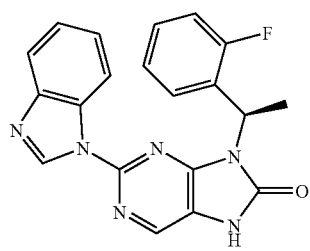 |
| | 212 | 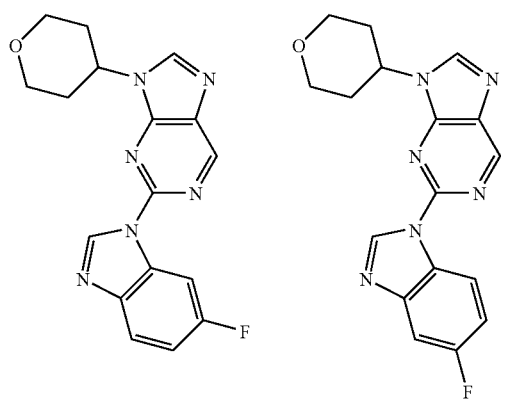 |
| | 213 | 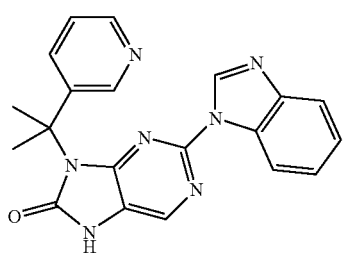 |
| | 214 | 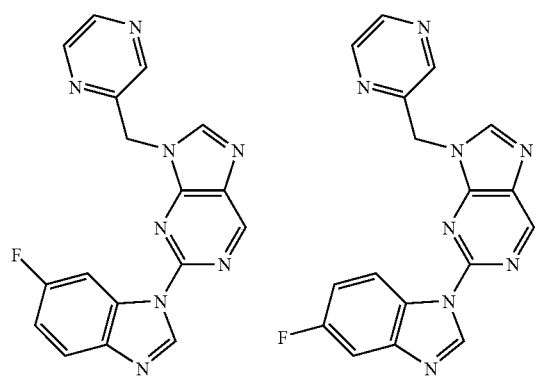 |

TABLE 2-continued
| Synthesis Example | Reference No. | |
|---|---|---|
| | 215 | 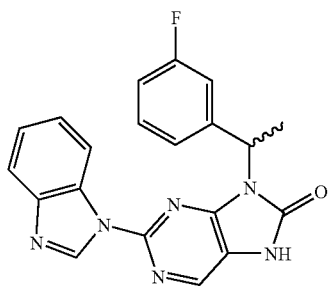 |
| | 216 | 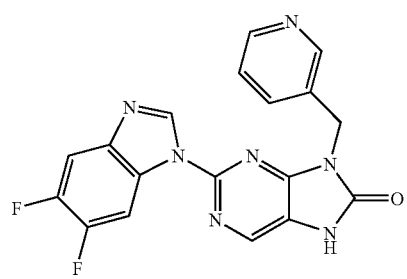 |
| | 217 | 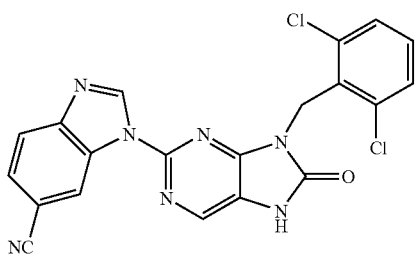 |
| | 218 | 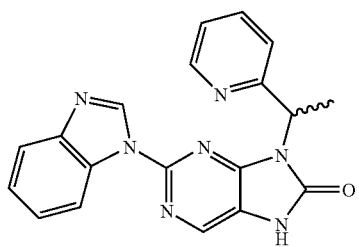 |
| | 219 | 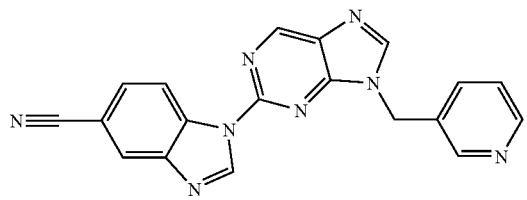 |
| | | 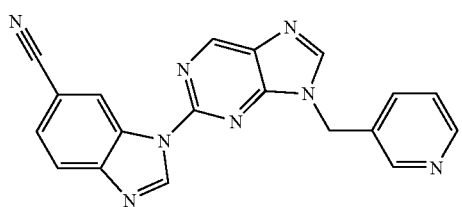 |

TABLE 2-continued
| Synthesis Example | Reference No. | |
|---|---|---|
| | 220 | 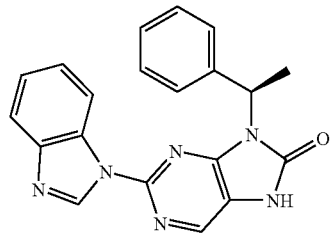 |
| | 221 | 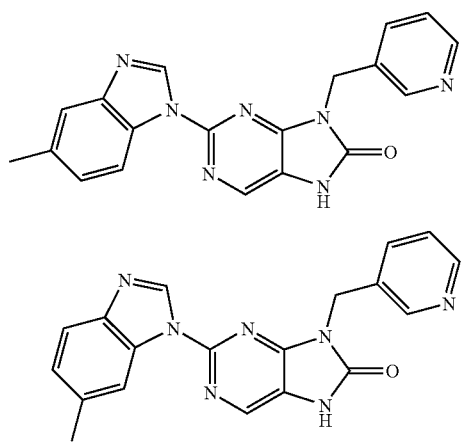 |
| | 222 | 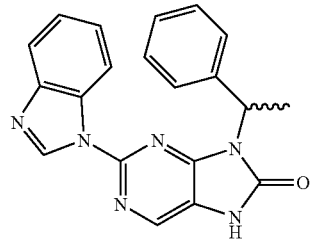 |
| | 223 | 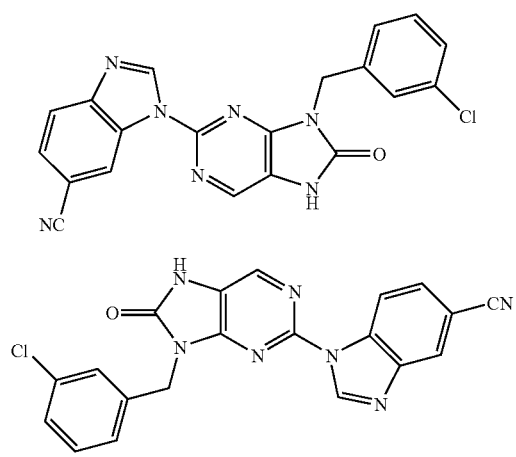 |

TABLE 2-continued
| Synthesis Example | Reference No. | |
|---|---|---|
| | 224 | 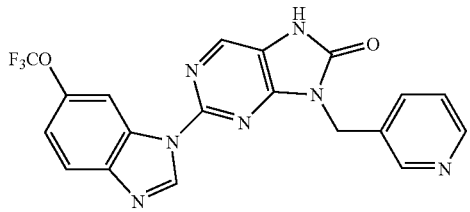 |
| | 225 | 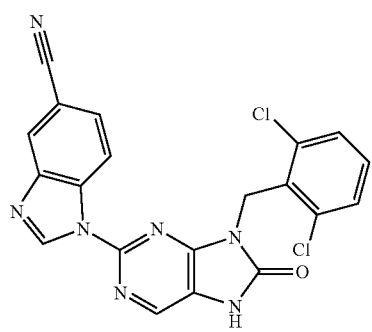 |
| | 226 | 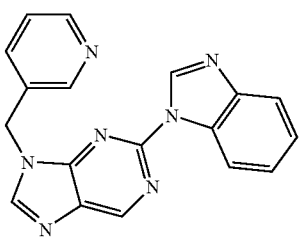 |
| | 227 | 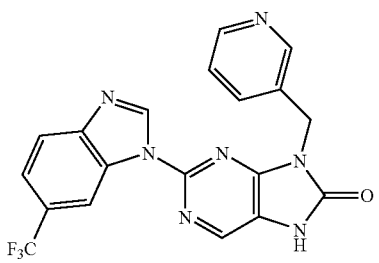 |
| | 228 | 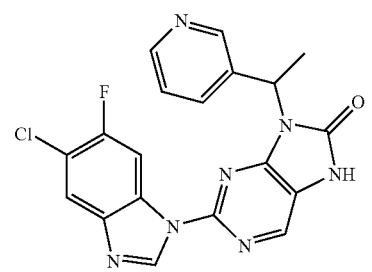 |

TABLE 2-continued
| Synthesis Example | Reference No. | |
|---|---|---|
| | 229 | 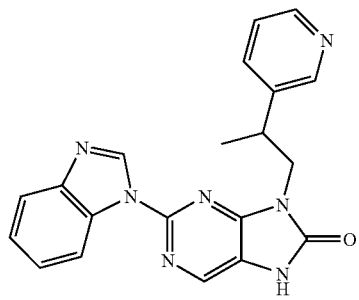 |
| | 230 | 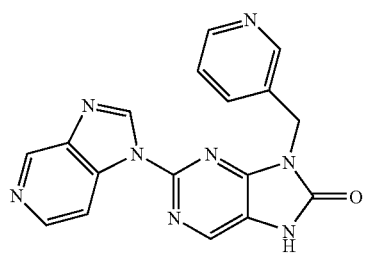 |
| | 231 | 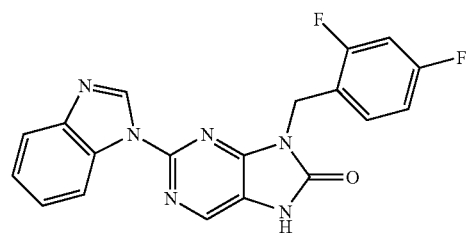 |
| | 232 | 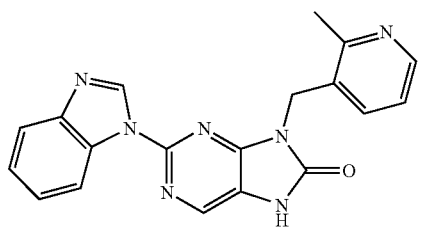 |
| | 233 | 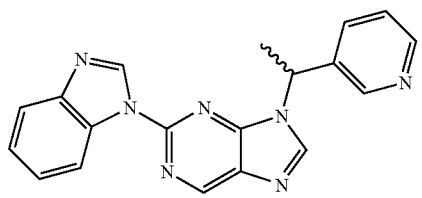 |
| | 234 | 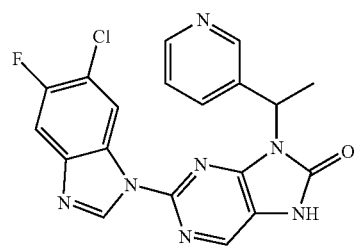 |

TABLE 2-continued
| Synthesis Example | Reference No. |
|---|---|
| | 235 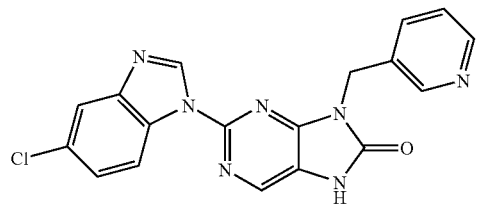 |
| | 236 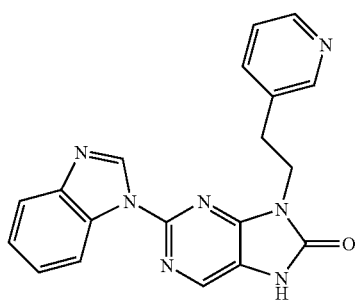 |
| | 237 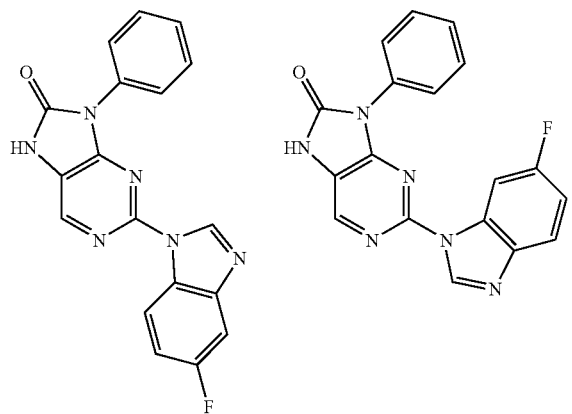 |
| | 238 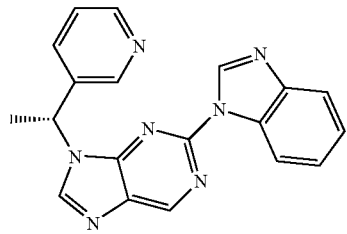 |
| | 239 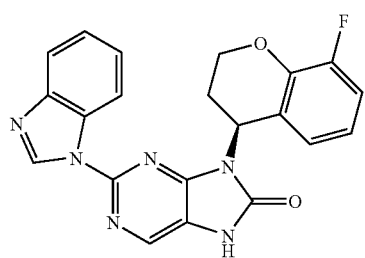 |

TABLE 2-continued
| Synthesis Example | Reference No. | |
|---|---|---|
| | 240 | 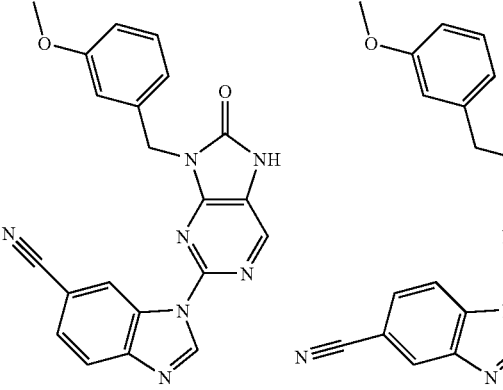 |
| | 241 | 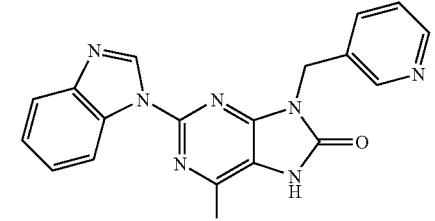 |
| | 242 | 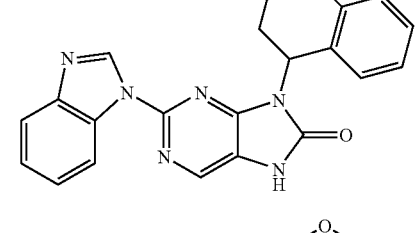 |
| | 403 | 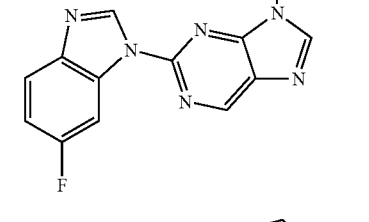 |
| | 413 | 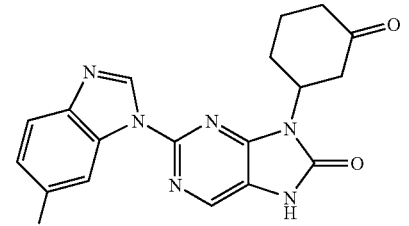 |

TABLE 2-continued
| Synthesis Example | Reference No. | |
|---|---|---|
| | 416 | 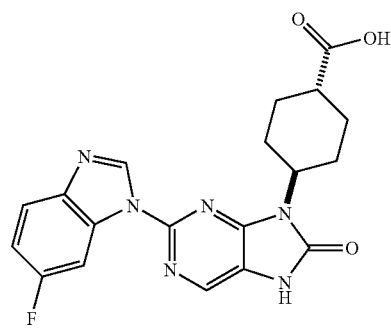 |
| | 421 | 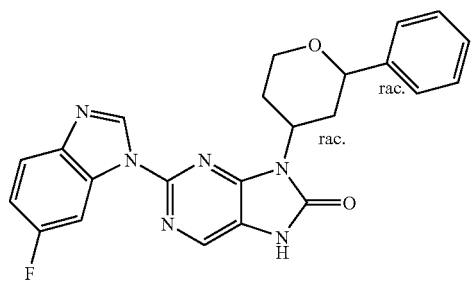 |
| | 422 | 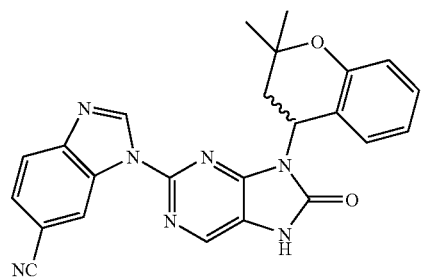 |
| | 423 | 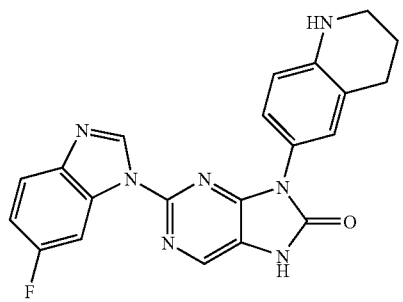 |
| Example 19 | 243 | 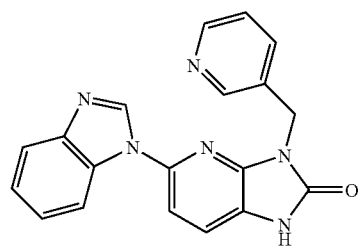 |

TABLE 2-continued
| Synthesis Example | Reference No. | |
|---|---|---|
| Example 17 | 244 | 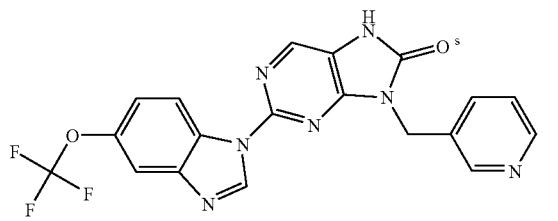 |
|  |  | 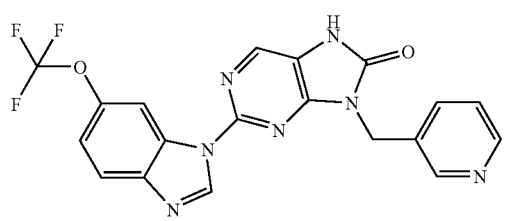 |
|  | 245 | 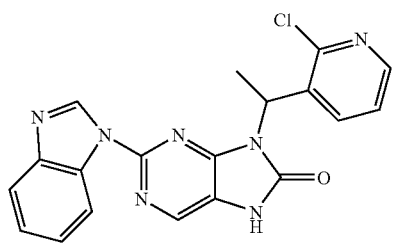 |
|  | 246 | 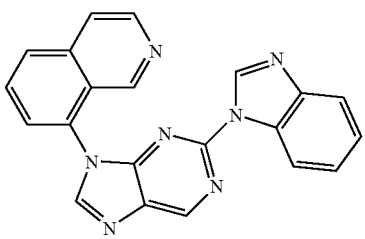 |
|  | 247 | 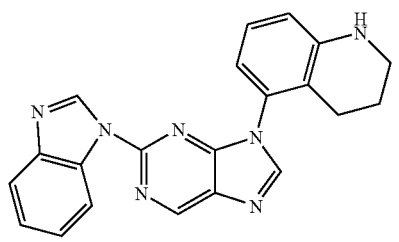 |
|  | 248 | 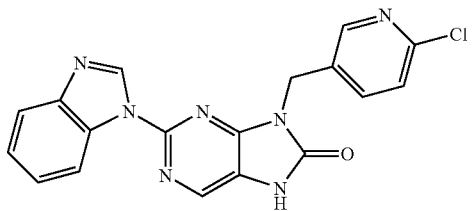 |

TABLE 2-continued
| Synthesis Example | Reference No. | |
|---|---|---|
| | 249 | 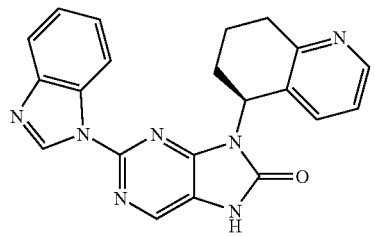 |
| | 250 | 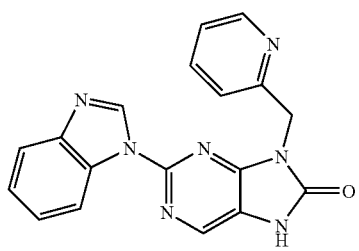 |
| | 251 | 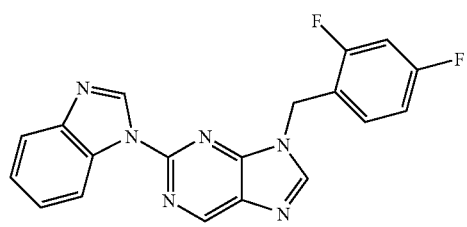 |
| Example 19 | 252 | 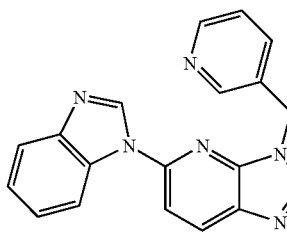 |
| | 253 | 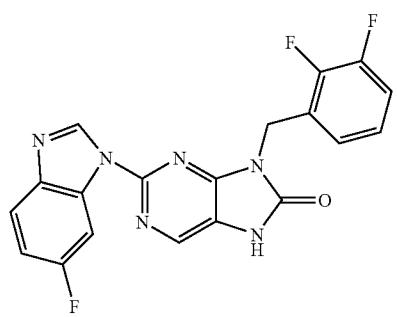 |
| Example 37 | 254 | 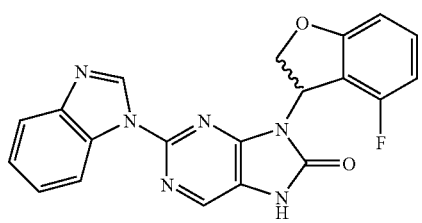 |

TABLE 2-continued
| Synthesis Example | Reference No. | |
|---|---|---|
| | 255 | 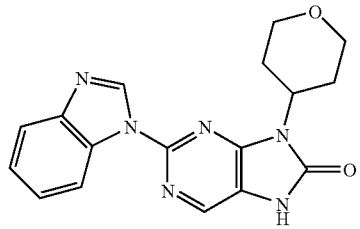 |
| | 256 | 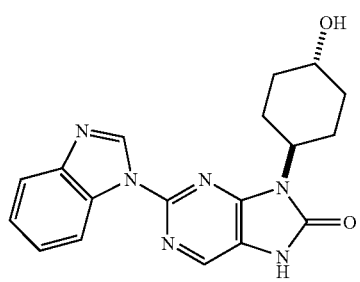 |
| | 257 | 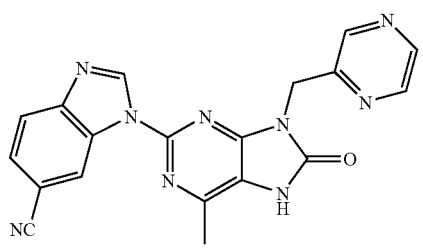 |
| | 258 | 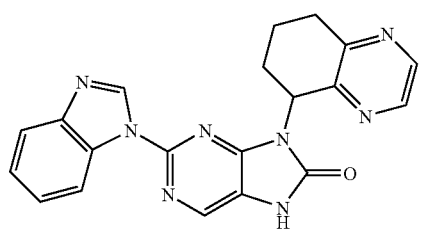 |
| | 259 | 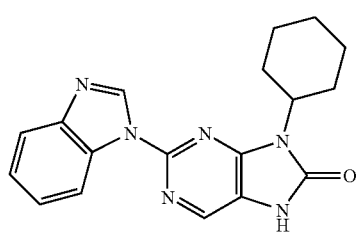 |
| | 260 | 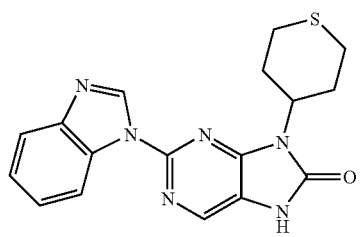 |

TABLE 2-continued
| Synthesis Example | Reference No. | |
|---|---|---|
| | 261 | 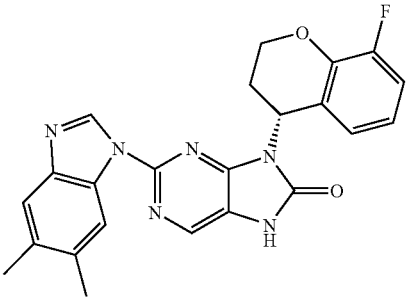 |
| | 262 | 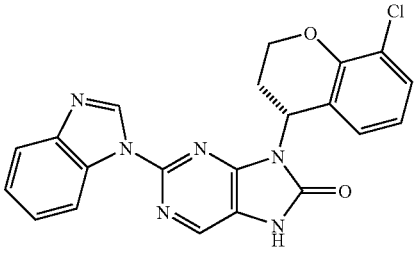 |
| | 263 | 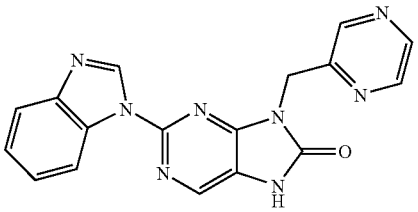 |
| Example 24 | 264 | 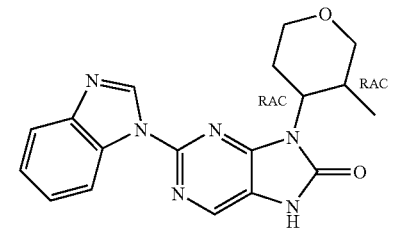 |
| | 265 | 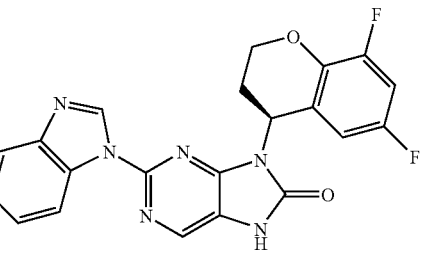 |
| | 266 | 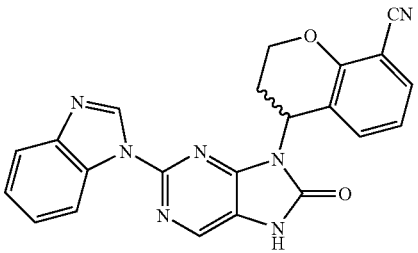 |

TABLE 2-continued
| Synthesis Example | Reference No. | |
|---|---|---|
| | 267 | 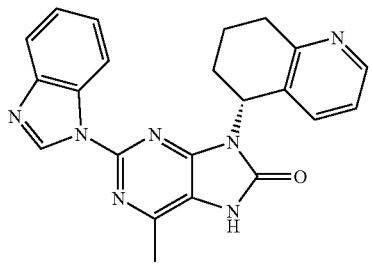 |
| | 268 | 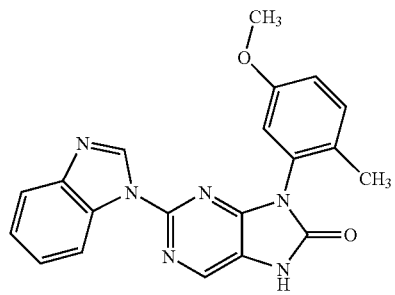 |
| | 269 | 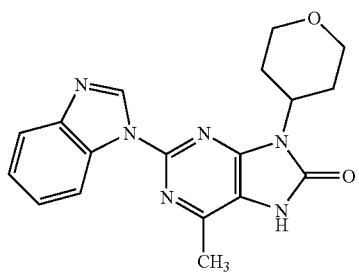 |
| | 270 | 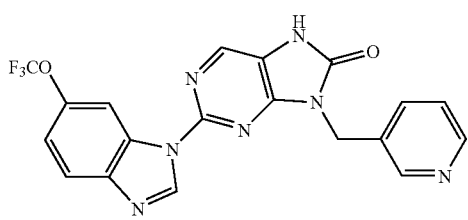 |
| | 271 | 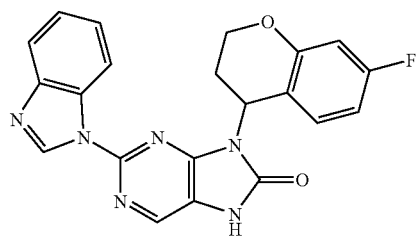 |
| | 272 | 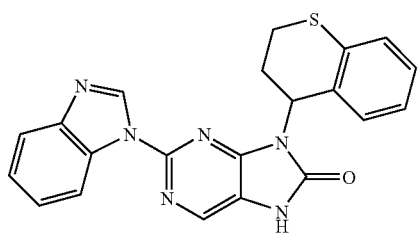 |

TABLE 2-continued
| Synthesis Example | Reference No. | |
|---|---|---|
| | 273 | 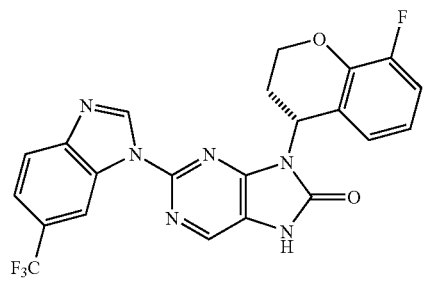 |
| | 274 | 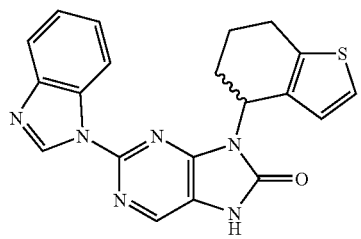 |
| | 275 | 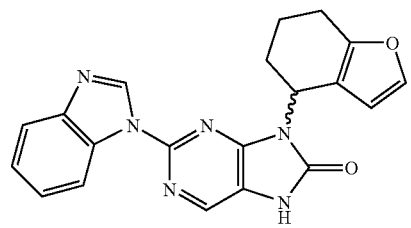 |
| Example 25 | 276 | 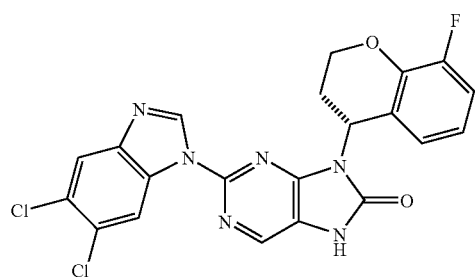 |
| | 277 | 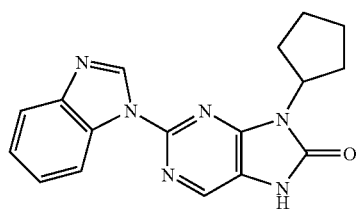 |
| | 278 | 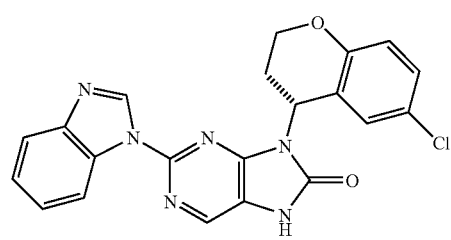 |

TABLE 2-continued
| Synthesis Example | Reference No. | |
|---|---|---|
| | 279 | 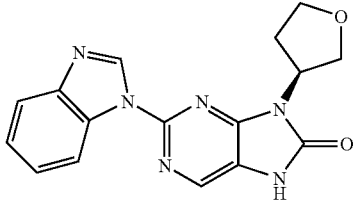 |
| | 280 | 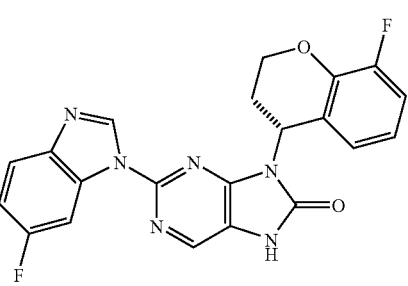 |
| | 281 | 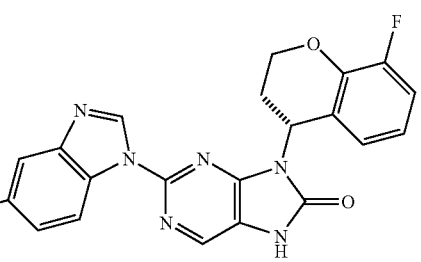 |
| | 282 | 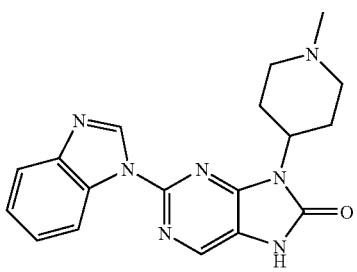 |
| | 283 | 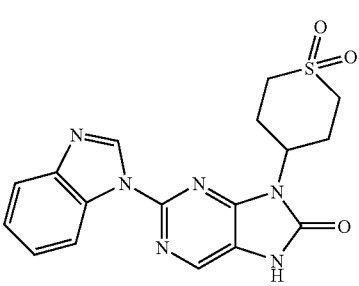 |
| | 400 | 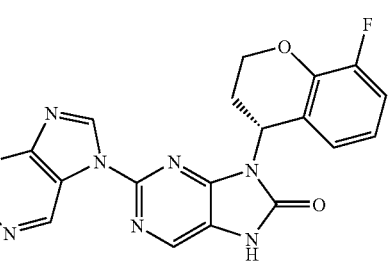 |

TABLE 2-continued
| Synthesis Example | Reference No. | |
|---|---|---|
| | 401 | 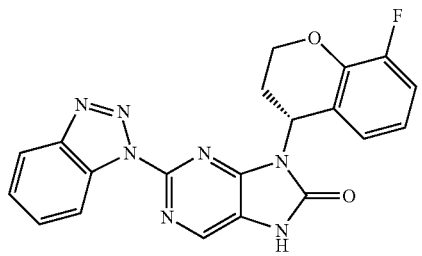 |
| Example 35 | 284 | 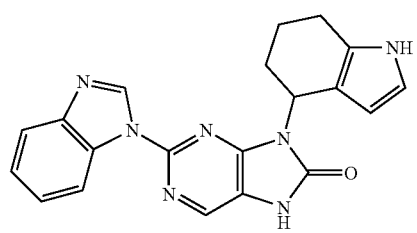 |
| | 285 | 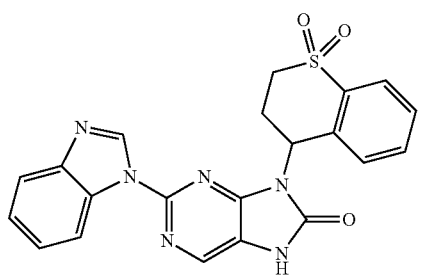 |
| | 286 | 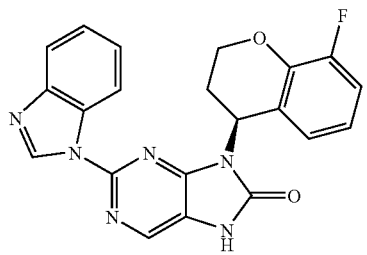 |
| | 287 | 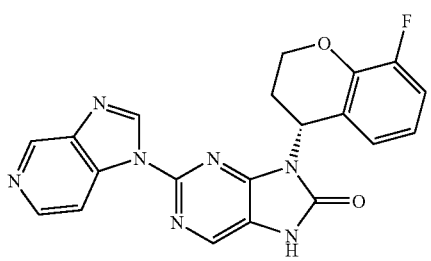 |
| | 288 | 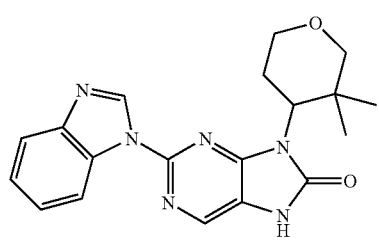 |

TABLE 2-continued
| Synthesis Example | Reference No. | |
|---|---|---|
| | 289 | 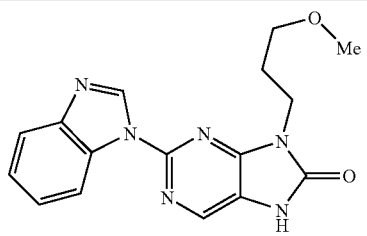 |
| | 290 | 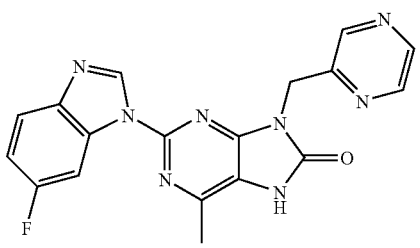 |
| | 291 | 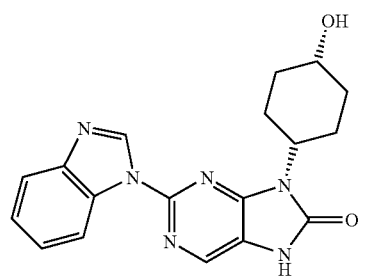 |
| | 292 | 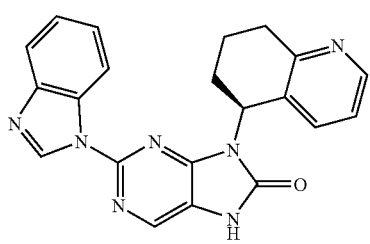 |
| | 293 | 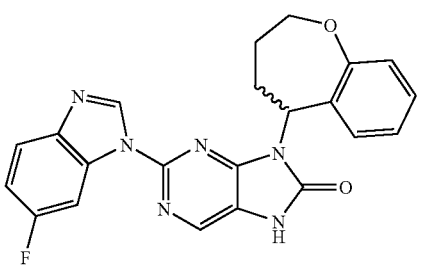 |
| | 294 | 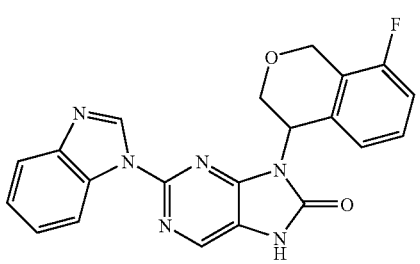 |

TABLE 2-continued
| Synthesis Example | Reference No. | |
|---|---|---|
| | 432 | 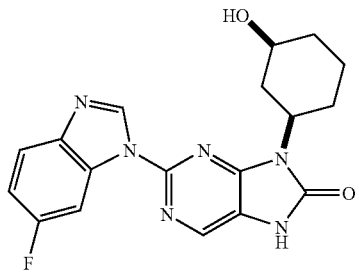 |
| | 433 | 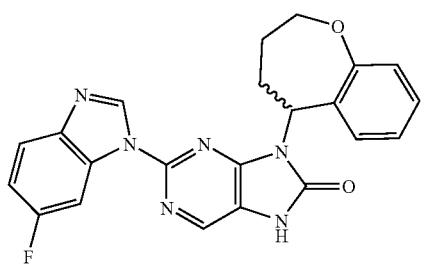 |
| | 434 | 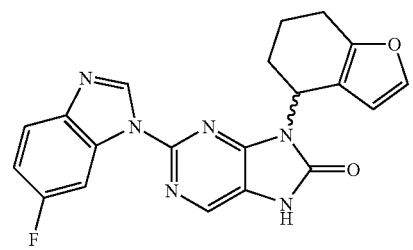 |
| | 435 | 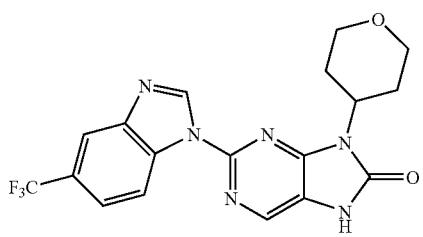 |
| | 436 | 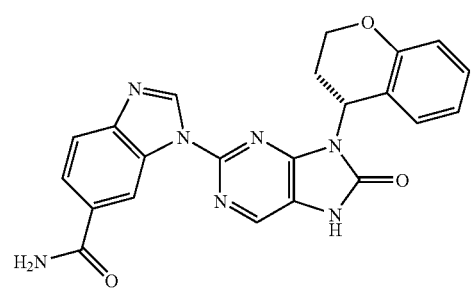 |

TABLE 2-continued
| Synthesis Example | Reference No. | |
|---|---|---|
| | 437 | 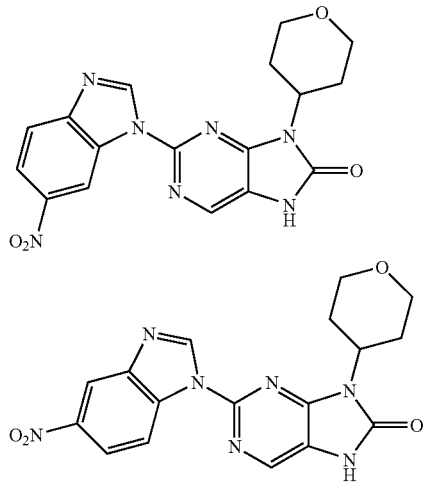 |
| | 438 | 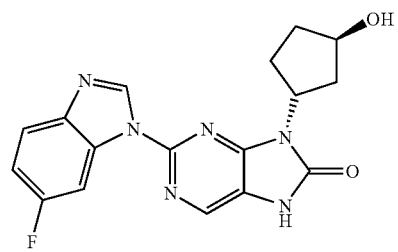 |
| | 439 | 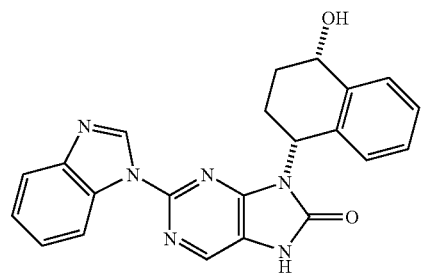 |
| | 440 | 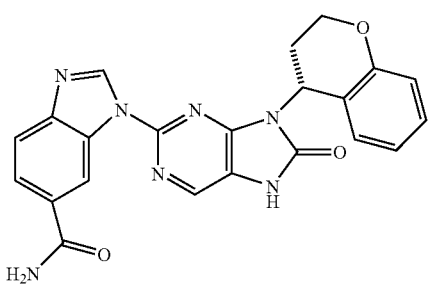 |

TABLE 3
| Synthesis Example | Reference No. | |
|---|---|---|
| | 301 | 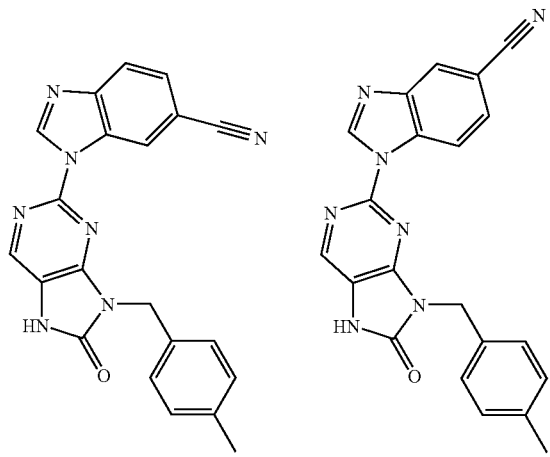 |
| | 302 | 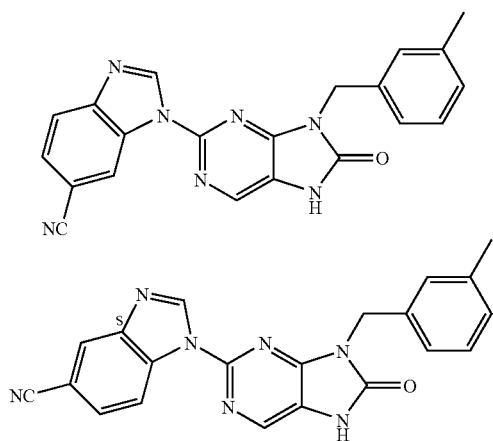 |
| | 303 | 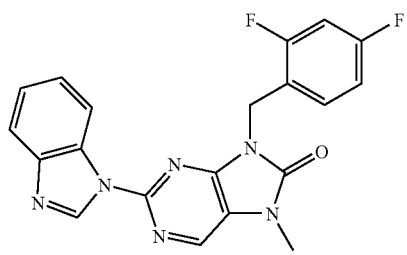 |
| | 304 | 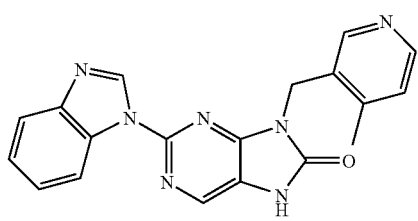 |

TABLE 3-continued
| Synthesis Example | Reference No. |
|---|---|
| | 305 |
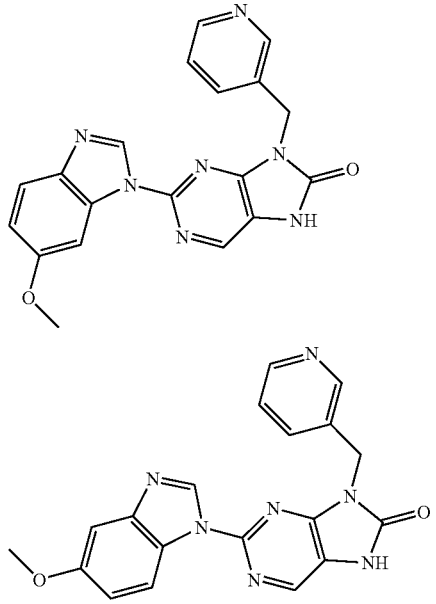
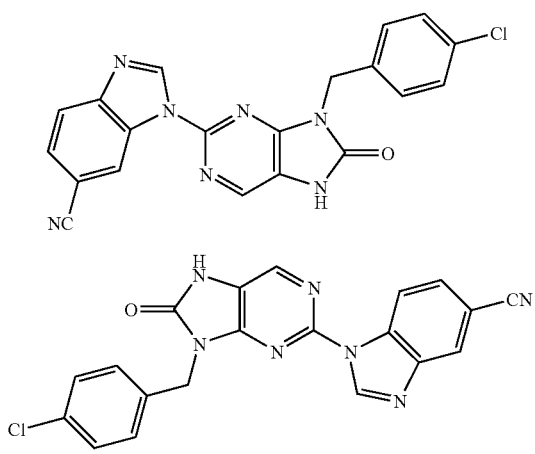
306
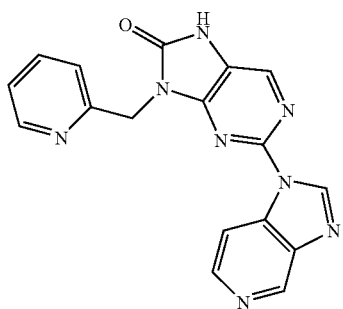
307

TABLE 3-continued
| Synthesis Example | Reference No. | |
|---|---|---|
| | 308 | 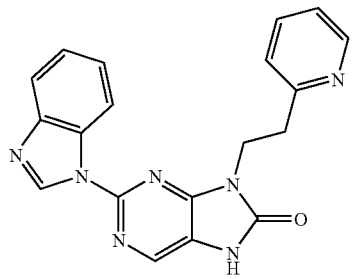 |
| | 309 | 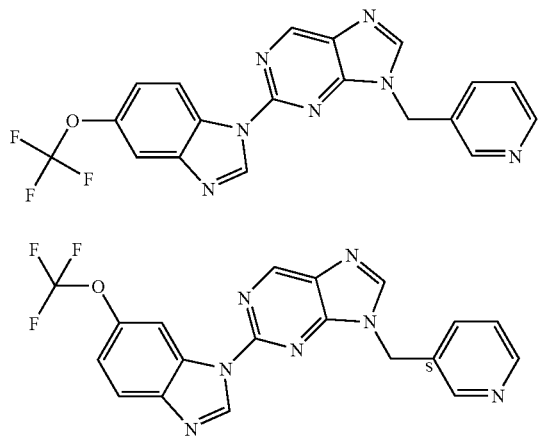 |
| | 310 | 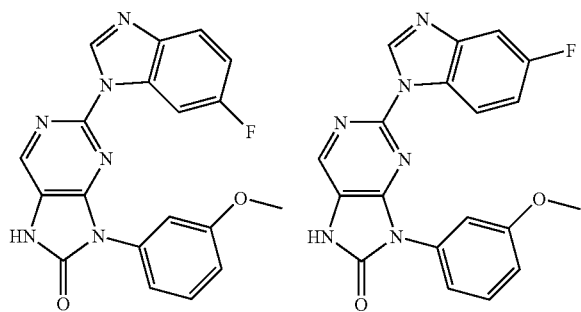 |
| | 311 | 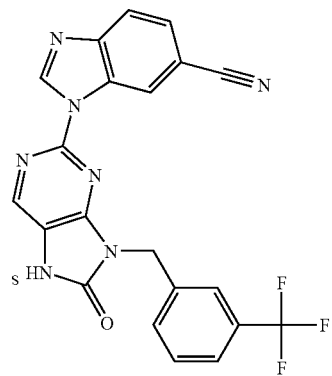 |

TABLE 3-continued
| Synthesis Example | Reference No. | |
|---|---|---|
| | | 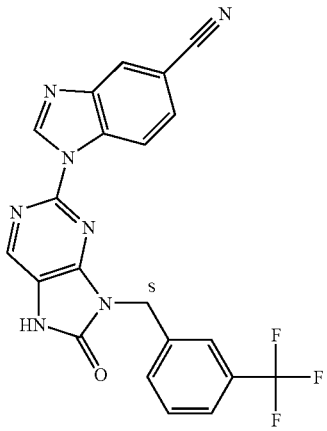 |
| | 312 | 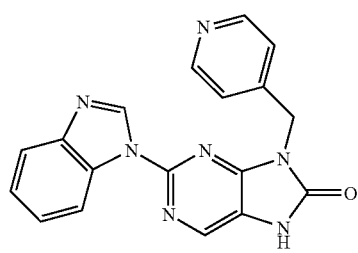 |
| | 313 | 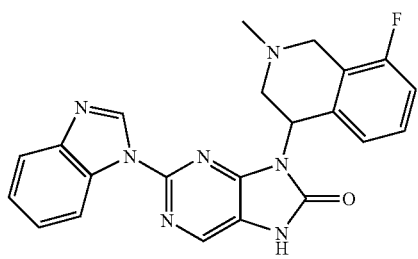 |
| | 314 | 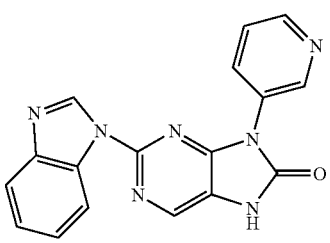 |
| | 315 | 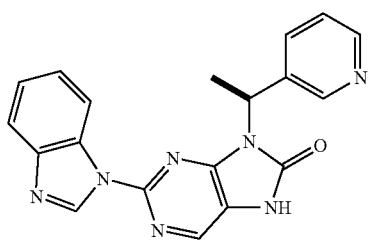 |

TABLE 3-continued
| Synthesis Example | Reference No. | |
|---|---|---|
| | 316 | 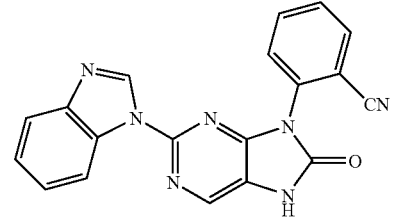 |
| | 317 | 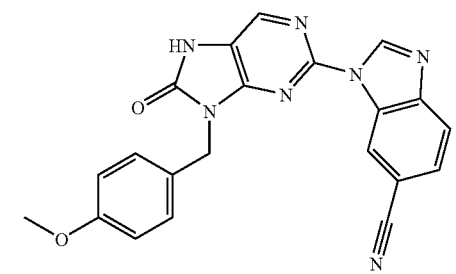 |
| | | 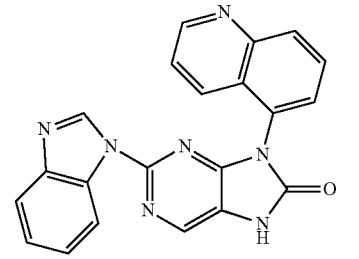 |
| | 318 | 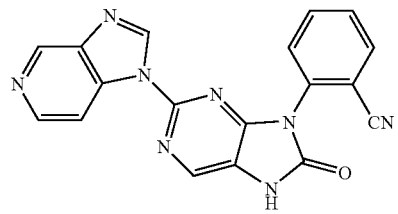 |
| | 320 | 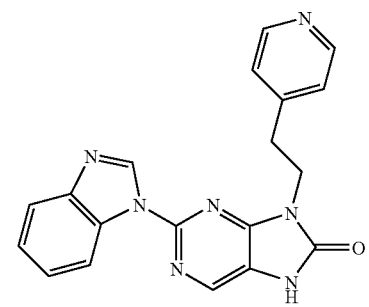 |
| | 321 | |

TABLE 3-continued
| Synthesis Example | Reference No. | |
|---|---|---|
| | 322 | 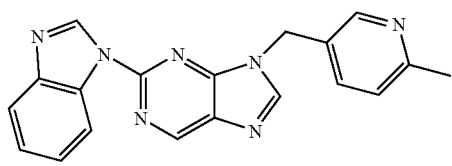 |
| | 323 | 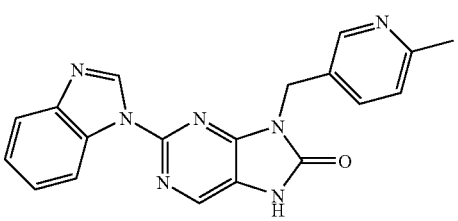 |
| | 324 | 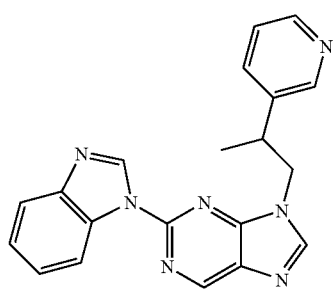 |
| | 325 | 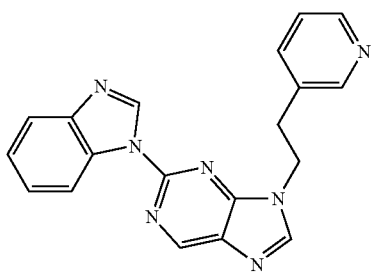 |
| | 326 | 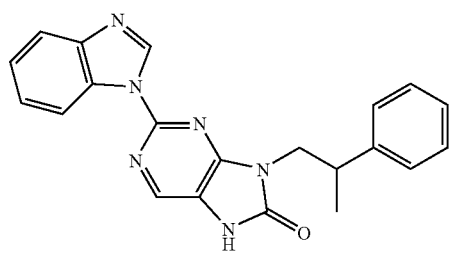 |
| | 327 | 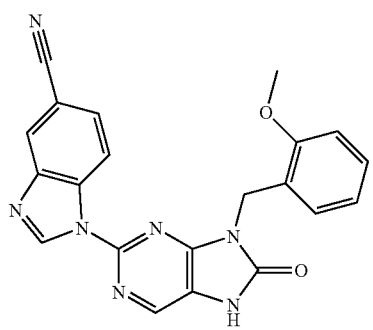 |

TABLE 3-continued
| Synthesis Example | Reference No. | |
| --- | --- | --- |
| | 328 | 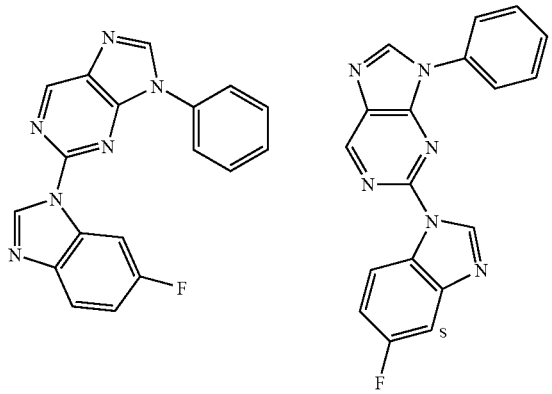 |
| | 329 | 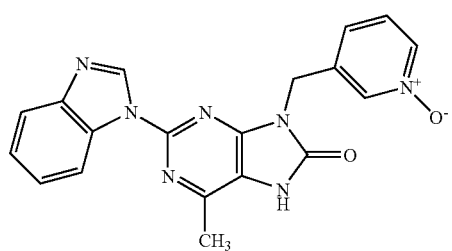 |
| | 330 | 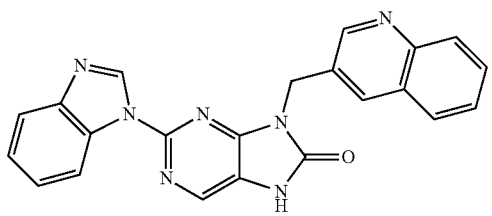 |
| | 331 | 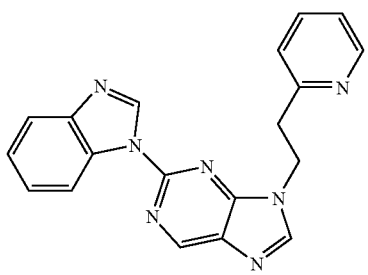 |
| | 332 | 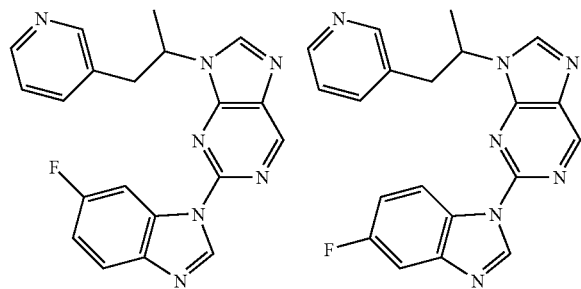 |

247
TABLE 3-continued
| Synthesis Example | Reference No. | |
|---|---|---|
| | 333 | 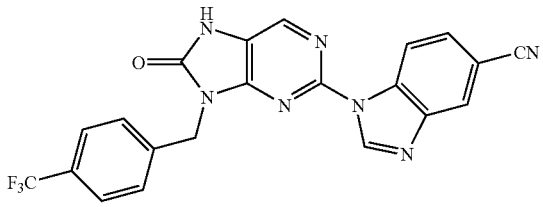 |
| | | 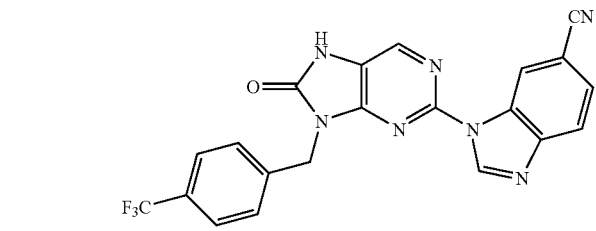 |
| | 334 | 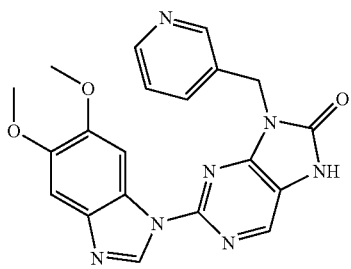 |
| | 335 | 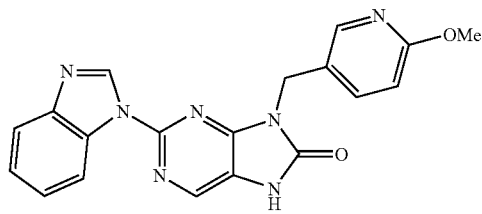 |
| | 336 | 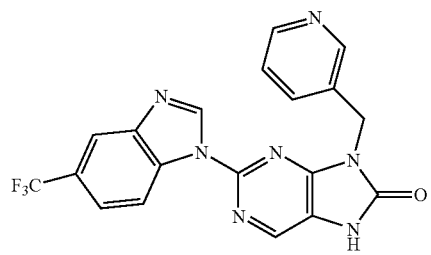 |
| | 337 | 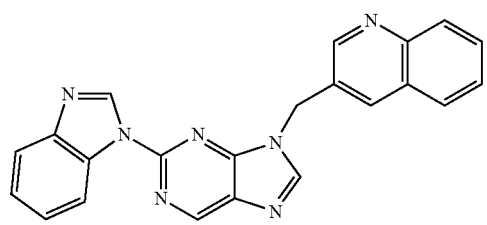 |

TABLE 3-continued
| Synthesis Example | Reference No. |
|---|---|
| | 338 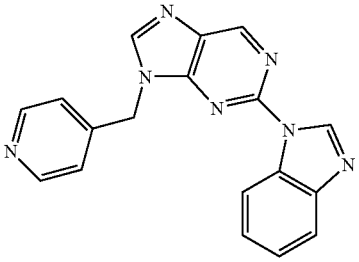 |
| | 339 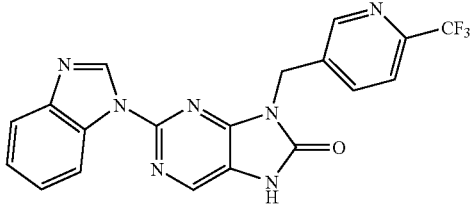 |
| | 340 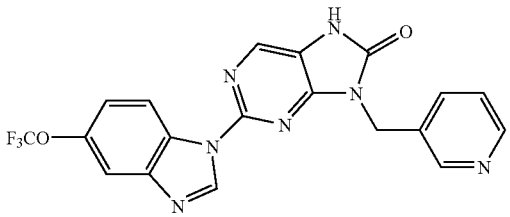 |
| | 341 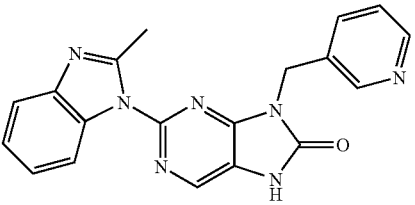 |
| | 342 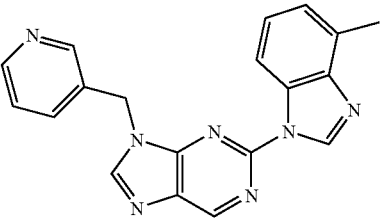 |
| | 345 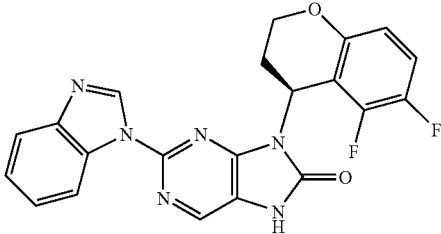 |

TABLE 3-continued
| Synthesis Example | Reference No. | |
|---|---|---|
| | 346 | 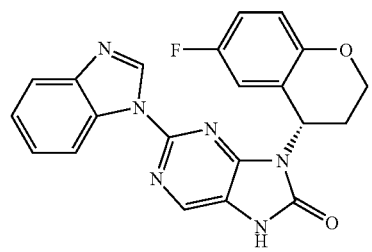 |
| | 347 | 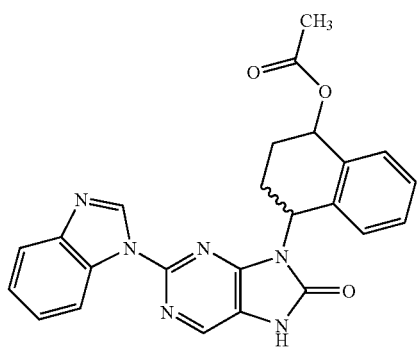 |
| | 348 | 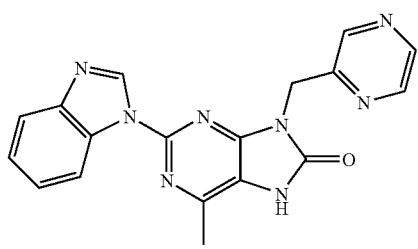 |
| | 349 | 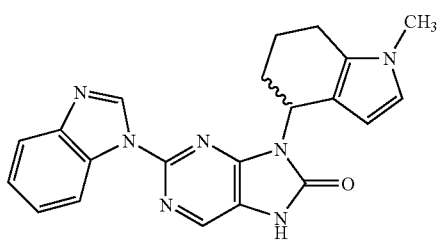 |
| | 350 | 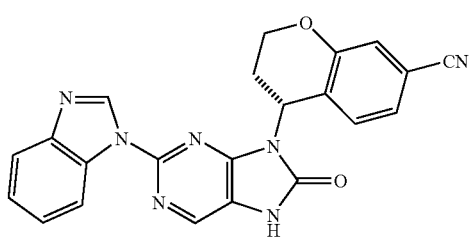 |

TABLE 3-continued
| Synthesis Example | Reference No. | |
|---|---|---|
| | 351 | 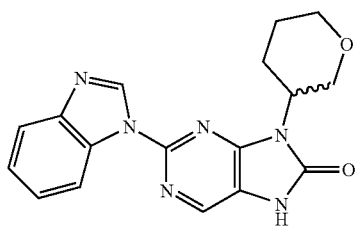 |
| | 352 | 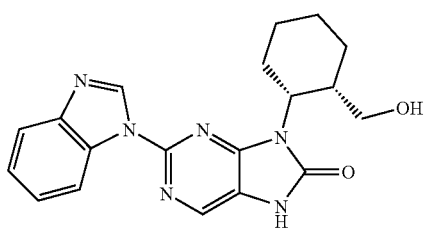 |
| | 353 | 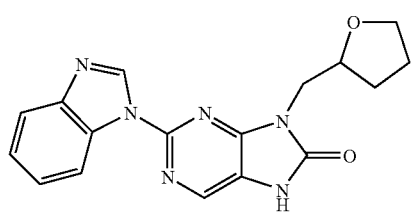 |
| | 354 | 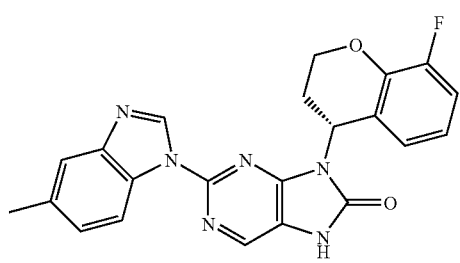 |
| | 355 | 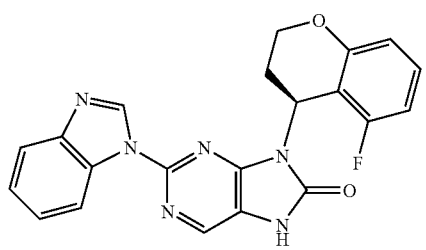 |
| | 356 | 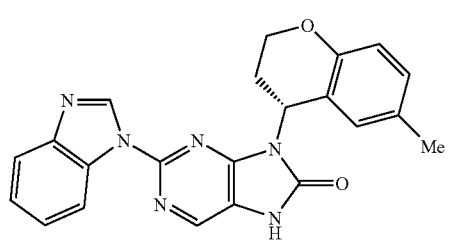 |

TABLE 3-continued

| Synthesis Example | Reference No. |
|---|---|
| | 357 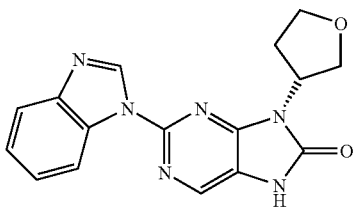 |
| | 358 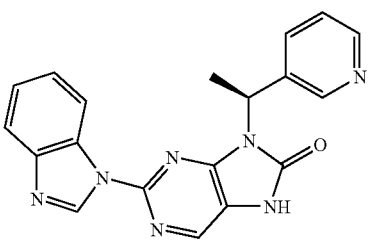 |
| | 359 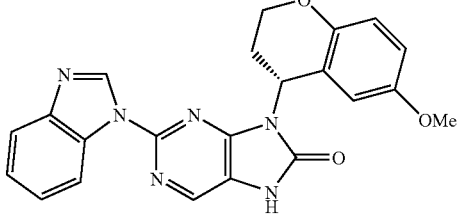 |
| | 360 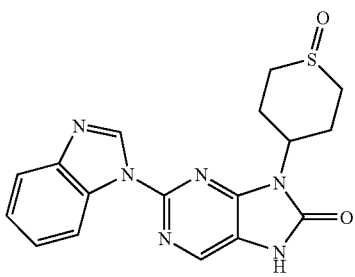 |
| | 361 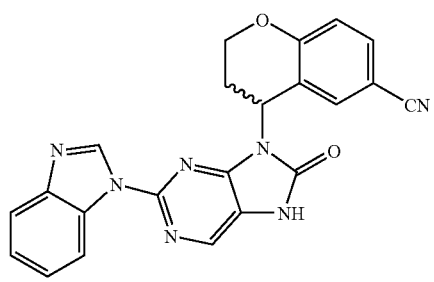 |

IL-2-Induced IFN-γ Production in the Mouse

Administration of IL-2 leads to an increase in serum IFN-γ in the mouse due to NK secretion of the cytokine (Thornton S, Kuhn K A, Finkelman F D and Hirsch R. NK cells secrete high levels of IFN-γ in response to in vivo administration of IL-2. Eur J Immunol 2001 31:3355-3360). The experiment was carried out essentially according to the protocol in Thornton et al. and the test compounds were administered in order to determine the level of inhibition attained. In summary, female BALB/c mice were fasted for 12-18 hours before a study but had free access to water at all times. Test compounds were administered by gavage one hour before intraperitoneal injection of IL-2 and capture antibody. At termination of the studies, the mice were sacrificed by carbon dioxide inhalation, terminal blood samples were collected by cardiac puncture and serum was generated. Serum was stored frozen until it was assayed for IFN-γ, as described by the kit manufacturer (BD Pharmingen™, San Diego, Calif.).

Using the above method, compounds 114, 120, 135, 137, 138, 139, 142, 143, 151, and 162 from Table 1 were shown to inhibit IL-2-induced IFN-gamma production by >40% at 30 mg/kg in vivo in the mouse. A reference compound, CP690550, exhibited 96% inhibition at 30 mg/kg in this screen.

Although the foregoing invention has been described in some detail for purposes of illustration, it will be readily apparent to one skilled in the art that changes and modifications may be made without departing from the scope of the invention described herein.

The invention claimed is:

1. A compound of formula:

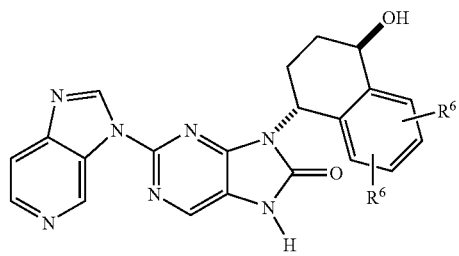

wherein $R^6$ is hydrogen or halogen.

2. A compound of formula:

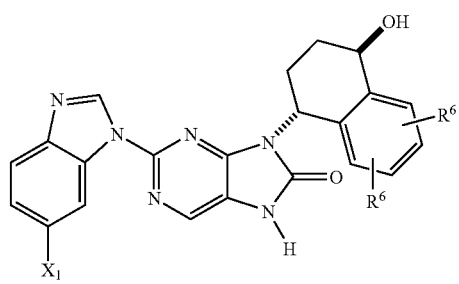

wherein $X_1$ is selected from hydrogen, cyano, halogen, halo($C_1$-$C_6$)alkyl and halo($C_1$-$C_6$)alkoxy, and $R^6$ is hydrogen or halogen.

3. A compound according to claim 2 selected from

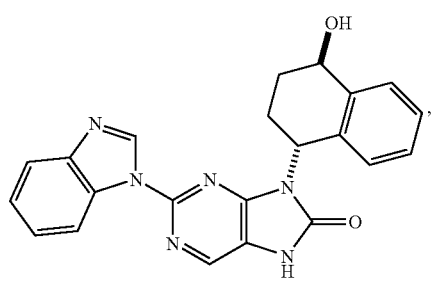

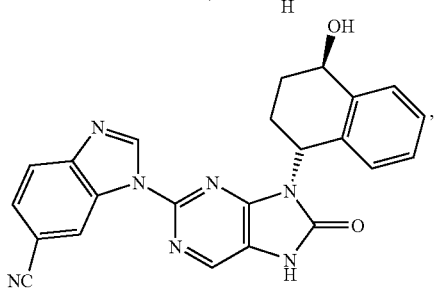

-continued

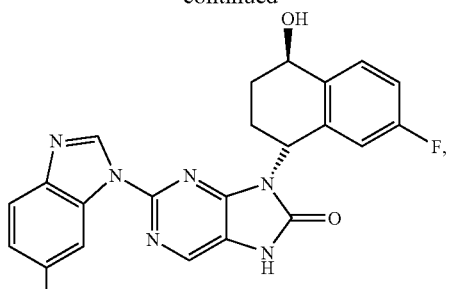

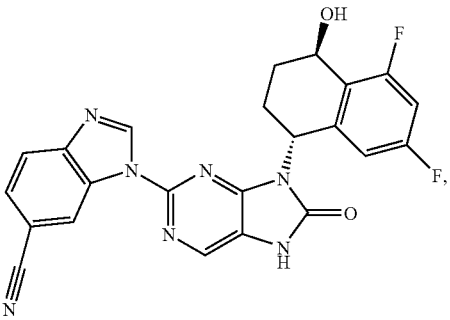

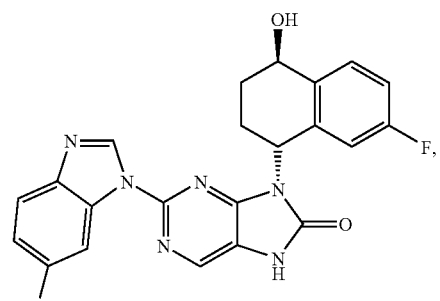

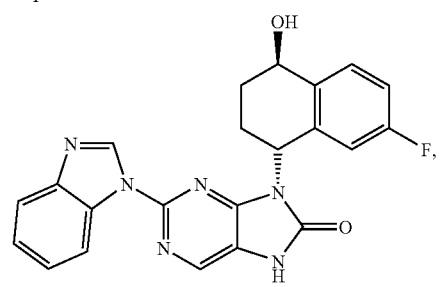

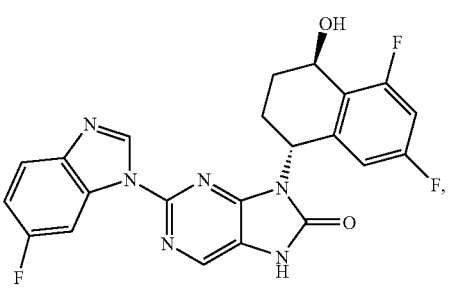

-continued
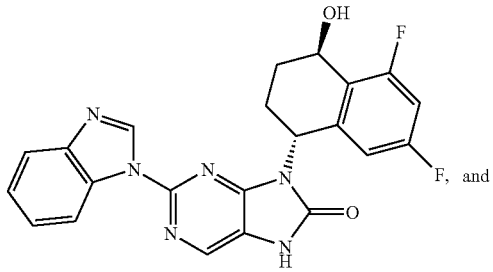
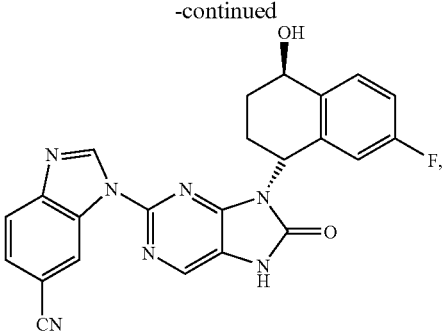
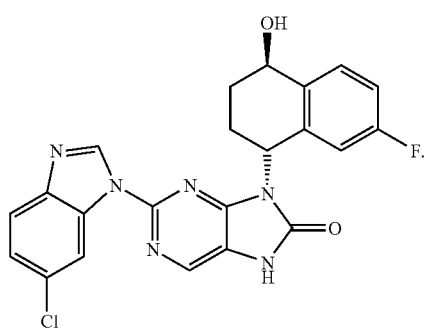
4. A compound according to claim 2, selected from
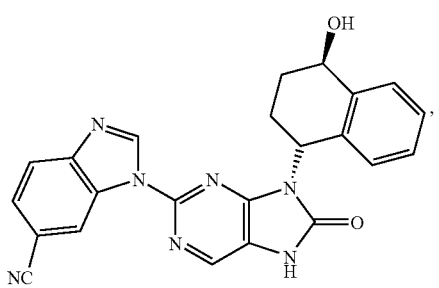
-continued
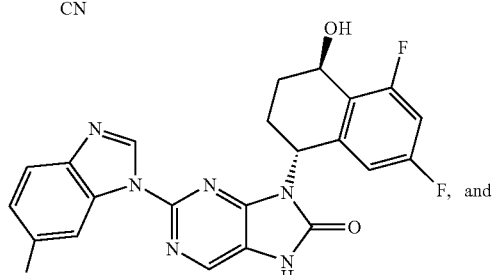
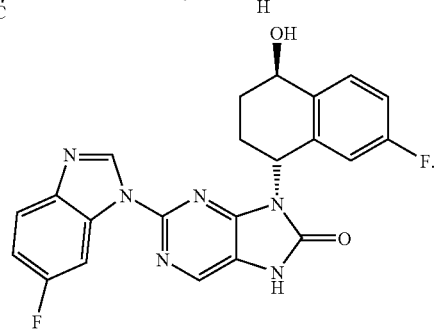
5. A pharmaceutical composition comprising a pharmaceutically acceptable carrier and a therapeutically effective amount of at least one compound according to claims 1 or 2-4.
* * * * *